(12) United States Patent
Hirata et al.

(10) Patent No.: US 7,902,369 B2
(45) Date of Patent: Mar. 8, 2011

(54) DIARYL-SUBSTITUTED FIVE-MEMBERED HETEROCYCLE DERIVATIVE

(75) Inventors: Yukari Hirata, Tsukuba (JP); Satoru Ito, Tsukuba (JP); Hiroshi Kawamoto, Tsuchiura (JP); Toshifumi Kimura, Tsukuba (JP); Yasushi Nagatomi, Tsukuba (JP); Hisashi Ohta, Tsukuba (JP); Akio Sato, Ushiku (JP); Atsushi Satoh, Tsukuba (JP); Gentaroh Suzuki, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 1200 days.

(21) Appl. No.: 10/590,586

(22) PCT Filed: Mar. 7, 2005

(86) PCT No.: PCT/JP2005/004379
§ 371 (c)(1),
(2), (4) Date: Aug. 24, 2006

(87) PCT Pub. No.: WO2005/085214
PCT Pub. Date: Sep. 15, 2005

(65) Prior Publication Data
US 2007/0173507 A1    Jul. 26, 2007

(30) Foreign Application Priority Data
Mar. 5, 2004   (JP) .................................. 2004-063243

(51) Int. Cl.
*C07D 401/00*   (2006.01)
*C07D 417/00*   (2006.01)
*C07D 403/00*   (2006.01)

(52) U.S. Cl. ...................... 546/268.4; 548/181; 548/255

(58) Field of Classification Search ............... 546/268.4; 548/255, 181
See application file for complete search history.

(56) References Cited

U.S. PATENT DOCUMENTS

| | | | |
|---|---|---|---|
| 6,399,641 B1 | 6/2002 | Jolidon et al. | |
| 6,969,730 B2 | 11/2005 | Cowart et al. | |
| 7,105,548 B2 | 9/2006 | Cosford et al. | |
| 7,417,053 B2 * | 8/2008 | Unoki et al. | 514/300 |
| 7,538,138 B2 | 5/2009 | Cowart et al. | |
| 2005/0256118 A1 * | 11/2005 | Altenbach et al. | 514/233.8 |

FOREIGN PATENT DOCUMENTS
JP   2003146990      5/2003
WO   WO 03051315  *  6/2003

OTHER PUBLICATIONS

Eistert et al. STN Abstract Document No. 73:14768, Justus Liebigs Annalen der Chemie (1970), 734, 56-69.*
L'abbe et al. STN Abstract Document No. 122:290182 Bulletin des Societes Chimiques Beiges (1994), 103(7-8), 321-7.*
International Search Report for JP PCT/JP2005/004379, dated May 24, 2005.
EP Search Report for EP JP PCT/JP2005/004379, dated Jun. 12, 2009.
International Preliminary Report on Patentability for JP PCT/JP2005/004379, Dec. 6, 2009.

* cited by examiner

*Primary Examiner* — Nizal S Chandrakumar
(74) *Attorney, Agent, or Firm* — J. Eric Thies; Gerard M. Devlin

(57) ABSTRACT

The present invention provides the compounds represented by formula (I):

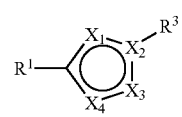

(I)

or pharmaceutical salts thereof, wherein:
$X_1$ represents oxygen atoms and the like, $X_2$ represents nitrogen atoms and the like, $X_3$ represents nitrogen atoms and the like, $X_4$ represents nitrogen atoms and the like, $R^1$ represents formula (II-1):

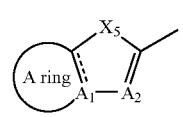

(II-1)

wherein $X_5$ represents sulfur atoms and the like, $A_1$ represents carbon atoms and the like, $A_2$ represents nitrogen atoms and the like and A ring represents phenyl group and the like,
having mGluR1 inhibiting effect, and being usefull for preventing or treating convulsion, acute pain, inflammatory pain, chronic pain, brain disorder such as cerebral infarction or transient ischemick attack, psychotic disorder such as schizophrenia, anxiety, drug dependence, Parkinson's disease, or gastrointestinal disorder.

13 Claims, No Drawings

DIARYL-SUBSTITUTED FIVE-MEMBERED HETEROCYCLE DERIVATIVE

CROSS REFERENCE TO RELATED APPLICATIONS

This application is a U.S. National Phase application under 35 U.S.C. §371 of PCT Application No. PCT/JP2005/004379, filed Mar. 7, 2005, which claims priority under 35 U.S.C. §119 from JP Application No. JP2004-062343, filed Mar. 5, 2004.

TECHNICAL FIELD

The present invention relates to a diaryl-substituted hetero-5-membered ring derivative.

BACKGROUND ART

Glutamic acid is a neurotransmitter mediating excitatory transmission in central nervous system. Glutamic acid is related to various important brain function such as life and death, differentiation and proliferation of neuron; development of neuron and glial cells, flexible change of neurotransmission efficiency of mature or developed brain, as well as various neurotransmission (see for example, Annual Review of Biophysics and Biomolecular Structure, Vol. 23, p. 319 (1994), etc.).

From pharmacological and molecular biological studies, glutamate receptors in mammal's central nervous system are classified into two classes, i.e. ion channel-glutamate receptor, and metabotropic glutamate receptor (hereinafter referred to as "mGluR"). Ion channel-glutamate receptors are comprised of a complex of different subunit proteins, and are ion channels gating with the bindings of ligands. On the other hand, mGluR conjugates with GTP binding protein, and acts by controlling production of intracellular second messengers, or activation of ion channel via GTP binding protein (see for example, Brain Research Reviews, Vol. 26, p. 230 (1998), etc.).

From studies so far, mGluR has been reported to exist as eight different subtypes of mGluR1 to MGluR8. These subtypes are classified into three subgroups based on homology of amino acid sequence, signaling, and pharmacological properties. Group I (mGluR 1 and 5) activates phospholipase C against intracellular signaling, while Group II (mGluR2 and 3) and Group III (mGluR4, 6, 7 and 8) regulates adenylate cyclase activity to suppress accumulation of cyclic adenosine monophosphate (CAMP) by forskolin stimulation. Moreover, Group II is selectively activated by LY354740 described in for example, Journal of Medicinal Chemistry, Vol. 42, p. 1027 (1999), etc., and Group III is selectively activated by L-AP4. Furthermore, various receptors other than mGluR6 which exists specifically in retina express widely in brain and nervous systems, each showing characteristic distribution within the brain, and each receptor is believed to have a different physiological function (see for example, Neurochemistry International, Vol. 24, p. 439 (1994); European Journal of Pharmacology, Vol. 375, p. 277 (1999), etc.).

Moreover, as for compounds structurally similar to formula (I), for example a compound shown by formula (A):

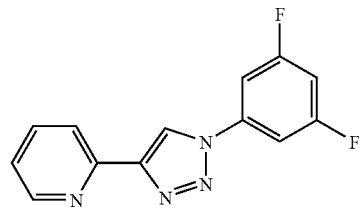

(A)

is described (see for example, WO03/051315, etc.).

The compound shown by the above formula (A) is common to the compound of the present invention on the point that the group bound to the 1$^{st}$ position of triazole group is a phenyl group substituted by a fluorine. However, while the group bound to the 4$^{th}$ position of triazole group of the formula (A) is a pyridyl group, the group bound to the 4$^{th}$ position of triazole ring of the compound (I) of the present invention, is different being a double ring group. Moreover, it is also different as the compound shown by (A) is a modulator of mGluR5, while the compound (I) of the present invention is a compound showing mGluR1 inhibiting effect.

DISCLOSURE OF THE INVENTION

Therefore, the object of the present invention is to provide a new substance having mGluR1 inhibiting effect.

The present inventors found that the specific diaryl substituted hetero 5 membered ring derivative has mGluR1 inhibiting effect, and the present invention has been thus accomplished.

In other words, the present invention provides the following compounds (1) to (20), or a pharmaceutically acceptable salt thereof, to achieve the above object.

(1) A compound represented by formula (I):

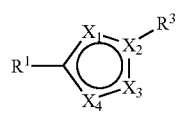

(I)

or a pharmaceutically acceptable salt thereof, wherein:
  $X_1$ represents an oxygen atom, nitrogen atom or $CR^2$;
  $X_2$ represents a nitrogen atom or a carbon atom;
  $X_3$ represents a nitrogen atom or a carbon atom;
  $X_4$ represents a nitrogen atom or a carbon atom;
  $R^1$ represents the following formula (II-1):

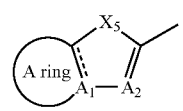

(II-1)

wherein:
    —$X_5$— represents —S— or -$A_4$=$A_3$-, $A_1$ is a carbon atom or a nitrogen atom, as for $A_2$ to $A_4$, either all of $A_2$ to $A_4$ are $CR^4$ or any one or two of $A_2$ to $A_4$ are nitrogen atoms and the remaining two or one of $A_2$ to $A_4$ are $CR^4$;
    ˭˭˭˭shows a double bond when $A_1$ is a carbon atom, and a single bond when $A_1$ is a nitrogen atom;

R⁴ represents a hydrogen atom, lower alkyl group, lower alkyloxy group, halogen atom, mono-or di-lower alkylamino atom, hydroxy group, lower alkyloxycarbonyl group, carbamoyl group or mono-or di-lower alkylcarbamoylamino group;

A ring is the following (1) or (2), that may have 1 to 3 substituted groups selected from the group comprising substituted group α, (1) saturated, partially saturated, or unsaturated 5-or 6-membered ring and the ring may be substituted by 1 or 2 oxo groups, wherein all of the constituting atoms of A ring are carbon atoms, or (2) saturated, partially saturated or unsaturated 5-or 6-membered ring that may have 1 to 3 hetero atoms selected from the group comprising N, S and O, besides carbon atoms, as for constituting atoms of A ring and the ring may be substituted by 1 or 2 oxo groups;

R² represents a group selected from the group consisting of hydrogen atom, lower alkyl group, cyano group, lower alkyloxy group, lower alkyloxycarbonyl group and trialkylsilyl group;

R³ is the following group (A) or (B) that may have 1 to 3 substituted groups selected from the group comprising halogen atom, lower alkyl group, cyano group, nitro group, lower alkyloxy group, hydroxy group and amino group;

said lower alkyl group may be substituted by a halogen atom;

group (A) a phenyl group;

group (B) an unsaturated or partially saturated 5-to 6-membered hetero ring group having 1 to 3 hetero atoms selected from the group comprising N, S and O in the ring;

with the proviso that the formula (I) excludes 4-[5-(2-naphthalenyl)1H-[1,2,4]triazole-3-yl]-pyridine, 3-(1-3-benzodioxol-5-yl)-5-(2-ethylphenyl)-1H-1,2,4-triazole, 6-[5-(4-pyridyl)-1H-1,2,4-triazole-4-yl]-quinoline, 3-(5-phenyl-4H-[1,2,4]triazole-3-yl)naphthalene-2-ol, 3-[5-pyridine-4-yl-1H-[1,2,4]triazole-3-yl]-naphthalene-2-ol, 5-(quinoline-2-yl)-2-(3-cyano-phenyl)-tetrazole, 3-[5-(3,5-dichloropyridine4-yl)-2-methyl-2H-[1,2,4]triazole-3-yl]-quinoline, 3-naphthalene-2-yl-5-phenyl-4H-[1,2,4]triazole, 3-benzo[1,3]dioxol-5-yl-1-methyl-5-o-tolyl-1H-[1,2,4]triazole, 5-(5-phenyl-4H-[1,2, 4]triazole-3-yl)isobenzofuran-1,3-dione.

Substituted group α lower alkyl group (the lower alkyl group may be substituted by a hydroxyl group, halogen atom, aryl group di-lower alkylamino group (two di-lower alkyl groups may bound each other and form a 5-to 7-membered aliphatic hetero ring together with nitrogen atom, or 1 of the carbon atom constituting the aliphatic hetero ring may be substituted by an oxygen atom), lower alkoxy group, oxo group, lower alkyloxycarbonyl group, alkanoyloxy group or lower alkyl-sulfonylamino group; or when the lower alkyl group is a branched-lower alkyl group, the branched alkyls group may bound each other to form a cycloalkyl group or a cycloalkylene group with 3 to 6 carbon atoms, when the lower alkyl group is a branched-lower alkyl group, the branched alkyl groups may be bound each other to form a cycloalkyl group (the cycloalkyl group may be substituted by a lower alkyl group, hydroxy group, aralkyl group, or lower alkoxy group), when the same carbon atom constituting A ring has 2 lower alkyl groups, the lower alkyl group may form together a cycloalkyl group), cycloalkyl group (any 1 of carbon atoms constituting the cycloalkyl group may be substituted by an oxygen atom), lower alkyloxy group, halogen atom, mono-or di-lower alkylamino group, alkanoyl group, alkylsulfonyl group, lower alkyloxycarbonyl group, carbamoyl group, mono-or di-lower alkylcarbamoyl group, mono-or di-lower alkylcarbamoylamino group, amino group and hydroxyl group.

(2) The compound according to (1), or a pharmaceutically acceptable salt thereof, wherein:

formula (I) is formula (I-1),

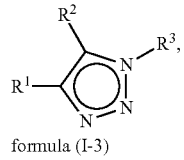
formula (I-2)

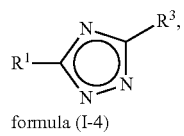
formula (I-3)

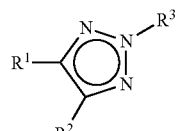
formula (I-4)

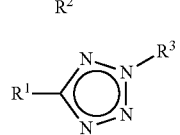

wherein each symbol is the same as above.

(3) The compound according to (1) or (2), or a pharmaceutically acceptable salt thereof, wherein:

R¹ is formula (II-A):

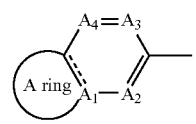

wherein each symbol is the same as above.

(4) The compound according to (3), or a pharmaceutically acceptable salt thereof, wherein:

formula (II-A)formula (II-B):

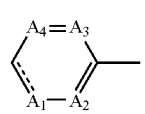

n formula (II-A) is a phenyl group.

(5) The compound according to (3) or (4), or a pharmaceutically acceptable salt thereof, wherein:

A ring has at least 1 nitrogen atom as a constituting atom of the A ring.

(6) The compound according to (3), or a pharmaceutically acceptable salt thereof, wherein:
formula (II-A) is a group represented by formula (II-C):

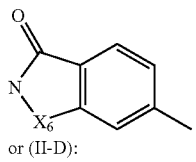

or (II-D):

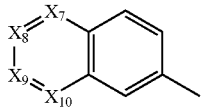

wherein $X^6$ represents $CH_2$, CH=CH or CH—CH, and as for $X_7$ to $X_{10}$, 1 of $X_7$ to $X_{10}$ is a nitrogen atom, and the rest are carbon atoms;
said group may have 1 to 3 substituted groups selected from the above mentioned substituted group α that ring A may have.
(7) The compound according to (6), wherein formula (II-A) is formula (II-C), or a pharmaceutically acceptable salt thereof.
(8) The compound according to (6), wherein formula (II-A) is formula (II-D), or a pharmaceutically acceptable salt thereof.
(9) The compound according to any one of (1), (2), (3) or (4), or a pharmaceutically acceptable salt thereof, wherein:
formula (I) is formula (I-1) or formula (I-4);
with the proviso that $R^1$ is a substituted or non-substituted naphthyl group.
(10) The compound according to (1), or a pharmaceutically acceptable salt thereof, wherein:
the compound represented by the formula (I) is:
5-methyl-1-phenyl-4-(quinoline-6-yl)-1H-[1,2,3]triazole,
5-methyl-4-(1-oxo-indene-5-yl)-1-phenyl-1H-[1,2,3]triazole,
5-methyl-4-(2-methylbenzothiazole-5-yl)-1-phenyl-1H-[1,2,3]triazole,
4-(1H-indole-5-yl)-5-methyl-1-phenyl-1H-[1,2,3]triazole,
1-(2-fluoropyridine3-yl)-5-methyl-4-(quinoline-6-yl)-1H[1,2,3]triazole,
5-methyl-4(naphthalene-2-yl)-5-methyl-1H-[1,2,3]triazole,
4-(3-cyclohexyl-5-fluoro-6-methyl-4-oxo-4H-chromen-7-yl)-5-methyl-1-phenyl-1H-[1,2,3]triazole,
1-(2-fluoropyridine3-yl)-5-methyl-4-(2-methyl-quinoline-6-yl)-1H-[1,2,3]triazole,
1-(2-fluoropyridine3-yl)-5-methyl-4-quinoxaline-6-yl)-1H-[1,2,3]triazole,
4-(1,3-dioxo-2,3-dihydro-1H-isoindole-5-yl)-5-methyl-1-phenyl-1H-[1,2,3]triazole,
4-(1,3-dioxo-2,3-dihidro-2-methyl-1H-isoindole-5-yl)-5-methyl-1-phenyl-1H-[1,2,3]triazole,
4-(2,2-dimethyl-1-oxo-indene-5-yl)-5-methyl-1-phenyl-1H-[1,2,3]triazole,
1-(2-fluoropyridine3-yl)-5-methyl-4-(2-methyl-imidazo[1,2-a]pyridine-6-yl)-1H-[1,2,3]triazole,
5-methyl-4-(4-oxo-4H-chromen-6-yl)-1-phenyl-1H-[1,2,3]triazole,
1-(2-fluoropyridine3-yl)-5-methyl-4-([1,2,4]triazolo[4,3-a]pyridine-7-yl)-1H-[1,2,3]triazole,
4-(3,4-dihydro-2H-1-oxa-9-aza-anthracene-6-yl)-1-(2-fluoropyridine3-yl)-5-methyl-1H-[1,2,3]triazole,
1-(2-fluoropyridine3-yl)-5-methyl-4-([1,2,4]triazolo[4,3-a]pyridine-6-yl-1H-[1,2,3]triazole,
1-(2-fluoropyridne3-yl)-4-isoquinoline-7-yl-5-methyl-1H-[1,2,3]triazole,
1-(2-fluoropyridine-3-yl)-4-isoquinoline-3-yl-5-methyl-1H-[1,2,3]triazole,
1-(2-fluoropyridine-3-yl)-4-(2,2-dimethyl-1-oxo-indene-5-yl)-5-methyl-1H-[1,2,3]triazole,
1-(2-fluoropyridine-5-yl)-5-methyl-4-(2-methyl-quinoline-6-yl)-1H-[1,2,3]triazole,
1-(6-chloro-[1,5]naphthyridine-2-yl)-4-(2-fluoropyridine-3-yl)-5-methyl-1H-[1,2,3]triazole,
1-(2-fluoropyridine-3-yl)-5-methtyl-4-(5,6,7,8-tetrahydro-[1,5]naphthyridine-2-yl)-1H-[1,2,3]triazole,
4-(5-acetyl-5,6,7,8-tetrahydro-[1,5]naphthyridine-2-yl)-1-(2-fluoropyridine-3-yl)-5-methyl-1H-[1,2,3]triazole,
4-(2-chloroquinoline-6-yl)-1-(2-fluoropyridine-3-yl)-1-methyl-1H-[1,2,3]triazole,
1-(2-fluoropyridine-3-yl)-5-methyl-4-(2-methyl-1-oxoindene-5-yl)-1H-[1,2,3]triazole,
1-(2-fluoropyridine-3-yl)-5-methtyl-4-((2R*)-methyl-1-oxoindene-5-yl)-1H-[1,2,3]triazole,
1-(2-fluoropyridine-3-yl)-5-methyl-4-((2S*)-methyl-1-oxoindene-5-yl)-1H-[1,2,3]triazole,
1-(2-fluoropyridine-5-yl)-4-(2,2-dimethyl-1-oxo-indene-5-yl)-5-methyl-1H-[1,2,3]triazole,
1-(2-fluoropyridine-3-yl)-4-(4-oxo-4H-chromen-7-yl)-5-methyl-1H-[1,2,3]triazole,
1-(2-fluoropyridine-3-yl)-4-(2-methoxyquinoline-6-yl)-5-methyl-1[1,2,3]triazole,
4-(2-tert-butyl-imidazo[1,2-a]pyridine-6-yl)-1-(2-fluoropyridine-3-yl)-5-methyl-1H-[1,2,3]triazole,
1-(2-fluoropyridine-3-yl)-5-methyl-4-(1-oxo-indene-2-spiro-1'-cyclobutane-5-yl)-1H-[1,2,3]triazole,
4-(2-dimethylamino-quinoline-6-yl)-1-(2-fluoropyridine-3-yl)-5-methyl-1[1,2,3]triazole,
1-(2-fluoropyridine-3-yl)-5-methyl-4-(1-oxo-indene-2-spiro-1'-cyclopropyl-5-yl)-1H-[1,2,3]triazole,
4-(2-chloro-3-ethyl-quinoline-6-yl)-1-(2-fluoropyridine-3-yl)-5-methyl-1H-[1,2,3]triazole,
4-(2-isopropyl-1-oxo-isoindoline-5-yl)-1-(2-fluoropyridine-3-yl)-5-methyl-1H-[1,2,3]triazole,
1-(2-fluoropyridine-3-yl)-4-(2-methoxy-1-oxo-indene-5-yl)-5-methyl-1-[1,2,3]triazole,
1-(2-fluoropyridine-3-yl)-5-methyl-4-(2-morpholine-4-yl-quinoline-6-yl)-1H-[1,2,3]triazole,
4-(3-methyl-4-oxo-4H-chromen-7-yl)-1-(2-fluoropyridine-3-yl)-5-methyl-1H-[1,2,3]]triazole,
1-(2-fluoropyridine-3-yl)-4-(2-(4-methylpiperazine-1-yl)-quinoline-6-yl)-5-methyl-1H-[1,2,3]triazole,
4-(2-isopropyl-imidazo[1,2-a]pyridine-6-yl)-1-(2-fluoropyridine-3-yl)-5-methyl-1H-[1,2,3]triazole,
1-(2-fluoropyridine-3-yl)-4-(5-oxo-5,6,7,8-tetrahydro-naphthalene-2-yl)-5-methyl-1H-[1,2,3]triazole,
1-(2-fluoropyridine-3-yl)-5-methyl-4-(2-methyl-1-oxo-isoindoline-5-yl)-1H-[1,2,3]triazole,
4-(2-ethyl-3-methyl-imidazo[1,2-a]pyridine-6-yl)-1-(2-fluoropyridine-3-yl)-5-methyl-1H-[1,2,3]triazole,
1-(2-fluoropyridine-3-yl)-4-(1-oxo-2-methylcarbonyloxy-indene-5-yl)-5-methyl-1[1,2,3]triazole,
1-(2-fluoropyridine-5-yl)-4-(2-isopropyl-imidazo[1,2-a]pyridine-6-yl)-5-methyl-1H-[1,2,3]triazole,
1-(2-fluoropyridine-3-yl)-4-(1-oxo-4-hydroxy-indene-5-yl)-5-methyl-1H-[1,2,3]triazole, 4-(2-cyclopropyl-imidazo[1,2-a]pyridine-6-yl)-1-(2-fluoro-pyridine-3-yl)-5-methyl-1H-[1,2,3]triazole,
4-(2-cyclopropyl-1-oxo-isoindoline-5-yl)-1-(2-fluoropyridine-3-yl)-5-methyl-1H-[1,2,3]triazole,
4-(2-isopropyl-1-oxo-indene-5-yl)-1-(2-fluoropyridine-3-yl)-5-methyl-1H-[1,2,3]triazole,
1-(2-fluoropyridine-3-yl)-4-(2-methyl-2-methylcarbonyloxy-1-oxo-indene-5-yl)-5-methyl-1H-[1,2,3]triazole,
1-(2-fluoropyridine-3-yl)-4-(2-hydroxy-2-methyl-1-oxo-indene-5-yl)-5-methyl-1H-[1,2,3]triazole,
1-(2-fluoropyridine-3-yl)-4-(2-methoxy-2-methyl-1-oxo-indene-5-yl)-5-methyl-1H-[1,2,3]triazole,
4-((2S*)-methoxy-(2R*)-methyl-1-oxoindene-5-yl)-1-(2-fluoropyridine-3-yl)-5-methyl-1H-[1,2,3]triazole,
4-((2R*)-methoxy-(2S*)-methyl-1-oxoindene-5-yl)-1-(2-fluoropyridine-3-yl)-5-methyl-1H-[1,2,3]triazole,
1-(2-fluoropyridine-3-yl)-4-(2-pyrrolidine-1-yl-quinoline-6-yl)-5-methyl-1H-[1,2,3]triazole,
1-(2-fluoropyridine-3-yl)-5-methyl-4-(2-methyl-4-oxo-4-methyl-chromen-7-yl)-1H-[1,2,3]triazole,
1-(2-fluoropyridine-5-yl)-4-(1-oxo-2-methyl-indene-5-yl)-5-methyl-1H-[1,2,3]triazole,
1-(2-fluoropyridine-3-yl)-5-methyl-4-(1-oxo-1H-indene-5-yl)-1H-[1,2,3]triazole,
1-(2-fluoropyridine-3-yl)-4-(2-methyl-1-oxo-1H-inden-5-yl)-5-methyl-1H-[1,2,3]triazole,
1-(2-fluoropyridine-5-yl)-4-(3-methyl-4-oxo-4H-chromen-7-yl)-5-methyl-1H-[1,2,3]triazole,
4-(2-cyclopropyl-1-oxo-isoindoline-5-yl)-1-(2-fluoropyridine-5-yl)-5-methyl-1H-[1,2,3]triazole,
4-(benzothiazole-6-yl)-1-(2-fluoropyridine-3-yl)-5-methyl-1H-[1,2,3]triazole,
4-(5-fluoro-3-methyl-4-oxo-4H-chromen-7-yl)-1-(2-fluoropyridine-3-yl)-5-methyl-1H-[1,2,3]triazole,
5-methyl-4-(3-methyl-4-oxo-4H-chromen-7-yl)-1-(pyridine-3-yl)-1H-[1,2,3]triazole,
1-(2-fluoropyridine-3-yl)-4-(2-methanesulfonyl-quinoline-6-yl)-5-methyl-1H-[1,2,3]triazole,
4-[(2-isopropyl-methyl-amino)-quinoline-6-yl]-1-(2-fluoropyridine-3-yl)-5-methyl-1H-[1,2,3]triazole,
4-(3-benzyl-4-oxo-3,4-dihidroquinazoline-6-yl)1-(2-fluoropyridine-3-yl)-5-methyl-1H-[1,2,3]triazole,
1-(2-fluoropyridine-3-yl)-4-(5-oxo-6-methyl-5,6,7,8-tetrahydro-naphthalene-2-yl)-5-methyl-1H-[1,2,3]triazole,
4-(3-benzy-4-oxo-3,4-dihydroquinazoline-6-yl)-1-phenyl-1H-[1,2,3]triazole,
4-(2-isopropyl-1-oxo-isoindoline-5-yl)-1-(2-fluoropyridine-4-yl)-5-methyl-1H-[1,2,3]triazole,
4-(2-tert-butyl-1-oxo-isoindoline-5-yl)-1-(2-fluoropyridine-3-yl)-5-methyl-1H-[1,2,3]triazole,
4-(2-ethyl-1-oxo-isoindoline-5-yl)-1-(2-fluoropyridine-3-yl)-5-methyl-1H-[1,2,3]triazole,
1-(2-fluoropyridine-3-yl)-4-(2-methoxy-4-oxo-4H-chromen-7-yl)-5-methyl-1H-[1,2,3]triazole,
1-(2-fluoropyridine-3-yl)-4-(3-methyl-4-oxo-3,4-dihydroquinazoline-7-yl)-5-methyl-1H-[1,2,3]triazole,
1-(2-fluoropyridine-3-yl)-4-(3-methyl-4-oxo-3,4-dihydroquinazoline-6-yl)-5-methyl-1H-[1,2,3]triazole,
1-(2-fluoropyridine-3-yl)-4-[2-(2-hydroxy-1-methyl-ethyl)-1-oxo-isoindoline-5-yl]-5-methyl-1H-[1,2,3]triazole,
1-(2-fluoropyridine-3-yl)-5-methyl-(2,3-dimethyl-4-oxo-3,4-dihydro-quinazoline-7-yl)-5-methyl-1H-[1,2,3]triazole,
4-(2-isopropyl-1-oxo-isoindoline-5-yl)-1-(2-fluoropyridine-3-yl)-1H-[1,2,3]triazole,
1-(2-fluoropyridine-3-yl)-4-(3-methyl-4-oxo-chroman-7-yl)-5-methyl-1H-[1,2,3]triazole,
1-(2-fluoropyridine-3-yl)-4-((3R*)-methyl-4-oxo-chroman-7-yl)-5-methyl-1H-[1,2,3]triazole,
1-(2-fluoropyridine-3-yl)-4-((3S*)-methyl-4-oxo-chroman-7-yl)-5-methyl-1H-[1,2,3]triazole,
1-(2-fluoropyridine-3-yl)-4-(1-oxo-isoindoline-5-yl)-5-methyl-1H-[1,2,3]triazole,
4-(3-benzyl-4-oxo-3,4-dihydroquinazoline-7-yl)-1-(2-fluoropyridine-3-yl)-5-methyl-1H-[1,2,3]triazole,
1-(2-fluoropyridine-5-yl)-4-(2-isopropyl-imidazo[1,2-a]pyridine-6-yl)-5-methyl-1H-[1,2,3]triazole,
4-(3-benzyl-2-ethyl-4-oxo-3,4-dihydroquinazorine-7-yl)-1-(2-fluoropyridine-3-yl)-5-methyl-1H-[1,2,3]triazole,
1-(2-fluoropyridine-3-yl)-5-methyl-4-(2-propyl-1-oxo-isoindoline-5-yl)-1H-[1,2,3]triazole,
4-(2-benzyl-1-oxo-isoindoline-5-yl)-1-(2-fluoropyridine-3-yl)-5-methyl-1H-[1,2,3]triazole,
4-(2-cyclopropyl-1-oxo-isoindoline-5-yl)-1-(2-fluoropyridine-3-yl)-5-methyl-1H-[1,2,3]triazole,
4-(2-cyclopropylmethyl-1-oxo-isoindoline-5-yl)-1-(2-fluoropyridine-3-yl)-5-methyl-1H-[1,2,3]triazole,
4-(2-isobutyl1-oxo-isoindoline-5-yl)-1-(2-fluoropyridine-3-yl)-5-methyl-1H-[1,2,3]triazole,
1-(2-fluoropyridine-3-yl)-5-methyl-4-(3-methyl-4-oxo-4H-pyrano[2,3-b]pyridine-7-yl)-1H-[1,2,3]triazole,
4-(3,3-dimethyl-4-oxo-chroman-7-yl)-1-(2-fluoropyridine-3-yl)-5-methyl-1H-[1,2,3]triazole,
4-(2-cyclopropyl-1-oxo-isoindoline-5-yl)-1-phenyl-5-methyl-1H-[1,2,3]triazole,
1-(2-fluoropyridine-3-yl)-5-methyl-4-(1a-methyl-2-oxo-1,1a,2,7a-tetrahydro-7-oxo-6-cyclopropa[b]naphthalene-5-yl)-1H-[1,2,3]triazole,
4-(2-methyl-1-oxo-isoquinoline-6-yl)-1-(2-fluoropyridine-3-yl)-5-methyl-1H-[1,2,3]triazole,
4-(2-ethyl-imidazo[1,2-a]pyridine-6-yl)-1-(2-fluoropyridine-3-yl)-5-methyl-1H-[1,2,3]triazole,
4-(2-methyl-1-oxo-3,4-dihydroisoquinoline-6-yl)-1-(2-fluoropyridine-3-yl)-5-methyl-1H-[1,2,3]triazole,
([1,8]naphthyridine-3-yl)-4-phenyl-5-methyl-1H-[1,2,3]triazole,
5-(2-cyclopropyl-1-oxo-isoindoline-5-yl)-1-2-fluoropyridine-3-yl)-4-carbonitril-1H-[1,2,3]triazole,
4-(2-isopropyl-1-oxo-isoindoline-5-yl)-1-(2,4-difluorophenyl)-5-methyl-1H-[1,2,3]triazole,
4-(2-(2,2-difluoroethyl)-1-oxo-isoindoline-5-yl)-1-(4-fluorophenyl)-5-methyl-1H-[1,2,3]triazole,
4-(2-(2-hydroxy-2-methyl-propyl)-1-oxo-isoindoline-5-yl)-1-(4-fluorophenyl)-5-methyl-1H-[1,2,3]triazole,
4-(2-(2-hydroxy-2-methyl-propyl)-1-oxo-isoquinoline-6-yl)-1-(4-fluorophenyl)-5-methyl-1H-[1,2,3]triazole, or
1-(4-fluorophenyl)-5-methyl-4-(2-(2-hydroxy-2-methyl-propyl)-quinoline-6-yl)-1-[1,2,3]triazole.
(11) The compound according to (1), or a pharmaceutically acceptable salt thereof, wherein: the compound represented by formula (I) is 1-(2-fluoropyridine-3-yl)-5-methyl-4-(1-oxoindene-2-spiro-1'-cyclopropyl-5-yl)-1H-[1,2,3]triazole.
(12) The compound according to (1), or a pharmaceutically acceptable salt thereof, wherein: the compound represented by formula (I) is 4-(2-isopropyl-1-oxo-isoindoline-5-yl)-1-(2-fluoropyridine-3-yl)-5-methyl-1H-[1,2,3]triazole.
(13) The compound according to (1), or a pharmaceutically acceptable salt thereof, wherein: the compound represented by formula (I) is 4-(2-isopropyl-1-oxo-isoindoline-5-yl)-1-(2-fluoropyridine-3-yl)-5-methyl-1H-[1,2,3]triazole.

(14) The compound according to (1), or a pharmaceutically acceptable salt thereof, wherein: the compound represented by formula (I) is 1-(2-fluoropyridine-3-yl)-5-methyl-4-(2-propyl-1-oxo-isoindoline-5-yl)-1H-[1,2,3]triazole.

(15) The compound according to (1), or a pharmaceutically acceptable salt thereof, wherein: the compound represented by formula (I) is 4-(2-cyclopropyl-1-oxo-isoindoline-5-yl)-1-(2-fluorobenzene-3-yl)-5-methyl-1H-[1,2,3]triazole.

(16) The compound according to (1), or a pharmaceutically acceptable salt thereof, wherein: the compound represented by formula (I) is 4-(2-isopropyl-1-oxo-isoindoline-5-yl)-1-(2,4-difluorophenyl)-5-methyl-1H-[1,2,3]triazole.

(17) The compound according to (1), or a pharmaceutically acceptable salt thereof, wherein: the compound represented by formula (I) is 4-(2-(2,2-difluoroethyl)-1-oxo-isoindoline-5-yl)-1-(4-fluorophenyl)-5-methyl-1H-[1,2,3]triazole.

(18) The compound according to (1), or a pharmaceutically acceptable salt thereof, wherein: the compound represented by formula (I) is 4-(2-(2-hydroxy-2-methyl-propyl)-1-oxo-isoindoline-5-yl)-1-(4-fluorophenyl)-5-methyl-1H-[1,2,3]triazole.

(19) The compound according to (1), or a pharmaceutically acceptable salt thereof, wherein: wherein the compound represented by formula (I) is 4-(2-(2-hydroxy-2-methyl-propyl)-1-oxo-isoquinoline-6-yl)-1-(4-fluorophenyl)-5-methyl-1H-[1,2,3]triazole, or a pharmaceutically acceptable salt thereof.

(20) The compound according to (1), or a pharmaceutically acceptable salt thereof, wherein: the compound represented by formula (I) is 1-(4-fluorophenyl)-5-methyl-4-2-(2-hydroxy-2-methyl-propyl)-quinoline-6-yl)-1H-[1,2,3]triazole.

The above compounds (1) to (20), or pharmaceutically acceptable salts thereof have an effect to inhibit mGluR1. In other words, the present invention provides an mGluR1 inhibitor comprising the compounds according to (1) to (20) or pharmaceutically acceptable salts thereof.

3,5-dihydroxyphenylglycine (hereinafter referred to as DHPG) which is a selective agonist to Group I, is reported to cause convulsion when administered into brain ventricle(for example, see Journal of Neuroscience Research, Vol. 51, p. 399 (1988), etc.).

On the other hand, in the examination using mGluR1 selective antagonist, in a pentylenetetrazole-inducing convulsion model which is generally used in evaluation of effect of anticonvulsants, RS-1-aminoindene-1,5-dicarboxylic acid (herein after referred to as AIDA) is reported to show a dose-dependent anti-convulsion effect (see for example, Neuropharmacology, vol. 37, p. 1465 (1998), etc.), as well as showing suppressing effect to convulsion induced by sound stimulation in mouse and rat showing genetical spasmophile (for example, see European Journal of Pharmacology, vol. 368, p. 17 (1999), etc.). Moreover, LY456236 being a different selective antagonist, is reported to decrease convulsion duration and its level in amygdala kindling rat, known to be human convulsion model (see for example, Neuropharmacology, vol. 43, p. 308, 2002, etc.).

The above knowledge suggests that mGluR1 inhibitor is useful for the prevention or treatment of convulsion.

Therefore, the compounds according to (1) to (20) having mGluR1 inhibiting effect, or pharmaceutically acceptable salts thereof, are believed to be effective for prevention or treatment of convulsion.

Moreover, when DHPG is administered into spinal cord, allodynia or hyper-colic to mechanical stimulation, or hyper-colic to heat stimulation is observed in rats (see for example, Neuroreport, vol. 9, p. 1169, 1998, etc.).

On the other hand, in investigation with antagonists, when AIDA is administered into brain, pain sensation threshold increases (see for example, The Journal of Pharmacology & Experimental Therapeutics, Vol. 281, p. 721, 1997, etc.), and when AIDA is administered into spinal cord, analgesic effect is observed for consecutive colic models such as spinal-cord-injury hyperalgesia models (see for example, Journal of Neurotrauma, vol. 19, p. 23, 2002, etc.), and arthritis models (see for example, The Journal of Pharmacology & Experimental Therapeutics, vol. 300, p. 149, 2002, etc.).

The above knowledge suggests that mGluR1 inhibitor has a possibility to have analgesic effect not only to acute pain, but also to inflammatory or chronic pain.

Therefore, the compounds according to (1) to (20) having mGluR1 inhibiting effect, or pharmaceutically acceptable salts thereof, are believed to be useful for prevention or treatment of acute, inflammatory or chronic pain.

Further, suppressing effect of AIDA to delayed neuronal death of hippocampus observed in transient cerebral ischemia-reperfusion model (see for example, Neuropharmacology, vol. 38, p. 1607, 1999, and Neuroscience Letters, vol. 293, p. 1, 2000, etc.); or reducing effect by mGluR1 selective antagonist (3aS,6aS)-6a-naphtalen-2-ylmethyl-5-methyliden-hexahydro-cyclopenta[c]furan-1-one (hereinafter referred to as BAY36-7620) of infarction of cerebral cortex volume in subdural hemorrhage model rat (see for example, European Journal of Pharmacology, vol. 428, p. 203, 2001, etc.) is observed. As for another selective antagonist, R128494, reduction of the whole volume of infarction in middle cerebral artery-ligation rat model is observed (see for example, Neuropharmacology, vol. 43, p. 295, 2002, etc.).

The above knowledge suggests that mGluR1 inhibitor has a possibility to have protecting effect to cerebral disorders such as brain infarction, or transient cerebral ischemia attack.

Therefore, the compounds according to (1) to (20) having mGluR1 inhibiting effect, or pharmaceutically acceptable salts thereof, are believed to be useful for prevention or treatment of cerebral disorders such as brain infarction, or transient cerebral ischemia attack.

Furthermore, when DHPG is administered into brain nucleus accumbens, increase of motor activity is observed, and the effect is similar to the reaction when dopamine receptor stimulating agent is administered (see for example, European Journal of Neuroscience, vol. 13, p. 2157, 2001, etc.); and further in Psychopharmacology, vol. 141, p. 405, 1999, etc., when DHPG is administered into brain nucleus accumbens, prepulse inhibition disorder occurs, as observed in experimental animal models and schizophrenics. Both of these reactions occurred from DHPG, are similar to reactions observed for dopamine receptor stimulating agents such as apomorphine, or dopamine-releasing agents such as amphetamine and methamphetamine are used. On the other hand, existing antipsychotic agents are believed to exhibit effects by suppressing dopamine nerves being excessively excited.

As reactions similar to dopamine stimulating effect by DHPG were observed, it was suggested that mGluR1 and mGluR5 are involved in deterioration in mental function in nucleus accumbens, and that mGluR1 inhibitor improves these symptoms.

Therefore, the compounds according to (1) to (20) having mGluR1 inhibiting effect, or pharmaceutically acceptable salts thereof, are believed to be useful for prevention or treatment of deterioration in mental function such as schizophrenia.

Moreover, in Vogel-type conflict test with rats, widely used as estimation system detecting antianxiety effect of agents, selective antagonist R128494 is reported to have increased drinking accompanied by punishment (see for example, Neuropharmacology, vol. 43, p. 295, 2002, etc).

The above knowledge suggests that mGluR1 inhibitor has a possibility to have antianxiety effect.

Therefore, the compounds according to (1) to (20) having mGluR1 inhibiting effect, or pharmaceutically acceptable salts thereof, are believed to be useful for prevention or treatment of anxiety.

In the above-mentioned non-patent document 16, it is described that the mGluR1 selective antagonist BAY36-7620 suppresses intracerebral autostimulation promoted by the NMDA receptor antagonist, MK-801. As many of NMDA receptor antagonists are clinically obvious to generate dependency, the present test system is believed to be a model reflecting a part of MK-801 dependency.

The above knowledge suggests that selective antagonist of mGluR1 receptor can be a preventive or treating agent of drug dependence.

Therefore, the compounds according to (1) to (20) having mGluR1 inhibiting effect, or pharmaceutically acceptable salts thereof, are believed to be useful for prevention or treatment of drug dependence.

Moreover, in a test wherein extracellular potential using brain slice containing rat hypothalamic nucleus, it was observed that occurrence frequency of action potential is increased according to local application of DHPG (see for example, Brain Research, vol. 766, p. 162, 1997, etc.), suggesting that activation of hypothalamic nucleus is due to mGluR1 or mGluR5. Excitement of hypothalamic nucleus is well known to be a characteristic of Parkinson disease.

The above knowledge suggests that mGluR1 inhibitor can be a preventive/treating agent of Parkinson disease.

Therefore, the compounds according to (1) to (20) or pharmaceutically acceptable salts thereof, are believed to be useful for prevention or treatment of Parkinson disease.

Furthermore, gastroesphageal reflux disease (GERD) is the most popular upper gastrointestinal tract disorder. Actual drug treatments are intended to suppress gastric acid secretion or gastric acid neutralization in esophagus. It was believed so far that the main mechanism related to the reflux was a chronic tension decline of lower esophageal-sphincter. However, for example, in Gastroenterol Clin. North Am., vol. 19, pp. 517-535, 1990, it has been reported that almost all reflux episodes are caused by a transient lower esophageal sphincter relaxation (TLESRS), that is relaxation other than swallowing. Moreover, normal gastric acid secretion of GERD patients have been found to be normal.

Lower esophageal sphincter (LES) are often intermittently relaxed. As a result, when sphincters are relaxed, as mechanical barrier are lost tentatively, the phenomenon where gastric juice can influx into esophagus is defined as "reflux".

The term "TLESR" showing transient relax of lower esophageal sphincter is a determination according to Gastroenterology, vol. 109 (2), pp. 601-610, 1995.

The term "reflux" is determined as gastric juice that can flow into the esophagus from the stomach. This is because in such condition, mechanical barrier is transiently lost. The word "GERD" for gastroespageal reflux disease is determined according to Baillière's Clinical Gastroenterology, Vol. 14, pp. 759-774, 2000.

From the above physiological and pathophysiological meanings, the above compounds (1) to (20) or pharmaceutically acceptable salts thereof are believed to be useful for prevention or treatment of gastrointestinal disorders.

BEST MODE FOR CARRYING OUT THE INVENTION

Meanings of the terms herein used will be first explained and then, the compounds of the present invention.

The "aryl group" includes aryl groups of cyclic hydrocarbons of 6 to 14 carbons.

The "lower alkyl group" means a straight or branched chain alkyl group of 1 to 6 carbons, including, for example, methyl group, ethyl group, propyl group, isopropyl group, butyl group, isobutyl group, sec-butyl group, tert-butyl group, pentyl group, isoamyl group, neopentyl group, isopentyl group, 1,1-dimethylpropyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,2,2-trimethylpropyl group, 1-ethyl-2-methylpropyl group, and the like.

The "cycloalkyl group" means a cycloalkyl group of 3 to 7 carbons, including, for example, cyclopropyl group, cyclobutyl group, cyclopentyl group, cyclohexyl group, cycloheptyl group, cyclooctyl group and cyclononyl group.

The "lower alkyloxy group" means a group wherein a hydrogen atom of the hydroxyl group is substituted by the above-mentioned lower alkyl group, and includes, for example, methoxy group, etoxy group, propoxy group, isopropoxy group, butoxy group, sec-butoxy group, tert-butoxy group, pentyloxy group, isopentyloxy group, hexyloxy group, isohexyloxy group.

The "halogen atom" includes, for example, fluorine atom, chlorine atom, bromine atom and iodine atom.

The "mono-lower alkyl amino group" means the amino group mono-substituted by the above-mentioned lower alkyl group, including, for example, methylamino group, ethylamino group, propylamino group, isopropylamino group, butylamino group, sec-butylamino group, or tert-butylamino group.

The "di-lower alkylamino group" means the amino group di-substituted by the same or different above-mentioned lower alkyl group, including, for example, dimethylamino group, diethylamino group, dipropylamino group, methylpropylamino group, or diisopropylamino group.

The "alkanoyl group" means the carbonyl group to which the above-mentioned lower alkyl group is attached, including, for example, methylcarbonyl group, ethylcarbonyl group, propylcarbonyl group, isopropylcarbonyl group.

The "lower alkyloxycarbonyl group" means the group wherein the hydrogen atom of the hydroxyl group is substituted by the above-mentioned alkanoyl group, including, for example, methoxycarbonyl group, etoxycarbonyl group, isopropyl carbonyl group.

The "mono-lower alkylcarbamoyl group" means the carbamoyl group mono-substituted by the above-mentioned alkyl group, including, for example methylcarbamoyl group, ethylcarbamoyl group, propylcarbamoyl group, isopropylcarbamoyl group, butylcarbamoyl group, sec-butylcarbamoyl group and tert-butylcarbamoyl group.

The "di-lower alkylcarbamoyl group" means the carbamoyl group di-substituted by the same or different above-mentioned lower alkyl group, including, for example, dimethylcarbamoyl group, diethylcarbamoyl group, ethylmethylcarbamoyl group, dipropylcarbamoyl group, methylpropylcarbamoyl group and diisopropylcarbamoyl group.

The "mono-lower alkylcarbamoylamino group" means the carbamoylamino group mono-substituted by the above-mentioned alkyl group, including for example, methylcarbamoylamino group, ethylcarbamoylamino group, and isopropylcarbamoylamino group.

The "di-lower alkylcarbamoylamino group" means the carbamoylamino group di-substituted by the same or different above-mentioned lower alkyl group, including for example, dimethylcarbamoylamino group, diethylcarbamoylamino group, ethylmethylcarbamoylamino group, and ethylisopropylcarbamoylamino group.

The "alkylsulfonyl group" means a sulfonyl group to which the above-mentioned alkyl group is attached, including, for example, methylsulfonyl group, ethylsulfonyl group, propylsulfonyl group, isopropylsulfonyl group, and butylsulfonyl group.

The "trialkylsilyl group" means the silyl group trisubstituted by the same or different above-mentioned lower alkyl group, including for example, trimethylsilyl group, and triethylsilyl group.

In order to further show specific examples of the compounds of formula (I) of the present invention,
formula (I):

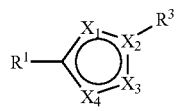
(I)

each symbol used in formula (I) will be explained by the following examples.

$X_1$ represents an oxygen atom, nitrogen atom or $CR^2$, and among these, nitrogen atom or $CR^2$ is preferable, $CR^2$ being more preferable.

$R^2$ represents a hydrogen atom, lower alkyl group, cyano group, lower alkyloxy group, lower alkyloxycarbonyl group or trialkylsilyl group, and among these, hydrogen atom, cyano group or lower alkyl group is preferable, cyano group or lower alkyl group being more preferable.

$X_2$ represents a nitrogen atom or a carbon atom, nitrogen atom being preferable for $X_2$.

$X_3$ represents a nitrogen atom or a carbon atom, nitrogen atom being preferable for $X_3$.

$X_4$ represents nitrogen atom or a carbon atom, nitrogen atom being preferable for $X_4$.

$R^1$ is a group represented by formula (II-1):

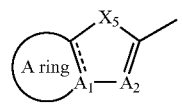
(II-1)

The group represented by formula (II-10) in the above-mentioned formula (II-1) will be explained.

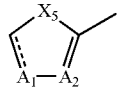
(II-10)

$A_1$ represents a carbon atom or a nitrogen atom.
—$X^5$— represents —S— or -$A_4$=$A_3$-.
$A_2$ to $A_4$ represent: all of $A_2$ to $A_4$ represent $CR^4$; or any one or two of $A_2$ to $A_4$ represent a nitrogen atom, and the remaining one or two of $A_2$ to $A_4$ represent $CR^4$.

$R^4$ represents a hydrogen atom, lower alkyl group, lower alkyloxy group, halogen atom, mono-or di-lower alkylamino group, hydroxy group, lower alkyloxycarbonyl group, carbamoyl group or mono-or di-loweralkylcarbamoylamino group.

In the above-mentioned formula (II-1) or (II-10), ═══ represents a double bound when $A_1$ is a carbon atom, and a single bond when $A_1$ is a nitrogen atom, and double bond is preferable.

From the above, as for formula (II-10), the compound represented by formula (II-A)

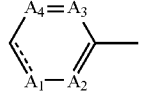
(II-A)

[wherein each symbol is the same as above]
is preferable, and specifically, the group represented by the following formula (II-11) can be exemplified,
(formula II-11)

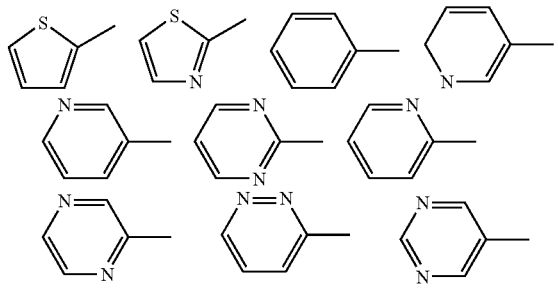
(II-11)

and among these, the group represented by formula (II-12) is preferable,
(formula II-12)

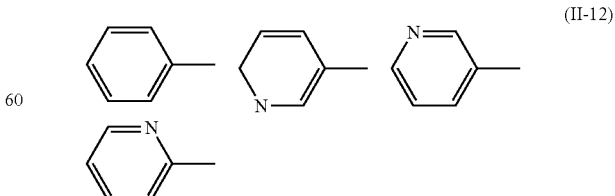
(II-12)

the group represented by the following formula (II-13) is more preferable.

(formula II-13)

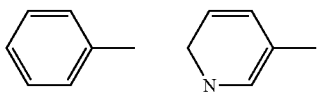

(II-13)

A ring represents either of the following:
1) saturated, partially saturated, or unsaturated 5-or 6-membered ring, wherein all of the constituting atoms of A ring are carbon atoms, or
2) saturated, partially saturated or unsaturated 5-or 6-membered ring that may have 1 to 3 hetero atoms selected from the group comprising N, S and O, besides carbon atoms, as for constituting atom of A ring.

As for A ring, a ring that has at least one nitrogen atom as constituting atoms of A ring is preferable.

A ring may have 1 to 3 substituted groups selected from the group consisting of lower alkyl group (the lower alkyl group may be further substituted by hydroxy group, halogen atom or aryl group, and when the same carbon atom constituting A ring has 2 lower alkyl groups, the lower alkyl group may form together a cycloalkyl group), cycloalkyl group, lower alkyloxy group, halogen atom, mono-or di-lower alkylamino group, alkanoyl group, alkylsulfonyl group, lower alkyloxycarbonyl group, carbamoyl group, mono-or di-lower alkylcarbamoyl group, mono-or di-lower alkylcarbamoylamino group and hydroxy group, and further, A ring may be substituted by 1 or 2 oxo groups.

As for the "lower alkyl group" of the substituted group, for example, methyl group, ethyl group, isopropyl group and the like are preferable.

When the same carbon atom constituting A ring has 2 lower alkyl groups, the lower alkyl groups may form together a cycloalkyl group.

As for the cycloalkyl group, for example, cyclopropyl group, cyclobutyl group, cyclopentyl group and cyclohexyl group and the like are preferable.

As for the "lower alkyl group substituted by hydroxy group" of the substituted group, hydroxymethyl group, 2-hydroxyethyl group, 1-hydroxyethyl group, 2-hydroxy-1-methylethyl group and the like are preferable.

As for the "lower alkyl group substituted by a halogen atom" of the substituted group, for example, chloromethyl group, chloromethyl group, bromomethyl group, fluoromethyl group and the like are preferable.

As for the "lower alkyl group substituted by an aryl group" of the substituted group, for example benzyl group, phenethyl group and the like are preferable.

As for the "cycloalkyl group" of the substituted group, for example, cyclopropyl group, cyclobutyl group, cyclopentyl group, cyclohexyl group and the like are preferable.

As for the "lower alkyloxy group" of the substituted group, for example, methoxy group, ethoxy group, isopropoxy group and the like are preferable.

As for the "halogen atom" of the substituted group, for example, fluorine atom, chlorine atom, bromine atom and the like are preferable.

As for the "mono-lower alkylamino group" of the substituted group, for example, methylamino group, ethylamino group, isopropylamino group are preferable.

As for the "di-lower alkyl amino group" of the substituted group, for example, dimethylamino group, diethylamino group, diisopropylamino group, ethylmethylamino group and the like are preferable.

Further, as for the di-lower alkylamino group, the same or different lower alkyl group forming 5-to 6-membered hetero ring are included, and further any one of methylene group constituting the 5-to 6-membered hetero ring may be substituted by O, N or S.

When the methylene group is substituted by N,N may be further substituted by a lower alkyl group.

As for the 5-to 6-membered hetero ring, for example, pyrrolidine-1-yl group, piperidine-1-yl group, 4-methylpiperidine-1-yl group, 4-ethylpiperidine-1-yl group, morpholine-4-yl group and the like are preferable.

As for the "alkanoyl group" of the substituted group, for example, acetyl group, propionyl group and the like are preferable.

As for the "alkylsulfonyl group" of the substituted group, for example, methylsulfonyl group, ethylsulfonyl group, isopropylsulfonyl group and the like are preferable.

As for the "mono-lower alkylcarbamoyl group" of the substituted group, for example, methylcarbamoyl group, ethylcarbamoyl group, isopropylcarbamoyl group and the like are preferable.

As for the "di-lower alkylcarbamoyl group" of the substituted group, for example, dimethylcarbamoyl group, diethylcarbamoyl group, ethylmethylcarbamoyl group and the like are preferable.

As for the "mono-lower alkylcarbamoylamino group" of the substituted group, for example, methylcarbamoylamino group, ethylcarbamoylamino group, isopropylcarbamoylamino group and the like are preferable.

As for the "di-lower lower alkylcarbamoylamino group" of the substituted group, for example, dimethylcarbamoylamino group, diethylcarbamoyl amino group, ethylmethylcarbamol group, diisopropylcarbamoylamino group and the like are preferable.

When A ring has alkyl group and lower alkyloxy group as a substituted groups, the lower alkyl group and the lower alkyloxy group may form together a 5-or 6-membered hetero ring.

As for R1, a group represented by formula (II-C):

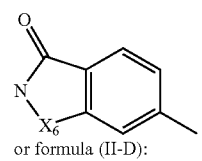

(II-C)

or formula (II-D):

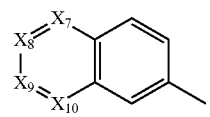

(II-D)

wherein $X_6$ represents $CH_2$, $CH=CH$ or $CH_2-CH_2$, as for $X_7$ to $X_{10}$, one of $X_7$ to $X_{10}$ represents a nitrogen atom, and others represent carbon atoms.
said group may have 1 to 3 substituted groups selected from the above-mentioned substituted group $\propto$ that A ring may have, is preferable; specifically, quinoline-6-yl group, quinoline-7-yl group, isoquinoline-7-yl group, isoquinoline-6-yl group, 2-methylquinoline-6-yl group, isoquinoline-3-yl group, 2-methoxyquinoline-6-yl group, 3-methoxyquinoline-6-yl group, 2-dimethylaminoquinoline-6-yl group, 2-chloro-3-ethyl-quinoline-6-yl group, 2-morpholine-4-yl-quinoline-6-yl group, 2-(4-methylpiperazine-1- yl)-quinoline-6-yl group, 2-pyrrolidine-1-yl-quinoline-6-yl group, 2-methanesulfonyl-quinoline-6-yl group, 2-isopropyl-methylamino-quinoline-6-yl group, 2-(2-hydroxy-2-methyl-propyl)-1-oxo-isoquinoline-6-yl group, quinoxaline-6-yl group, 1-oxo-isoindoline-5-yl group, 2-isopropyl-1-oxo-isoindoline-5-yl group, 2-(2,2-difluoroethyl)-1-oxo-isoindoline-5-yl group, 2-(2-hydroxy-2-methylpropyl)-1-oxo-isoindoline-5-yl group, 2-methyl-1-oxo-isoindoline-5-yl group, 2-cyclopropyl-1-oxo-isoindoline-5-yl group, 2-ethyl-1-oxo-isoindoline-5-yl group, and 2-(2-hydroxy-1-methylethyl)-1-oxo-isoindoline-5-yl group can be exemplified.

$R^3$ represents either:

(A) a phenyl group, or
(B) an unsaturated or partially saturated 5-to 6-membered hetero ring group having 1 to 3 hetero atoms selected from the group comprising N, S and O.

$R^3$ may have 1 to 3 substituted groups selected from the group comprising halogen atom, lower alkyl group, cyano group, nitro group, lower alkyloxy group and hydroxy group. When $R^3$ has 2 or 3 of the substituted groups, the substituted groups may be the same of different.

As for the "halogen atom" of the substituted group, for example, fluorine atom, chlorine atom, bromine atom are preferable.

As for the "lower alkyl group" of the substituted group, for example, methyl group, ethyl group, isopropyl group and the like are preferable.

As for the "lower alkyloxy group" of the substituted group, for example, methoxy group, ethoxy group, isopropyloxy group and the like are preferable.

From the above, as for $R^3$ that may have the substituted group, for example,

As for the compound represented by the above-mentioned formula (I), a compound represented by the following formula (I-A):

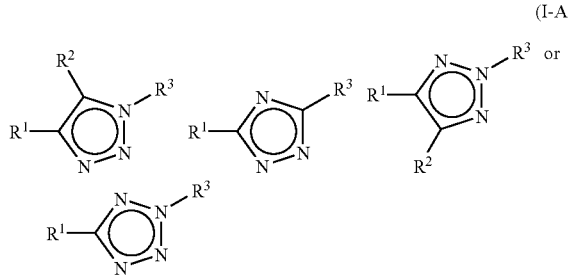

(I-A)

wherein each symbol is the same as above,
is preferable; a compound represented by the following formula (I-B):

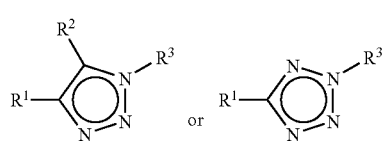

(I-B)

wherein each symbol is the same as above,
is more preferable, and a compound represented by the above-mentioned formula (I-1):

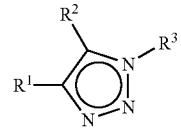

(I-1)

wherein each symbol is the same as above,
is further preferable.

However among the compounds described in the above (I), the following compounds are excluded: 4-[5-(naphthalenyl)-1H-[1,2,4]triazole-3-yl]-pyridine, 3-(1,3-benzodioxole-5-yl)-5-(2-ethylphenyl)-1H-1,2,4-triazole, 6-[5-(4-pyridyl)-1H-1,2,4-triazole4-yl]-quinoline, 3-(5-phenyl-4H-[1,2,4]triazole-3-yl)naphthalene-2-ol, 3-[5-pyridine4-yl-1H-[1,2,4]triazole-3-yl]-naphthalene-2-ol, 5-(quinoline-2-yl)-2-(3-cyano-phenyl)-tetrazole, 3-[5-(3,5-dichloropyridine-4-yl)-2-methyl-2H-[1,2,4]triazole-3-yl]-quinoline, 3-naphthalene-2-yl-5-phenyl-4H-[1,2,4]triazole, 3-benzo[1,3]dioxysole-5-yl-1-methyl-5-o-tolyl-1H-[1,2,4]triazole, 5-(5-phenyl-4H-[1,2,4]triazole-3-yl)isobenzofuran-1,3-dion. Further, substituted or unsubstituted naphthyl group wherein R1s of (I-B) and (I-1) are substituted is also excluded.

Meanwhile, any of the preferred embodiments of $X_1, X_2, X_3, X_4, X_5, X_6, X_7, X_8, X_9, X_{10}, R^1, R^2, R^3, A_1, A_2, A_3, A_4, A_5$, A ring - - -, may be combined.

As for the compound of the present invention, more specifically, for example,
5-methyl-1-phenyl-4-(quinoline-6-yl)-1H-[1,2,3]triazole,
5-methyl-4-(1-oxo-indene-5-yl)-1-phenyl-1H-[1,2,3]triazole,
5-methyl-4-(2-methylbenzothiazole-5-yl)-1-phenyl-1H-[1,2,3]triazole,
4-(1H-indole-5-yl)-5-methyl-1-phenyl-1H-[1,2,3]triazole,
1-(2-fluoropyridine3-yl)-5-methyl-4-(quinoline-6-yl-1H-[1,2,3]triazole,
5-methyl-4-(naphthalene-2-yl)-5-methyl-1H-[1,2,3]triazole,
4-(3-cyclohexyl-5-fluoro-6-methyl-4-oxo-4H-chromen-7-yl)-5-methyl-1-phenyl-1H-[1,2,3]triazole,
1-(2-fluoropyridine3-yl)-5-methyl-4-(2-methyl-quinoline-6-yl)-1H-[1,2,3]triazole,
1-(2-fluoropyridine3-yl)-5-methyl-4-quinoxaline-6-yl)-1H-[1,2,3]triazole,
4-(1,3-dioxo-2,3-dihydro-1H-isoindole-5-yl)-5-methyl-1-phenyl-1H-[1,2,3]triazole,
4-(1,3-dioxo-2,3-dihydro-2-methyl-1H-isoindole-5-yl)-5-methyl-1-phenyl-1H-[1,2,3]triazole,
4-(2,2-dimethyl-1-oxo-indene-5-yl)-5-methyl-1-phenyl-1H-[1,2,3]triazole,
1-(2-fluoropyridine3-yl)-5-methyl-4-(2-methyl-imidazo[1,2-a]pyridine-6yl)-1H-[1,2,3]triazole,
5-methyl-4-(4-oxo-4H-chromen-6-yl)-1-phenyl-1H-[1,2,3]triazole,
1-(2-fluoropyridine3-yl)-5-methyl-4-([1,2,4]triazolo[4,3-a]pyridine-7-yl)-1H-[1,2,3]triazole,
4-(3,4-dihydro-2H-1-oxa-9-aza-anthracen-6-yl)-1-(2-fluoropyridine3-yl)-5-methyl-1H-[1,2,3]triazole,
1-(2-fluoropyridine-3-yl)-5-methyl-4-([1,2,4]triazolo[4,3-a]pyridine-6-yl-1H-[1,2,3]triazole,
1-(2-fluoropyridine-3-yl)-4-isoquinoline-7-yl-5-methyl-1H-[1,2,3]triazole,
1-(2-fluoropyridine-3-yl)-4-isoquinoline-3-yl-5-methyl-1H-[1,2,3]triazole,
1-(2-fluoropyridine-3-yl)-4-(2,2-dimethyl-1-oxo-indene-5-yl)-5-methyl-1H-[1,2,3]triazole, 1-(2-fluoropyridine-5-yl)-5-methyl-4-(2-methyl-quinoline-6-yl)-1H-[1,2,3]triazole,
1-(6-chloro-[1,5]naphthyridine-2-yl)-4-(2-fluoropyridine-3-yl)-5-methyl-1H-[1,2,3]triazole,
1-(2-fluoropyridine-3-yl)-5-methyl-4-(5,6,7,8-tetrahydro-[1,5]naphthyridine-2-yl)-1H-[1,2,3]triazole,
4-(5-acetyl-5,6,7,8-tetrahydro-[1,5]naphthyridine-2-yl)-1-(2-fluoropyridine-3-yl)-5-methyl-1H-[1,2,3]triazole,
4-(2-chloroquinoline-6-yl)-1-(2-fluoropyridine-3-yl)-1-methyl-1H-[1,2,3]triazole,
1-(2-fluoropyridine-3-yl)-5-methyl-4-(2-methyl-1-oxoindene-5-yl)-1H-[1,2,3]triazole,
1-(2-fluoropyridine-3-yl)-5-methyl-4-((2R*)-methyl-1-oxoindene-5-yl)-1H-[1,2,3]triazole,
1-(2-fluoropyridine3-yl)-5-methyl-4-((2S*)-methyl-1-oxoindene-5-yl)-1H-[1,2,3]triazole,
1-(2-fluoropyridine-5-yl)-4-(2,2-dimethyl-1-oxo-indene-5-yl)-5-methyl-1H-[1,2,3]triazole,
1-(2-fluoropyridine-3-yl)-4-(4-oxo-4H-chromen-7-yl)-5-methyl-1H-[1,2,3]triazole,
1-(2-fluoropyridine-3-yl)-4-(2-methoxyquinoline-6-yl)-5-methyl-[1,2,3]triazole,
4-(2-tert-butyl-imidazo[1,2-a]pyridine-6-yl)-1-(2-fluoropyridine-3-yl)-5-methyl-1H-[1,2,3]triazole,
1-(2-fluoropyridine-3-yl)-5-methyl-4-(1-oxo-indene-2-spiro-1'-cyclobutane-5-yl)-1H-[1,2,3]triazole,
4-(2-dimethylamino-quinoline-6-yl)-1-(2-fluoropyridine-3-yl)-5-methyl-[1,2,3]triazole,
1-(2-fluoropyridine-3-yl)-5-methyl-4-(1-oxo-indene-2-spiro-1-cyclopropyl-5-yl)-1H-[1,2,3]triazole,
4-(2-chloro-3-ethyl-quinoline-6-yl)-1-(2-fluoropyridine-3-yl)-5-methyl-1H-[1,2,3]triazole,
4-(2-isopropyl-1-oxo-isoindoline-5-yl)-1-(2-fluoropyridine-3-yl)-5-methyl-1H-[1,2,3]triazole,
1-(2-fluoropyridine-3-yl)-4-(2-methoxy-1-oxo-indene-5-yl)-5-methyl-1H-[1,2,3]triazole,
1-(2-fluoropyridine-3-yl)-5-methyl-4-(2-morpholine-4-yl-quinoline-6-yl)-1H-[1,2,3]triazole,
4-(3-methyl-4-oxo-4H-chromen-7-yl)-1-(2-fluoropyridine-3-yl)-5-methyl-1H-[1,2,3]triazole,
1-(2-fluoropyridine-3-yl)-4-(2-(4-methylpiperazine-1-yl)-quinoline-6-yl)-5-methyl-[1,2,3]triazole,
4-(2-isopropyl-imidazo[[1,2-a]pyridine-6-yl]-1-(2-fluoropyridine-3-yl)-5-methyl-1H-[1,2,3]triazole,
1-(2-fluoropyridine-3-yl)-4-(5-oxo-5,6,7,8-tetrahydroanaphthalene-2-yl)-5-methyl-1H-[1,2,3]triazole,
1-(2-fluoropyridine-3-yl)-5-methyl-4-(2-methyl-1-oxoisoindoline-5-yl)-1H-[1,2,3]triazole,
4-(2-ethyl-3-methyl-imidazo[1,2-a]pyridine-6-yl)-1-(2-fluoropyridine-3-yl)-5-methyl-1H-[1,2,3]triazole,
1-(2-fluoropyridine-3-yl)-4-(1-oxo-2-methylcarbonyloxy-indene-5-yl)-5-methyl-1H-[1,2,3]triazole,
1-(2-fluoropyridine-5-yl)-4-(2-isopropyl-imidazo[1,2-a]pyridine-6-yl)-5-methyl-1H-[1,2,3]triazole,
1-(2-fluoropyridine-3-yl)-4-(1-oxo-4-hydroxy-indene-5-yl)-5-methyl-1H-[1,2,3]triazole,
4-(2-cyclopropyl-imidazo[1,2-a]pyridine-6-yl)-1-(2-fluoropyridine-3-yl)-5-methyl-1H-[1,2,3]triazole,
4-(2-cyclopyropyl-1-oxo-isoindoline-5-yl)-1-(2-fluoropyridine-3-yl)-5-methyl-1H-[1,2,3]triazole,
4-(2-isopropyl-1-oxo-indene-5-yl)-1-(2-fluoropyridine-3-yl)-5-methyl-1H-[1,2,3]triazole,
1-(2-fluoropyridine-3-yl)-4-(2-methyl-2-methylcarbonyloxy-1-oxo-indene-5-yl)-5-methyl-1H-[1,2,3]triazole,
1-(2-fluoropyridine-3-yl)-4-(2-hydroxy-2-methyl-1-oxo-indene-5-yl)-5-methyl-1H-[1,2,3]triazole,
1-(2-fluoropyridine-3-yl)-4-(2-methoxy-2-methyl-1-oxo-indene-5-yl)-5-methyl-1H-[1,2,3]triazole,
4-((2S*)-methoxy-(2R*)-methyl-1-oxoindene-5-yl)-1-(2-fluoropyridine-3-yl)-5-methyl-1H-[1,2,3]triazole,
4-((2R*)-methoxy-(2S*)-methyl-1-oxoindene-5-yl)-1-(2-fluoropyridine-3-yl)-5-methyl-1H-[1,2,3]triazole,
1-(2-fluoropyridine-3-yl)-4-(2-pyrrolidine-1-yl-quinoline-6-yl)-5-methyl-1H-[1,2,3]triazole,
1-(2-fluoropyridine-3-yl)-5-methyl-4-(2-methyl-4-oxo-4-methyl-chromen-7-yl)-1H-[1,2,3]triazole,
1-(2-fluoropyridine-5-yl)-4-(1-oxo-2-methyl-indene-5-yl)-5-methyl-1H-[1,2,3]triazole,
1-(2-fluoropyridine-3-yl)-5-methyl-4-(1-oxo-1H-indene-5-yl)-1H-[1,2,3]triazole,
1-(2-fluoropyridine-3-yl)-4-(2-methyl-1-oxo-1H-indene-5-yl)-5-methyl-1H-[1,2,3]triazole,
1-(2-fluoropyridine-5-yl)-4-(3-methyl-4-oxo-4H-chromen-7-yl)-5-methyl-1H-[1,2,3]triazole,
4-(2-cyclopropyl-1-oxo-isoindoline-5-yl)-1-(2-fluoropyridine-5-yl)-5-methyl-1H-[1,2,3]triazole,
4-(benzothiazole-6-yl)-1-(2-fluoropyridine-3-yl)-5-methyl-1H-[1,2,3]triazole,
4-(5-fluoro-3-methyl-4-oxo-4H-chromen-7-yl)-1-(2-fluoropyridine-3-yl)-5-methyl-1H-[1,2,3]triazole,
5-methyl-4-(3-methyl-4-oxo-4H-chromen-7-yl)-1-(pyridine-3-yl)-1H-[1,2,3]triazole,
1-(2-fluoropyridine-3-yl)-4-(2-methanesulfonyl-quinoline-6-yl)-5-methyl-1H-[1,2,3]triazole,
4-[(2-isopropyl-methyl-amino)-quinoline-6-yl]-1-(2-fluoropyridine-3-yl)-5-methyl-1H-[1,2,3]triazole,
4-(3-benzyl-4-oxo-3,4-dihydroquinazoline-6-yl)1-(2-fluoropyridine-3-yl)-5-methyl-1H-[1,2,3]triazole,
1-(2-fluoropyridine-3-yl)-4-(5-oxo-6-methyl-5,6,7,8-tetrahydro-naphthalene-2-yl)-5-methyl-1H-[1,2,3]triazole,
4-(3-benzyl-4-oxo-3,4-dihydroquinazoline-6-yl)-1-phenyl-1H-[1,2,3]triazole,
4-(2-isopropyl-1-oxo-isoindoline-5-yl)-1-(2-fluoropyridine-4-yl)-5-methyl-1H-[1,2,3]triazole,
4-2-tert-butyl-1-oxo-isoindoline-5-yl)-1-(2-fluoropyridine-3-yl)-5-methyl-1H-[1,2,3]triazole,
4-(2-ethyl-1-oxo-isoindoline-5-yl)-1-(2-fluoropyridine-3-yl)-5-methyl-1H-[1,2,3]triazole,
1-(2-fluoropyridine-3-yl)-4-(2-methoxy-4-oxo-4H-chromen-7-yl)-5-methyl-1H-[1,2,3]triazole,
1-(2-fluoropyridine-3-yl)-4-(3-methyl-4-oxo-3,4-dihydroquinazoline-7-yl)-5-methyl-1H-[1,2,3]triazole,
1-(2-fluoropyridine-3-yl)-4-(3-methyl-4-oxo-3,4-dihydroquinazoline-6-yl)-5-methyl-1H-[1,2,3]triazole,
1-(2-fluoropyridine-3-yl)-4-[2-(2-hydroxy-1-methyl-ethyl)-1-oxo-isoindoline-5-yl]-5-methyl-1H-[1,2,3]triazole,
1-(2-fluoropyridine-3-yl)-5-methyl-(2,3-dimethyl-4-oxo-3,4-dihydro-quinazoline-7-yl)-5-methyl-1H-[1,2,3]triazole,
4-(2-isopropyl-1-oxo-isoindoline-5-yl)-1-(2-fluoropyridine-3-yl)-1H-[1,2,3]triazole,
1-(2-fluoropyridine-3-yl)-4-(3-methyl-4-oxo-chroman-7-yl)-5-methyl-1H-[1,2,3]triazole,
1-(2-fluoropyridine-3-yl)-4-((3R*)-methyl-4-oxo-chroman-7-yl)-5-methyl-1H-[1,2,3]triazole,
1-(2-fluoropyridine-3-yl)-4-((3S*)-methyl-4-oxo-chroman-7-yl)-5-methyl-1H-[1,2,3]triazole,
1-(2-fluoropyridine-3-yl)-4-(1-oxo-isoindoline-5-yl)-5-methyl-1H-[1,2,3]triazole,
4-(3-benzyl-4-oxo-3,4-dihydroquinazoline-7-yl)-1-(2-fluoropyridine-3-yl)-5-methyl-1H-{1,2,3}triazole,
1-(2-fluoropyridine-5-yl)-4-(2-isopropyl-imidazo-[1,2-a]pyridine-6-yl)-5-methyl-1H-[1,2,3]triazole, 4-(3-benzyl-2-ethyl-4-oxo-3,4,-dihydroquinazoline-7-yl)-1-(2-fluoropyridine-3-yl)-5-methyl-1H-[1,2,3]triazole,
1-(2-fluoropyridine-3-yl)-5-methyl-4-(2-propyl-1-oxo-isoindoline-5-yl)-1H-[1,2,3]triazole,
4-(2-benzyl-1-oxo-isoindoline-5-yl)-1-(2-fluoropyridine-3-yl)-5-methyl-1H-[1,2,3]triazole,
4-(2-cyclopropyl-1-oxo-isoindoline-5-yl)-1-(2-fluoropyridine-3-yl)-5-methyl-1H-[1,2,3]triazole,
4-(2-cyclopropylmethyl-1-oxo-isoindoline-5-yl)-1-(2-fluoropyridine-3-yl)-5-methyl-1H-[1,2,3]triazole,
4-(2-isobutyl1-oxo-isoindoline-5-yl)-1-(2-fluoropyridine-3-yl)-5-methyl-1H-[1,2,3]triazole,
1-(2-fluoropyridine-3-yl)-5-methyl-4-(3-methyl-4-oxo-4H-pyrano[2,3-b]pyridine-7-yl)-1H-[1,2,3]triazole,
4-(3,3-dimethyl-4-oxo-chroman-7-yl)-1-(2-fluoropyridine-3-yl)-5-methyl-1H-[1,2,3]triazole,
4-(2-cyclopropyl-1-oxo-isoindoline-5-yl)-1-phenyl-5-methyl-1H-[1,2,3]triazole,
1-(2-fluoropyridine-3-yl)-5-methyl-4-(1a-methyl-2-oxo-1,1a-2-7a-tetrahydro-7-oxo-6-cyclopropa[b]naphthalene-5-yl)-1H-[1,2,3]triazole,
4-(2-methyl-1-oxo-isoquinoline-6-yl)-1-(2-fluoropyridine-3-yl)-5-methyl-1H-[1,2,3]triazole,
4-(2-ethyl-imidazo[1,2-a]pyridine-6-yl)-1-(2-fluoropyridine-3-yl)-5-methyl-1H-[1,2,3]triazole,
4-(2-methyl-1-oxo-3,4-dihydroisoquinoline-6-yl)-1-(2-fluoropyridine-3-yl)-5-methyl-1H-[1,2,3]triazole,
([1,8]naphthylidine-3-yl)-4-phenyl-5-methyl-1H-[1,2,3]triazole,
5-(2-cyclopropyl-1-oxo-isoindoline-5-yl)-1-(2-fluoropyridine-3-yl)-4-carbonitrile-1H-[1,2,3]triazole,
4-(2-isopropyl-1-oxo-isoindoline-5-yl)-1-(2,4-difluorophenyl)-5-methyl-1H-[1,2,3]triazole,
4-(2-(2,2-difluoroethyl)-1-oxo-isoindoline-5-yl)-1-(4-fluorophenyl)-5-methyl-1H-[1,2,3]triazole,
4-(2-(2-hydroxy-2-methyl-propyl)-1-oxo-isoindoline-5-yl)-1-(4-fluorophenyl)-5-methyl-1H-[1,2,3]triazole,
4-(2-(2,2hydroxy-2-methyl-propyl)-1-oxo-isoqyinoline-6-yl)-1-(4-fluorophenyl-5-methyl-1H-[1,2,3]triazole, or
1-(4-fluorophenyl)-5-methyl-4-(2-(2-hydroxy-2-methyl-propyl)-quinoline-6-yl)-1-[1,2,3]triazole, and pharmaceutically acceptable salts thereof can be exemplified. Among these,
1-(2-fluoropyridine-3-yl)-5-methyl-4-(1-oxoindene-2-spiro-1'-cyclopropyl-5-yl)-1H-[1,2,3]triazole,
4-(2-isopropyl-1-oxo-isoindoline-5-yl)-1-(2-fluoropyridine-3-yl)-5-methyl-1H-[1,2,3]triazole,
1-(2-fluoropyridine-3-yl)-5-methyl-4-(2-propyl-1-oxo-isoindoline-5-yl)-1H-[1,2,3]triazole,
4-(2-cyclopropyl-1-oxo-isoindoline-5-yl)-1-(2-fluorobenzene-3-yl)-5-methyl-1H-[1,2,3]triazole,
4-(2-isopropyl-1-oxo-isoindoline-5-yl)-1-(2,4-difluorophenyl)-5-methyl-1H-[1,2,3]triazole,
4-(2-(2,2-difluoroehtyl)-1-oxo-isoindoline-5-yl)-1-(4-fluorophenyl)-5-methyl-1H-[1,2,3]triazole,
4-(2-(2-hydroxy-2-methyl-propyl)-1-oxo-isoindoline-5-yl)-1-(4-fluorophenyl)-5-methyl-1H-[1,2,3]triazole,
4-(2-(2-hydroxy-2-methyl-propyl-1-oxo-isoquinoline-6-yl)-1-(4-fluorophenyl)-5-methyl-1H-[1,2,3]triazole, or
1-(4-fluorophenyl)-5-methyl-4-(2-(2-hydroxy-2-methyl-propyl)-quinoline-6-yl-1H-[1,2,3]triazole, and pharmaceutically acceptable salts thereof are preferable.

The compounds (I) of the present invention can be produced according to a well-known reaction method or a per se known method. The compounds (I) of the invention can be produced in a conventional synthetic method carried out in a liquid phase, or in a recently developed striking solid phase method, such as combinatorial synthetic method or parallel synthetic process.

The compound (I) of the present invention

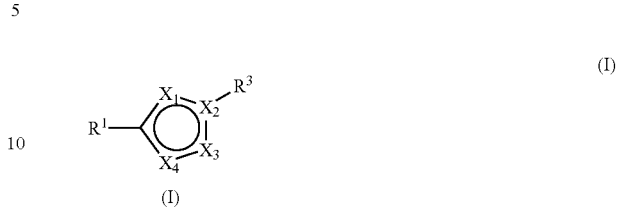

(I)

wherein each symbol is the same as above, can be produced for example by the following method.

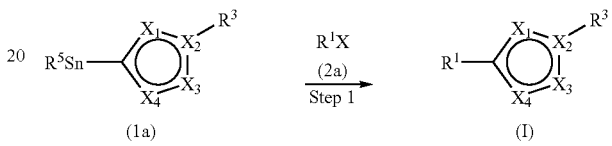

wherein $R^5$ represents a lower alkyl group, X represents a leaving group, and the other symbols are the same as above.

(Step 1)

In this step, the compound (1a) is reacted with the compound (2a) in the presence of a catalyst, to produce the compound (I) of the present invention.

$R^5$ in the compound (1a) represents a lower alkyl group, and for example, methyl group, ethyl group, propyl group, butyl group and the like are preferable.

As for X in the compound (2a), there is no specific limitation as long as it leaves in the reaction of the compounds (1a) and (2a) to generate the compound (I), while halogen atom or $OSO_3CF_3$ is preferable.

The reaction in this step is what is called Stille coupling reaction.

The amount used of the compound (2a) is usually 1 to 10 equivalent, preferably 1 to 3 equivalent for 1 equivalent of compound (1a).

As for catalysts used in this step, $Pd(PPh_3)_4$, $Pd_2(dba)_3$ and the like are exemplified.

The amount used of catalyst is usually 1 to 200% mol, preferably 5 to 20% mol for 1 equivalent of compound (1).

The ligands used in this step include for example, $PPh_3$, $P(o-ttolyl)_3$, dppp, BINAP, $AsPh_3$.

The amount used of ligand is usually 1 to 20% mol, preferably 5 to 20% mol for 1 equivalent of compound (1).

As for reaction solvent, there is no particular limitation as long as it does not affect the reaction, and for example, toluene, DMF, NMP, THF, DMSO and the like are exemplified, and among these, toluene, DMF, NMP and the like are preferable.

The reaction temperature is usually 0° C. to 150° C., preferably 50° C. to 120° C.

The reaction time is usually 30 min to 7 days, preferably 6 to 12 hours.

Thus resulting compound (I) of the present invention may be separated and purified by means of a conventional way, for example, concentration, vacuum concentration, extract with solvent, crystallization, reprecipitation, chromatography, and so on.

The compound (I) of the present invention may be further produced by the following method.

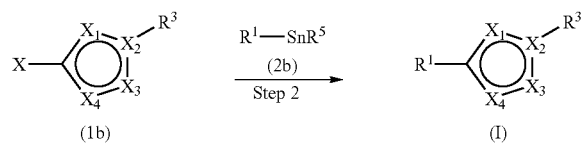

wherein each symbol is the same as above.
(Step 2)

In this step, the compound (1b) is reacted with the compound (2b) in the presence of a catalyst, to produce the compound (I) of the present invention.

The reaction in this step is what is called Stille coupling reaction, as for the above step 1.

The present step will be explained in detail in the following.

The amount of the compound (2b) used in this step is usually 1 to 10 equivalent, preferably 1 to 3 equivalent for 1 equivalent of compound (1b).

The types and amount of catalysts used in this step is the same as those in the above step 1.

Further, the types and amount of lignads used are the same as those in the above step 1.

Moreover, the reaction solvent used in this step, the reaction temperature and the reaction time are the same as above.

Thus resulting compound (I) of the present invention may be separated and purified by means of a conventional way, for example, concentration, vaccum concentration, extract with solvent, crystallization, reprecipitation, chromatography, and so on.

The compound (I) of the present invention may be further produced by the following method.

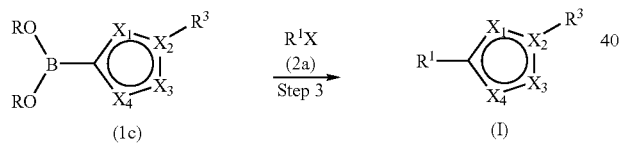

wherein R represents alkyl group and the like, and the other symbols are the same as above.
(Step 3)

In this step, the compound (1c) is reacted with the compound (2a) in the presence of catalyst and base, to produce the compound (I) of the present invention.

The reaction in this step is what is called Suzuki coupling reaction.

The amount used of the compound (2a) is usually 1 to 10 equivalent, preferably 1 to 3 equivalent for 1 equivalent of the compound (1c).

As for catalyst used, for example, Pd (PPh$_3$)$_4$, Pd$_2$(dba)$_3$, PdCl$_2$(dppf)$_2$ can be exemplified.

The amount used of catalyst is usually 1 to 200% mol, preferably 5 to 20% mol for 1 equivalent of compound (1c).

As for base used, for example, sodium carbonate, potassium carbonate are included.

The amount of base used is usually 1 to 10 equivalent, preferably 1 to 5 equivalent for 1 equivalent of compound (1c).

As for reaction solvent, there is no particular limitation as long as it does not affect the reaction, and for example, toluene, DMF, NMP, dioxane, THF, DMSO, water and the like are exemplified, and among these, toluene, DMF, and NMP are preferable.

The reaction temperature is usually 0° C. to 150° C., preferably 50° C. to 120° C.

The reaction time is usually 30 min to 7 days, preferably 6 to 12 hours.

Thus resulting compound (I) may be separated and purified by means of a conventional way, for example, concentration, vaccum concentration, extraction with solvent, crystallization, reprecipitation, chromatography, and so on.

The compound (I) of the present invention may be further produced by the following method.

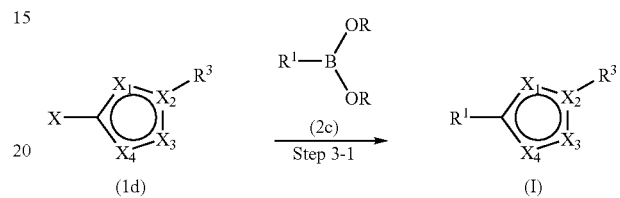

wherein each symbol is the same as above.
(Step 3-1)

In this step, the compound (1d) is reacted with the compound (2c), to produce the compound (I) of the present invention.

The reaction in this step is what is called Suzuki coupling reaction, and the reaction conditions may be the same as the above step 3.

Thus resulting compound (I) of the present invention may be separated and purified by means of a conventional way, for example, concentration, vaccum concentration, extraction with solvent, crystallization, reprecipitation, chromatography, and so on.

Among the compound (1a) used in the above step 1, the compound represented by the formula (1a-1),

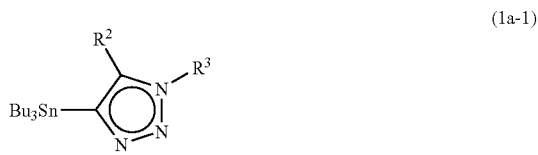

wherein each symbol is the same as above, for example can be produced by the following method.

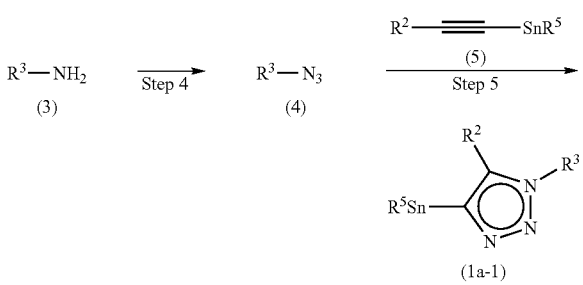

wherein each symbol is the same as above.
(Step 4)

In this step, the compound (3) is reacted with NaNO$_2$ and NaN$_3$ in the presence of water and hydrogen chloride, to produce the compound (4).

The amount of NaNO$_2$ used in the present reaction is usually 1 to 50 equivalent, preferably 1 to 5 equivalent, for 1 equivalent of compound (3).

The amount of NaN$_3$ used in the present step is usually 1 to 50 equivalent, preferably 1 to 5 equivalent, for 1 equivalent of compound (3).

The amount of water and hydrogen chloride used is usually 1 to 1000 equivalent, preferably 1 to 100 equivalent for 1 equivalent of compound (3).

As for reaction solvent, there is no particular limitation as long as it does not affect the reaction, and for example, mixed solvent of water-ether, THF, ethyl acetate, chloroform can be exemplified, and among these, mixed solvent of water-ether is preferable.

The reaction temperature is usually 0° C. to 100° C., preferably 0° C. to room temperature.

The reaction time is usually 30 min to 24 hours, preferably 1 to 12 hours.

Thus resulting compound (1a-1) may be separated and purified by means of a conventional way, for example, concentration, vaccum concentration crystallization, extract with solvent, reprecipitation, chromatography, and so on.

(Step 5)

In this step, the compound (4) obtained in the above step 4 is reacted with the compound (5) to produce the compound (1a-1).

As for the compound (5) used in the present step, for example, tributyl (1-propynyl) tin, ethinyltri-N-butyltin are included.

The compound (5) used in the present invention can be produced by using a commercially available compound, or by reacting the compound represented by the formula (5A)

(formula 5A)

(5A)

wherein each symbol is the same as above, with the compounds represented by the formula (4A) or (4B)

(4A)

(4B)

wherein each symbol is the same as above. The reaction can be performed by a method described previously (for example, J. Org. Chem. 1987, 52(19), 4296; Tetrahedron Lett. 1984, 25(28), 3019, etc.), by a method according thereof, or by a combination of these and ordinary methods.

The amount used of the compound (4) is usually 1 to 50 equivalent, preferably 2 to 10 equivalent for 1 equivalent of compound (3).

As for solvent used, there is no particular limitation as long as it does not affect the reaction, and for example, toluene, benzene, xylene, DMF, NMP, dioxane, THF, and DMSO are included, and among these, toluene, benzene, and xylene are preferable.

The reaction temperature is usually 0° C. to 150° C., preferably 5 to 150° C.

The reaction time is usually 30 min to 7 days, preferably 2 to 12 hours.

Thus resulting compound (1a-1) may be separated and purified by means of a conventional way, for example, concentration, vaccum concentration, extract with solvent, crystallization, reprecipitation, chromatography, and so on.

Moreover, the compound (I-1) of the present invention can be also produced by the following method with the use of the compound (4).

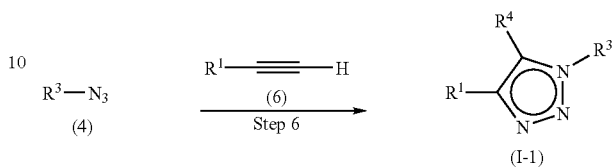

(Step 6)

In this step, the above compound (4) is reacted with the compound (6) in the presence of cuprate, to produce the compound (I-1) of the present invention.

The amount used of the compound (6) is usually 1 to 10 equivalent, preferably 1 to 3 equivalent for 1 equivalent of compound (4).

As for cuprate used in the present step include, copper sulfate pentahydrate/sodium ascorbate, copper iodide, copper bromide, and CuOTf-C$_6$H$_6$ complex.

The amount used of cuprate is usually 0.1 to 20% mol, preferably 1 to 10% mol, for 1 equivalent of compound (4).

As for solvent used, there is no particular limitation as long as it does not affect the reaction, and for example, mixed solvent of water-tert-butanol, or water-ethanol, and the like can be exemplified.

The reaction temperature is usually 0° C. to 60° C., preferably 20° C. to 30° C.

The reaction time is usually 1 to 36 hours, preferably 3 to 24 hours.

Thus resulting compound (I-1) of the present invention may be separated and purified by means of a conventional way, for example, concentration, vaccum concentration, extract with solvent, crystallization, reprecipitation, chromatography, and so on.

The compound (6) used in the present step can be produced in the presence of cuprate such as copper iodide, and bases such as triethylamine, by using the above mentioned compound (2a) and trimethylsilylacetylene, with the use of Pd catalyst such as PdCl$_2$(PPh$_3$)$_2$, with the use of a solvent such as DMF. The reaction can be performed by a method described previously (for example, J. Chem. Soc., Perkin Trans. 1, 2000, 4339-4346, Angew. Chem. Int. Ed. 2002, 41, No. 14, 2596-2599, etc.), by a method according thereof, or by a combination of these and ordinary methods.

Moreover, the compound represented by the compound (I-1) of the present invention I-1)

(I-1)

wherein each symbol is the same as above, for example can be produced by the following method.

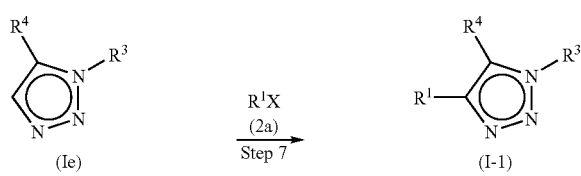

wherein each symbol is the same as above.
(Step 7)

In this step, the compound (1e) is reacted with the compound (2a) in the presence of bases and catalyst, to produce the compound (I-1) of the present invention.

The reaction in this step is what is called Heck reaction.

X in the compound (2a) used in this step represents a leaving group, and include for example, chlorine atom, bromine atom, iodine atom, and trifluoromethansulfonyloxy group.

The amount of the compound (2a) used is usually 1 to 5 equivalent, preferably 1 to 2 equivalent for 1 equivalent of compound (1e).

As for catalyst used in the present step, palladium catalyst is preferable, and include for example, $Pd(OAc)_2$, $Pd(PPh_3)_4$, $Pd_2(dba)_3$, and $pdCl_2(dppf)_2$.

The amount of catalyst used is usually 0.01 to 1 equivalent, preferably 0.1 to 0.2 equivalent for 1 equivalent of compound (1e).

Moreover, ligands are used in the present reaction, and as for the ligands, for example, $PPh_3$, $P(O\text{-tolyl})_3$, dppf, BINAP are included.

The amount of ligands used is usually 1 to 20% mol, preferably 5 to 20% mol, for 1 equivalent of compound (1e).

As for bases used in the present step, for example triethylamine, sodium acetate, sodium carbonate, potassium carbonate are included.

The amount of bases used is usually 1 to 2 equivalent, preferably 1.1 to 1.5 equivalent for 1 equivalent of compound (1e).

The reaction temperature is usually 0 to 150° C., preferably 50 to 120° C.

As for reaction solvent, there is no particular limitation as long as it does not affect the reaction, and for example, toluene, DMF, NMP, dioxane, THF, DMSO, and water are included, and among these, toluene, DMF and NMP are preferable.

The reaction time is usually 30 min to 7 days, preferably 6 to 12 hours.

Thus resulting compound (I-1) may be separated and purified by means of a conventional way, for example, concentration, vaccum concentration, extract with solvent, crystallization, reprecipitation, chromatography, and so on.

The compound of the present invention may be converted to salt or ester medically acceptable by an ordinary method, and reciprocally, conversion from salt or ester to free compound can be also performed by an ordinary method.

Specifically when the above compounds (I), (I-A), (I-B), (I-1) and (Ia-1) have a basic group(s) originated in an amino or pyridyl group within the molecule, they may be converted into the corresponding pharmaceutically acceptable salts by treating the compounds with acid.

The acid-added salts include, for example, hydrohalic acid salts such as hydrochloride, hydrofluoride, hydrobromide and hydroiodide; inorganic acid salts such as nitrate, perchlorate, sulfate, phosphate and carbonate; lower alkylsulfonates such as methanesulfonate, trifluoromethanesulfonate and ethanesulfonate; arylsulfonates such as benzenesulfonate and p-toluenesulfonate; organic acid salts such as fumarate, succinate, citrate, tartrate, oxalate and maleate; and acid-added salts of organic salts such as glutamate and aspartate.

When the compounds of the present invention have an acid group(s) in the group, for example, carboxyl group, they may be converted into the corresponding pharmaceutically acceptable salts by treating with a base. The base-added salts include, for example, alkali metal salts such as sodium and potassium; alkaline earth metal salts such as calcium or magnesium; and organic base salts such as ammonium salt, guanidine, triethylamine and dicyclohexylamine.

In addition, the compounds of the present invention may exist in optional forms of the hydrates or solvates of the free compounds or salts thereof.

Moreover, the conversion from salt or ester to free compound can be performed by an ordinary method, reciprocally.

In some cases, the compounds of the present invention exist as stereoisomers or tautomers such as optical isomers, diastereomers, or geometrical isomers depending on the embodiments of the substituents. Such isomers all are naturally included in the present invention. In addition, the mixtures of these isomers in the optional ratio are also included in the compound of the present invention.

When the compound of the present invention is used clinically, it can be formulated by adding a pharmaceutically acceptable additive according to its administration form. The additives then used, may be various additives usually used in the formulation field, and include: gelatin, lactose, sucrose, titanium oxide, starch, crystalline cellulose, hydroxypropyl methylcellulose, carboxymethylcellulose, corn starch, microcrystalline wax, white petrolatum, magnesium aluminometasilicate, calcium dihydrogen phophate, citric acid, trisodium citrate, hydroxypropylcellulose, sorbitol, sorbitan fatty acid ester, polysorbate, sucrose fatty acid ester polyoxyethylene, castor wax, polyvinylpyrrolidone, magnesium stearate, light anhydrous silic acid, talc, vegetable oil, benzyl alcohol, gum arabic, propylene glycol, polyalkylene glycol, cyclodextrin, and hydroxypropylcyclodextrin.

The mixture of the compound of the present invention and the above additives may be used as solid formulation (tablet, capsule, granule, powder, suppository, etc.) or liquid formulation (syrup, elixir, injection, etc.). These formulations may be prepared according to general methods in the formulation field. The liquid formulation may be in a form to dissolve or suspended in water or other suitable medium at the time of usage. Moreover, particularly in case of injection, it may be dissolved or suspendeded in physiological saline or in glucose solution according to need, and buffer or preservative may be further added. These formulations may contain the compound of the present invention by a rate of 1.0 to 100 wt %, preferably 1.0 to 60 w %.

The formulation of the compound of the present invention may be performed for example according to the following preparation examples.

PREPARATION EXAMPLE 1

The compound of Example 1 described in the following (10 parts), 15 parts of heavy magnesium oxide and 75 parts of lactose were homogeneously mixed to prepare a powdery preparation in powder or fine powder of not larger than 350 µm. The powdery preparation was placed in capsule containers to prepare capsule preparations.

PREPARATION EXAMPLE 2

The compound of Example 1 described in the following (45 parts), 15 parts of starch, 16 parts of lactose, 21 parts of crystalline cellulose, 3 parts of polyvinyl alcohol and 30 parts of distilled water were homogeneously mixed, disintegrated, granulated, dried and sieved to give a granular preparation having a size of 1410 to 177 μm diameter.

PREPARATION EXAMPLE 3

After a granular preparation was manufactured by the same method as in Production Example 2, 3 parts of calcium stearate were added to 96 parts of the granular preparation followed by subjecting to a compression molding to prepare tablets having 10 mm diameter.

PREPARATION EXAMPLE 4

To 90 parts of the granular preparation manufactured by the method of Production Example 2 were added 10 parts of crystalline cellulose and 3 parts of calcium stearate followed by subjecting to a compression molding to give tablets of 8 mm diameter. A mixed suspension of syrup gelatin and precipitated calcium carbonate was added thereto to prepare sugar-coated tablets.

When the compound of the present invention is used clinically, the dosage and number of times of administration differ from the sex, age, body weight, symptom levels, type and scope of intended treatment effect of the patient. Generally, in case of oral administration, 0.01 to 100 mg/kg per day for adult, preferably 0.03 to 1 mg/kg per day is administered in 1 or more times. In case of parenteral administration, 0.001 to 10 mg/kg, preferably 0.001 to 0.1 mg/kg per day is administered in 1 or more times.

Physician, veterinary or clinician can normally determine easily the necessary effective dosage to block, suppress or stop the development of diseases.

EXAMPLES

The present invention will be explained in detail referring to examples, while the present invention is not limited at all by these Examples.

Wakogel (registered trademark) C-300 (Wako Pure Chemicals) or KP-Sil (registered trademark) Silica prepacked column (Biotage) was used for silicagel chromatography in the Examples. For a preparative thin-layer chromatography, Kieselgel™ 60F 254, Art. 5744 (Merck) was used. For basic silicagel column chromatography, Chromatorex (registered trademark) NH (100-250 mesh or 200-350 mesh) (Fuji Silysia Chemical) was used. Mass spectrum was measured with the use of micromass ZQ (Waters) by electrospray ionization method (ESI) or atmosphere pressure chemical ionization method (APCI).

NMR spectrum was measured with the use of dimethylsulfoxide as internal standard when measured with heavy dimethylsulfoxide solution, measured with Gemini-200 (200 MHz; Varian), Gemini-300 (300 MHz; Varian), Mercury 400 (400 MHz; Varian) or InovA400 (400 MHz; Varian)-types spectrometers, and all δ levels were shown by ppm.
Meanings of the Abbreviations in the Following Examples are as shown Below.
    i-Bu: isobutyl group
    n-Bu: n-butyl group
    t-Bu: t-butyl group
    Me: methyl group
    Et: ethyl group
    Ph: phenyl group
    i-Pr: isopropyl group
    n-Pr: n-propyl group CDCl$_3$: heavy chloroform
    CD$_3$OD: heavy methanol
    DMSO-d$_6$: heavy dimethyl sulfoxide Meanings of abbreviations in nuclear magnetic resonance spectrum are as shown below.
    s: singlet
    d: doublet
    dd: double doublets
    t: triplet
    m: multiplet
    br: broad
    q: quartet
    J: coupling constant
    Hz: hertz Example 1

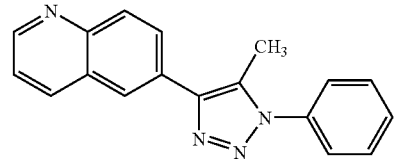

5-methyl-1-phenyl-4-(quinoline-6-yl)-1H-[1,2,3]triazole

Under nitrogen atmosphere, 2.0 ml of dimethylformamide solution with 20 mg of 6-bromo-quinoline, 30 g of the tin reagent, 1-phenyl-5-methyl-4-tributylstanyl-1H-[1,2,3]triazole obtained in Reference Example 5, and 11 mg of tetrakistriphenylphosphinepalladium was stirred all night at 115° C. After adding water, the product was extracted with ethyl acetate. Organic layer was washed with water, and then dried with anhydrous sodium sulfate. Residues obtained by distilling out the solvent under reduced pressure were purified by preparative thin-layer silicagel chromatography (hexane: ethyl acetate=1.1), to obtain 8.5 mg of the above compound as a white solid.

$^1$HNMR (300 MHz, CDCl$_3$), δ: 2.60 (3H, s), 7.40-7.50 (1H, m), 7.51-7.66 (5H, m), 8.08-8.28 (4H, m), 8.90-8.98 (1H, m), ESI-MS Found: m/z 287.2 [+H]$^+$.

Example 2

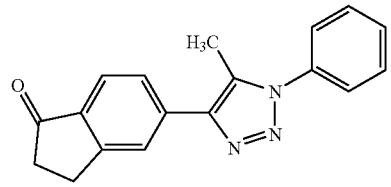

5-methyl-4-(1-oxoindene-5-yl)-1-phenyl-1H-[1,2,3]triazole

Under nitrogen atmosphere, 21 mg of 5-bromo-1-oxoindene and 30 mg of the compound 1-phenyl-5-methyl-4-tributylstanyl-1H-[1,2,3]triazole of Reference Example 5, were dissolved in 3 ml of dimethylformamide. 11 mg of Tetrakistriphenylphosphinepalladium was added, and the mixture was stirred all night by heating at 115° C. The reaction solution was cooled down to room temperature, and insoluble matters were removed by celite filtration. Water was added to the filtrate, the products were extracted with ethyl acetate. Ethyl acetate layer was washed with saturated saline solution, and then dried with anhydrous sodium sulfate. After distilling out the solvents under reduced pressure, residues were separated and purified with preparative thin-layer chromatography (ethyl acetate/hexane=1/2) to obtain 2.8 mg of the above compound as a white solid.

$^1$HNMR (400 MHz, CDCl$_3$), δ: 2.53 (3H, s), 2.74-2.77 (2H, m), 3.21-3.24 (2H, m), 7.49-4.56 (5H, m), 7.76 (21, d, J=8.0 Hz), 7.85 (1H, J=8.0 Hz), 7.96 (1H, s), ESI-MS Found: m/z 290.2[M+H]$^+$.

Example 3

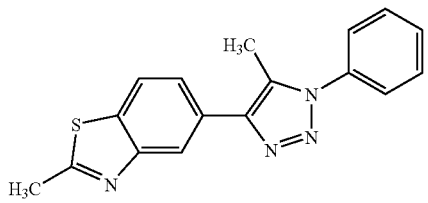

5-methyl-4-(2-methylbenzothiazole-5-yl)-1-phenyl-1H-[1.2,3]triazole

Under nitrogen atmosphere, 21 mg of 5-bromo-2-methyl-benzothiazole and 30 mg of the compound 1-phenyl-5-methyl-4-tributylstanyl-1H-[1,2,3]triazole of Reference Example 5 were dissolved in 3 ml of toluene. 11 mg of tetrakistriphenylphosphinepalladium was added, and the mixture was stirred all night by heating at 98° C. The reaction solution was cooled down to room temperature, and insoluble matters were removed by celite filtration. After distilling out the solvents under reduced pressure, residues were separated and purified with preparative thin-layer chromatography (ethyl acetate/hexane=1/2) to obtain 2.8 mg of the above compound as a white solid.

$^1$HNMR (400 MHz, CDCl$_3$), δ: 2.54 (3H, s), 2.87 (3H, s), 7.51-4.57 (5H, m), 7.92-7.93 (2H, m), 8.21 (1H, s), ESI-MS Found: m/z 307.2 [M+H]$^+$.

Example 4

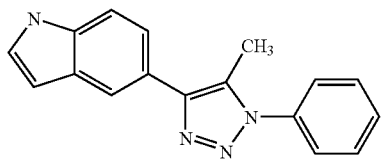

4-(1H-indole-5-yl)-5-methyl-1-phenyl-1H-[1,2,3]triazole

The above compound was obtained in the same manner as Example 1, with the use of 5-bromo-1H-indole and the tin reagent 1-phenyl-5-methy-4-tributylstanyl-1H-[1,2,3]triazole obtained in Reference Example 5.

$^1$HNMR (300 MHz, CDCl$_3$) δ: 1.56 (3H, s), 6.60-6.68 (1H, m), 7.48-7.62 (7H, m), 7.62-7.71 (1H, m), 7.99 (1H, s), 8.20-8.30 (1H, brs), ESI-MS Found: m/z 275.1 [M+H]$^+$.

Example 5

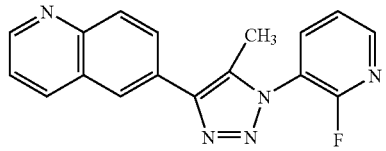

1-(2-fluoropyridine-3-yl)-5-methyl-4-(quinoline-6-yl)-1H[1,2,3]triazole

Under nitrogen atmosphere, 42 mg of 6-bromoquinoline and 30 mg of the compound 1-(2-fluoropyridine-3-yl)-5-methyl-4-tributylstanyl-1H-[1,2,3]triazole of Reference Example 1, were dissolved in 3 ml of dimethylformamide, 11 mg of tetrakistriphenylphosphinepalladium was added, and the mixture was stirred all night by heating at 115° C. under reflux.

The reaction solution was cooled down to room temperature, and insoluble matters were removed by celite filtration. Water was added to the filtrate, the products were extracted with ethyl acetate. Ethyl acetate layer was washed with saturated saline solution, and then was dried with anhydrous sodium sulfate. After distilling out the solvents under reduced pressure, residues were separated and purified with preparative thin-layer chromatography (chloroform/methanol=50/1) to obtain 2.4 mg of the above compound as a white solid.

$^1$HNMR (400 MHz, CDCl$_3$), δ: 2.56 (3H, d, J=2.4 Hz), 7.24-7.50 (2H, m), 8.06-8.11 (1H, m), 8.15-8.16 (1H, m), 8.18-8.23 (3H, m), 8.44-8.45 (1H, m), 8.93-8.94 (1H, m), ESI-MS Found: m/z 306.2 [M+H]$^+$.

Example 6

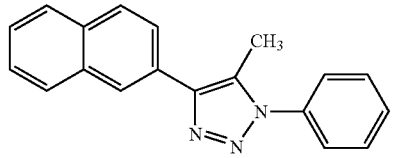

5-methyl-4-(naphthalene-2-yl)-5-methyl-1H-[1,2,3]triazole

The above compound was obtained in the same manner as Example 1, with the use of 2-bromo-naphthalene and the tin reagent 1-phenyl-5-methyl-4-tributylstanyl-1H-[1,2,3]triazole obtained in Reference Example 5.

¹HNMR (300 MHz, CDCl₃), δ: 2.59 (3H, s), 7.48-7.65 (7H, m), 7.82-8.02 (4H, m), 8.21 (1H, s), ESI-MS Found: m/z 286.2 [M+H]⁺.

Example 7

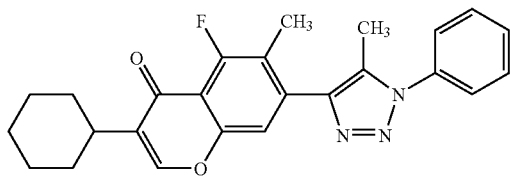

4-(3-cyclohexyl-5-fluoro-6-methyl-4-oxo-4H-chromen-7-yl)-5-methyl-1-phenyl-1H-[1,2,3]triazole 1) Manufacture of 1-(3-bromo-2-fluoro-4,6-dimethoxyphenyl)-2-cyclohexylethane-1-one Under nitrogen atmosphere, 6 ml of dichloroethane solution with 2.3 g of 2-bromo-3,5-dimethoxy-1-fluorobenzene and 6 ml of dichloroethane solution with 2.3 g of cyclohexylacetylchloride were dropped sequentially to 15 ml of dichloroethane solution with 1.8 g of alminium trichloride, 180 mg of zinc dichloride at −10° C., and then the mixture was stirred at room temperature for 2 hours. 20% of hydrochloric acid solution was added to the reaction solution, extracted with chloroform. Chloroform layer was washed with saturated saline solution and then dried with anhydrous sodium sulfate. After distilling out the solvents under reduced pressure, residues were separated and purified with silicagel chromatography (hexane/ethyl acetate=5/1) to obtain 780 mg of the above compound as a white solid.

¹HNMR (400 MHz, CDCl₃), δ: 0.90-1.78 (10H, m), 1.85-1.97 (1H, m), 2.66 (2H, dd, J=1.0, 2.6 Hz), 3.85 (3H, s), 3.93 (3H, s), 6.27 (1H, d, J=2.0 Hz), ESI-MS Found: m/z 359.2 [M+H]⁺.

2) Manufacture of 2-cyclohexyl-1-(2-fluoro-3-methyl-4,6-dimethoxyphenyl)ethane-1-one Under nitrogen atmosphere, 400 mg of methylboronic acid, 77 g of tetrakistriphenylphosphinepalladium, and 2.3 g of potassium carbonate were added sequentially at room temperature to 15 m of dioxane solution with 600 mg of the compound obtained in the above 1), and the mixture was stirred at 95° C. for 26 hours. Water was added to the reaction solution, extracted with ethyl acetate. Ethyl acetate layer was washed with saturated saline solution, and then dried with anhydrous sodium sulfate. After distilling out the solvents under reduced pressure, residues were separated and purified with silicagel chromatography (hexane/ethyl acetate=20/1) to obtain 370 mg of the above compound as a white solid.

¹HNMR (400 MHz, CDCl₃). δ: 0.90-1.78 (10H, m), 1.83-1.97 (1H, m), 2.03 (3H, d, J=2.4 Hz), 2.67 (2H, d, J=7.2 Hz), 3.81 (3H, s), 3.85 (3H, s), 6.20 (1H, d, J=2.0 Hz), ESI-MS Found: m/z 295.3 [M+H]⁺.

3) Manufacture of 2-cyclohexyl-1-(6-fluoro-2,4-dihydroxy-5-methylphenyl)ethane-1-one Under nitrogen atmosphere, 500 mg of aluminum trichloride was added to 10 ml of toluene solution with 370 mg of the compound obtained in the above 2), and the mixture was stirred at 95° C., for 2 hours. Water was added to the reaction solution, and extracted with ethyl acetate. Ethyl acetate layer was washed with saturated saline solution, and then dried with anhydrous sodium sulfate. After distilling out the solvents under reduced pressure, residues were separated and purified with silicagel chromatography (hexane/ethyl acetate=30/1) to obtain 230 mg of the above compound as a white solid.

¹HNMR (400 MHz, CDCl₃), δ: 0.98-1.90 (10H, m), 1.93-1.98 (1H, m), 2.08 (3H, d, J=2.4 Hz), 2.82 (1H, dd, J=4.4, 6.8 Hz), 5.80 (1H, brs), 6.17 (1H, d, J=2.0 Hz), ESI-MS Found: m/z 267.3 [M+H]⁺.

4) Manufacture of 3-cyclohexyl-5-fluoro-7-hydroxy-6-methyl-4H-chromen-4-one

Under nitrogen atmosphere, 1.4 ml of dimethylformamide was dropped at 0° C. to 0.37 ml solution of borontrifluoride-ethylether complex with 230 mg of the compound obtained in the above 3), and the mixture was stirred at 0° C. for 15 min. A mixed solution of 283 mg of phosphorus pentachloride and 7 ml of dimethylformamide was dropped at 0° C. to the reaction solution, and the mixture was stirred at room temperature for 12 hours. Water was added to the reaction solution, and extracted with ethyl acetate. Ethyl acetate layer was washed with saturated saline solution, and then dried with anhydrous sodium sulfate. After distilling out the solvents under reduced pressure, residues were separated and purified with silicagel chromatography (hexane/ethyl acetate=3/1) to obtain 110 mg of the above compound as a white solid.

¹HNMR (400 MHz, CDCl₃),δ: 1.15-1.95 (10H, m), 2.19 (3H, d, J=2.4 Hz), 2.73-2.83 (1H, m), 5.70 (1H, s), 6.59 (1H, d, J=2.0 Hz), 7.47 (1H, s), ESI-MS Found: m/z 277.3 [M+H]⁺.

5) Manufacture of 3-cyclohexyl-5-fluoro-7-(trifluoromethyl)sulfonyloxy)-6-methyl-4H-chromen-4-one Under nitrogen atmosphere, 0.1 ml of trifluoromethyl sulfonate anhydride was added at room temperature to 1 ml of pyridine solution with 20 mg of the compound obtained in the above 4), and the mixture was stirred at room temperature for 1 hour. Water was added to the reaction solution, extracted with chloroform. Chloroform layer was washed with saturated saline solution, and then dried with anhydrous sodium sulfate. After distilling out the solvents under reduced pressure, residues were separated and purified with preparative thin-layer chromatography (hexane/ethyl acetate=3/1) to obtain 7 mg of the above compound as a white solid.

ESI-MS Found: m/z 409.1 [+H]⁺.

6) Manufacture of 4-(3-cyclohexyl-5-fluoro-6-methyl-4-oxo-4H-chromen-7-yl)-5-methyl-1-phenyl-1H-[1,2,3]triazole The above compound was obtained by performing coupling reaction in the same manner as Example 1, with the use of the compound obtained in the above 5) and the alkyl tin reagent 1-phenyl-5-methyl-4-tributylstanyl-1H-[1,2,3]triazole similar as Reference Example 5.

¹HNMR (400 MHz, CDCl₃), δ: 1.18-1.32 (3H, m), 1.39-1.53 (2H, m), 1.70-1.98 (5H, m), 2.32 (3H, d, J=3.2 Hz), 2.34

(3H, J=3.2 Hz), 2.79-2.89 (1H, m), 7.50-7.61 (6H, m), ESI-MS Found: m/z 418.2 [M+H]+.

Example 8

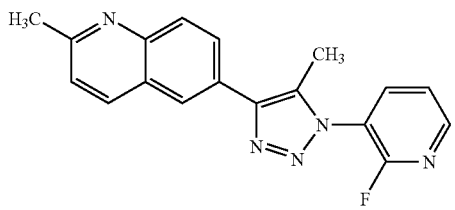

1-(2-fluoropyridine-3-yl)-5-methyl-4-(2-methyl-quinolline-6-yl)-1H-[1,2,3]triazole The above compound was obtained in the same manner as Example 1, with the use of 6-bromo-2-methyl-quinoline and the tin reagent 1-(2-fluoropyridine-3-yl)-5-methyl-4-tributylstanyl-1H-[1,2,3]triazole, obtained in Reference Example 1.
$^1$HNMR (300 MHz, CDCl$_3$), δ: 2.55 (3H, d, J=2.0 Hz), 2.79 (3H, s), 7.34 (1 h, d, J=7.6 Hz), 7.48-7.52 (1H, m), 8.05-8.22 (5H, m), 8.41-8.50 (1H, m), ESI-MS Found: m/z 320.2 [M+H]+.

Example 9

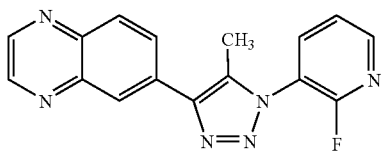

1-(2-fluoropyridine-3-yl)-5-methyl-4-quinoxaline-6-yl)-1H-[1,2,3]triazole

The above compound was obtained by performing the reaction in the same manner as Example 5, except using 6-bromoquinoxaline instead of 6-bromoquinoline which was used in Example 5. $^1$HNMR (400 MHz, CDCl$_3$), δ: 2.60 (3H, d, J=2.0 Hz), 7.48-7.51 (1H, m), 8.07-8.11 (1H, m), 8.21-8.24 (1H, m), 8.37-8.46 (3H, m), 8.85-8.88 (2H, m), ESI-MS Found: m/z 307.2 [M+H]+.

Example 10

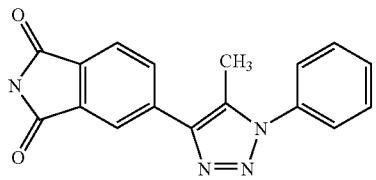

4-(1,3-dioxo-2,3-dihydro-1H-isoindole-5-yl)-5-methyl-1-phenyl-1H-[1,2,3]triazole The above compound was obtained by performing the reaction in the same manner as Example 2, except using 4-bromophthalimide instead of 5-bromo-1-oxoindane which was used in Example 2.
$^1$HNMR (400 MHz, CDCl$_3$), δ: 2.56 (3H, s), 7.49-7.51 (2H, m), 7.57-7.59 (3H, m), 7.95-7.97 (1H, m), 8.20-8.21 (1H, m), 8.28-8.30 (1H, m), ESI-MS Found: m/z 305.1 [M+H]+.

Example 11

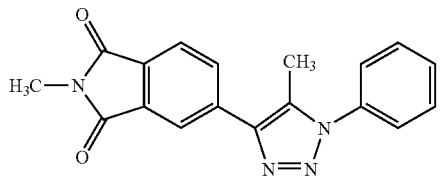

4-(1,3-dioxo-2,3-dihydro-2-methyl-1H-isoindole-5-yl)-5-methyl-1-phenyl-1H-[1,2,3]triazole Under nitrogen atmosphere, 10 mg of the compound 4-(1,3-dioxo-2,3-dihydro-1H-isoindole-5-yl)-5-methyl-1-phenyl-1H-[1,2,3]triazole obtained in the above Example 10 was dissolved in 2 ml of dimethylformamide. Sodium hydride and methyl iodide were added and the mixture was stirred at room temperature for 30 min. Water was added to the reaction solution, extracted with ethyl acetate. Ethyl acetate layer was washed with saturated saline solution, and then dried with anhydrous sodium sulfate. After distilling out the solvents under reduced pressure, residues were separated and purified with preparative thin-layer chromatography (ethyl acetate/hexane=1/2) to obtain 10 mg of the above compound as a brown solid.
$^1$HNMR (400 MHz, CDCl$_3$), δ: 2.56 (3H, s), 3.21 (3H, s), 7.48-7.51 (2H, m), 7.55-7.59 (3H, m), 7.94 (1H, d, J=8.0 Hz), 8.19 (1H, m), 8.22-8.24 (1H, m), ESI-MS Found: m/z 319.2 [M+H]+.

Example 12

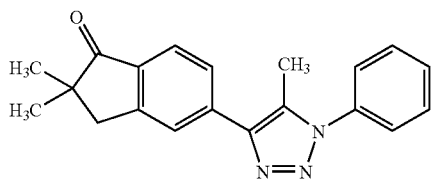

4-(2,2-dimethyl-1-oxoindene-5-yl)-5-methyl-1-phenyl-1H-[1,2,3]triazole

Under nitrogen atmosphere, 35 mg of 5-bromo-2,2-dimethyl-1-oxoindane and 30 mg of the compound 1-phenyl-5-methyl-4-tributylstanyl-1H-[1,2,3]triazole of the Reference Example 5 were dissolved in 3 ml of toluene. 11 mg of tetrakistriphenylphosphinepalladium was added and the mixture was stirred all night by heating at 95° C. The reaction solution was cooled down to room temperature, and insoluble matters were removed by celite filtration. Water was added to the filtrate, the products were extracted with ethyl acetate. Ethyl acetate layer was washed with saturated saline solution, and dried with anhydrous sodium sulfate. After distilling out the solvents under reduced pressure, residues were separated and purified with preparative thin-layer chromatography (ethyl acetate/hexane=1/2) to obtain 5.87 mg of the above compound as a white solid.

$^1$HNMR (400 MHz, CDCl$_3$), δ: 1.27 (6H, s), 2.53 (3H, s), 3.07 (2H, s), 7.49-7.60 (5H, m), 7.74-7.76 (1H, m), 7.83-7.85 (1H, m), 7.91 (1H, s), ESI-MS Found: m/z 318.2 [M+H]$^+$.

Example 13

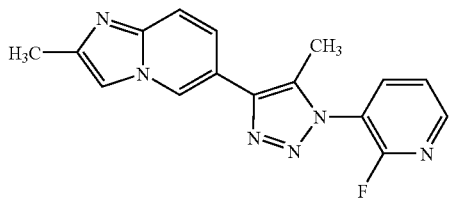

1-(2-fluoropyridine-3-yl)-5-methyl-4-(2-methyl-imidazo[1,2-a]pyridine-6-yl)-1H-[1,2,3]triazole The above compound was obtained in the same manner as Example 1, with the use of 6-bromo-2-methyl-imidazo[1,2-a]pyridine and the tin reagent 1-(2-fluoropyridine-3-yl)-5-methyl-4-tributylstanyl-1H-[1,2,3]triazole obtained in Reference Example 1.

$^1$HNMR (300 MHz, CDCl$_3$), δ: 2.48 (3H, d, J=2.0 Hz), 2.50 (3H, s), 7.44 (1H, s), 7.47-7.53 (2H, m), 7.63 (1H, d, J=7.0 Hz), 8.02-8.12 (1H, m), 8.43-8.50 (1H, m), 8.54 (1H, s), ESI-MS Found: m/z 309.2 [M+H]$^+$.

Example 14

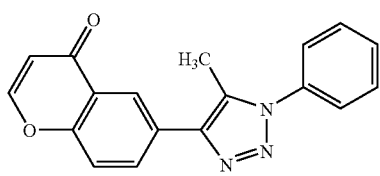

5-methyl-4-(4-oxo-4H-chromen-6-yl)-1-phenyl-1H-[1,2,3]triazole

The above compound was obtained as a white solid, by performing coupling reaction in the same manner as Example 1, with the use of 6-bromochromone and the alkyl tin compound 1-phenyl-5-methyl-4-tributylstanyl-1H-[1,2,3]triazole, similar as Reference Example 5.

$^1$HNMR (400 MHz, DCl$_3$), δ: 2.57 (3H, s), 6.37 (1H, d, J=6.4 Hz), 7.47-7.59 (6H, m), 7.88 (1H, d, J=6.0 Hz), 8.32-8.42 (2H, m), ESI-MS Found: m/z 304.2 [M+H]$^+$.

Example 15

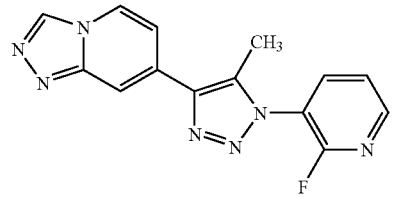

1-(2-fluoropyridine-3-yl)-5-methyl-4-([1,2,4]triazolo[4,3-a]pyridine-7-yl)-1H-[1,2,3]triazole 1) Manufacture of 7-iodo-[1,2,4]triazolo[4,3-a]pyridine 1 g of 2-fluoro-4-iodo-pyridine and 5 ml of hydrazine monohydrate were dissolved in 6 ml of acetonitrile, and the mixture was stirred at 80° C. for 2 hours, and the solvents were distilled outunder reduced pressure. 5 ml of dimethylformamide and 3 ml of ethyl orthoformate were added to the residues, stirred at 150° C. for 2 hours, cooled down to room temperature and the reaction was stopped after adding water. The products were extracted with chloroform, and after drying with anhydrous sodium sulfate, the solvents were distilled outunder reduced pressure. The obtained residues were washed with ethyl acetate and 680 g of the above compound was obtained as a white solid.

$^1$HNMR (400 MHz, DMSO), δ: 7.18-7.22 (1H, m), 8.29-8.38 (2H, m), 9.21 (1H, s), ESI-MS Found: m/z 245.9 [M+H]$^+$.

2) Manufacture of 1-(2-fluoropyridine-3-yl)-5-methyl-4-([1,2,4]triazolo[4,3-a]pyridine-7-yl)-1H-[1,2,3]triazole The above compound was obtained in the same manner as Example 1, with the use of halide obtained above and the tin reagent 1-phenyl-5-methyl-4-tributylstanyl-1H-[1,2,3]triazole obtained in Reference Example 5.

$^1$HNMR (300 MHz, CDCl$_3$), δ: 2.58 (3H, s), 7.48-7.55 (1H, m), 7.70 (1H, d, J=7.4 Hz), 8.00 (1H, s), 8.02-8.12 (1H, m), 8.24 (1H, d, J=7.4 Hz), 8.42-8.51 (1H, m), 8.87 (1H, s), ESI-MS Found: m/z 296.1 [M+H]$^+$.

Example 16

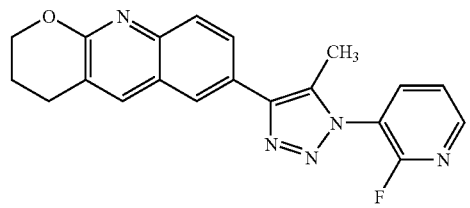

4-(3,4-dihydro-2H-1-oxa-9-aza-anthracene-6-yl)-1-(2-fluoropyridine-3-yl)-5-methyl-1H-[1,2,3]triazole The above compound was obtained in the same manner as Example 1, with the use of 6-bromo-3,4-dihydro-2H-1-oxa-9-aza-anthracene and the tin reagent 1-(2-fluoropyridine-3-yl)-5-methyl-4-tributylstanyl-1H-[1,2,3]triazole, obtained in Reference Example 1.

$^1$HNMR (300 MHz, CDCl$_3$), δ: 2.05-2.18 (2H, m), 2.52 (3H, d, J=2.0 Hz), 3.06 (2H, t, J=6.4 Hz), 4.50 (2H, t, J=5.3 Hz), 7.45-7.52 (1H, m), 7.89-8.15 (5H, m), 8.41-8.50 (1H, m), ESI-MS Found: m/z 362.1 [M+H]$^+$.

Example 17

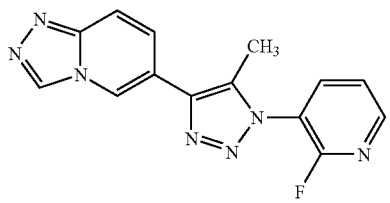

1-(2-fluoropyridine-3-yl)-5-methyl-4-([1,2,4]triazolo[4,3-a]pyridine-6-yl)-1H-[1,2,3]triazole The above compound was obtained in the same manner as Example 1, with the use of 6-bromo-[1,2,4]triazolo[4,3-a]pyridine and the tin reagent 1-(2-fluoropyridine-3-yl)-5-methyl-4-tributylstanyl-1H-[1,2,3]triazole, obtained in Reference Example 1.

$^1$HNMR (300 MHz, CDCl$_3$), δ: 2.52 (3H, d, J=1.6 Hz), 7.49-7.58 (1H, m), 7.74 (1H, d, J=9.6 Hz), 7.93 (1H, d, J=9.6 Hz), 8.02-8.12 (1H, m), 8.43-9.51 (1H, m), 8.43-9.51 (1H, m), 8.60 (1H, s), 8.92 (1H, s), ESI-MS Found: m/z 296.1 [M+H]$^+$.

Example 18

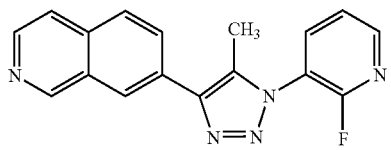

1-(2-fluoropyridine-3-yl)-4-isoquinoline-7-yl-5-methyl-1H-[1,2,3]triazole

The above compound was obtained by performing the reaction in the same manner as Example 5, except using trifluorosulfonate isoquinoline-7-ylester instead of 6-bromoquinoline which was used in Example 5.

$^1$HNMR (400 Mz, CDCl$_3$), δ: 2.57 (3H, d, J=2.0 Hz), 7.47-7.51 (1H, m), 7.69 (1H, d, J=6.0 Hz), 7.95 (1H, d, J=8.4 Hz), 8.06-8.11 (1H, m), 8.20-8.23 (1H, m), 8.30 (1H, s), 8.44-8.46 (1H, m), 8.55 (1H, d, J=6.0 Hz), 9.32 (1H, s), ESI-MS Found: m/z 306.2 [M+H]$^+$.

Example 19

1-(2-fluoropyridine-3-yl)-4-isoquinoline-3-yl-5-methyl-1H-[1,2,3]triazole

The above compound was obtained by performing the reaction in the same manner as Example 5, except using trifluorosulfonate isoquinoline-3-ylester instead of 6-bromoquinoline which was used in Example 5.

$^1$HNMR (400 MHz, CDCl$_3$), δ: 2.76-2.77 (3H, m), 7.45-7.48 (1H, m), 7.57-7.61 (1H, m), 7.68-7.72 (1H, m), 7.92 (1H, d, J=8.0 Hz), 7.97 (1H, d, J=8.0 Hz), 8.02-8.06 (1H, m), 8.42-8.44 (1H, m), 8.58 (1H, s), 8.27 (1H, m), ESI-MS Found: m/z 306.2 [M+H]$^+$.

Example 20

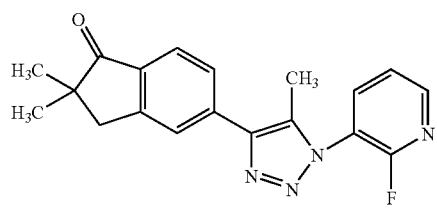

1-(2-fluoropyridine-3-yl)-4-(2,2-dimethyl-1-oxoindane-5-yl)-5-methyl-1H-[1,2,3]triazole Under nitrogen atmosphere, 35 mg of 5-bromo-2,2-dimethyl-1-oxoindane and 30 mg of the compound 1-(2-fluoropyridine-3-yl)-5-methyl-4-tributylstanyl-1H-[1,2,3]triazole of Reference Example 1 were dissolved in 3 ml of toluene. 11 mg of tetrakistriphenylphosphinepalladium was added and the mixture was stirred all night by heating at 115° C. under reflux. The reaction solution was cooled down to room temperature, and insoluble matters were removed by celite filtration. After distilling out the solvents under reduced pressure, residues were separated and purified with preparative thin-layer chromatography (ethyl acetate/hexane=1/2) to obtain 21.8 mg of the above compound as a white solid.

$^1$HNMR (400 MHz, CDCl$_3$), δ: 1.28 (6H, s), 2.51 (3H, m), 3.08 (2H, s), 7.47-7.50 (1H, m), 7.77 (1H, d, J=7.6 Hz), 7.85

(1H, d, J=8.0 Hz), 7.89 (1H, s), 8.04-8.09 (1H, m), 8.43-8.45 (1H, m), ESI-MS Found: m/z 337.2 [M+H]⁺.

Example 21

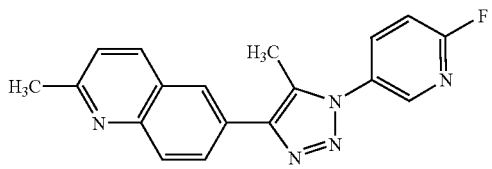

1-(2-fluoropyridine-5-yl)-5-methyl-4-(2-methyl-quinoline-6-yl)-1H-[1,2,3]triazole The above compound was obtained as a white solid by performing coupling reaction in the same manner as Example 1, with the use of 2-methyl-6-bromoquinoline and the alkyl tin compound 1-(2-fluoropyridine-5-yl)-5-methyl-4-tributyl-stanyl-1H-[1,2,3]triazole, similar as Reference Example 3.
¹HNMR (300 MHz, CDCl₃), δ: 2.60 (3H, s), 2.78 (4H, s), 7.20 (1H, dd, J=3.6, 8.8 Hz), 7.33 (1H, d, J=8.4 Hz), 8.01-8.09 (1H, m), 8.09-8.14 (3H, m), 8.17 (1H, d, J=1.6 Hz), 8.45 (1H, dd, J=0.8, 2.0 Hz), ESI-MS Found: m/z 320.2 [M+H]⁺.

Example 22

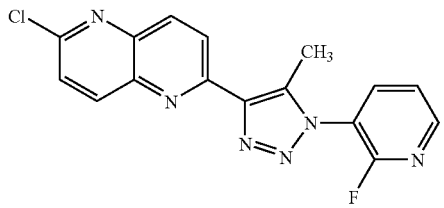

1-(6-chloro-[1,5]naphthyridine-2-yl)-4-(2-fluoropyridine-3-yl)-5-methyl-1H-[1,2,3]triazole The above compound was obtained in the same manner as Example 1, with the use of 2-chloro-6-chloro-[1,5]naphthyridine and the tin reagent 1-(2-fluoropyridine-3-yl)-5-methyl-4-tributylstanyl-1H-[1,2,3]triazole obtained in Reference Example 1.
¹HNMR (300 MHz, CDCl₃), δ: 2.80-2.89 (3H, m), 7.47-7.57 (1H, m), 7.68-7.77 (1H, m), 8.02-8.13 (1H, m), 8.41 (1H, td, J=1.7, 8.5 Hz), 8.47-8.51 (1H, m), 8.80-8.87 (1H, m), 9.02-9.11 (1H, m), ESI-MS Found: m/z 341.0 [M+H]⁺.

Example 23

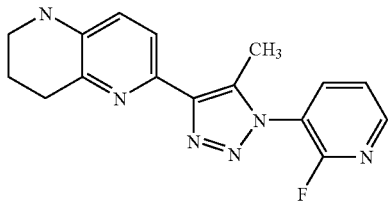

1-(2-fluoropyridine-3-yl)-5-methyl-4-(5,6,7,8-tetrahydro-[1,5]naphthyridine-2-yl)-1H-[1,2,3]triazole After dissolving 7.0 mg of the compound of the Example 22, in 1.5 ml of ethanol and 1.5. ml of ethyl acetate, 3.0 mg of palladium hydroxide was added, and the mixture was stirred for 30 min at room temperature under hydrogen atmosphere. The catalysts were filtrated, the solvents were distilled out and the residues were purified by preparative thin-layer silicagel chromatography (hexane:ethyl acetate:50:50) to obtain 2.6. mg of the above compound.
¹HNMR (300 MHz, CDCl₃), δ: 2.00-2.12 (2H, m), 2.60-2.67 (3H, m), 2.97 (2H, t, J=6.6 Hz), 3.36 (2H, t, J=5.5 Hz), 3.92 (1H, brs), 6.8106.88 (1H, m), 7.40-7.49 (1H, m), 7.78 (1H, d, J=8.2 Hz), 7.83-8.03 (1H, m), 8.42 (1H, d, J=4.9 Hz), ESI-MS Found: m/z 311.1 [M+H]⁺.

Example 24

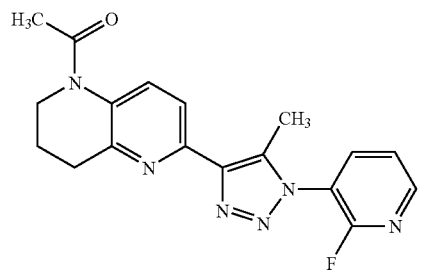

4-(5-acetyl-5,6,7,8-tetrahydro-[1,5]naphthyridine-2-yl)-(2-fluoropyridine-3-yl)-5-methyl-1H-[1,2,3]triazole After dissolving 2.0 mg of the compound of Example 23 in 400 µl of pyridine, 40 µl of acetic acid anhydride was added and the mixture was stirred all night at room temperature. The solvents were distilled out, and the residues were purified by preparative thin-layer silicagel chromatography (hexane:ethyl acetate=50:50, 3 drops of ammonia water) to obtain 2.0 mg of the above compound.
¹HNMR (300 MHz, CDCl₃), δ: 2.02-2.17 (2H, m), 2.31 (3H, s), 2.65-2.70 (3H, m), 3.01 (2H, t, J=6.6 Hz), 3.84 (2H, t, J=6.3 Hz), 7.22-7.38 (1H, m), 7.43-7.50 (1H, m), 7.99-8.09 (2H, m), 8.40-8.48 (1H, m), ESI-MS Found: m/z 353.1 [M+H]⁺.

Example 25

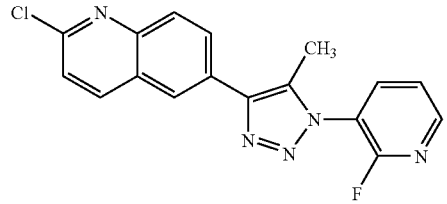

4-(2-chloroquinoline-6-yl)-1-(2-fluoropyridine-3-yl)-1-methyl-1H-[1,2,3]triazole The above compound was obtained in the same manner as Example 1, with the use of 6-bromo-2-chloroquinoline and the tin reagent 1-(2-fluoropyridine-3-yl)-5-methyl-4-tributylstanyl-1H-[1,2,3]triazole obtained in Reference Example 1. ¹HNMR (300 MHz, CDCl₃), δ: 2.56 (3H, d, J=1.1 Hz), 7.45 (1H, d, J=8.6 Hz), 7.47-7.54 (1H, m), 8.03-8.44 (4H, m), 8.26 (1H, d, J=0.3 Hz), 8.42-8.50 (1H, m), ESI-MS Found: m/z 340.0 [M+H]⁺.

Example 26

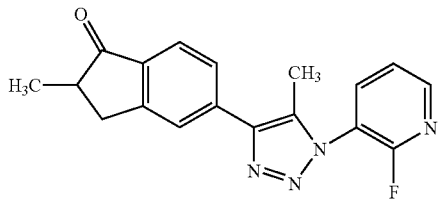

1-(2-fluoropyridine-3-yl)-5-methyl-4-(2-methyl-1-oxoindane-5-yl)-1H-[1,2,3]triazole The above compound was obtained by the same manner as Example 20, except using 5-bromo-2-methyl-1-oxoindane instead of 5-bromo-2,2-dimethyl-1-oxoindane which was used in Example 20.

¹HNMR (400 MHz, CDCl₃), δ: 1.36 (3H, d, J=7.2 Hz), 2.51 (3H, d, J=2.4 Hz), 2.76-2.84 (2H, m), 3.45-3.52 (1H, m), 7.49-7.52 (1H, m), 7.77-7.80 (1H, m), 7.87 (1H, d, J=8.4 Hz), 7.94 (1H, s), 8.07-8.11 (1H, m), 8.46-8.48 (1H, m), ESI-MS Found: m/z 323.2 [M+H]⁺.

Example 27

1-(2-fluoropyridine-3-yl)-5-methyl-4-((2R*)-methyl-1-oxoindene-5-yl)-1H-[1,2,3]triazole and 1-(2-fluoropyridine-3-yl)-5-methyl-4-((2S*)-methyl-1-oxoindene-5-yl)-1H-[1,2,3]triazole 10 mg of 1-(2-fluoropyridine-3-yl)-5-methyl-4-(2-methyl-1-oxoindene-5-yl)-1H-[1,2,3]triazole obtained in the above Example 26 was optically resolved by optically active column (Daicel; CHIRALPAKAD-H column; hexane/ethanol=2/3). From the first fraction, 4.35 mg of the compound named (2R*) of the above compound for convenience, and 4.59 mg of the compound named (2S*) of the above compound for convenience were obtained both as white solid, respectively.

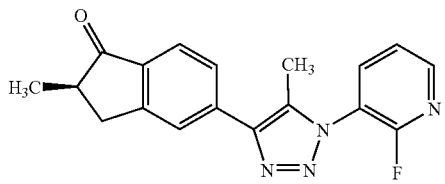

1-(2-fluoropyridine-3-yl)-5-methyl-4-((2R*)-methyl-1-oxoindane-5-yl)-1H-[1,2,3]triazole ¹HNMR (400 MHz, CDCl₃), δ: 1.36 (3H, d, J=7.2 Hz), 2.51 (3H, d, J=2.4 Hz), 2.76-2.84 (2H, m), 3.45-3.52 (1H, m), 7.49-7.52 (1H, m), 7.77-7.80 (1H, m), 7.87 (1H, d, J=8.4 Hz), 7.94 (1H, s), 8.07-8.11 (1H, m), 8.46-8.48 (1H, m), ESI-MS Found: m/z 323.2 [M+H]⁺.

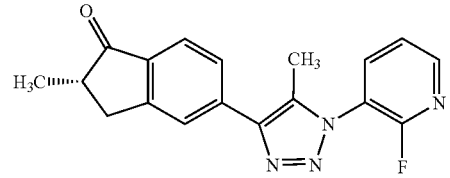

1-(2-fluoropyridine-3-yl)-5-methly-4-((2S*)-methyl-1-oxoindane-5-yl)-1H-[1,2,3]triazole ¹HNMR (400 MHz, CDCl₃), δ: 1.36 (3H, d, J=7.2 Hz), 2.51 (3H, d, J=2.4 Hz), 2.76-2.84 (2H, m), 3.45-3.52 (1H, m), 7.49-7.52 (1H, m), 7.77-7.80 (1H, m), 7.87 (1H, d, J=8.4 Hz), 7.94 (1H, s), 8.07-8.11 (1H, m), 8.46-8.48 (1H, m), ESI-MS Found: m/z 323.2 [M+H]⁺.

Example 28

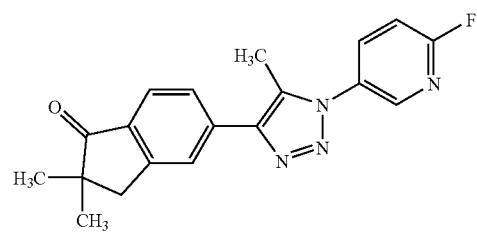

1-(2-fluoropyridine-5-yl)-4-(2,2-dimethyl-1-oxoindane-5-yl)-5-methyl-1H-[1,2,3]triazole The above compound was obtained as white solid by performing coupling reaction in the same manner as Example 1, with the use of 5-bromo-2,2-dimethylindane-1-one and the alkyl tin compound 1-(2-fluoropyridine-5-yl)-5-methyl-4-tributylstanyl-1H-[1,2,3]triazole similar as Reference Example 3.

¹HNMR (400 MHz, CDCl₃), δ: 1.28 (6H, s), 2.58 (3H, s), 3.09 (2H, s), 7.22 (1H, dd, J=3.6, 8.4 Hz), 7.76 (1H, d, J=8.0 Hz), 7.88 (1H, d, J=8.0 Hz), 7.91 (1H, s), 8.01-8.07 (1H, m), 8.45 (1H, d, J=2.0 Hz), ESI-MS Found: m/z 337.2 [M+H]⁺.

Example 29

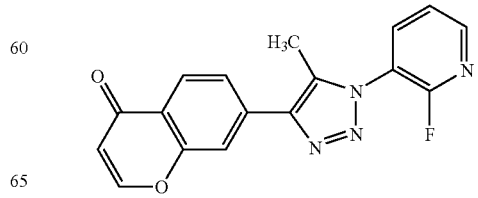

1-(2-fluoropyridine-3-yl)-4-(4-oxo-4H-chromen-7-yl)-5-methyl-1H-[1,2,3]triazole

1) Manufacture of 7-((trifluoromethyl)sulfonyloxy)-4H-chromen-4-one

Under nitrogen atmosphere, 0.24 ml of trifluoromethansulfonic anhydride was added at 0° C. to 4 ml of pyridine solution with 180 g of 7-hydroxy-4H-chromen-4-one, and the mixture was stirred at room temperature for 5 hours. Water was added to the reaction solution, extracted with chloroform. Chloroform layer was washed with saturated saline solution, and then dried with anhydrous sodium sulfate. After distilling out the solvents under reduced pressure, residues were separated and purified with preparative thin-layer chromatography (chloroform/methanol=10/1) to obtain 83 mg of the above compound as a white solid.

ESI-MS Found: m/z 295.0 [M+H]$^+$.

2) Manufacture of 1-(2-fluoropyridine-3-yl)-4-(4-oxo-4H-chromen-7-yl)-5-methyl-1H-[1,2,3]triazole The above compound was obtained as white solid by performing coupling reaction in the same manner as Example 1, with the use of the compound obtained in the above 1 and the alkyl tin compound 1-(2-fluoropyridine-3-yl)-5-methyl-4-tributylstanyl-1H-[1,2,3]triazole similar as Reference Example 1.

$^1$HNMR (400 MHz, CDCl$_3$), δ: 2.55 (3H, d, J=2.0 Hz), 6.39 (1H, d, J=6.4 Hz), 7.47-7.57 (1H, m), 7.86 (1H, dd, J=1.4, 8.0 Hz), 7.90 (1H, d, J=5.6 Hz), 7.96 (1H, d, J=1.6 Hz), 8.05-8.15 (1H, m), 8.32 (1H, d, J=8.4 Hz), 8.44-8.52 (1H, m), ESI-MS Found: m/z 323.1 [M+H]$^+$.

Example 30

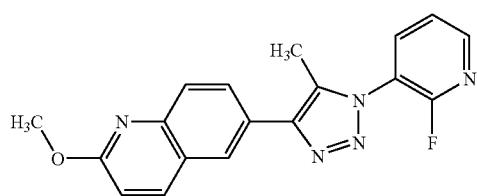

1-(2-fluoropyridine-3-yl)-4-(2-methoxyquinoline-6-yl)-5-methyl-[1,2,3]triazole

The above compound was obtained as white solid, by performing coupling reaction in the same manner as Example 20, with the use of 2-methoxy-6-bromoquinoline and the alkyl tin compound 1-(2-fluoropyridine-3-yl)-5-methyl-4-tributylstanyl-1H-[1,2,3]triazole similar as Reference Example 1.

$^1$HNMR (400 MHz, CDCl$_3$), δ: 2.53 (3H, s), 4.11 (3H, d, J=1.2 Hz), 6.96 (1H, dd, J=0.8, 8.8 Hz), 7.45-7.55 (1H, m), 8.05 (1H, d, J=4.4 Hz), 8.05-8.13 (3H, m), 8.14 (1H, s), 8.46 (1H, dd, J=0.8, 3.6 Hz), ESI-MS Found: m/z 336.2 [M+H]$^+$.

Example 31

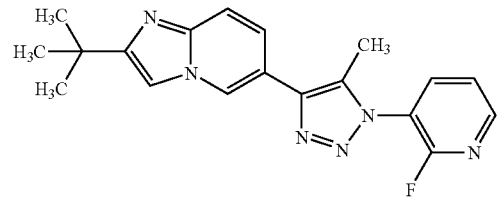

4-(2-tert-butyl-imidazo[1,2-a]pyridine-6-yl)-1-(2-fluoropyridine-3-yl)-5-methyl-1H-[1,2,3]triazole 1) Manufacture of 6-bromo-2-tert-butyl-imidazo[1,2-a]pyridine 1-bromopinacolone (178 mg) was dissolved in 2.0 ml of ethanol, 156 mg of 2-amino-5-bromopyridine was added, and the mixture was stirred all night by heating under reflux. After cooled down to room temperature, the solvents were distilled outunder reduced pressure, ethyl acetate followed by saturated sodium hydrogen carbonate aqueous solution were added. Organic layer was dried with anhydrous sodium sulfate, and the solvents were distilled outunder reduced pressure. The obtained residues were purified by preparative thin-layer silicagel chromatography (hexane:ethyl acetate=75:25) to obtain 186 mg of the above compound as a white solid.

$^1$HNMR (300 MHz, CDCl$_3$), δ: 1.39 (9H, s), 7.16 (1H, dd, J=1.8, 9.5 Hz), 7.31 (1H, s), 7.47 (1H, d, J=9.5 Hz), 8.19 (1H, d, J=1.8 Hz), ESI-MS Found: m/z 253.2 [M+H]$^+$.

2) Manufacture of 4-(2-tert-butyl-imidazo[1,2-a]pyridine-6-yl)-1-(2-fluoropyridine-3-yl)-5-methyl-1H-[1,2,3]triazole The above compound was obtained in the same manner as Example 1, with the use of halide obtained above, and the tin reagent 1-(2-fluoropyridine-3-yl)-5-methyl-4-tributylstanyl-1H-[1,2,3]triazole, obtained in Reference Example 1.

$^1$HNMR (300 MHz, CDCl$_3$), δ: 1.43 (9H, s), 2.47 (3H, d, J=1.7 Hz), 7.44 (1H, s), 7.45-7.53 (2H, m), 7.68 (1H, d, J=9.6 Hz), 8.02-8.13 (1H, m), 8.42-8.49 (1H, m), 8.54 (1H, s), ESI-MS Found: m/z 351.2 [M+H]$^+$.

Example 32

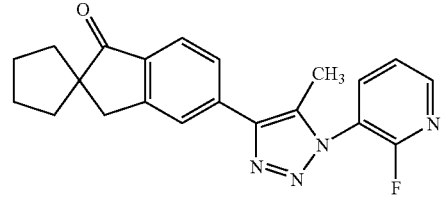

1-(2-fluoropyridine-3-yl)-5-methyl-4-(1-oxoindane-2-spiro-1'-cyclobutane-5-yl)-1H-[1,2,3]triazole 1) Manufacture of
5-bromo-1-oxoindane-2-spiro-1'-cyclobutane 100 mg of 5-bromo-1-oxoindane was dissolved in 10 ml of toluene, 0.3 ml of 1,4-dibromobutan and 132 mg of tert-butoxypotassium were added, and the mixture was stirred all night by heating at 130° C. under reflux. The reaction solution was cooled down to room temperature, the solvents were distilled outunder reduced pressure and the residues were separated and purified by silicagel chromatography (ethyl acetate/hexane=1/2) to obtain 71 mg of the above compound as a yellow oily matter.

2) Manufacture of 1-(2-fluoropyridine-3-yl)-5-methyl-4-(1-oxoindane-2-spiro-1'-cyclobutane-5-yl)-1H-[1,2,3]triazole The above compound was obtained by performing the reaction in the same manner as Example 20, except using 5-bromo-1-oxoindane-2-spiro-1'-cyclobutane obtained in the above 1) instead of 5-bromo-2,2-dimethyl-1-oxoindane which was used in Example 20. ¹HNMR (400 MHz, CDCl₃), δ: 1.63-1.68 (2H, m), 1.80-1.83 (2H, m), 1.94-1.97 (2H, m), 2.02-2.07 (2H, m), 2.51 (3H, d, J=1.6 Hz), 3.12 (2H, s), 7.49-7.52 (1H, m), 7.78 (1H, d, J=8.4 Hz), 7.87 (1H, d, J=8.4 Hz), 7.91 (1H, m), 8.08-8.11 (1H, m), 8.46-8.47 (1H, m), ESI-MS Found: m/z 363.2 [M+H]⁺.

Example 33

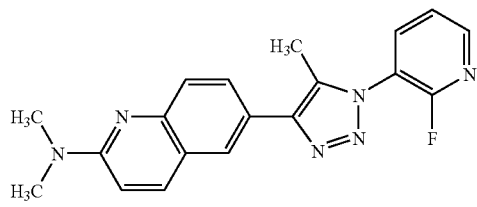

4-(2-dimethylamino-quinoline-6-yl)-1-(2-fluoropyridine-3-yl)-5-methyl-[1,2,3]triazole The above compound was obtained as a white solid by performing coupling reaction in the same manner as Example 20, with the use of 2-dimethylamino-6-bromoquinoline and the alkyl tin compound 1-(2-fluoropyridine-3-yl)-5-methyl-4-tributylstanyl-1H-[1,2,3]triazole, similar as Reference Example 1.

¹HNMR (400 MHz, CDCl₃), δ: 2.51 (3H, d, J=2.0 Hz), 3.27 (6H, s), 6.95 (1H, d, 9.2 Hz), 7.45-7.55 (1H, m), 7.81 (1H, d, J=8.4 Hz), 7.95 (2H, t, J=9.0 Hz), 8.01 (1H, brs), 8.09 (1H, t, J=7.4 Hz), 8.44 (1H, d, 5.2 Hz), ESI-MS Found: m/z 349.2 [M+H]⁺.

Example 34

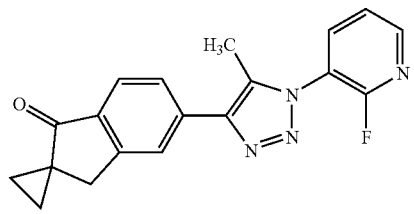

1-(2-fluoropyridine-3-yl)-5-methyl-4-(1-oxoindane-2-spiro-1'-cyclopropyl-5-yl)-1H-[1,2,3]triazole 1) Manufacture of
5-bromo-1-oxo-2-spiro-1'-cyclopropylindane 500 mg of 60% sodium hydride was added by ice-cooling to 15 ml solution of dimethylformamide with 1.0 g of 5-bromo-1-indanon. The reaction solution was stirred for 10 min, and after adding 1.2 ml of dibromoethane, the mixture was heated to room temperature and stirred for 1 hour. The reaction solution was diluted with ethyl acetate, washed with water and saturated saline solution, dried with anhydrous sodium sulfate. The residues obtained by distilling out the solvents under reduced pressure were purified by silicagel column chromatography (hexane:ethyl acetate=95:5) to obtain 700 mg of the above compound as a white solid.

¹HNMR (300 MHz, CDCl₃), δ: 1.14-1.22 (2H, m), 1.42-1.50 (2H, m), 3.20 (2H, s), 7.51-7.56 (1H, m), 7.63-7.70 (2H, m).

2) Manufacture of 1-(2-fluoropyridine-3-yl)-5-methyl-4-(1-oxoindane-2-spiro-1'-cyclopropyl-5-yl)-1H-[1,2,3]triazole The above compound was obtained according to the method of Example 1, with the use of the compound obtained in the above 1) and the compound 1-(2-fluoropyridine-3-yl)-5-methyl-4-tributylstanyl-1H-[1,2,3]triazole of Reference Example 1.

¹HNMR (300 MHz, CDCl₃), δ: 1.19-1.22 (2H, m), 1.48-1.52 (2H, m), 2.53 (3H, s), 3.31 (2H, s), 7.498-7.53 (1H, m), 7.81 (1H, d, J=8.1 Hz), 7.90 (1H, d, J=8.1 Hz), 8.00 (1H, s), 8.06-8.12 (1H, m), 8.40-8.50 (1H, m), ESI-MS Found: m/z 335.2 [M+H]$^+$.

Example 35

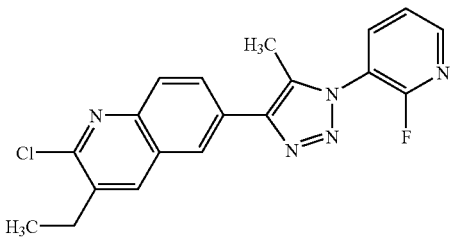

4-(2-chloro-3-ethyl-quinoline-6-yl)-1-(2-fluoropyridine-3-yl)-5-methyl-1H-[1,2,3]triazole The above compound was obtained as a white solid by performing coupling reaction in the same manner as Example 20, with the use of 2-chloro-3-ethyl-6-bromoquinoline and the alkyl tin compound 1-(2-fluoropyridine-3-yl)-5-methyl-4-tributylstanyl-1H-[1,2,3]triazole, similar as Reference Example 1.

$^1$HNMR (400 MHz, CDCl$_3$), δ: 1.40 (3H, t, J=7.4 Hz), 2.56 (3H, d, J=1.6 Hz), 2.95 (2H, q, J=7.6, 14.8 Hz), 7.48-7.54 (1H, m), 8.05 (1H, s), 8.09-8.16 (3H, m), 8.21 (1H, s), 8.47 (1H, dd, J=1.2, 4.8 Hz), ESI-MS Found: m/z 368.1 [M+H]$^+$.

Example 36

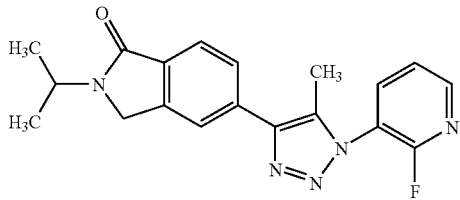

4-(2-isopropyl-1-oxo-isoindoline-5-yl)-1-(2-fluoropyridine-3-yl)-5-methyl-1H-[1,2,3]triazole 1) Manufacture of 5-bromo-2-isopropyl-1-oxo-isoindoline Under nitrogen atmosphere, 500 mg of 4-bromo-2-bromomethyl methyl benzoate was dissolved in 10 ml of methanol, 0.42 ml of isopropylamine and 0.67 ml of triethylamine were added, and the mixture was stirred all night by heating at 100° C. under reflux. The reaction solution was cooled down to room temperature, and after distilling out the solvents under reduced pressure, residues were separated and purified by silicagel column chromatography (ethyl acetate/hexane=1/2), to obtain 222 mg of the above compound as a white solid.

$^1$HNMR (400 MHz, CDCl$_3$), δ: 1.39 (6H, d, J=6.8 Hz), 4.31 (2H, s), 4.62-4.69 (1H, m), 7.59 (1H, d, J=8.0 Hz), 7.61(1H, s), 7.70 (1H, d, J=8.0 Hz), ESI-MS Found: m/z 254.1 [M+H]$^+$.

2) Manufacture of 4-(2-isopropyl-1-oxo-isoindoline-5-yl)-1-(2-fluoropyridine-3-yl)-5-methyl-1H-[1,2,3]triazole Under nitrogen atmosphere, 280 mg of 5-bromo-2-isopropyl-1-oxo-isoindoline and 171 mg of the compound 1-(2-fluoropyridine-3-yl)-5-methyl-4-tributylstanyl-1H-[1,2,3]triazole of Reference Example 1 were dissolved in 10 ml of toluene, 42 g of tetrakistriphenylphosphinepalladium was added, and the mixture was stirred for 12 hours by heating at 115° C. under reflux. The reaction solution was cooled down to room temperature and insoluble matters were removed by celite filtration. After distilling out the solvents under reduced pressure, residues were separated and purified with silicagel column chromatography (ethyl acetate/hexane=3/1) to obtain 179 mg of the above compound as a white solid.

$^1$HNMR (400 MHz, CDCl$_3$), δ: 1.33 (6H, d, J=7.2 Hz), 2.50 (3H, d, J=2.0 Hz), 4.43 (2H, s), 4.68-4.75 (1H, m), 7.49-7.52 (1H, m), 7.81 (1H, d, J=8.0 Hz), 7.96 (1H, d, J=8.0 Hz), 7.99 (1H, s), 8.06-8.11 (1H, m), 8.46-8.47 (1H, m), ESI-MS Found: m/z 352.2 [M+H]$^+$.

Example 37

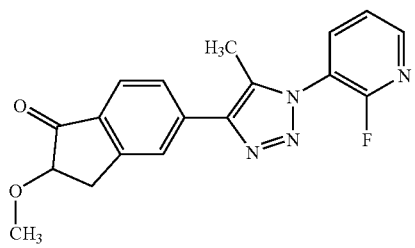

1-(2-fluoropyridine-3-yl)-4-(2-methoxy-1-oxoindane-5-yl)-5-methyl-1H-[1,2,3triazole 1) Manufacture of 5-bromo-2-methoxy-1-indanone 232 mg of [Hydroxy (p-nitrobenzensulfonyloxy)iodo]benzene was added at room temperature to 15 ml solution of acetonitrile with 100 mg of 5-bromo-1-indanone, and then heated under reflux for 4 hours. The reaction solution was cooled down to room temperature, the solvents were distilled outunder reduced pressure. The obtained residues were dissolved in 20 ml of methanol and refluxed all night. The reaction solution was cooled down to room temperature, the solvents were distilled outunder reduced pressure, and the obtained residues were dissolved in chloroform, washed with water and saturated saline solution, then dried with anhydrous sodium sulfate. The residues obtained by distilling out the solvents under reduced pressure were purified by silicagel column chromatography (hexane:ethyl acetate=95:5) to obtain 59 mg of the above compound as a white solid.

$^1$HNMR (300 MHz, CDCl$_3$), δ: 3.00 (1H, dd, J=4.8, 17.1 Hz), 3.44 (1H, dd, J=7.5 Hz), 4.16 (1H, dd, J=4.8, 7.5 Hz), 7.52-7.66 (3H, m).

2) Manufacture of 1-(2-fluoropyridine-3-yl)-4-(2-methoxy-1-oxoindene-5-yl)-5-methyl-1H-[1,2,3]triazole The above compound was obtained according to the method of Example 1, with the use of the compound obtained in the above 1) and the compound 1-(2-fluoropyridine-3-yl)-5-methyl-4-tributylstanyl-1H-[1,2,3]triazole of Reference Example 1.

¹HNMR (300 MHz, CDCl₃), δ: 2.52 (3H, d, J=2.1 Hz), 3.10 (1H, dd, J=3.9, 16.8 Hz), 3.60 (1H, dd, J=7.8, 16.8 Hz), 3.68 (3H, s), 4.26 (1H, dd, J=3.9, 7.8 Hz), 7.48-7.59 (1H, m), 7.82 (1H, d, J=8.1 Hz), 7.89 (1H, d, J=8.1 Hz), 7.94 (1H, s), 8.06-8.12 (1H, m), 8.45-8.50 (1H, m), ESI-MS Found: m/z 339.1 [M+H]⁺.

Example 38

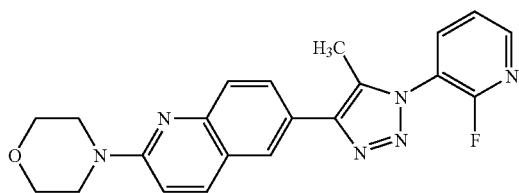

1-(2-fluoropyridine-3-yl)-5-methyl-4-(2-morpholine-4-yl-quinoline-6-yl)-1H-[1,2,3]triazole 1) Manufacture of 2-morpholine-6-bromoquinoline Under nitrogen atmosphere, 0.28 ml of morpholine and 490 mg of potassium carbonate were sequentially added at room temperature to 2 ml solution of dimethylsulfonamide with 78 mg of 2-chloro-6-bromoquinoline, and the mixture was stirred at 115° C. for 7 hours. Water was added to the reaction solution, and extracted with diethylether. Diethylether layer was washed with saturated saline solution, and then dried with anhydrous sodium sulfate. After distilling out the solvents under reduced pressure, residues were separated and purified with silicagel chromatography (hexane/ethyl acetate=3/1) to obtain 63 mg of the above compound as a white solid.

ESI-MS Found: m/z 293.1 [M+H]⁺.

2) Manufacture of 1-(2-fluoropyridine-3-yl)-5-methyl-4-(2-morpholine-4-yl-quinoline-6-yl)-1H-[1,2,3]triazole The above compound was obtained as a white solid by performing coupling reaction in the same manner as Example 20 with the use of the compound obtained in the above 1) and the alkyl tin compound 1-(2-fluoropyridine-3-yl)-5-methyl-4-tributylstanyl-1H-[1,2,3]triazole, similar as Reference Example 1.

¹HNMR (400 MHz, CDCl₃), δ: 2.52 (3H, d, J=2.0 Hz), 3.76 (4H, t, J=4.8 Hz), 3.88 (4H, t, J=4.8, 9.6 Hz), 7.02 (1H, d, J=9.6 Hz), 7.49 (1H, t, J=4.8 Hz), 7.82 (1H, d, J=9.2 Hz), 8.00 (2H, dd, J=2.2, 9.0 Hz), 8.04 (1H, d, J=2.0 Hz), 8.10 (1H, t), 8.44 (1H, d, J=4.4 Hz), ESI-MS Found: m/z 391.2 [M+H]⁺.

Example 39

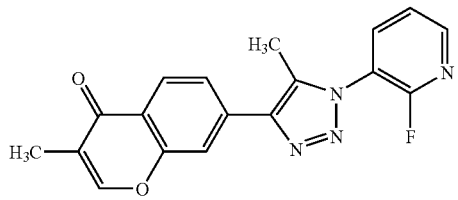

4-(3-methyl-4-oxo-4H-chromen-7-yl)-1-(2-fluoropyridine-3-yl)-5-methyl-1H-[1,2,3]triazole 1) Manufacture of 7-((trifluoromethyl)sulfonyloxy)-3-methyl-4H-chromen-4-one Under nitrogen atmosphere, 0.23 ml of trifluoromethansulfonic anhydride was added at 0° C. to 3 ml solution of pyridine with 120 mg of 7-hydroxy-3-methyl-4H-chromen-4-one, and the mixture was stirred at room temperature for 2 hours. Water was added to the reaction solution, and extracted with ethyl acetate. Ethyl acetate layer was washed with saturated saline solution, and then dried with anhydrous sodium sulfate. After distilling out the solvents under reduced pressure, residues were separated and purified with silicagel chromatography (hexane/ethyl acetate=10/1) to obtain 183 mg of the above compound as a white solid.

¹HNMR (400 MHz, CDCl₃), δ: 2.05 (3H, d, J=0.8 Hz), 7.30 (1H, dd, J=2.0, 8.4 Hz), 7.40 (1H, d, J=2.0 Hz), 7.83 (1H, d, J=1.2 Hz), 8.83 (1H, d, J=9.2 Hz), ESI-MS Found: m/z 309.1 [M+H]⁺.

2) Manufacture of 4-(3-methyl-4-oxo-4H-chromen-7-yl)-1-(2-fluoropyridine-3-yl)-5-methyl-1H-[1,2,3]triazole The above compound was obtained as a white solid by performing coupling reaction in the same manner as Example 20 with the use of the compound obtained in the above 1) and the alkyl tin compound 1-(2-fluoropyridine-3-yl)-5-methyl-4-tributylstanyl-1H-[1,2,3]triazole, similar as Reference Example 1.

¹HNMR (400 MHz, CDCl₃), δ: 2.08 (3H, d, J=1.2 Hz), 2.54 (3H, d, J=2.0 Hz), 7.51 (1H, t, J=4.8 Hz), 7.84 (2H, dd, J=1.2, 8.4 Hz), 7.92 (1H, s), 8.09 (1H, t, J=8.2 Hz), 8.35 (1H, d, J=8.4 Hz), 8.48 (1H, d, J=4.8 Hz), ESI-MS Found: m/z 359.1 [M+H]⁺.

Example 40

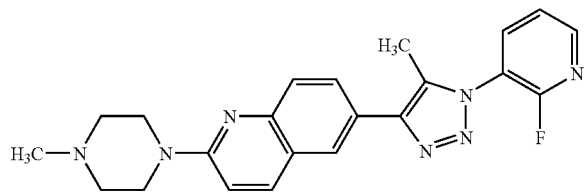

1-2-fluoropyridine-3-yl)-4-(2-(4-methylpyperazine-
1-yl)-quinoline-6-yl)-5-methyl-[1,2,3]triazole

1) Manufacture of 2-(4-methylpyperazine)-6-bromoquinoline

Under nitrogen atmosphere, 130 mg of 1-methylpiperazine was added sequentially at room temperature to 3 ml solution of dioxane with 63 mg of 2-chloro-6-bromoquinoline, and the mixture was stirred at 115° C. for 11 hours. Water was added to the reaction solution, extracted with diethylether. Diethylether layer was washed with saturated saline solution, and then dried with anhydrous sodium sulfate. After distilling out the solvents under reduced pressure, residues were separated and purified with silicagel chromatography (hexane/ethyl acetate=3/1) to obtain 45 mg of the above compound as a white solid.

ESI-MS Found: m/z 306.1 [M+H]$^+$.

2) Manufacture of 1-(2-fluoropyridine-3-yl)-4-(2-(4-methylpiperazine-1-yl)-quinoline-6-yl)-5-methyl-[1,2,3]triazole The above compound was obtained as a white solid by performing coupling reaction in the same manner as Example 20 with the use of the compound obtained in the above 1) and the alkyl tin compound 1-(2-fluoropyridine-3-yl)-5-methyl-4-tributylstanyl-1H-[1,2,3]triazole, similar as Reference Example 1.

$^1$HNMR (400 MHz, CDCl$_3$), δ: 2.38 (3H, s), 2.52 (3H, d, J=1.6 Hz), 2.58 (4H, t, J=5.2 Hz), 3.82 (4H, t, J=4.8 Hz), 7.04 (1H, d, J=8.8 Hz), 7.49 (1H, dd, J=4.8, 7.6 Hz), 7.81 (1H, d, J=8.4 Hz), 7.94-8.00 (2H, m), 8.02 (1H, d, J=1.6 Hz), 8.09 (1H, t, J=8.2 Hz), 8.45 (1H, d, J=4.8 Hz), ESI-MS Found: m/z 404.2 [M+H]$^+$.

Example 41

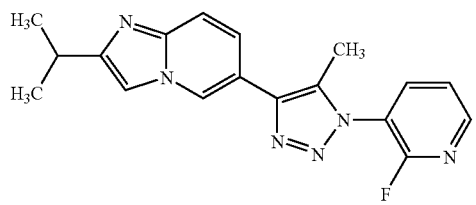

4-(2-isopropyl-imidazo[1,2-a]pyridine-6-yl)-1-(2-fluoropyridine-3-yl)-5-methyl-1H-[1,2,3]triazole

1) Manufacture of 6-bromo-2-isopropyl-imidazo[1,2-a]pyridine 20 ml solution of anhydrous methanol with 2.24 mg of 3-methyl-2-butanone was cooled down to −15° C., and 866 μl of bromine was dropped thereto. After stirring the mixture for 5 min at −15° C., and 1 hour at room temperature, 20 ml of water was further added and stirred 2 more hours. After adding 2.6 g of potassium carbonate, the products were extracted with diethylether, dried with anhydrous sodium sulfate, and the solvents were distilled outunder reduced pressure. The obtained residues were dissolved in 80 ml of ethanol, 2.94 g of 2-amino-5-bromopyridine was added and the resultant was stirred all night by heating under reflux. After cooling down to room temperature, the solvents were distilled outunder reduced pressure, and ethyl acetate followed by saturated sodium hydrogen carbonate aqueous solution were added. After drying organic layer with anhydrous sodium sulfate, the solvents were distilled outunder reduced pressure. The obtained residues were purified by silicagel column chromatography (hexane:ethyl acetate=75:25) to obtain 1.46 g of the above compound as a white solid.

$^1$HNMR (300 MHz, CDCl$_3$), δ: 1.35 (6H, d, J=6.9 Hz), 3.09 (1H, sept, J=6.9 Hz), 7.16 (1H, dd, J=1.9, 9.6 Hz), 7.30 (1H, s), 7.44 (1H, d, J=9.6 Hz), 8.19 (1H, d, J=1.9 Hz), ESI-MS Found: m/z 239.1 [M+H]$^+$.

2) Manufacture of 4-(2-isopropyl-imidazo[1,2-a]pyridine-6-yl)-1-(2-fluoropyridine-3-yl)-5-methyl-1H-[1,2,3]triazole The above compound as obtained in the same manner as Example 1 with the use of halide obtained above, ant the tin reagent 1-(2-fluoropyridine-3-yl)-5-methyl-4-tributylstanyl-1H-[1,2,3]triazole obtained in Reference Example 1.

$^1$HNMR (300 MHz, CDCl$_3$), δ: 1.40 (6H, d, J=6.8 Hz), 2.47 (3H, d, J=2.2 Hz), 3.15 (1H, sept, J=6.8 Hz), 7.43 (1H, t, =0.7 Hz), 7.48-7.52 (2H, m), 7.66 (1H, dt, J=9.3, 0.7 Hz), 8.06-8.11 (1H, m), 8.45-8.47 (1H, m), 8.54 (1H, dd, J=1.0, 1.7 Hz), ESI-MS Found: m/z 337.1 [+H]$^+$.

Example 42

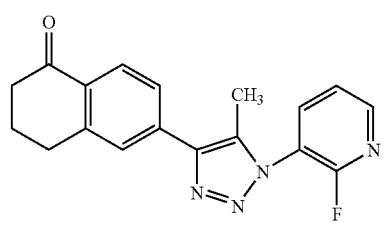

1-(2-fluoropyridine-3-yl)-4-(5-oxo-5,6,7,8-tetrahydro-naphthalene-2-yl)-5-methyl-1H-[1,2,3]triazole The above compound was obtained by performing the reaction in the same manner as Example 5, except using trifluoromethansulfonate 5-oxo-5,6,7,8-tetrahydro-naphthalene-2-ylester instead of 6-bromoquinoline, which was used in Example 5.

¹HNMR (400 MHz, CDCl₃), δ: 2.16-2.23 (2H, m), 2.50 (3H, d, J=2.0 Hz), 2.69-2.72 (2H, m), 3.05-3.08 (2H, m), 7.48-7.51 (1H, d, J=8.4 Hz), 7.80 (1H, m), 8.06-8.14 (1H, m), 8.15 (1H, d, J=8.0 Hz), 8.45-8.47 (1H, m), ESI-MS Found: m/z 323.2[M+H]⁺.

Example 43

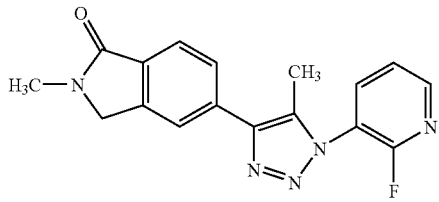

1-(2-fluoropyridine-3-yl)-5-methyl-4-(2-methyl-1-oxo-isoindoline-5-yl)-1H-[1,2,3triazole

1) Manufacture of 5-bromo-2-methyl-1-oxo-isoindoline

The above compound was obtained by performing the reaction in the same manner as Example 36-1, except using methylamine instead of isopropylamine which was used in Example 36-1.

2) Manufacture of 1-(2-fluoropyridine-3-yl)-5-methyl-4-(2-methyl-1-oxo-isoindolin-5-yl)-1H-[1,2,3]triazole The above compound was obtained by performing the reaction in the same manner as Example 36-2, except using 5-bromo-2-methyl-1-oxo-isoindoline, obtained in the above 1), instead of 5-bromo-2-isopropyl-1-oxo-isoindoline, which was used in Example 36-2.

¹HNMR (400 MHz, CDCl₃), δ: 2.51 (3H, d, J=2.0 Hz), 3.24 (3H, s), 4.47 (2H, s), 7.49-7.52 (1H, m), 7.81 (1H, d, J=8.0 Hz), 7.95 (1H, d, J=8.4 Hz), 7.97 (1H, s), 8.07-8.11 (1H, m), 8.46-8.47 (1H, m), ESI-MS Found: m/z 324.2[M+H]⁺.

Example 44

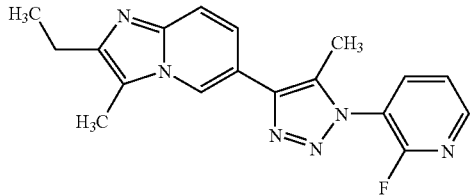

4-(2-ethyl-3-methyl-imidazo[1,2a]-pyridine-6-yl)-1-(2-fluoropyridine-3-yl)-5-methyl-1H-[1,2,3]triazole

1) Manufacture of N-(5-iodo-1H-pyridine-2-ylidene)-toluene-4-sulfonamide

Pyridine solution of 125 ml with 25 g of 5-iodo-2-aminopyridine, 23.9 g of paratoluenesulfonylchloride was stirred at 100° C. After cooling down to room temperature, 250 ml of water was added and stirred at room temperature for 3 hours. The deposits were filtered, dried under reduced pressure to obtain 44.1 g of the above compound.

2) Manufacture of 2-[2-(toluene-4-sulfonylimino-2H-pyridine-1-yl)-pentane-3-one The compound obtained in the above 1) (25.6 g) and 13.56 g of 2-bromo-pentane-3-one were dissolved in 260 ml of tetreahydrofuran, and after cooling down to 0° C., 35.8 ml of diisopropylamine was dropped. After stirring all night at room temperature, saturated sodium hydrogen carbonate solution was added, the reaction was stopped, and the products were extracted with ethyl acetate. Organic layer was dried with anhydrous sodium sulfate, and the solvents were distilled outunder reduced pressure. The obtained residues were purified by silicagel column chromatography (hexane: ethyl acetate=50:50) to obtain 22.4 g of the intended compound as yellow amorphous.

3) Manufacture of 6-iodo-2-ethyl3-methyl-imidazo[1.2-a]pyridine

The compound obtained in the above 2)(22.4 g) was dissolved in 220 ml of chloroform, cooled down to 0° C., and 17.3 ml of trifluoroacetic anhydride was dropped thereto. After stirring the mixture all night at room temperature, the solvents were distilled outunder reduced pressure. After adding saturated sodium hydrogen carbonate aqueous solution, the obtained residues were extracted with chloroform. After drying organic layer with anhydrous sodium sulfate, the solvents were distilled outunder reduced pressure. The residues were washed with diisopropylether, to obtain 11.4 g of the above compound as a pale yellow solid.

¹HNMR (400 MHz, CDCl₃), δ: 1.32 (3H, t, J=7.6 Hz), 2.39 (3H, s), 2.76 (2H, q, J=7.6 Hz), 7.26 (1H, dd, J=1.6, 9.4 Hz), 7.34 (1H, dd, J=8, 9.4 Hz), 8.04 (1H, dd, J=0.8, 1.6 Hz).

4) Manufacture of 4-(2-ethyl-3-methyl-imidazo[1,2-a]pyridine-6-yl)-1-(2-fluoropyridine-3-yl)-5-methyl-1H-[1,2,3]triazole The above compound was obtained in the same manner as Example 1, with the use of halide obtained in the above 3), and 1-(2-fluoropyridine-3-yl)-5-methyl-4-tributylstanyl-1H-[1,2,3]triazole obtained in Reference Example 1.

¹HNMR (300 MHz, CDCl₃), δ: 1.37 (3H, t, J=7.6 Hz), 1.59 (3H, s), 2.49 (3H, s), 2.82 (2H, q, J=7.6 Hz), 7.40-7.52 (2H, m), 7.66 (1H, d, J=9.2 Hz), 8.02-8.11 (1H, m), 8.34 (1H, s), 8.42-8.50 (1H, m), ESI-MS Found: m/z 337.2 [M+H]⁺.

Example 45

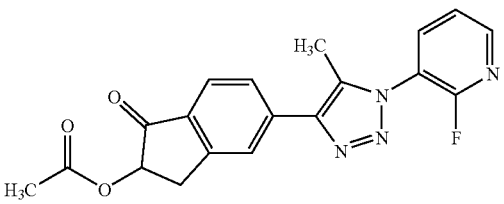

1-(2-fluoropyridine-3-yl)-4-(1-oxo-2-methylcarbo-nyloxy-indane-5-yl)-5-methyl-1H-[1,2,3]triazole

1) Manufacture of 5-bromo-1-methylcarbonyloxy-1-indanone

[Hydroxy(p-nitrobenzenesulfonyloxy)iodo]benzene (465 mg) was added to 30 ml solution of acetonitrile with 200 mg of 5-bromo-1-indanone at room temperature, and was refluxed for 4 hours under heating. The reaction solution was cooled down to room temperature, and the solvents were distilled out under reduced pressure. The obtained residues were dissolved in 40 ml of acetic acid, 340 mg of silver carbonate was added at room temperature, and refluxed for 12 hours under heating. The reaction solution was cooled down to room temperature, the solvents were distilled out under reduced pressure, and dissolved in chloroform. Organic layer was washed with water and saline solution, dried with anhydrous sodium sulfate. The residues obtained by distilling out the solvents under reduced pressure, were purified by silicagel column chromatography (hexane:ethyl acetate=90:10) to obtain 200 mg of the above compound as a white solid.

$^1$HNMR (300 MHz, CDCl$_3$), δ: 2.18 (3H, s), 3.03 (1H, dd, J=4.5, 17.1 Hz), 3.64 (1H, dd, J=7.5, 17.1 Hz), 5.39 (1H, dd, J=4.5 Hz), 7.5 Hz), 7.55-7.69 (3H, m).

2) Manufacture of 1-(2-fluoropyridine-3-yl)-4-(1-oxo-2-methylcarbonyloxy-indane-5-yl)-5-methyl-1H-1,2,3]triazole The above compound was obtained according to the method of Example 1, with the use of the compound obtained in the above 1), and the compound 1-(2-fluoropyridine-3-yl)-5-methyl-4-tributylstanyl-1H-[1,2,3]triazole of Reference Example 1.

$^1$HNMR (300 MHz, CDCl$_3$), δ: 2.21 (3H, s), 2.52 (3H, d, J=2.1 Hz), 3.13 (1H, dd, J=5.1, 17.1 Hz), 3.75 (1H, dd, J=7.8, 17.1 Hz), 5.49 (1H, dd, J=5.1, 7.8 Hz), 7.48-7.54 (1H, m), 7.85 (1H, d, J=8.1 Hz), 7.92 (1H, d, J=8.1 Hz), 7.96 (1H, s), 8.05-8.12 (1H, m), 8.45-8.49 (1H, m), ESI-MS Found: m/z 367.1 [M+H]$^+$.

Example 46

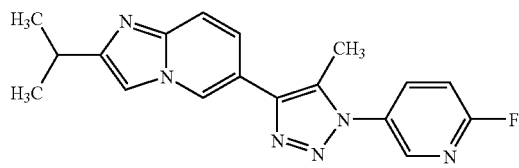

1-(2-fluoropyridine-5-yl)-4-(2-isopropyl-imidazo[1,2-a]pyridine-6-yl)-5-methyl-1H-[1,2,]triazole The above compound was obtained in the same manner as Example 1, with the use of halide obtained in Example 41, and the tin reagent 1-(2-fluoropyridine-5-yl)-5-methyl-4-tributylstanyl-1H-[1,2,3]triazole, obtained in Reference Example 3.

$^1$HNMR (300 MHz, CDCl$_3$), δ: 1.40 (6H, d, J=6.9 Hz), 2.53 (3H, s), 3.15 (1H, sept, J=6.9 Hz), 7.19-7.29 (1H, m), 7.40-7.50 (2H, m), 7.67 (1H, d, J=9.6 Hz), 7.99-8.09 (1H, m), 8.45 (1H, s), 8.53 (1H, s), ESI-MS Found: m/z 337.0 [M+H]$^+$.

Example 47

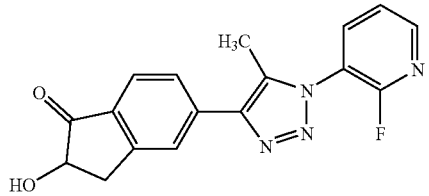

1-(2-fluoropyridine-3-yl)-4-(1-oxo-4-hydroxy-indane-5-yl)-5-methyl-1H-[1,2,3]triazole Three drops of 2 M sodium hydroxide aqueous solution was added at room temperature to 1 ml solution of tetrahydrofuran with 6 mg of 1-(2-fluoropyridine-3-yl)-4-(1-oxo-2-methylcarbonyloxy-indane-5-yl)-5-methyl-1H-[1,2,3]triazole, obtained in Example 45. After stirring at room temperature for 1 hour, the resultant was diluted with chloroform, washed with water and saturated saline solution, and dried with anhydrous sodium sulfate. The solvents were distilled out under reduced pressure, and the obtained residues were purified by silicagel column chromatography (hexane:ethyl acetate=80:20) to obtain 1.3 mg of the above compound as a white solid.

$^1$HNMR (300 MHz, CDCl$_3$), δ: 2.52 (3H, d, J=2.1 Hz), 2.89 (1H, brs), 3.10 (1H, dd, J=5.1, 16.5 Hz), 3.66 (1H, dd, J=7.5, 16.5 Hz), 4.61 (1H, dd, J=5.1, 7.5 Hz), 7.49-7.53 (1H, m), 7.86 (1H, d, J=7.8 Hz), 7.90 (1H, d, J=7.8 Hz), 7.96 (1H, s), 8.06-8.13 (1H, m), 8.47-8.50 (1H, m), ESI-MS Found: m/z 325.2 [M+H]$^+$.

Example 48

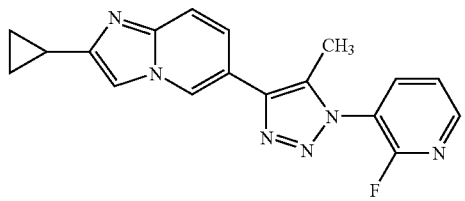

4-(2-cyclopropyl-imidazo[1,2-a]pyridine-6-yl)-1-(2-fluoropyridine-3-yl)-5-methyl-1H-[1,2,3]triazole

1) Manufacture of 6-bromo-2-cyclopropyl-imidazo[1,2-a]pyridine 20 ml of anhydrous methanol solution with 2.24 g of cyclopropylmethylketone was cooled down to −15° C., and 866 μl of bromide was dropped thereto. The mixture was stirred 5 min at 0° C., then 1 hour at room temperature, and 20 ml of water was added and stirred for further 2 hours. Potassium carbonate (2.6 g) was added and the products were extracted with diethylether, dried with anhydrous sodium sulfate, and the solvents were distilled out under pressure. The obtained residues were dissolved in 80 ml of ethanol, 2-amino-5-bromopyridine 2.94 g was added and the resultant was stirred all night by heating under reflux. After cooling down to room temperature, the solvents were distilled out under reduced pressure, and ethyl acetate followed by saturated sodium hydrogen carbonate aqueous solution were added. Organic layer was dried with anhydrous sodium sulfate, and the solvents were distilled out under reduced pressure. The obtained residues were purified by silicagel column chromatography (hexane:ethyl acetate=80:20) to obtain 1.77 g of the above compound as a white solid.

$^1$HNMR (300 MHz, CDCl$_3$), δ: 0.82-1.08 (4H, m), 1.93-2.08 (1H, m), 7.16 (1H, d, J=9.6 Hz), 7.33 (1H, s), 7.38 (1H, d, J=9.6 Hz), 8.16 (1H, s), ESI-MS Found: m/z 237.1 [M+H]$^+$.

2) Manufacture of 4-(2-cyclopropyl-imidazo[1,2-a]pyridine-6-yl)-1-(2-fluoropyridine-3-yl)-5-methyl-1H-[1,2,3]triazole The above compound was obtained in the same manner as Example 1, with the use of halide obtained in the above 1) and the tin reagent 1-(2-fluoropyridine-3-yl)-5-methyl-4-tributylstanyl-1H-[1,2,3]triazole, obtained in Reference Example 1.

$^1$HNMR (400 MHz, CDCl$_3$), δ: 0.98-1.03 (4H, m), 2.00-2.18 (1H, m), 2.47 (3H, d, J=1.2 Hz), 7.45-7.52 (3H, m), 7.60 (1H, d, J=9.3 Hz), 8.06-8.10 (1H, m), 8.46 (1H, td, J=1.7, 4.8 Hz), 8.5 1(1H, dd, J=1.0, 1.7 Hz), ESI-MS Found: m/z 335.2 [M+H]$^+$.

Example 49

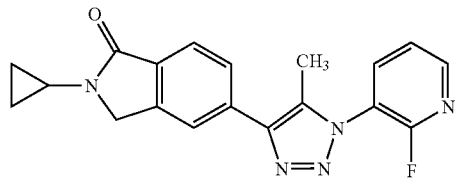

4-(2-clycloropropyl-1-oxo-isoindoline-5-yl)-1-(2-fluoropyridine-3-yl)-5-methyl-1H-[1,2,3]triazole 1) Manufacture of 5-bromo-2-cyclopropyl-1-oxo-isoindoline Under nitrogen atmosphere, 700 mg of 4-bromo-2-bromomethyl benzoate was dissolved in 20 ml of toluene, 0.40 ml of cyclopropyl amine and 1.0 ml of triethylamine were added and the mixture was stirred all night by heating under reflux. The reaction solution was cooled down to room temperature, the solvents were distilled out under reduced pressure, and the residues were separated and purified by silicagel column chromatography (ethyl acetate:hexane=1/2) to obtain 336 mg of the above compound as a white solid.

$^1$HNMR (400 MHz, CDCl$_3$), δ: 0.68-0.93 (4H, m), 2.88-2.93 (1H, m), 4.29(2H, s), 7.56-7.59(2H, m), 7.68 (1H, d, J=8.0 Hz), ESI-MS Found: m/z 252.1 [M+H]$^+$.

2) Manufacture of 4-(2-cyclopropyl-1-oxo-isoindoline-5-yl)-1-(2-fluoropyridine-3-yl)-5-methyl-1H-[1,2,3]triazole Under nitrogen atmosphere, 300 mg of 5-bromo-2-cyclopropyl-1-oxo-isoindoline and 185 mg of 1-(2-fluoropyridine-3-yl)-4-tri-n-butyltin-5-methyl-1H-[1,2,3]triazole were dissolved in 10 ml of toluene, 45 g of tetrakistriphenylphosphinepalladium was added, and the mixture was stirred all night by heating under reflux. The reaction solution was cooled down to room temperature, and insoluble matters were removed by celite filtration. The solvents were distilled out under reduced pressure, and the residues were separated and purified by silicagel column chromatography (ethyl acetate/hexane=3/1, 5/1) to obtain 87.7 mg of the above compounds as a white solid.

$^1$HNMR (400 MHz, CDCl$_3$), δ: 0.88-0.98 (4H, m), 2.50 (3H, d, J=2.4 Hz), 2.95-3.00 (1H, m), 4.41 (2H, s), 7.48-7.52 (1H, m), 7.93 (1H, m), 7.94-7.95 (2H, m), 8.06-8.10 (1H, m), 8.45-8.47 (1H, m), ESI-MS Found: m/z 350.2 [M+H]$^+$.

Example 50

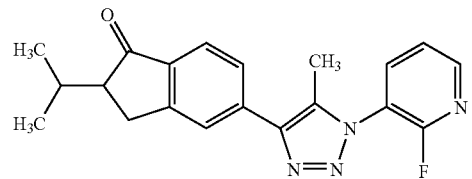

4-(2-isopropyl-1-oxoindane-5-yl)-1-(2-fluoropyridine-3-yl)-5-methyl-1H-[1,2,3]triazole 1) Manufacture of 5-bromo-2-isopropyl-1-oxoindane Under nitrogen atmosphere, 100 mg of 5-bromo-1-oxoindene was dissolved in 2 ml of tetrahydrofuran, and cooled down to −78° C. 0.4 ml of hexamethylphosphoramide, 0.3 ml of 1.57 M n-butyllitium hexane solution, and 1.0 ml of isopropyl iodide were added, and the mixture was stirred at −78° C. for 2 hours. Water was added to the reaction solution, and the mixture was extracted with ethyl acetate. Ethyl acetate layer was washed with saturated saline solution, and dried with anhydrous sodium sulfate. The solvents were distilled out under reduced pressure, and the residues were separated and purified by preparative thin-layer chromatography (ethyl acetate/hexane=1/2) to obtain 26 mg of the above compound as a white solid.

2) Manufacture of 4-(2-isopropyl-1-oxoindane-5-yl)-1-(2-fluoropyridine-3-yl)-5-methyl-1H-[1,2,3]triazole The above compound was obtained by performing the reaction by the same method as Example 20, except using 5-bromo-2-isopropyl-1-oxoindane obtained in the above 1), instead of 5-bromo-2,2-dimethyl-1-oxoindane which was used in Example 20.

$^1$HNMR (400 MHz, CDCl$_3$), δ: 0.83 (3H, d, J=6.8 Hz), 1.08 (3H, d, J=7.2 Hz), 2.43-2.47 (1H, m), 2.51 (3H, d, J=2.0 Hz), 2.70-2.76 (1H, m), 2.99-3.04 (1H, m), 3.20-3.26 (1H, m), 7.49-7.52 (1H, m), 7.77 (1H, d, J=8.0 Hz), 7.86 (1H, d,

J=8.0 Hz), 7.97 (1H, s), 8.07-8.11 (1H, m), 8.46-8.47 (1H, m), ESI-MS Found: m/z 351.2 [M+H]⁺.

Example 51

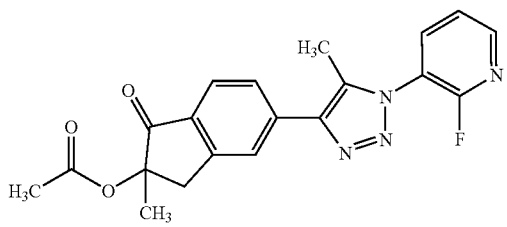

1-(2-fluoropyridine-3-yl)-4-(2-methyl-2-methylcarbonyloxy-1-oxoindane-5-yl)-5-methyl-1H-[1,2,3]triazole At room temperature, 3 mg of 60% of sodium hydride was added to 1 ml solution of dimethylformamide with 10 mg of 1-(2-fluoropyridine-3-yl)-4-(1-oxo-2-methylcarbonyloxy-indane-5-yl)-5-methyl-1H-[1,2,3]triazole, obtained in Example 45. After stirring 30 min at room temperature, 5 drops of methyl iodide was added and the mixture was further stirred for 1 hour at room temperature.

The resultant was diluted with ethyl acetate, washed with water and saturated saline solution, and dried with anhydrous sodium sulfate. The residues obtained by distilling out the solvents under reduced pressure were purified by silicagel column chromatography (hexane:ethyl acetate=80:20) to obtain 3.5 g of the above compound as a white solid.

¹HNMR (300 MHz, CDCl₃), δ: 1.52 (3H, s), 2.12 (3H, s), 2.51 (3H, d, J=2.1 Hz), 3.24 (1H, d, J=16.8 Hz), 3.59 (1H, d, J=16.8 Hz), 7.47-7.55 (1H, m), 7.81(1H, d, J=8.1 Hz), 7.91 (1H, s), 7.93 (1H, d, J=8.1 Hz), 8.06-8.12 (1H, m), 8.45-8.49 (1H, m), ESI-MS Found: m/z 381.1 [M+H]⁺.

Example 52

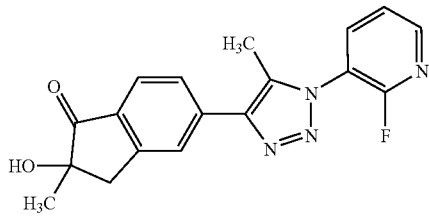

1-(2-fluoropyridine-3-yl)-4-(2-hydroxy-2-methyl-1-oxoindane-5-yl)-5-methyl-1H-[1,2,3]triazole At room temperature, 100 µl of 2M sodium hydride aqueous solution was added to 1 ml solution of tetrahydrofuran with 30 mg of 1-(2-fluoropyridine-3-yl)-4-(2-methyl-2-methylcarbonyloxy-1-oxoindane-5-yl)-5-methyl-1H-[1,2,3]triazole obtained in Example 51. The mixture was stirred at room temperature for 1 hour, diluted with ethyl acetate, washed with water and saturated saline solution, and dried with anhydrous sodium sulfate. The residues obtained by distilling out the solvents under reduced pressure were purified by silicagel column chromatography (hexane:ethyl acetate=80:20) to obtain 10 mg of the above compound as a white solid.

¹HNMR (300 MHz, CDCl₃), δ: 1.49 (3H, s), 2.52 (3H, d, J=1.8 Hz), 2.70(1H, brs), 3.32 (3H, s), 7.47-7.59 (1H, m), 7.83 (1H, d, J=8.1 Hz), 7.90 (1H, d, J=8.1 Hz), 7.93 (1H, s), 8.05-8.12 (1H, s), 8.42-8.49 (1H, m), ESI-MS Found: m/z 351.2 [M+H]⁺.

Example 53

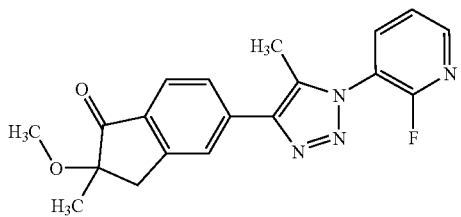

1-(2-fluoropyridine-3-yl)-4-(2-methoxy-2-methyl-1-oxoindane-5-yl)-5-methyl-1H-[1,2,3]triazole 1) Manufacture of 5-bromo-2-methylcarbonyloxy-1-indanone At room temperature, 2.1 g of [hydroxyl(p-nitrobenzensulfonyloxy)iodo]benzene was added to 150 ml solution of acetonitrile with 1.0 g of 5-bromo-1-indanone, and the mixture was heated under reflux for 3 hours. The reaction solution was cool down to room temperature, and then the solvents were distilled outunder reduced pressure. The obtained residues were dissolved in 200 ml of acetic acid, 1.7 g of silver carbonate was added at room temperature, and heated under reflux for 12 hours. The reaction solution was cooled down to room temperature, the solvents were distilled outunder reduced pressure, dissolved in chloroform, washed with water and saturated saline solution, and dried with anhydrous sodium sulfate. The residues obtained by distilling out the solvents under reduced pressure were purified by silicagel column chromatography (hexane:ethyl acetate=90:10) to obtain 910 mg of the above compound as a white solid.

¹HNMR (300 MHz, CDCl₃), δ: 2.18 (3H, s), 3.03 (1H, dd, J=4.5, 17.1 Hz), 3.64 (1H, dd, J=7.5, 17.1 Hz), 5.39 (1H, dd, J=4.5 Hz), 7.5 Hz), 7.55-7.69 (3H, m).

2) Manufacture of 5-bromo-2-methyl-2-methoxy-1-indanone 640 mg of 60% of sodium hydroxide was added at room temperature to 20 ml solution of dimethylformamide with 850 mg of 5-bromo-2-methylcarbonyloxy-1-indanone obtained in the above 1). After stirring for 10 min at room temperature, 3.5 ml of methyl iodide was added and the mixture was stirred for 1 hour at room temperature. Then, 2 ml of dimethylformamide containing 5% water was added and further stirred for 1 hour at room temperature.

The reaction solution was diluted with ethyl acetate, washed with water and saturated saline solution, dried with anhydrous sodium sulfate. The residues obtained by distilling out the solvents under reduced pressure were purified by silicagel column chromatography (hexane:ethyl acetate=90:10) to obtain 400 mg of the above compound as a white solid.

¹HNMR (300 MHz, CDCl₃), δ: 1.44 (3H, s), 3.05 (1H, d, J=17.5 Hz), 3.28 (3H, s), 3.33 (1H, d, J=17.5 Hz), 7.52-7.66 (3H, m).

3) Manufacture of 1-(2-fluoropyridine-3-yl)-4-(2-methoxy-2-methyl-1-oxoindene-5-yl)-5-methyl-1H-[1,2,3]triazole The above compound was obtained according to the method of Example 1, with the use of the compound obtained in the above 2) and the compound 1-(2-fluoropyridine-3-yl)-5-methyl-4-tributylstanyl-1H-[1,2,3]triazole of Reference Example 1.

¹HNMR (300 MHz, CDCl₃), δ: 1.48 (3H, s), 2.51 (3H, d, J=2.1 Hz), 3.15 (1H, d, J=17.4 Hz), 3.33 (3H, s), 3.44 (1H, d, J=17.4 Hz), 7.45-7.53 (1H, m), 7.81 (1H, d, J=8.1 Hz), 7.79 (1H, d, J=8.1 Hz), 8.05-8.12 (1H, m), 8.44-8.50 (1H, m), ESI-MS Found: m/z 381.1 [M+H]⁺.

Example 54

4-((2S*)-methoxy-1-(2R*)-methyl-1-oxoindane-5-yl)-1-(2-fluoropyridine-3-yl)-5-methyl-1H-[1,2,3]triazole; and 4-((2R*)-methoxy-(2S*)-methyl-1-oxoindane-5-yl)-1-(2-fluoropyridine-3-yl)-5-methyl-1H-[1,2,3]triazole 7.0 mg of the racemic compound, 1-(2-fluoropyridine-3-yl)-4-(2-methoxy-2-methyl-1-oxoindane-5-yl)-5-methyl-1H-[1,2,3]triazole, obtained in Example 53, was optically resolved by optically active column (Daicel, CHIRALPAK AD-H column; hexane/etanol=400/600). From the first fraction, 2.5 mg of the compound named (2S*,2R*) of the above compound for convenience, and from the latter fraction, 2.5 mg of the compound named (2R*,2S*) of the above compound for convenience were obtained, both as white solid, respectively.

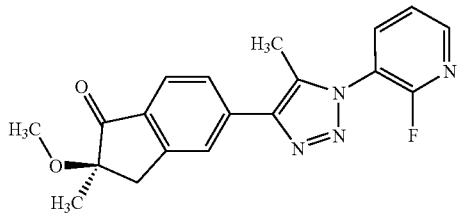

4-((2S*)-methoxy-(2R*)-methyl-1-oxoindane-5-yl)-1-(2-fluoropyridine-3-yl)-5-methyl-1H-[1,2,3]triazole ¹HNMR (300 MHz, CDCl₃), 1.48 (3H, s), 2.51 (3H, d, J=2.1 Hz), 3.15 (1H, d, J=17.4 Hz), 3.33 (3H, s), 3.44 (1H, d, J=17.4 Hz), 7.45-7.53 (1H, m), 7.81 (1H, d, J=8.1 Hz), 7.79 (1H, d, J=8.1 Hz), 8.05-8.12 (1H, m), 8.44-8.50 (1H, m), ESI-MS Found: m/z 381.1 [M+H]⁺.

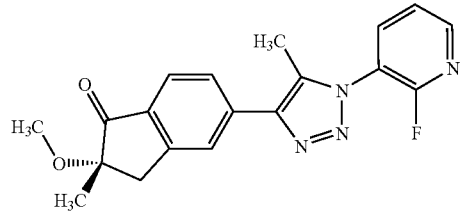

4-((2R*)-methoxy-(2S*)-methyl-1-oxoindane-5-yl)-1-(2-fluoropyridine-3-yl)-5-methyl-1H-[1,2,3]triazole 1.48 (3H, s), 2.51 (3H, d, J=2.1 Hz), 3.15 (1H, d, J=17.4 Hz), 3.33 (3H, s), 3.44 (1H, d, J=17.4 Hz), 7.45-7.53 (1H, m), 7.81 (1H, d, J=8.1 Hz), 7.79 (1H, d, J=8.1 Hz), 8.05-8.12 (1H, m), 8.44-8.50 (1H, m), ESI-MS Found: m/z 381.1 [M+H]⁺.

Example 55

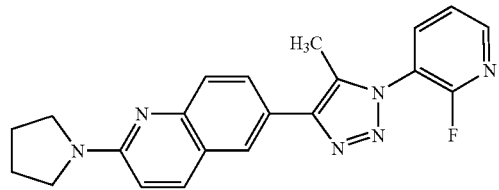

1-(2-fluoropyridine-3-yl)-4-(2-pyrrolidine-1-yl-quinoline-6-yl)-5-methyl-1H-[1,2,3]triazole 1) Manufacture of 2-pyrrolidine-6-bromoquinoline Under nitrogen atmosphere, 100 mg of pyrrolidine was added sequentially to 2 ml solution of dioxane with 40 mg of 2-chloro-6-bromoquinoline at room temperature, and the mixture was stirred at 115° C. for 6 hours. Water was added to the reaction solution, extracted with diethylether. Diethylether layer was washed with saturated saline solution, and dried with anhydrous sodium sulfate. The solvents were distilled outunder reduced pressure, and the residues were separated and purified by silicagel chromatography (hexane/ethyl acetate=3/1) to obtain 35 mg of the above compound as a white solid.

ESI-MS Found: m/z 277.0 [M+H]⁺.

2) Manufacture of 1-(2-fluoropyridine-3-yl)-4-(2-pyrrolidine-1-yl-quinoline-6-yl)-5-methyl-1H-[1,2,3]triazole The above compound was obtained as a white solid by performing coupling reaction in the same manner as Example 20, with the use of the compound obtained in the above 1) and the alkyl tin compound 1-(2-fluoropyridine-3-yl)-5-methyl-4-tributylstanyl-1H-[1,2,3]triazole, similar as Reference Example 1.

¹HNMR (400 MHz, CDCl₃), δ: 2.07 (3H, t, J=6.8 Hz), 2.52 (3H, d, J=2.0 Hz), 3.66 (4H, brs), 6.78 (1H, d, J=8.8 Hz), 7.49 (1H, t, J=6.2 Hz), 7.80 (1H, d, J=8.4 Hz), 7.93 (2H, t, J=10.6

Hz), 8.01 (1H, d, J=2.0 Hz), 8.01 (1H, t, J=8.4, 16.8 Hz), 8.45 (1H, d, J=4.4 Hz), ESI-MS Found: m/z 375.2 [M+H]⁺.

Example 56

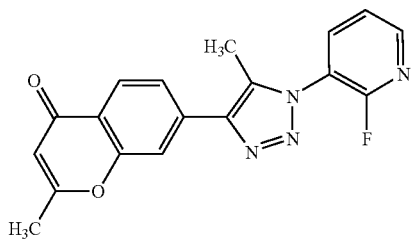

1-(2-fluoropyridine-3-yl)-5-methyl-4-(2-methyl-4-oxo-4-methyl-chromen-7-yl)-1H-[1,2,3]triazole 1) Manufacture of 7-(((trifluoromethyl)sulfonyloxy)-2-methyl-4H-chromen-4-on Under nitrogen atmosphere, 0.2 ml of trifluoromethansulfonic anhydride was added at 0° C. to 3 ml solution of pyridine with 10 mg of 7-hydroxy-2-methyl-4H-chromen-4-one, and the mixture was stirred at room temperature for 2 hours. Water was added to the reaction solution, extracted with ethyl acetate. Ethyl acetate layer was washed with saturated saline solution, and dried with anhydrous sodium sulfate. The solvents were distilled outunder reduced pressure, and the residues were separated and purified by silicagel chromatography (hexane/ethyl acetate=10/1) to obtain 112 mg of the above compound as a white solid.
ESI-MS Found: m/z 309.1 [M+H]⁺.

2) Manufacture of 1-(2-fluoropyridine-3-yl)-5-methyl-4-(2-methyl-4-oxo-4-methyl-chromen-7-yl)-1H-[1,2,3]triazole The above compound was obtained as a white solid by performing coupling reaction in the same manner as Example 20, with the use of the compound obtained in the above 1) and the alkyl tin compound 1-(2-fluoropyridine-3-yl)-5-methyl-4-tributylstanyl-1H-[1,2,3]triazole, similar as Reference Example 1.
¹HNMR (400 MHz, CDCl₃), δ: 2.43 (3H, s), 2.55 (3H, s), 6.21 (1H, s), 7.48-7.56 (1H, m), 7.83 (1H, dd, J=1.2, 8.4 Hz), 7.91 (1H, d, J=1.2 Hz), 8.05-8.15 (1H, m), 8.29 (1H, J=8.0 Hz), 8.48 (1H, J=4.8 Hz), ESI-MS Found: m/z 337.1 [M+H]⁺.

Example 57

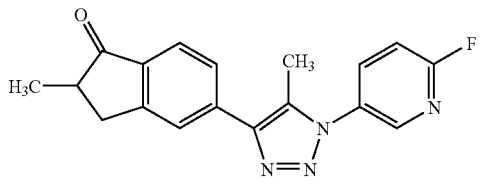

1-(2-fluoropyridine-5-yl)-4-(1-oxo-2-methyl-indane-5-yl)-5-methyl-1H-1,2,3]triazole The above compound was obtained by performing the reaction in the same manner as Example 20, except using 5-bromo-2-methyl-1-oxoindane instead of 5-bromo-2,2-dimethyl-1-oxoindane which was used in Example 20, and the compound 1-(2-fluoropyridine-5-yl)-5-methyl-4-tributylstanyl-1H-[1,2,3]triazole of Reference Example 3, instead of the compound 1-(2-fluoropyridine-3-yl)-5-methyl-4-tributylstanyl-1H-[1,2,3]triazole of Reference Example 1.
¹HNMR (400 MHz, CDCl₃), δ: 1.36 (3H, d, J=6.8 Hz), 2.57 (3H, s), 2.79-2.83 (1H, br), 3.46-3.52 (1H, m), 7.21-7.23 (1H, m), 7.75 (1H, d, J=8.0 Hz), 7.87 (1H, d, J=8.0 Hz), 7.93 (1H, s), 8.02-8.05 (1H, m), 8.45 (1H, s), ESI-MS Found: m/z 323.2 [M+H]⁺.

Example 58

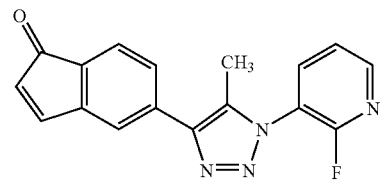

1-(2-fluoropyridine-3-yl)-5-methyl-4-(1-oxo-1H-indene-5-yl)-1H-[1,2,3]triazole

The above compound was obtained by performing the reaction in the same manner as Example 20, except using 5-bromo-1-oxo-1H-indene instead of 5-bromo-2,2-dimethyl-1-oxoindane which was used in Example 20.
¹HNMR (400 MHz, CDCl₃), δ: 2.37 (3H, d, J=1.2 Hz), 3.87 (1H, m), 4.55 (1H, m), 7.44-7.47 (1H, m), 7.58-7.66 (2H, m), 7.81 (1H, s), 7.99-8.03 (1H, m), 8.43-8.44 (1H, m), ESI-MS Found: m/z 613.3 [2M+H]+.

Example 59

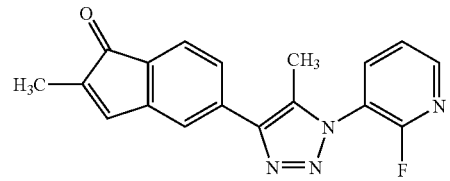

1-(2-fluoropyridine-3-yl)-4-(2-methyl-1-oxo-1H-indene-5-yl)-5-methyl-1H-[1,2,3]triazole The above compound was obtained by performing the reaction in the same manner as Example 20, except using 5-bromo-2-methyl-1-oxo-1H-indene instead of 5-bromo-2,2-dimethyl-1-oxoindane which was used in Example 20.

¹HNMR (400 MHz, CDCl₃), δ: 1.92 (3H, d, J=2.0 Hz), 2.48(3H, d, J=2.4 Hz), 7.21-7.22 (1H, m), 7.48-7.51 (4H, m), 8.05-8.09 (1H, m), 8.45-8.47 (1H, m), ESI-MS Found: m/z 321.1 [M+H]⁺.

Example 60

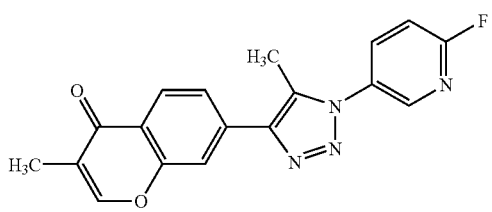

1-(2-fluoropyridine-5-yl)-4-(3-methyl-4-oxo-4H-chromen-7-yl)-5-methyl-1H-[1,2,3]triazole The above compound was obtained as a white solid by performing coupling reaction in the same manner as Example 20, with the use of 7-((trifluoromethyl)sulfonyloxy)-3-methyl-4H-chromen-4-one and the alkyl tin compound 1-(2-fluoropyridine-5-yl)-5-methyl-4-tributylstanyl-1H-[1,2,3] triazole, similar as Reference Example 3.

¹HNMR (400 MHz, CDCl₃), δ: 2.07 (3H, d, J=1.2 Hz), 2.60 (3H, s), 7.22 (1H, dd, J=3.6, 8.8), 7.80 (1H, dd, J=1.6, 8.4 Hz), 7.84 (1H, s), 7.90 (1H, s), 8.00-8.07 (1H, m), 8.35 (1H, d, J=8.4 Hz), 8.44-8.47 (1H, d, m), ESI-MS Found: m/z 337.1 [M+H]⁺.

Example 61

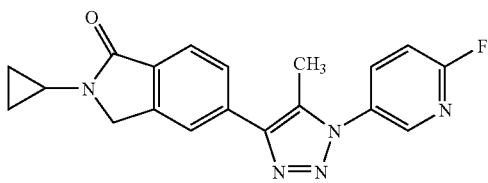

4-(2-cyclopropyl-1-oxo-isoindoline-5-yl)-1-(2-fluoropyridine-5-yl)-5-methyl-1H-[1,2.3]triazole 1) Manufacture of 5-bromo-2-cyclopropyl-1-oxo-isoindoline The above compound was obtained by performing the reaction in the same manner as Example 49-1.

2) Manufacture of 4-(2-cyclopropyl-butyl-1-oxo-isoindoline-5-yl)-1-(2-fluoropyridine-2-yl)-5-methyl-1H-[1,2,3]triazole The above compound was obtained in the same manner as Example 49-2, except using the compound 1-(2-fluoropyridine-5-yl)-4-tributyltin-5-methyl-1H-[1,2,3]triazole of Reference Example 3, instead of the compound 1-(2-fluoropyridine3-yl)--4-tributyltin-5-methyl-1H-[1,2,3]triazole of Reference Example 1, which was used in Example 49-2.

¹HNMR (400 MHz, CDCl₃), δ: 0.88-0.98 (4H, m), 2.55 (3H, s), 2.96-3.00 (1H, m), 4.41 (2H, s), 7.20-7.23 (1H, m), 7.77 (1H, d, J=8.4 Hz), 7.93-7.95 (2H, m), 8.01-8.05 (1H, m), 8.45 (1H, m), ESI-MS Found: m/z 350.0 [M+H]⁺.

Example 62

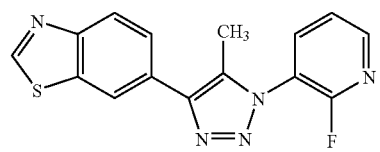

4-(benzothiazole-6-yl)-1-(2-fluoropyridine-3-yl)-5-methyl-1H-[1,2,3]triazole

The above compound was obtained as a colorless solid by performing the reaction in the same manner as Example 1, with the use of 6-bromobenzothiazole and the tin reagent 1-(2-fluoropyridine-3-yl)-5-methyl-4-tributylstanyl-1H-[1,2,3]triazole of Reference Example 1.

¹HNMR (300 MHz, CDCl₃). δ: 2.53 (3H, d, J=2.0 Hz), 7.48-8.48 (6H, m), 9.06 (1H, s), ESI-MS Found: m/z 312.0 [M+H]⁺.

Example 63

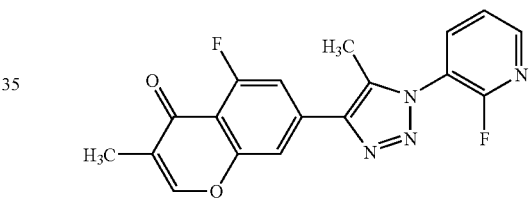

4-(5-fluoro-3-methyl-4-oxo-4H-chromen-7-yl)-1-(2-fluoropyridine-3-yl)-5-emthyl-1H-[1,2,3]triazole 1) Manufacture of 1-(2-fluoro-4,6-dimethoxyphenyl)propane-1-one Under nitrogen atmosphere, 5 ml solution of dichloroethane with 2 g of 3,5-dimethoxy-1-fluorobenzene, and 5 ml solution of dichloroethane with 1.3 mg of propionyl chloride were dropped sequentiallly at −10° C. to 40 ml solution of dichloroethane with 2.4 g of alumimium trichloride and 240 mg of zinc dichloride, and the mixture was stirred at room temperature for 2 hours. 20% hydrochloric acid aqueous solution was added to the reaction solution, extracted with chloroform. Chloroform layer was washed with saturated saline solution, dried with anhydrous sodium sulfate. The solvents were distilled outunder reduced pressure and the residues were separated and purified by silicagel chromatography (hexane/ethyl acetate=5/1), to obtain 1.5 g of the above compound as a white solid.

2) Manufacture of 1-(6-fluoro-2,4-dihydroxyphenyl)propane-1-one

Under nitrogen atmosphere, 2.4 g of aluminium trichloride was added to 20 ml solution of toluene with 1.5 g of the compound obtained in the above 1), and the mixture was stirred at 95° C. for 8 hours. After adding water to the reaction solution, the white solid deposited was filtered to obtain 930 mg of the above compound as a white solid.

ESI-MS Found: m/z 185.0 [M+H]$^+$.

3) Manufacture of 5-fluoro-7-hydroxy-3-methyl-4H-chromen-4-one

Under nitrogen atmosphere, 8.4 ml of dimethylformamide was dropped at 0° C. to 2.2 ml solution of borone trifluoride ethylether complex with 930 mg of the compound obtained in the above 2), and the mixture was stirred at 0° C. for 15 min. A mixture solution of 1.74 g of phosphorous pentachloride and 45 ml of dimethylformamide was dropped to the reaction solution at 0° C., and stirred at room temperature for 2 hours. Hydrogen chloride methanol solution was added to the reaction solution, and stirred at 70° C. for 20 min. Methanol was distilled outunder reduced pressure, water was added and the resultant was extracted with chloroform. Chloroform layer was washed with saturated saline solution, and dried with anhydrous sodium sulfate. The solvents were distilled outunder reduced pressure and the residues were separated and purified by silicagel chromatography (chloroform/methanol=10/1), to obtain 980 mg of the above compound as a white solid.

ESI-MS Found: m/z 195.0 [M+H]$^+$.

4) Manufacture of 5-fluoro-7-((trifluoromethyl)sulfonyloxy)-3-methyl-4H-chromen-4-one Under nitrogen atmosphere, 1.7 ml of trifluoromethylsulfonate anhydride was added at 0° C. to 10 ml solution of pyridine of 980 mg of the compound obtained in the above 3), and the mixture was stirred at room temperature for 2 hours. Water was added to the reaction solution, extracted with chloroform. Chloroform layer was washed with saturated saline solution, and dried with anhydrous sodium sulfate. The solvents were distilled outunder reduced pressure, and the residues were separated and purified by preparative thin-layer chromatography (hexane/ethyl acetate=3/1) to obtain 760 mg of the above compound as a white solid.

ESI-MS Found: m/z 327.0 [M+H]$^+$.

5) Manufacture of 4-(5-fluoro-3-methyl-4-oxo-4H-chromen-7-yl)-1-(2-fluoropyridine-3-yl)-5-methyl-1H-[1,2,3]triazole The above compound was obtained as a white solid by performing coupling reaction in the same manner as Example 20, with the use of the compound obtained in the above 4) and the alkyl tin compound 1-(2-fluoropyridine-3-yl)-5-methyl-4-tributylstanyl-1H-[1,2,3]triazole, similar as Reference Example 1.

$^1$HNMR (400 MHz, CDCl$_3$), δ: 2.03 (3H, d, J=0.8 Hz), 2.54 (3H, d, J=2.0 Hz), 7.49-7.54 (2H, m), 7.72 (1H, s), 7.76 (1H, d, J=1.2 Hz), 8.09 (1H, t, J=8.2 Hz), 8.49 (1H, d, J=4.8 Hz), ESI-MS Found: m/z 355.0 [M+H]$^+$.

Example 64

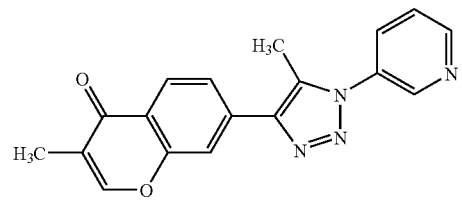

5-methyl-4-(3-methyl-4-oxo-4H-chromen-7-yl)-1-pyridine-3-yl)-1H-[1,2,3]triazole

The above compound was obtained as a white solid by performing coupling reaction in the same manner as Example 20, with the use of 7-((trifluoromethyl)sulfonyloxy-3-methyl-4H-chromen-4-one and the alkyl tin compound 1-(3-pyridyl)-5-methyl-4-tributylstanyl-1H-[1,2,3]triazole, similar as Reference Example 6.

$^1$HNMR (400 MHz, CDCl$_3$), δ: 2.08 (3H, d, J=1.2 Hz), 2.61 (3H, s), 5.59 (1H, dd, J=5.0, 8.2 Hz), 7.82 (1H, dd, J=1.6, 8.4 Hz), 7.85 (1H, d, J=1.2 Hz), 7.90-7.96 (2H, m), 8.35 (1H, d, J=8.4 Hz), 8.81-8.86 (2H, m), ESI-MS Found: m/z 319.1 [M+H]$^+$.

Example 65

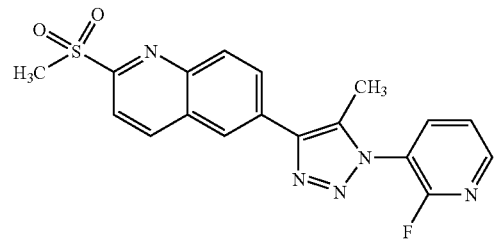

1-(2-fluoropyridine-3-yl)-4-(2-methanesulfonyl-quinoline-6-yl)-5-methyl-1H-[1,2,3]triazole The above compound was obtained by the same method as Example 1 with the use of 6-bromo-2-methanesulfonyl-quinoline and the tin reagent 1-(2-fluoropyridine-3-yl)-5-methyl-4-tributylstanyl-1H-[1,2,3]triazole, obtained in Reference Example 1.

¹HNMR (300 MHz, CDCl₃), δ: 2.60 (3H, d, J=2.0 Hz), 3.40-3.55 (3H, m), 7.49-7.57 (1H, m), 8.05-8.56 (7H, m), ESI-MS Found: m/z 384.0 [M+H]⁺.

Example 66

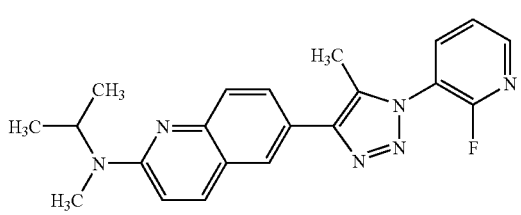

4-[(2-isopropyl-methyl-amino)-quinoline-6-yl]-1-(2-fluoropyridine-3-yl)-5-methyl-1H-[1,2,3]triazole 1) Manufacture of (6-bromo-2-quinolyl)-methyl(methylethyl)amine Under nitrogen atmosphere, 180 mg of N-methylisopropylamine, and 200 g of potassium carbonate were added at room temperature sequentially to 5 ml solution of dimethylsulfonamide with 63 g of 2-chloro-6-bromoquinoline, and the mixture was stirred at 110° C. for 4 hours. Water was added to the reaction solution, extracted with ethyl acetate. Ethyl acetate layer was washed with saturated saline solution, and dried with anhydrous sodium sulfate. The solvents were distilled outunder reduced pressure, and the residues were separated and purified by silicagel chromatography (hexane/ethyl acetate=3/1) to obtain 18 mg of the above compound as a white solid.

¹HNMR (400 MHz, CDCl₃), δ: 1.23 (6H, d, J=6.8 Hz), 2.99 (3H, s), 4.94-5.03 (1H, m), 6.88 (1H, d, J=9.2 Hz), 7.49-7.58 (2H, m), 7.69 (1H, dd, J=0.8, 2.0 Hz), 7.74 (1H, d, J=9.2 Hz), ESI-MS Found: m/z 279.1 [M+H]⁺.

2) Manufacture of 4-[(2-isopropyl-methyl-amino)-quinoline-6-yl]-1-(2-fluoropyridine-3-yl)-5-methyl-1H-[1,2,3]triazole The above compound was obtained as a white solid by performing coupling reaction in the same manner as Example 20, with the use of the compound obtained in the above 1) and the alkyl tin compound 1-(2-fluoropyridine-3-yl)-5-methyl-4-tributylstanyl-1H-[1,2,3]triazole, similar as Reference Example 1.

¹HNMR (400 MHz, CDCl₃), δ: 1.22-1.30 (6H, m), 2.51 (3H, d, J=2.4 Hz), 3.04 (3H, s), 5.00-5.10 (1H, m), 6.94 (1H, d, J=9.2 Hz), 7.45-7.52 (1H, m), 7.77 (1H, d, J=8.8 Hz), 7.94 (2H, t, J=6.6 Hz), 7.99 (1H, brs), 8.05-8.15 (1H, m), 8.45 (1H, dt, J=1.6, 3.2, 4.8 Hz), ESI-MS Found: m/z 377.2 [M+H]⁺.

Example 67

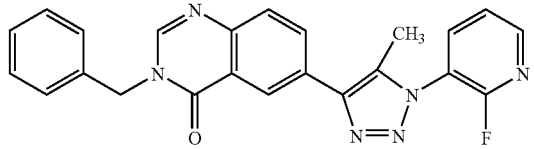

4-(3-benzyl-4-oxo-3,4-dihydroquinazoline-6-yl)-1-(2-fluoropyridine-3-yl)-5-methyl-1H-[1,2,3]triazole Under nitrogen atmosphere, 78.4 mg of 1-(2-fluoropyridine-3-yl)-4-tributylstanyl-1H-[1,2,3]triazole obtained in Reference Example 1, 8.8 mg of tris(benzylideneacetone) dipalladium and 18.7 mg of triphenylarsine were added to 3 ml solution of 102 g of 6-bromo-3-benzyl-4-oxo-3,4-dihydroquinazoline, and the mixture was stirred at 80° C. for 8 hours. Water was added to the reaction solution, extracted with ethyl acetate. Ethyl acetate layer was washed with saturated saline solution, and dried with anhydrous sodium sulfate. The solvents were distilled outunder reduced pressure, and the residues were separated and purified by preparative thin-layer chromatography (chloroform/methanol=19/1) to obtain 6.0 mg of the above compound as a colorless solid.

¹HNMR (300 MHz, CDCl₃), δ: 2.55 (3H, d, J=1.9 Hz), 5.24 (2H, s), 7.33~7.39 (5H, m), 7.50 (1H, dd, J=4.7 and 6.9 Hz), 7.85 (1H, d, J=8.4 Hz), 8.06-8.12 (1H, m), 8.15 (1H, s), 8.38-8.47 (2H, m), 8.59 (1H, d, J=2.2 Hz), ESI-MS Found: m/z 413.1 [M+H]⁺.

Example 68

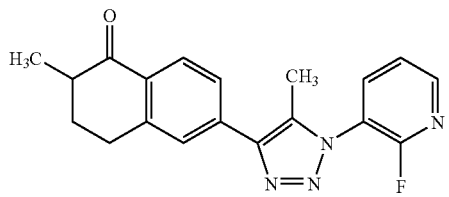

1-(2-fluoropyridine-3-yl)-4-(5-oxo-6-methyl-5,6,7,8-tetrahydro-naphthalene-2-yl)-5-methyl-1H-[1,2,3]triazole 1) Manufacture of trifluoromethanesulfonate 6-methyl-5-oxo-5,6,7,8-tetrahydro-naphthalene-2-ylester Under nitrogen atmosphere, 200 mg of trifluoromethanesulfonate 5-oxo-5,6,7,8-tetrahydro-naphthalene-2-ylester was dissolved in 3 ml of dimethylformamide. 54 mg of 60% sodium hydroxide and 1.0 ml of methyl iodide were added and the mixture was stirred at room temperature for 2 hours. Water was added to the reaction solution, extracted with ethyl acetate. Ethyl acetate layer was washed with saturated saline solution, and dried with anhydrous sodium sulfate. The solvents were distilled outunder reduced pressure, and the residues were separated and purified by preparative thin-layer chromatography (ethyl acetate/hexane=1/2) to obtain 42 mg of the above compound as a yellow oily matter.

2) Manufacture of 1-(2-fluoropyridine-3-yl)-4-(5-oxo-6-methyl-5,6,7,8-tetrahydro-naphthalene-2-yl)-5-methyl-1H-[1,2,3]triazole The above compound was obtained by performing the reaction in the same manner as Example 20, except using trifluoromethanesulfonate 6-methyl-5-oxo-5,6,7,8-tetrahydro-naphthalene-2-ylester obtained in the above 1), instead of 5-bromo-2,2-dimethtyl-1-oxoindane which was used in Example 20.

$^1$HNMR (400 MHz, CDCl$_3$). δ: 1.31 (3H, d, J=6.4 Hz), 1.88-1.99 (1H, m), 2.22-2.29 (1H, m), 2.50 (3H, d, J=1.6 Hz), 2.62-2.68 (1H, m), 3.05-3.16 (2H, m), 7.48-7.51 (1H, m), 7.68 (1H, d, J=8.4 Hz), 7.77 (1H, s), 8.06-8.10 (1H, m), 8.15 (1H, d, J=7.6 Hz), 8.45-8.46 (1H, m), ESI-MS Found: m/z 337.2 [M+H]$^+$.

Example 69

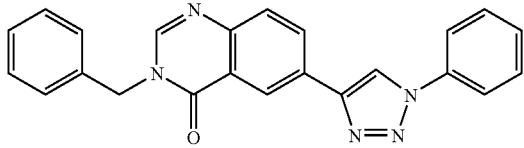

4-(3-benzyl-4-oxo-3,4-dihydroquinazoline-6-yl)-1-phenyl-1H-[1,2,3]triazole

1) Manufacture of 3-benzyl-4-oxo-6-(2-trimethylsilylethynyl)-3,4-dihydroquinazoline Under nitrogen atmosphere, 947 mg of trimethylsilylacetylene, 54.7 mg of copper iodide (I), 54.2 mg bis(triphenylphosphine) palladium dichloride (II) and 3 ml of triethylamine were added sequentially to 1.5 ml solution of dimethylformamide with 501 mg of 3-benzyl-6-bromo4-oxo-3,4-dihydroquinazoline, and the mixture was stirred at 100° C. for 14 hours. After distilling out the solvents under reduced pressure, water was added to the reaction solution, and extracted with ether. Ether layer was washed with saturated saline solution, and dried with anhydrous sodium sulfate. The solvents were distilled outunder reduced pressure, and the residues were separated and purified by silicagel column chromatography (ethyl acetate/hexane=3/7) to obtain 570 mg of the above compound as a colorless oily matter.

2) Manufacture of 3-benzyl-6-ethynyl-5-oxo-3,4-dihydroquinazoline

Under nitrogen atmosphere, 1.16 mg of potassium carbonate was added to 34 ml solution of methanol with 570 mg of the compound obtained in the above 1), and the resultant was stirred at room temperature for 2 hours. After distilling out the solvents under reduced pressure, water was added to the reaction solution, extracted with ether. Ether layer was washed with saturated saline solution, and dried with anhydrous magnesium sulfate. The solvents were distilled outunder reduced pressure, and the residues were separated and purified by silicagel column chromatography (ethyl acetate/hexane=1/1) to obtain 322 mg of the above compound as a colorless oily matter.

$^1$HNMR (300 MHz, CDCl$_3$). δ: 3.19 (1H, s), 5.20 (2H, s), 7.31-7.37 (5H, m), 7.65 (1H, d, J=8.5 Hz), 7.81 (1H, dd, J=1.9 and 8.5 Hz), 8.10 (1H, s), 8.45 (1H, d, J=1.9 Hz).

3) Manufacture of 4-(3-benzyl-4-oxo-3,4-dihydroquinazoline-6-yl)-1-phenyl-1H-[1,2,3]triazole Under nitrogen atmosphere, 1 M of sodium ascorbate aqueous solution and copper sulfate (II) 5-hydrate were added sequentially to 3 ml solution of water-tert-buthanol (1:1) with 114 mg of the compound obtained in the above 2), and 52.4 g of phenylazide, and the mixture was stirred at room temperature for 3 hours. Water was added to the reaction solution, extracted with ethyl acetate. Ethyl acetate layer was washed with saturated saline solution, and dried with anhydrous sodium sulfate. After distilling out the solvents under reduced pressure, the residues were separated and purified by preparative thin-layer chromatography (ethyl acetate/hexane=1/1) to obtain 23.0 of the above compound as a colorless solid.

$^1$HNMR (300 MHz, CDCl$_3$, δ: 5.24 (2H, s), 7.31-7.39 (5H, m), 7.46-7.61 (3H, m), 7.80-7.84 (3H, m), 8.13 (1H, s), 8.36 (1H, s), 8.52 (1H, dd, J=2.0 and 8.6 Hz), 8.69 (1H, d, J=1.9 Hz), ESI-MS Found: m/z 352.0 [M+H]$^+$.

Example 70

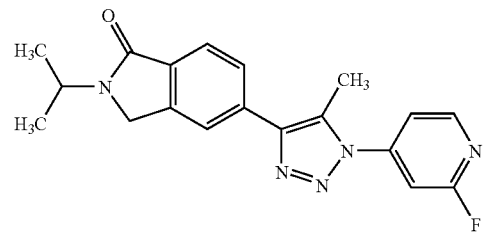

4-(isopropyl-1-oxo-isoindoline-5-yl)-1-(2-fluoropyridine-4-yl)-5-methyl-1H-[1,2,3]triazole 1) Manufacture of 4-azide-5-bromo-2-fluoro-pyridine Under nitrogen atmosphere, 20 ml solution of tetrahydrofuran with 1.39 ml of diisopropylamine was cooled down to −78° C., and 3.8 ml of 2.66 M n-butyllithium/hexane solution was dropped. The reaction solution was heated to 0° C., stirred for 5 min, and cooled down again to −78° C. Then, 5.0 ml solution of tetrahydrofuran with 1.74 g of 5-bromo2-fluoro-pyridine was added. After stirring at −78° C. for 10 min, 5.0 ml solution of tetrahydrofuran with n-dodecylbenzenesulfoneazide was added and the resultant was stirred. Then, the reaction solution was heated to −60° C., and water was added to stop the reaction. The products were extracted with ethyl acetate, dried with anhydrous sodium sulfate and the solvents were extracted under reduced pressure. The obtained residues were purified by silicagel column chromatography (hexane:ethyl acetate=80:20) to obtain 1.70 g of the above compound as a brown oily crude substance.

2) Manufacture of 1-(5-bromo-2-fluoro-pyridine-4-yl)-5-methyl-4-tributylstanyl-1H-[1,2,3]triazole 2.20 g of tributyl(1-propinyl)tin was added to 3.0 ml solution of toluene with 1.70 g of the compound obtained in the above 1), and the mixture was stirred all night at 120° C. The obtained solution was cooled down to room temperature, and purified by silicagel column chromatography (hexane:ethyl acetate=90:10) to obtain 670 mg of the above compound as a mixture of 1-(5-bromo-2-fluoro-pyridine-3-yl)-5-methyl-4-tributylstanyl-1H-[1,2,3]triazole.

3) Manufacture of 4-(2-isopropyl-1-oxo-isoindoline-5-yl)-1-(5-bromo-2-fluoro-pyridine4-yl)-5-methyl-1H-[1,2,3]triazole 6.0 mg of the above compound was obtained, as a mixture of 4-(2-isopropyl-1-oxo-isoindoline-5-yl)-1-(5-bromo-2-fluoro-pyridine-3-yl)-5-methyl-1H-[1,2,3]triazole, with the use of the mixture of the tin reagent obtained in the above 2) and halide obtained in Example 36.

2.5 mg of the mixture of the compound obtained in the above was dissolved in methanol, 2.5 mg of 10% palladium-carbon was added, and the mixture was stirred at room temperature for 20 min. After filtrating the catalyst, the solvents were distilled out, and the residues were purified by preparative thin-layer silicagel chromatography (ethyl acetate) to obtain 0.68 mg of the above compound.

$^1$HNMR (300 MHz, CDCl$_3$), δ: 1.32 (6H, d, J=6.8 Hz), 2.67 (3H, s), 4.47 (2H, s), 4.72 (1H, sept, J=6.8 Hz), 7.49-7.56 (1H, m), 7.73-7.80 (1H, m), 7.93-7.99 (2H, m), 8.47-8.51 (1H, m), ESI-MS Found: m/z 352.0 [M+H]$^+$.

Example 71

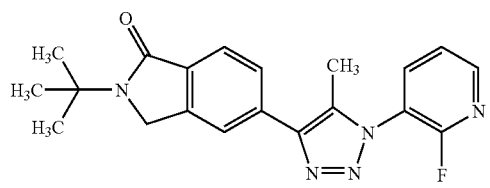

4-(2-tert-butyl-1-oxo-isosindoline-5-yl)-1-(2-fluoro-pyridine-3-yl)-5-methyl-1H-[1,2,3]triazole 1) Manufacture of 5-bromo-2-tert-butyl-1-oxoisoindoline The above compound was obtained by performing the reaction in the same manner as Example 49-1, expect using tert-butylamine instead of cyclopropylamine which was used in Example 49-1.

$^1$HNMR (400 MHz, CDCl$_3$), δ: 1.56 (9H, s), 4.43 (2H, s), 7.55-7.63 (3H, m), ESI-MS Found: m/z 268.1 [M+H]$^+$, 2) Manufacture of 4-(2-tert-butyl-1-oxo-isoindoline-5-yl)-1-(2-fluoropyridine-3-yl)-5-methyl-1H-[1,2,3] triazole The above compound was obtained by performing the reaction in the same manner as Example 49-2, except using 5-bromo-2-tert-butyl-1-oxoinsoindoline obtained in the above 1), instead of 5-bromo-2-cyclopropyl-1-oxoisoindoline which was used in Example 49-2.

$^1$HNMR (400 MHz, CDCl$_3$), δ: 1.60 (9H, s), 2.49 (3H, d, J=2.0 Hz), 4.55 (2H, s), 7.48-7.52 (1H, m), 7.78-7.80 (1H, m), 7.89-7.91 (1H, m), 7.93 (1H, s), 8.05-8.11 (1H, m), 8.45-8.47 (1H, m), ESI-MS Found: m/z 366.2 [M+H]$^+$.

Example 72

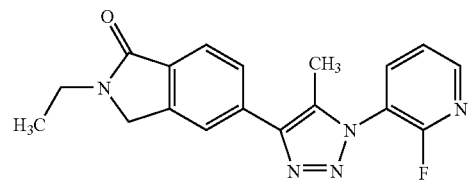

4-(2-ethyl-1-oxo-isoindoline-5-yl)-1-(2-fluoropyridine-3-yl)-5-methyl-1H-[1,2,3]triazole 1) Manufacture of 5-bromo-2-ethyl-1-oxoisoindoline The above compound was obtained by performing the reaction in the same manner as Example 50-1, except using ethylamine instead of cycloproplyamine which was used in Example 49-1.

$^1$HNMR (400 MHz, CDCl$_3$), δ: 1.27 (3H, t, J=7.2 Hz), 3.66 (2H, q, J=7.2 Hz), 4.36 (2H, s), 7.58-7.61 (2H, m), 7.69-7.71 (1H, m), ESI-MS Found: m/z 240.1 [M+H]$^+$.

2) Manufacture of 4-(2-ethyl-1-oxo-isoindoline-5-yl)-1-(2-fluoropyridine-3-yl)-5-methyl-1-[1,2,3]triazole The above compound was obtained by performing the reaction in the same manner as Example 49-2, except using 5-bromo-2-ethyl-1-oxoisoindoline obtained in the above 1), instead of 5-bromo-2-cyclopropyl-1-oxoisoindoline which was used in Example 49-2.

$^1$HNMR (400 MHz, CDCl$_3$), δ: 1.31 (3H, t, J=7.2 Hz), 2.51 (3H, d, J=2.0 Hz), 3.72 (2H, q, J=7.2 Hz), 4.48 (2H, s), 7.49-7.52 (1H, m), 7.80-7.83 (1H, m), 7.84-7.96 (1H, m), 7.98 (1H, s), 8.06-8.11 (1H, m), 8.45-8.47 (1H, m), ESI-MS Found: m/z 338.2 [M+H]$^+$.

Example 73

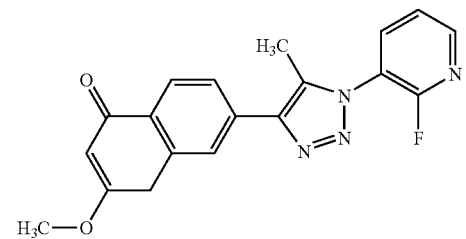

1-fluoropyridine-3-yl)-4-(2-methoxy-4-oxo4H-chromen-7-yl)-5-methyl-1H-[1,2,3]triazole 1) Manufacture of
7-hydroxy-2-methoxy-4H-chromen-4-on Under nitrogen atmosphere, 170 mg of aluminium trichloride was added to 5 ml solution of toluene with 103 mg of 2,7-dimethoxy-4H-chromen-4-one, and the mixture was stirred at 90° C. for 4 hours. Water was added to the reaction solution, the deposited white solid was filtered, separated and purified by preparative thin-layer chromatography (chloroform/methanol=9/1), to obtain 62 mg of the above compound as a white solid.
$^1$HNMR (400 MHz, CD$_3$OD), δ: 4.02 (3H, s), 5.58 (1H, s), 6.81 (1H, d, J=2.0 Hz), 6.90 (1H, dd, J=2.3, 8.8 Hz), 7.91 (1H, d, J=8.8 Hz), ESI-MS Found: m/z 193.0 [M+H]$^+$.

2) Manufacture of 7-((trifluoromethyl)sulfonyloxy)-2-methoxy-4H-chromen-4-on

Under nitrogen atmosphere, 0.11 ml of trifluoromethylsulfonate anhydride was added to 2 ml solution of pyridine with 62 mg of the compound obtained in the above 1), and the mixture was stirred at room temperature for 20 min. Water was added to the reaction solution, extracted with chloroform. Chloroform layer was washed with saturated saline solution and dried with anhydrous sodium sulfate. After distilling out the solvents under reduced pressure, the residues were separated and purified by preparative thin-layer chromatography (chloroform/methanol=9/1), to obtain 18 mg of the above compound as a white solid.
ESI-MS Found: m/z 325.0 [M+H]$^+$.

3) Manufacture of 1-(2-fluoropyridine-3-yl)-4-(2-methoxy-4-oxo-chromen-7-yl)-5-methyl-1H-[1,2,3]triazole The above compound was obtained as a white solid, by performing coupling reaction in the same manner as Example 67, with the use of the compound obtained in the above 2), and the alkyl tin compound 1-(2-fluoropyridine-3-yl)-5-methyl-4-tributylstanyl-1H-[1,2,3]triazole, similar as Reference Example 1.
$^1$HNMR (400 MHz, CDCl$_3$), δ: 2.54 (3H, d, J=2.0 Hz), 4.02 (3H, s), 5.66 (1H, s), 7.49-7.54 (1H, m), 7.84 (1H, dd, J=1.2, 8.0 Hz), 7.91 (1H, d, J=1.2 Hz), 8.06-8.13 (1H, m), 8.28 (1H, d, J=8.0 Hz), 8.48 (1H, d, J=4.8 Hz), ESI-MS Found: m/z 353.1 [M+H]$^+$.

Example 74

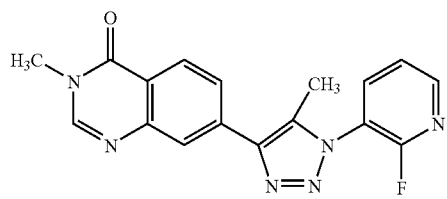

1-(2-fluoropyridine-3-yl)-4-(3-methyl-4-oxo-3,4-dihydro-quinazoline-7-yl)-5-methyl-1H-[1,2,3]triazole 16.7 mg of the above compound was obtained as a colorless solid, by performing the reaction in the same manner as Example 69, except using 101 mg of 7-bromo-3-methyl-4-oxo-3,4-dihydroquinazoline, instead of 6-bromo-3-benzyl-4-oxo-3,4-dihydroquinazoline, which was used in Example 69.
$^1$HNMR (300 MHz, CDCl$_3$), δ: 2.56 (3H, d, J=2.1 Hz), 3.64 (3H, s), 7.49-7.53 (1H, m), 8.05-8.13 (4H, m), 8.42-8.48 (2H, m), ESI-MS Found: m/z 337.0 [M+H]$^+$.

Example 75

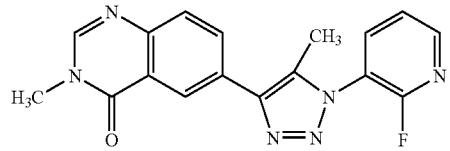

1-(2-fluoropyridine-3-yl)-4-(3-methyl-4-oxo-3,4-dihydro-quinazoline-6-yl)-5-methyl-1H-[1,2,3]triazole 21.0 mg of the above compound was obtained as a colorless solid, by performing the reaction in the same manner as Example 69, except using 109 mg of 6-bromo-3-methyl-4-oxo-3,4-dihydroquinazoline, instead of 6-bromo-3-benzyl-4-oxo-3,4-dihydroquinazoline, which was used in Example 69.
$^1$HNMR (300 MHz, CDCl$_3$), δ: 2.56 (3H, d, J=1.6 Hz), 3.64 (3H, s), 7.48-7.53 (1H, m), 7.85 (1H, d, J=8.6 Hz), 8.06-8.12 (2H, m), 8.36-8.48 (2H, m), 8.59 (1H, d, J=1.7 Hz), ESI-MS Found: m/z 337.0 [M+H]$^+$.

Example 76

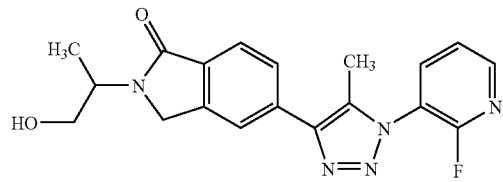

1-(2-fluoropyridine-3-yl)-4-[2-(2-hydroxy-1-methyl-ethyl)-1-oxo-isoindolline-5-yl]-5-methyl-1H-[1,2,3]triazole 1) Manufacture of 5-bromo-2-(2-hydroxy-1-mehtyl-ethyl)-1-oxo-isoindoline The above compound was obtained by performing the reaction in the same manner as Example 49-1, except using 2-hydroxy-1-methyl-ethylamine instead of cyclopropylamine, which was used in Example 49-1.
$^1$HNMR (400 MHz, CDCl$_3$), δ: 1.33 (3H, d, J=7.2 Hz), 3.72-3.76 (1H, m), 3.85-3.89 (1H, m), 4.35-4.50 (3H, m), 7.58-7.61 (2H, m), 7.66 (1H, d, J=8.0 Hz), ESI-MS Found: m/z 270.0 [M+H]$^+$.

2) Manufacture of 1-(2-fluoropyridine-3-yl)-4-[2-(2-hydroxy-1-methyl-ethyl)-1-oxo-isoindoline-5-yl]-5-methyl-1H-[1,2,3]triazole The above compound was obtained by performing the reaction in the same manner as Example 49-2, except using 5-bromo-2-(2-hydroxy-1-methyl-ethyl)-1-oxo-isoindoline obtained in the above 1), instead of 5-bromo-2-cyclopropyl-1-oxoisoindoline which was used in Example 49-2.

¹HNMR (400 MHz, CDCl₃), δ: 1.38 (3H, d, J=7.2 Hz), 1.63 (1H, br), 2.50 (3H, d, J=2.0 Hz), 3.77-3.82 (1H, m), 3.90-3.93 (1H, m), 4.42-4.48 (1H, m), 4.47-4.61 (2H, m), 7.49-7.52 (1H, m), 7.80-7.82 (1H, m), 7.94 (1H, d, J=8.0 Hz), 7.97 (1H, s), 8.07-8.11 (1H, m), 8.45-8.47 (1H, m), APCI-MS Found: m/z 368.0 [M+H]⁺.

Example 77

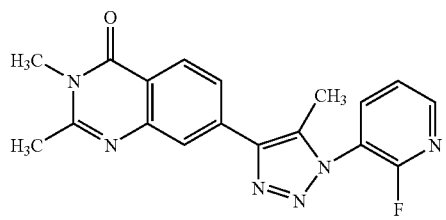

1-(2-floropyridine-3-yl)-5-methyl-(2,3-dimethyl-4-oxo-3,4-dihydro-quinazoline-7-yl)-5-methyl-1H-[1,2,3]triazole

1) Manufacture of N-methyl-2-amino-4-bromobenzamide 30 ml of 2.0 M methylamine-methanol solution was added to 6.28 mg of 7-bromo-1H-benzo[1,3]oxazine-2,4-dion, and the mixture was stirred at room temperature for 2 hours. The reaction solution was distilled out under reduced pressure, to obtain 6.57 mg of the above compound.

2) Manufacture of 7-bromo-2,3-dimethyl-4-oxo-3,4-dihydroquinazoline 5 ml of acetic acid anhydride was added to 979 mg of N-methyl-2-amino-4-bromobenzamide, and the resultant was heated under reflux for 7 hours. After distilling out excess reagent under reduced pressure, saturated sodium bicarbonate aqueous solution was added, extracted with ethyl acetate. Ethyl acetate layer was washed with saturated saline solution, dried with anhydrous sodium sulfate. After distilling out the solvents under reduced pressure, the residues were separated and purified by silicagel column chromatography (hexane/ethyl acetate=4/1), to obtain 618 mg of the above compound as a colorless compound.

¹HNMR (300 MHz, CDCl₃), δ: 2.61 (3H, s), 3.61 (3H, s), 7.51-8.11 (3H, m), ESI-MS Found: m/z 254.9 [M+H]⁺.

3) Manufacture of 1-(2-fluoropyridine-3-yl)-5-methyl-(2,3-dimethyl-4-oxo-3,4-dihydro-quinazoline-7-yl)-5-methyl-1H-[1,2,3]triazole The above compound was obtained in the amount of 7.6 mg as a colorless solid, by performing the reaction by the same method as Example 69, except using 41.7 mg of the compound obtained in the above 2), instead of 6-bromo-3-benzyl-4-oxo-3,4-dihydroquinazoline which was used in Example 69.

¹HNMR (300 MHz, CDCl₃), δ: 2.55 (3H, d, J=2.1 Hz), 2.66 (3H, s), 3.66 (3H, s), 7.48-7.53 (1H, m), 7.93 (1H, d, J=1.4 Hz), 8.03-8.12 (2H, m), 8.38 (1H, d, J=8.2 Hz), 8.45-8.47 (1H, m), ESI-MS Found: m/z 351.0 [M+H].

Example 78

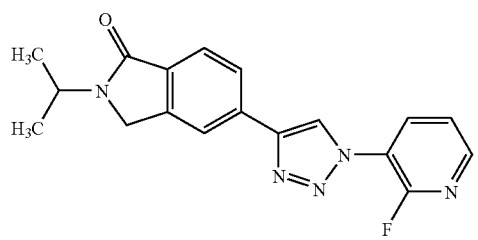

4-(2-isopropyl-1-oxo-isoindoline-5-yl)-1-(2-fluoro-pyridine-3-yl)-1H-[1,2,3]triazole The above compound was obtained in the same manner as Example 1, with the use of halide obtained in Example 36, and the tin reagent 1-(2-fluoropyridine-3-yl)-4-tributylstanyl-1H-[1,2,3]triazole, obtained in Reference Example 2.

¹HNMR (300 MHz, CDCl₃), δ: 1.33 (6H, d, J=6.8 Hz), 4.43 (2H, s), 4.71 (1H, sept, J=6.8 Hz), 7.47-7.51 (1H, m), 7.94 (2H, d, J=1.0 Hz), 8.13 (1H, d, J=1.0 Hz), 8.33-8.36 (1H, m), 8.49 (1H, d, J=2.7 Hz), 8.57-8.62 (1H, m), ESI-MS Found: m/z 338.1 [M+H]⁺.

Example 79

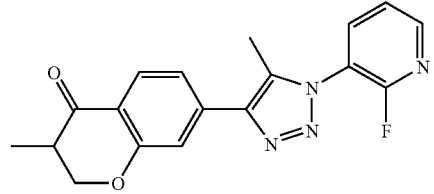

1-(2-fluoropyridine-3-yl)-4-(3-methyl-4-oxo-chroman-7-yl)-5-methyl-1H-[1,2,3]triazole

1) Manufacture of 7-((trifluoromethyl)sulfonyloxy-3-methylchroman-4-one

Under nitrogen atmosphere, 0.13 ml of trifluoromethylsulfonate anhydride was added to 1 ml solution of pyridine with 70 mg of 7-hydroxy-3-methyl-chroman-4-one at 0° C., and the mixture was stirred at room temperature for 1 hour. Water was added to the reaction solution, extracted with ethyl acetate. Ethyl acetate layer was washed with saturated saline solution and dried with anhydrous sodium sulfate. After distilling out the solvents under reduced pressure, the residues were separated and purified by silicagel chromatography (hexane/ethyl acetate=10/1), to obtain 92 mg of the above compound as a white solid.

¹HNMR (40 MHz, CDCl₃), δ: 1.24 (3H, d, J=6.8 Hz), 2.80-2.96 (1H, m), 4.21 (1H, t, J=11.4 Hz), 4.58 (1H, dd, J=5.4, 11.4 Hz), 6.90-6.96 (2H, m), 7.99 (1H, d, J=9.2 Hz), ESI-MS Found: m/z 311.0 [M+H]⁺.

2) Manufacture of 1-(2-fluoropyridine-3-yl)-4-((3SR)-methyl-4-oxo-chroman-7-yl)-5-methyl-1H-[1,2,3]triazole The above compound was obtained by performing coupling reaction in the same manner as Example 67, with the use of the compound obtained in the above 1), and the alkyl tin compound 1-(2-fluoropyridine-3-yl)-5-methyl-4-tribuylstanyl-1H-[1,2,3]triazole, similar as Reference Example 1.

$^1$HNMR (400 MHz, CDCl$_3$), δ: 1.26 (3H, d, J=7.2 Hz), 2.50 (3H, d, J=2.0 Hz), 2.87-2.97 (1H, m), 4.22 (1H, t, J=11.2 Hz), 4.57 (1H, dd, J=5.0, 11.4 Hz), 7.42 (1H, s), 7.46-7.55 (2H, m), 8.01 (1H, d, J=8.0 Hz), 8.04-8.13 (1H, m), 8.46 (1H, dt, J=1.6, 4.4 Hz), ESI-MS Found: m/z 339.1 [M+H]$^+$.

Example 80

1-(2-fluoropyridine-3-yl)-4-((3R*)-methyl-4-oxo-chroman-7yl)-5-methyl-1H-[1,2,3]triazole and 1-(2-fluoropyridine-3-yl)-4-((3S*)-methyl-4-oxo-chroman-7-yl)-5-methyl-1H-[1,2,3]triazole 1-(2-fluoropyridine-3-yl)-4-((3SR)-methyl-4-oxo-chroman-7-yl)-5-methyl-1H-[1,2,3]tirazole, obtained in Example 79, was optically resolved by optically active column (Daicel; CHIRALPAK-AD column; 0.1% diethylamine, hexane/isopropryl alcohol=80/200). From the first fraction, the compound named (3R*) of the above compound for convenience, and from the latter fraction, the compound named (3S*) of the above compound for convenience were obtained both as white solid, respectively.

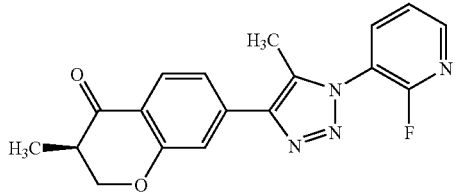

1-(2-fluoropyridine-3yl)-4-((3R*)-methyl-4-oxo-chroman-7-yl)-5-methyl-1H-[1,2,3]triazole $^1$HNMR (400 MHz, CDCl$_3$), δ: 1.26 (3H, d, J=7.2 Hz), 2.50 (3H, d, J=2.0 Hz), 2.87-2.97 (1H, m), 4.22 (1H, t, J=11.2, 22.4 Hz), 4.57 (1H, dd, J=5.0, 11.4 Hz), 7.42 (1H, s), 7.46-7.55 (2H, m), 8.01 (1H, d, J=8.0 Hz), 8.04-8.13 (1H, m), 8.46 (1H, dt, J=1.6, 3.2, 4.4 Hz), ESI-MS Found: m/z 339.1 [M+H]$^+$.

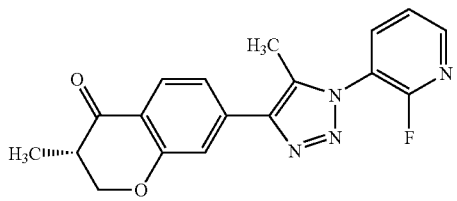

1-(2-fluoropyridine-3-yl)-4-((3S*)-methyl-4-oxo-chroman-7-yl)-5-methyl-1H-[1,2,3]triazole $^1$HNMR (400 MHz, CDCl$_3$), δ: 1.26 (3H, d, J=7.2 Hz), 2.50 (3H, d, J=2.0 Hz), 2.87-2.97 (1H, m), 4.22 (1H, t, J=11.2, 22.4 Hz), 4.57 (1H, dd, J=5.0, 11.4 Hz), 7.42 (1H, s), 7.46-7.55 (2H, m), 8.01 (1H, d, J=8.0 Hz), 8.04-8.13 (1H, m), 8.46 (1H, dt, J=1.6, 3.2, 4.4 Hz), ESI-MS Found: m/z 339.1 [M+H]$^+$.

Example 81

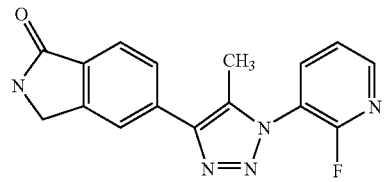

1-(2-fluoropyridine-3-yl)-4-(1-oxo-isoindoline-5-yl)-5-methyl-1H-[1,2,3]triazole 1) Manufacture of 5-bromo-2-tert-butoxycarbonyl-1-oxo-isoindoline Under nitrogen atmosphere, 70 mg of 5-bromo-1-oxo-isoindoline was dissolved in 2 ml of tetrahydrofuran, cooled down to 0° C., and then 4 mg of N,N-dimethylaminopyridine and 144 mg of di-tert-butylcarbonate were added. The mixture was stirred at room temperature for 30 min. Methanol was added to the reaction solution, and the solvents were distilled outunder reduced pressure. Water was added to the residues, extracted with ethyl acetate. Ethyl acetate layer was washed with saturated saline solution, and dried with anhydrous sodium sulfate. After distilling out the solvents under reduced pressure, the residues were separated and purified by silicagel column chromatography (ethyl acetate/hexane=1/2), to obtain 51.2 mg of the above compound as a white solid.

$^1$HNMR (400 MHz, CDCl$_3$), δ: 1.60 (9H, s), 4.74 (2H, s), 7.62-7.65 (2H, m), 7.76 (1H, d, J=8.0 Hz).

2) Manufacture of 1-(2-fluoropyridine-3-yl)-4-(2-tert-butoxycarbonyl-1-oxo-isoindoline-5-yl)-5-methyl-1H-[1,2,3]triazole The above compound was obtained by performing the reaction in the same manner as Example 5, except using 5-bromo-2-tert-butoxycarbonyl-1-oxo-isoindoline obtained in the above 1), instead of 6-bromoquinoline which was used in Example 5.

3) Manufacture of 1-(2-fluoropyridine-3-yl)-4-(1-oxo-isoindoline-5-yl)-5-methyl-1H-[1,2,3]triazole Under nitrogen atmosphere, 25 mg of 1-(2-fluoropyridine-3-yl)-4-(2-tert-butoxycarbonyl-1-oxo-isoindoline-5-yl)-5-methyl-1H-[1,2,3]triazole, obtained in the above 2) was dissolved in 1.0 ml of 5% trifluoroacetate chloroform solution, and the mixture was stirred at room temperature for 10 min. Water was added to the reaction solution, extracted with chloroform. Chloroform layer was washed with saturated sodium bicarbonate aqueous solution and saturated saline solution, and dried with anhydrous sodium sulfate. After distilling out the solvents under reduced pressure, the residues were separated and purified by preparative thin-layer chromatography (chloroform/methanol=50/1), to obtain 4.1 mg of the above compound as a white solid.

¹HNMR (400 MHz, CD₃OD), δ: 2.49 (3H, d, J=1.2 Hz), 4.56 (2H, s), 7.65-7.68 (1H, m), 7.96-7.98 (2H, m), 8.04 (1H, br), 8.25-8.30 (1H, m), 8.52-8.53 (1H, m), ESI-MS Found: m/z 310.2 [M+H]⁺.

Example 82

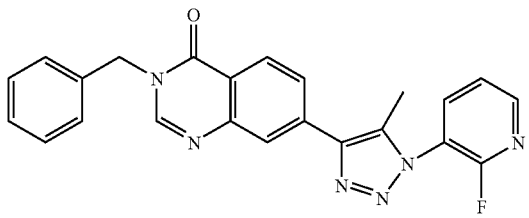

4-(3-benzyl-4-oxo-3,4-dihydroquinazoline-7-yl)-1-(2-fluoropyridine-3-yl)-5-methyl-1H-{1,2,3}triazole 1) Manufacture of N-benzyl-2-amino-4-bromobenzamide The above compound was obtained by performing the reaction in the same manner as Example 79-4, except using benzylamine instead of methylamine, which was used in Example 79-1.

2) Manufacture of 3-benzyl-7-bromo-4-oxo-3,4-dihydroquinazoline 10 ml of formic acid was added to 18.5 g of N-benzyl-2-amino-4-bromobenzamide, and was heated under reflux for 2 hours. After distilling out excess reagent under reduced pressure, saturated sodium bicarbonate aqueous solution was added, and extracted with ethyl acetate. Ethyl acetated layer was washed with saturated saline solution, and dried with anhydrous sodium sulfate. The solvents were distilled out under reduced pressure, and the residues were separated and purified by silicagel column chromatography (hexane/ethyl acetate=7/3), to obtain 821 mg of the above compound as a colorless solid.

¹HNMR (300 MHz, CDCl₃), δ: 5.18 (2H, s), 3.61 (3H, s), 7.7.34 (5H, s), 7.59-7.63 (1H, m), 7.87 (1H, s), 8.09 (1H, s), 8.16 (1H, d, J=8.6 Hz).

3) Manufacture of 4-(3-benzyl-4-oxo-3,4-dihydroquinazoline-7-yl)-1-(2-fluoropyridine-3yl)-5-methyl-1H-[1,2,3]triazole The above compound was obtained by performing the reaction in the same manner as Example 69, except using 3-benzyl-7-bromo-4-oxo-3,4-dihydroquinazoline obtained in the above 2), instead of 6-bromo-3-benzyl-4-oxo-3,4-dihydroquinaoline, which was used in Example 69.

¹HNMR (300 MHz, CDCl₃), δ: 2.55 (3H, d, J=1.9 Hz), 5.24 (2H, s), 7.33-7.41 (5H, m), 7.50 (1H, dd, J=5.0, 7.6 Hz), 8.05-8.12 (3H, m), 8.15 (1H, s), 8.44 (1H, s), 8.45-8.48 (1H, m), ESI-MS Found: m/z 337.2 [M+H]⁺.

Example 83

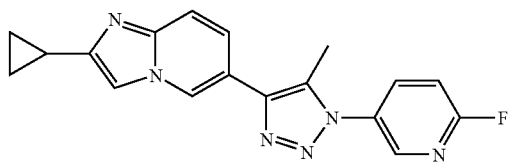

1-(2-fluoropyridine-5-yl)-4-(2-cyclopropyl-imidazo[1,2-a]pyridine-6-yl)-5-methyl-1H-[1,2,3]triazole The above compound was obtained in the same manner as Example 1, with the use of halide obtained in Example 48, and the tin reagent 1-(2-fluoropyridine-5-yl)-5-methyl-4-tributylstanyl-1H-[1,2,3]triazole, obtained in Reference Example 3.

¹HNMR (300 MHz, CDCl₃), δ: 0.88-0.98 (4H, m), 2.51 (3H, s), 2.94-3.02 (1H, m), 4.41 (2H, s), 7.25-7.33 (2H, m), 7.49-7.54 (2H, m), 7.76-7.80 (1H, m), 7.92-7.96 (2H, m), ESI-MS Found: m/z 349.3 [M+H]⁺.

Example 84

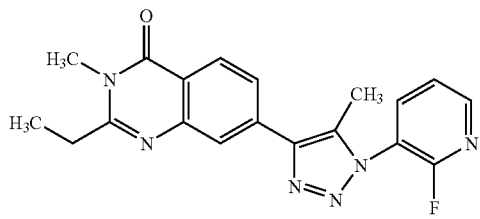

4-(3-benzyl-2-ethyl-4-oxo-3,4,-dihydroquinazoline-7-yl)-1-(2-fluoropyridine-3-yl)-5-methyl-1H-[1,2,3]triazole 1) Manufacture of 7-bromo-2-ethyl-3-methyl-4-oxo-3,4-dihydroquinazoline 1.5 ml of triethyl orthopropionate and 30 μL of acetic acid were added to 1 ml solution of N-methyl-2-pyrolidine with 796 mg of N-methyl-2-amino4-bromobenzamide, and the mixture was stirred at 100° C. for 1 hour. Saturated sodium bicarbonate aqueous solution was added to the reaction solution, and extracted with ether. Ether layer was washed with saturated saline solution, and dried with anhydrous magnesium sulfate. After distilling out the solvents under reduced pressure, the residues were separated and purified by silicagel column chromatography (hexane/ethyl acetate=4/1), to obtain 653 mg of the above compound as a colorless solid.

2) Manufacture of 4-(3-benzyl-2-ethyl-4-oxo-3,4,-dihydroquinazoline-7-yl)-1-(2-fluoropyridine-3-yl)-5-methyl-1H-[1,2,3]triazole The above compound was obtained as a colorless solid by performing the reaction in the same manner as Example 69, except using the compound obtained in the above 1), instead of 6-bromo-3-benzyl-4-oxo-3,4-dihydroquinazoline, which was used in Example 69.

¹HNMR (300 MHz, CDCl₃), δ: 1.43 (3H, t, J=7.4 Hz), 2.56 (3H, d, J=2.2 Hz), 2.90 (2H. q. J=7.4 Hz), 3.66 (3H, s), 7.248-7.52 (1H, m), 7.98-8.13 (3H, m), 8.37 (1H, d, J=8.3 Hz), 8.45-8.47 (1H, m), ESI-MS Found: m/z 365.0 [M+H]⁺.

Example 85

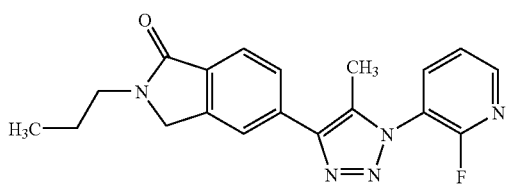

1-(2-fluoropyridine-3-yl)-5-methyl-4-(2-propyl-1-oxo-isoindoline-5-yl)-1H-[1,2,3]triazole 1) Manufacture of 5-bromo-2-propyl-1-oxo-isoindoline Under nitrogen atmosphere, 300 mg of 4-bromo-2-bromomethyl methyl benzoate was dissolved in toluene, 0.2 ml of propylamine and 0.1 ml of triethylamine were added and heated under reflux for 1 hour. The reaction solution was cooled down to room temperature, and after distilling out the solvents under reduced pressure, the residues were separated and purified by silicagel column chromatography (ethyl acetate/hexane=1/2), to obtain 289 mg of the above compound as a white solid.

¹HNMR (400 MHz, CDCl₃), δ: 0.96 (3H, t, J=7.6 Hz), 1.66-1.71 (2H, m), 3.56 (2H, t, J=7.6 Hz), 4.35 (2H, s), 7.58-7.60 (2H, m), 7.70 (1H, d, J=8.8 Hz), ESI-MS Found: m/z 254.2 [M+H]⁺.

2) Manufacture of 1-(2-fluoropyridine-3-yl)-5-methyl-4-(2-1-propyl-1-oxo-isoindoline-5-yl)-1H-[1,2,3]triazole Under nitrogen atmosphere, 480 mg of 5-bromo-2-propyl-1-oxo-isoindoline obtained in the above 1), and 300 mg of 1-(2-chloropyridine-3-yl)-4-tri-n-butyltin-5-methyl-[1,2,3]triazole, prepared in Reference Example 1 were dissolved in N,N-dimethylformamide. 73 mg of tetrakistriphenylphosphinepalladium was added, the mixture heated at 115° C., and was stirred for 3 hours. The reaction solution was cooled down to room temperature, insoluble matters were removed by celite filtration. Water was added to filtrate, extracted with ethyl acetate. Ethyl acetate was washed with saturated saline solution, and dried with anhydrous sodium sulfate. After distilling out the solvents under reduced pressure, the residues were separated and purified by silicagel column chromatography (ethyl acetate/hexane=2/1), to obtain 128 mg of the above compound as white solid.

¹HNMR (400 MHz, CDCl₃), δ: 0.99 (3H, t, J=7.4 Hz), 1.71-1.78 (2H, m), 2.51 (3H, d, J=2.1 Hz), 3.62 (2H, dd, J=7.2, 7.6 Hz), 4.47 (2H, s), 7.49-7.52 (1H, m), 7.81-8.82 (1H, m), 7.92-7.98 (2H, m), 8.06-8.11 (1H, m), 8.45-8.47 (1H, m), ESI-MS Found: m/z 352.3 [M+H]⁺.

Example 86

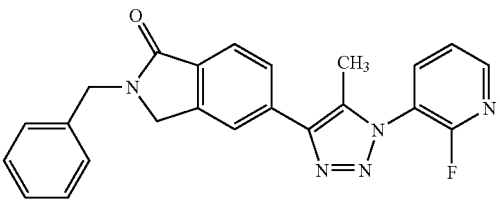

4-(2-benzyl-1-oxo-isoindoline-5-yl)-1-(2-fluoropyridine-3-yl)-5-methyl-1H-[1,2,3]triazole 1) Manufacture of 5-bromo-2-benzyl-1-oxo-isoindoline The above compound was obtained by performing the reaction in the same manner as Example 49-1, except using benzylamine instead of cyclopropylamine which was used in Example 49-1.

¹HNMR (400 MHz, CDCl₃), δ: 4.24 (2H, s), 4.78 (2H, s), 7.26-7.36 (5H, m), 7.54 (1H, s), 7.59-7.62 (1H, m), 7.75 (1H, d, J=8.0 Hz), ESI-MS Found: m/z 302.1 [M+H]⁺.

2) Manufacture of 4-(2-benzyl-1-oxo-isoindoline-5-yl)-1-(2-fluoropyridine-3-yl)-5-methyl-1H-[1,2,3]triazole The above compound was obtained by performing the reaction in the same manner as Example 49-2, except using 5-bromo-2-benzyl-1-oxoisoindoline obtained in the above 1), instead of 5-bromo-2-cyclopropyl-1-oxoisoindoline, which was used in Example 49-2.

¹HNMR (400 MHz, CDCl₃), δ: 2.49 (3H, d, J=1.2 Hz), 4.36 (2H, s), 4.84 (2H, s), 7.28-7.38 (5H, m), 7.48-7.51 (1H, m), 7.84 (1H, d, J=8.0 Hz), 7.90 (1H, s), 8.01 (1H, d, J=8.0 Hz), 8.06-8.10 (1H, m), 8.45-8.46 (1H, m), ESI-MS Found: m/z 400.2 [M+H]⁺.

Example 87

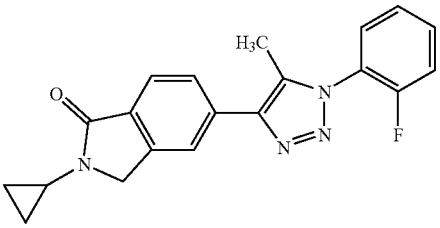

4-(2-cyclopropyl-1-oxo-isoindoline-5-yl)-1-(2-fluorobenzene-3-yl)-5-methyl-1H-[1,2,3]triazole The above compound was obtained in the same manner as Example 20, with the use of 5-bromo-2-cyclopropyl-1-oxoisoindoline obtained in Example 49-1, and the compound 1-(2-fluorophenyl)-5-methyl-4-tributylstanyl-1H-[1,2,3]triazole of Reference Example 4.

¹HNMR (300 MHz, CDCl₃), δ: 0.88-0.98 (4H, m), 2.51 (3H, s), 2.94-3.02 (1H, m), 4.41 (2H, s), 7.25-7.33 (2H, m), 7.49-7.54 (2H, m), 7.76-7.80 (1H, m), 7.92-7.96 (2H, m), ESI-MS Found: m/z 349.3 [M+H]⁺.

Example 88

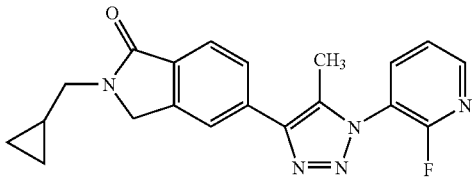

4-(2-cyclopropylmethyl-1-oxo-isoindoline-5-yl)-1-(2-fluoropyridine-3-yl)-5-methyl-1H-[1,2,3]triazole 1) Manufacture of 5-bromo-2-cyclopropylmethyl-1-oxo-isoindoline The above compound was obtained by performing the reaction in the same manner as Example 49-1, except using 2-cyclopropylmethylamine instead of cyclopropylamine, which was used in Example 49-1.

¹HNMR (400 MHz, CDCl₃), δ: 0.31-0.56 (2H, m), 0.56-0.60 (2H, m), 0.99-1.08 (1H, m), 3.47 (2H, d, J=7.2 Hz), 4.47 (2H, s), 7.58-7.62 (2H, m), 7.71 (1H, d, J=8.0 Hz), ESI-MS Found: m/z 266.1 [M+H]⁺.

2) Manufacture of 4-(2-cyclopropylmethyl-1-oxo-isoindoline-5-yl)-1-(2-fluoropyridine-3-yl)-5-methyl-1H-[1,2,3]triazole The above compound was obtained by performing the reaction in the same manner as Example 49-2, except using 5-bromo-2-cyclopropylmethyl-1-oxo-isoindoline obtained in the above 1), instead of 5-bromo-2-cyclopropyl-1-oxoisoindoline, which was used in Example 49-2.

¹HNMR (400 MHz, CDCl₃), δ: 0.35-0.38 (2H, m), 0.59-0.63 (2H, m), 1.04-1.14 (1H, m), 2.51 (3H, d, J=2.1 Hz), 3.53 (2H, d, J=7.2 Hz), 4.59 (2H, s), 7.49-7.52 (1H, m), 7.81-7.83 (1H, m), 7.95-7.99 (2H, m), 8.07-8.11 (1H, m), 8.45-8.47 (1H, m), ESI-MS Found: m/z 364.3 [M+H]⁺.

Example 89

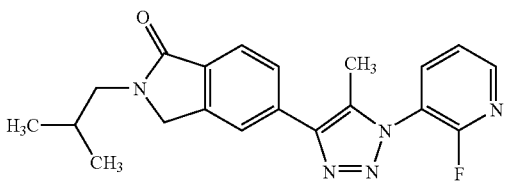

4-(2-isobutyl-1-oxo-isoindoline-5-yl)-1-(2-fluoropyridine-3-yl)-5-methyl-1H-[1,2,3]triazole 1) Manufacture of 5-bromo-2-isobutyl1-oxo-isoindoline The above compound was obtained by performing the reaction in the same manner as Example 49-1, except using 2-isobutylamine instead of cycloproplamine which was used in Example 49-1.

¹HNMR (400 MHz, CDCl₃), δ: 0.95 (6H, d, J=6.4 Hz), 2.01-2.08 (1H, m), 3.41 (2H, d, J=7.6 Hz), 4.36 (2H, s), 7.58-7.60 (2H, m), 7.70-7.72 (1H, m), ESI-MS Found: m/z 268.2 [M+H]⁺.

2) Manufacture of 4-(2-isobutyl1-oxo-isoindoline-5-yl)-1-(2-fluoropyridine-3-yl)-5-methyl-1H-[1,2,3]triazole The above compound was obtained by performing the reaction in the same manner as Example 49-2, except using 5-bromo-2-isobutyl1-oxo-isoindoline obtained in the above 1), instead of 5-bromo-2-cyclopropyl-1-oxoisoindoline which was used in Example 49-2.

¹HNMR (400 MHz, CDCl₃), δ: 0.99 (6H, d, J=6.6 Hz), 2.04-2.13 (1H, m), 2.51 (3H, d, J=2.1 Hz), 3.46-3.48 (2H, m), 4.47 (2H, s), 7.48-7.52 (1H, m), 7.80-7.82 (1H, m), 7.95-7.98 (2H, m), 8.06-8.11 (1H, m), 8.45-8.47 (1H, m), ESI-MS Found: m/z 366.3 [M+H]⁺.

Example 90

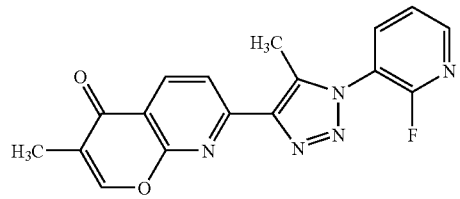

1-(2-fluoropyridine-3-yl)-5-methyl-4-(3-methyl-4-oxo-4H-pyrano[2,3-b]pyridine-7-yl)-1H-[1,2,3]triazole 1) Manufacture of 1-(2,6-dimethoxy-3-pyridyl)propane-1-one Under nitrogen atmosphere, 15% hexane solution of triethyl aluminium was dropped at 0° C. to 26 m solution of toluene with 0.6 ml of N,N'-dimethyl-ethan-1,2-diamine, and the mixture was stirred at room temperature for 1 hour. Then, 5 ml solution of toluene with 1 g of 2,6-dimethoxy-nicotinic acid methylester was dropped at room temperature, and the mixture was stirred at 130° C. for 1 hour. The reaction solution was cooled down under ice temperature, 1M of hydrochloric acid was added, and extracted with ethyl acetate. Ethyl acetate layer was washed with saturated saline solution, dried with anhydrous sodium sulfate. The solvents were distilled outunder reduced pressure to obtain 156 mg of the above compound.

ESI-MS Found: m/z 196.1 [M+H]⁺.

2) Manufacture of 3-methyl-7-methoxy-8-azA4H-chromen-4-one

Under nitrogen atmosphere, 261 mg of aluminium trichloride was added to 5 ml solution of toluene with 150 mg of the compound obtained in the above 1), the mixture was stirred at 90° C. for 3 hours. Water was added to the reaction solution, extracted with chloroform. Chloroform layer was washed with saturated saline solution, dried with anhydrous sodium sulfate, and the solvents were distilled outunder reduced pressure. Under nitrogen atmosphere, 0.3 ml of dimethylformamide was dropped at 0° C. to 0.1 ml solution of borone trifluolide ethylether complex with 37 mg of the obtained residues, and the resultant was stirred at 0° C. for 15 min. A mixed solution of 68 mg of phosphorus pentachloride and 1.6 ml of dimethylformamide was dropped at 0° C., and the mixture was stirred at room temperature for 3 hours. Methanol hydrochloride solution was added to the reaction solution, and stirred at 70° C. for 20 min. Methanol was distilled outunder reduced pressure, water was added and extracted with chloroform. Chloroform layer was washed with saturated saline solution, and dried with anhydrous sodium sulfate. After distilling out the solvents under reduced pressure, residues were separated and purified by preparative thin-layer chromatography (hexane:ethyl acetate=3/1) to obtain 26 mg of the above compound as a white solid.

$^1$HNMR (400 MHz, CDCl$_3$), δ: 2.03 (3H, d, J=1.2 Hz), 4.05 (3H, s), 6.83 (1H, d, J=8.4 Hz), 7.78 (1H, d, J=1.2 Hz), 8.44 (1H, d, J=8.4 Hz), ESI-MS Found: m/z 192.1 [M+H]$^+$.

3) Manufacture of 7-hydroxy-3-methyl-8-azA4H-chromen-4-one

Under nitrogen atmosphere, 75 mg of aluminium trichloride was added to 2 ml solution of toluene with 26 mg of the compound obtained in the above 2), the mixture was stirred at 90° C. for 8 hours. Water was added to the reaction solution, extracted with chloroform. Chloroform layer was washed with saturated saline solution, dried with anhydrous sodium sulfate. After distilling out the solvents under reduced pressure, the residues were separated and purified by preparative thin-layer chromatography (chloroform/methanol=9/1) to obtain 11 mg of the above compound as a white solid.

ESI-MS Found: m/z 378.0 [M+H]$^+$.

4) Manufacture of 7-((trifluoromethyl)sulfonyloxy)-3-methyl-8-azA4H-chromen-one Under nitrogen atmosphere, 0.01 ml of 4-methyl-2,6-ditertialbutylpyridine, 0.015 ml of trifluoromethylsulfonate anhydride were added sequentially to 1 ml solution of dichloromethane with 7 mg of the compound obtained in the above 3), and the mixture was stirred at room temperature for 1 hour. Water was added to the reaction solution and extracted with chloroform. Chloroform layer was washed with saturated saline solution and dried with anhydrous sodium sulfate. After distilling out the solvents under reduced pressured, residues were separated and purified by preparative thin-layer chromatography (hexane/ethyl acetate=3/1) to obtain 10 mg of the above compound as a white solid.

$^1$HNMR (400 MHz, CDCl$_3$), δ: 2.07 (3H, d, J=1.2 Hz), 7.26 (1H, d, J=8.4 Hz), 7.90 (1H, d, J=1.2 Hz), 8.79 (1H, d, J=8.4 Hz), ESI-MS Found: m/z 310.0 [M+H]$^+$.

5) Manufacture of 1-(2-fluoropyridine-3-yl)-5-methyl-4-(3-methyl-4-oxo-4H-pirano[2,3-b]pyridine-7-yl)-1H-[1,2,3]triazole The above compound was obtained as a white solid by performing coupling reaction in the same manner as Example 67, with the use of the compound obtained in the above 4) and the alkyl tin compound 1-(2-fluoropyridine-3-yl)-5-methyl-4-tributylstanyl-1H-[1,2,3]triazole similar as Reference Example 1.

$^1$HNMR (400 MHz, CDCl$_3$), δ: 1.26 (3H, d, J=7.2 Hz), 2.50 (3H, d, J=2.0 Hz), 2.87-2.97 (1H, m), 4.22 (1H, t, J=11.2 Hz), 4.57 (1H, dd, J=5.0, 11.4 Hz), 7.42 (1H, s), 7.46-7.55 (2H, m), 8.01 (1H, d, J=8.0 Hz), 8.04-8.13 (1H, m), 8.46 (1H, dt, J=1.6, 4.4 Hz), ESI-MS Found: m/z 338.2 [M+H]$^+$.

Example 91

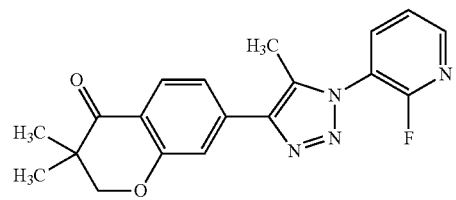

4-(3,3-dimethyl-4-oxo-chroman-7-yl)-1-(2-fluoropyridine-3-yl)-5-methyl-1H-[1,2,3]triazole

1) Manufacture of 3,3-dimethyl-7-methoxychroman-4-one

Under nitrogen atmosphere, 0.4 ml of methyl iodide was added to 10 ml solution tetrahydrofuran with 240 mg of 3-methyl-7-methoxychroman-4-one, 100 mg of potassium hydrogenate was added and the mixture was stirred at room temperature for 3 hours. Water was added to the reaction solution, extracted with chloroform. Chloroform layer was washed with saturated saline solution and dried with anhydrous sodium sulfate. After distilling out the solvents under reduced pressure, residues were separated and purified by silicagel chromatography (hexane/ethyl acetate=5/1) to obtain 145 mg of the above compound as a white solid.

$^1$HNMR (400 MHz, CDCl$_3$), δ: 1.19 (6H, d, J=0.8 Hz), 3.84 (3H, d, J=0.8 Hz), 4.14 (2H, s), 6.40 (1H, d, J=2.4 Hz), 6.57-6.62 (1H, m), 7.84 (1H, d, J=8.4 Hz), ESI-MS Found: m/z 207.1 [M+H]$^+$.

2) Manufacture of 7-hydroxy-3,3-dimethylchroman-4-one

Under nitrogen atmosphere, 110 mg of aluminium trichloride was added to 3 ml solution of toluene with 67 mg of the compound obtained in the above 1), and the mixture was stirred at 90° C. for 2 hours. Water was added to the reaction solution, and extracted with chloroform. Chloroform layer was washed with saturated saline solution and dried with anhydrous sodium sulfate. After distilling out the solvents under reduced pressure, residues were separated and purified by preparative thin-layer chromatography (chloroform/methanol=9/1) to obtain 50 mg of the above compound as a white solid.

¹HNMR (400 MHz, CDCl₃), δ: 1.20 (6H, s), 4.13 (2H, s), 6.43 (1H, d, J=2.0 Hz), 6.57 (1H, dd, J=2.0, 8.4 Hz), 7.81 (1H, d, J=8.4 Hz), ESI-MS Found: m/z 193.1 [M+H]⁺.

3) Manufacture of 7-((trifluoromethyl)sulfonyloxy-3,3-dimethylchroman-4-one

Under nitrogen atmosphere, 0.06 ml of 4-methyl-2,6-ditertialbutylpyridine, 0.05 ml of trifluoromethylsulfonate anhydride were added sequentially to 2 ml solution of dichloromethane with 50 mg of the compound obtained in the above 3), and the mixture was stirred at room temperature for 2 hours. Water was added to the reaction solution, extracted with chloroform. Chloroform layer was washed with saturated saline solution, and dried with anhydrous sodium sulfate. After distilling out the solvents under reduced pressure, residues were separated and purified by preparative thin-layer chromatography (hexane/ethyl acetate=3/1) to obtain 40 mg of the above compound as a white solid.

¹HNMR (400 MHz, CDCl₃), δ: 1.22 (6H, s), 4.21 (2H, s), 6.90-6.97 (2H, m), 8.00 (1H, dd, J=0.4, 8.4 Hz), ESI-MS Found: m/z 325.0 [M+H]⁺.

4) Manufacture of 4-(3,3-dimethyl-4-oxo-chroman-7-yl)-1-(2-fluoropyridine-3-y)-5-methyl-1H-[1,2,3]triazole The above compound was obtained as a white solid by performing coupling reaction in the same manner as Example 67, with the use of the compound obtained in the above 3) and the alkyl tin compound 1-(2-fluoropyridine-3-yl)-5-methyl-4-tributylstanyl-1H-[1,2,3]triazole similar as Reference Example 1.

¹HNMR (400 MHz, CDCl₃), δ: 1.25 (6H, s), 2.50 (3H, d, J=2.0 Hz), 4.21 (2H, s), 7.42 (1H, d, J=1.6 Hz), 7.47-7.54 (2H, m), 8.03 (1H, d, J=8.0 Hz), 8.05-8.11 (1H, m), 8.43-8.49 (1H, m), ESI-MS Found: m/z 353.1 [M+H]⁺.

Example 92

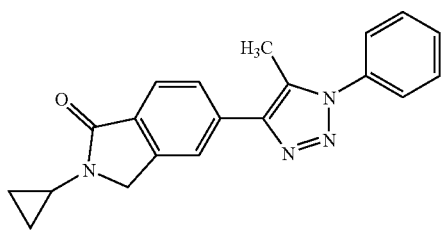

4-(2-cyclopropyl-1-oxo-isoindoline-5-yl)-1-phenyl-5-methyl-1H-[1,2,3]triazole

The above compound was obtained by the same method as Example 20 with the use of 5-bromo-2-cyclopropyl-1-oxoisoindoline obtained in Example 49-1 and the compound 1-phenyl-5-methyl-4-tributylstanyl-1H-[1,2,3]triazole of Reference Example 5.

¹HNMR (300 MHz, CDCl₃), δ: 0.89-0.98 (4H, m), 2.53 (3H, s), 2.93-3.02 (1H, m), 4.41 (2H, s), 7.50-7.62 (5H, m), 7.77-7.82 (1H, m), 7.91-7.97 (2H, m), ESI-MS Found: m/z 331.3 [M+H]⁺.

Example 93

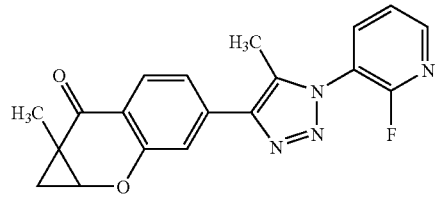

1-(2-fluoropyridine-3-yl)-5-methyl-4-(1a-methyl-2-oxo-1,1a,2,7a-tetrahydro-7-oxo-6-cyclopropa[b]naphthalene-5-yl)-1H-[1,2,3]triazole Under nitrogen atmosphere, 3 ml of dimethylsulphoneamide was added to the mixture of 3 mg of sodium hydride and 13 mg of trimethylsulfoxoniumiodide, and the mixture was stirred at room temperature for 20 min. Then 3 ml solution of dimethylsulphonamide with 20 mg of 4-(3-methyl-4-oxo-4H-chromen-7-yl)-1-(2-fluoropyridine-3-yl)-5-methyl-1H-[1,2,3]triazole was added, and the mixture was stirred at room temperature for 2 hours, and then at 50° C. for 1 hour. Cold water was added to the reaction solution, extracted with ditheylether. Diethylether layer was washed with saturated saline solution, and dried with anhydrous sodium sulfate. After distilling out the solvents under reduced pressure, the residues were separated and purified by preparative thin-layer chromatography (hexane/ethyl acetate=3/1) to obtain 13 mg of the above compound as a white solid.

¹HNMR (400 MHz, CDCl₃), δ: 1.34-1.54 (2H, m), 1.40 (3H, s), 2.48 (3H, d, J=2.4 Hz), 4.44 (1H, dd, J=4.0, 5.2 Hz), 7.39 (1H, d, J=1.6 Hz), 7.47-7.53 (2H, m), 8.01 (1H, d, J=7.6 Hz), 8.03-8.10 (1H, m), 8.46 (1H, dt, J=1.0, 4.4 Hz), ESI-MS Found: m/z 351.0 [+H]+

Example 94

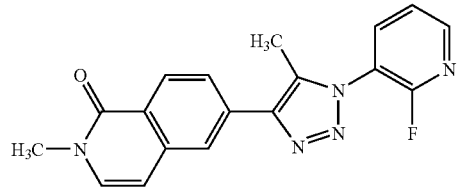

4-(2-methyl-1-oxo-isoquinoline-6-yl)-1-(2-fluoropyridine-3-yl)-5-methyl-1H-[1,2,3]triazole 1) Manufacture of 6-bromo-2-methylisoquinoline-1-one Under nitrogen atmosphere, 60% sodium hydrogenate (18 mg) was added at 0° C. to 2 ml solution of dimethylformamide with 100 mg of 6-bromo-2H-isoquinoline-1-one, and the mixture was stirred for 30 min. Then, 0.03 ml of methyl iodide was added at 0° C., stirred at room temperature for 2 hours. Cold water was added to the reaction solution, extracted with chloroform. Chloroform layer was washed with saturated saline solution, dried with anhydrous sodium sulfate. After distilling out the solvents under reduced pressure, residues were separated and purified by preparative thin-layer chromatography (hexane/ethyl acetate=3/1) to obtain 24 mg of the above compound as a white solid.

¹HNMR (400 MHz, CDCl₃), δ: 3.59 (3H, s), 6.39 (1H, d, J=7.2 Hz), 7.09 (1H, d, J=7.2 Hz), 7.56 (1H, dd, J=2.0, 8.4 Hz), 7.67 (1H, d, J=2.0 Hz), 8.27 (1H, d, J=8.4 Hz), ESI-MS Found: m/z 238.1 [M+H]⁺.

2) Manufacture of 4-(2-methyl-1-oxo-isoquinoline-6-yl)-1-(2-fluoropyridine-3-yl)-5-mehtyl-1H-[1,2,3]triazole The above compound was obtained as a white solid, by performing coupling reaction in the same manner as Example 67, with the use of the compound obtained in the above 1) and the alkyl tin compound 1-(2-fluoropyridine-3-yl)-5-methyl-4-tributylstanyl-1H-[1,2,3]triazole similar as Reference Example 1.

¹HNMR (400 MHz, CDCl₃), δ: 2.54 (3H, d, J=2.0 Hz), 3.64 (3H, s), 6.58 (1H, d, J=7.6 Hz), 7.13 (1H, d, J=7.6 Hz), 7.48-7.54 (1H, m), 7.89 (1H, dd, J=1.6, 8.0 Hz), 8.00 (1H, d, J=1.6 Hz), 8.06-8.14 (1H, m), 8.45-8.49 (1H, m), 8.55 (1H, d, J=8.4 Hz), ESI-MS Found: m/z 323.3 [M+H]⁺.

Example 95

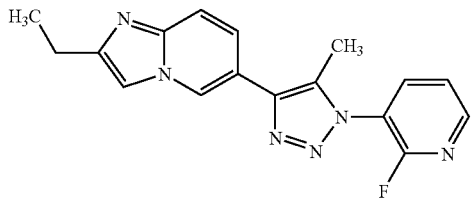

4-(2-ethyl-imidazo[1,2-a]pyridine-6-yl)-1-(-fluoro-pyridine-3-yl)-5-methyl-1H-[1,2,3]triazole 1) Manufacture of 6-bromo-2-ethyl-imidazo[1,2-a]pyridine 5.0 g of 1-bromo-2-butanone was dissolved in 80 ml of ethanol, 5.71 g of 2-amino-5-bromopyridine was added, and the mixture was stirred all night by heating under reflux. After cooling down to room temperature, the solvents were distilled outunder reduced pressure, and ethyl acetated followed by saturated sodium bicarbonate aqueous solution were added. After drying organic layer with anhydrous sodium sulfate, the solvents were distilled outunder reduced pressure. The obtained residues were purified by preparative thin-layer silicagel chromatography (hexane:ethyl acetate=75:25), to obtain 4.82 g of the above compound as a white solid.

¹HNMR (300 MHz, CDCl₃), δ: 1.34 (3H, t, J=7.6 Hz), 2.82 (2H, d, J=7.6 Hz), 7.17 (1H, dd, J=1.9, 9.5 Hz), 7.32 (1H, s), 7.42 (1H, d, J=9.5 Hz), 8.19 (1H, d, J=1.9 Hz), ESI-MS Found: m/z 225.1 [M+H]⁺.

2) Manufacture of 4-(2-ethyl-imidazo[1,2-a]pyridine-6-yl)-1-(2-fluoropyridine-3-yl)-5-methyl-1H-[1,2,3]triazole The above compound was obtained in the same manner as Example 1, with the use of halide obtained in the above 1), and the tin reagent 1-(2-fluoropyridine-3-yl)-5-methyl-4-tributylstanyl-1H-[1,2,3]triazole obtained in Reference Example 1.

¹HNMR (400 MHz, CDCl₃), δ: 1.39 (3H, t, J=7.6 Hz), 2.48 (3H, d, J=2.0 Hz), 2.87 (2H, dq, J=0.76, 7.6 Hz), 7.44 (1H, d, J=0.73 Hz), 7.48-7.54 (2H, m), 7.64 (1H, td, J=0.7, 9.3 Hz), 8.05-8.11 (1H, m), 8.45-8.48 (1H, m), 8.54-8.55 (1H, m), ESI-MS Found: m/z 323.3 [M+H]⁺.

Example 96

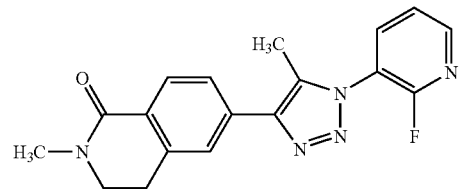

4-(2-methyl-1-oxo-3,4-dihydroisoquinoline-6-yl-1-(2-fluoropyridine-3-yl)-5-methyl-1H-[1,2,3]triazole 20 mg of palladium carbon was added to 10 ml solution of ethanol with 5 mg of 4-(2-methyl-1-oxo-isoquinoline-6-yl)-1-(2-fluoropyridine-3-yl)-5-methyl-1H-[1,2,3]triazole, and hydrogen was added under 4 atm of hydrogen atomosphere. 8 hours later, the reaction solution was filtered, and after distilling out the solvents of the filtrate, the residues were separated and purified by preparative thin-layer chromatography (chloroform/methanol=10/1) to obtain 1 mg of the above compound as a white solid.

¹HNMR (400 MHz, CDCl₃), δ: 2.54 (3H, d, J=2.0 Hz), 3.64 (3H, s), 6.58 (1H, d, J=7.6 Hz), 7.13 (1H, d, J=7.6 Hz), 7.48-7.54 (1H, m), 7.89 (1H, dd, J=1.6, 8.0 Hz), 8.00 (1H, d, J=1.6 Hz), 8.06-8.14 (1H, m), 8.45-8.49 (1H, m), 8.55 (1H, d, J=8.4 Hz), ESI-MS Found: m/z 336.2 [M+H]⁺.

Example 97

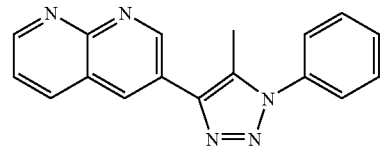

([1.8]naphthylidine-3-yl)-4-phenyl-5-methyl-1H-[1,2,3]triazole

1) Manufacture of (6-bromo-[1,8]naphthylidine-3-yl)-4-phenyl-5-methyl-1H-[1,2,3]triazole Under nitrogen atmosphere, 79 mg of 5-methyl-1-phenyl-1H-[1,2,3]triazole, 46 mg of sodium acetate, and 55 mg of trans-di-μ-acetatebis[2-(di-o-trylphosphino)benzyl]dipalladium (II) were added to 1 ml solution of dimethylformamide with 149 mg of 3,6-dibromo-[1,8]naphthylidine, and the mixture was stirred at 140° C. for 23 hours. Saturated sodium bicarbonate aqueous solution was added to the reaction solution and the products were extracted with chloroform. Chloroform layer was washed with saturated saline solution, dried with anhydrous sodium sulfate. After distilling out the solvents under reduced pressure, the residues were separated and purified by preparative thin-layer chromatography (chloroform/methanol=19/1) to obtain 8.6 mg of the above compound as a colorless solid.

2) Manufacture of ([1,8]naphthylidine-3-yl-4-phenyl-5-methyl-1H-[1,2,3]triazole 1 ml of alcoholic potassium hydroxide solution and palladium hydroxide-carbon in an amount of catalyst were added to 8.6 mg of the compound obtained in the above 1), and the mixture was stirred under hydrogen atmosphere for 30 min. After filtrating the reaction solution, the solvents were distilled outunder reduced pressure, and the residues were separated and purified by preparative thin-layer chromatography (ethyl acetate) to obtain 0.52 mg of the above compound as a colorless solid.
$^1$HNMR (300 MHz, CDCl$_3$), δ: 2.63 (3H, s), 7.50-7.60 (5H, m), 8.20-8.33 (2H, m), 8.68 (1H, d, J=2.7 Hz), 9.15-9.19 (1H, m), 9.57 (1H, d, J=2.5 Hz), ESI-MS Found: m/z 288.1 [M+H]$^+$.

Example 98

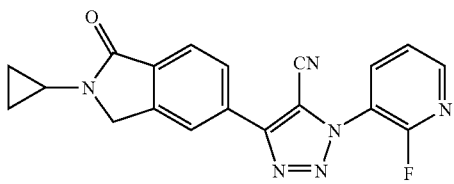

5-(2-cyclopropyl-1-oxo-isoindoline-5-yl)-1-(2-fluoropyridine-3-yl)-4-carbonitrile-1H-[1,2,3]triazole 1) Manufacture of 2-isopropyl-1-oxo-5-(4,4,5,5-tetramethyl[1,3,2]-dioxoborane-2-yl)-isoindoline Under nitrogen atmosphere, 15 ml solution of 1,4-dioxane with 1.01 g of 5-bromo-2-cyclopropyl-1-oxo-indoline obtained in Example 39, 1.02 g of bis(pinacolate)diborane, 1.18 g of potassium acetate, 110 mg of 1,1-bis(diphenylphosphino)-ferrocene, 163.2 mg of [1,1-bis(diphenylphosphino)-ferrocen]dichloropalladium was stirred at 90° C. for 8 hours. After cooling down to room temperature, insoluble matters were filtrated with celite, and the solvents were distilled outunder reduced pressure. The obtained residues were purified by silicagel colum chromatography (hexane:ethyl acetate=50:50) to obtain 1.70 g of the above compound as a white solid.
$^1$HNMR (400 MHz, CDCl$_3$), δ: 0.85-0.94 (4H, m), 1.24 (6H, s), 1.27 (6H, s), 2.90-3.00 (1H, m), 4.30 (2H, s), 7.81-7.95 (3H, m).

2) Manufacture of 3-(2-fluoropyridine-3-yl)-5-trimethylsilanyl-1H-[1,2,3]triazole-2-ethyl carbonate 1.3 ml of 3-(trimethylsilyl)ethyl propinate was added to 5 ml solution of toluene with 800 mg of 3-azido-2-fluoropyridine of Reference Example 1-1, the mixture was stirred at 120° C. for 1 hour. The obtained solution was cooled down to room temperature, and purified by silicagel column chromatography (hexane/ethyl acetate=5/1) to obtain 512 mg of the above compound as a yellow oily matter.
$^1$HNMR (400 MHz, CDCl$_3$), δ: 1.22-1.31 (3H, m), 4.09-4.14 (2H, m), 7.41-7.45 (1H, m), 7.97-8.01 (1H, m), 8.38-8.40 (1H, m), ESI-MS Found: m/z 309.2 [M+H]$^+$.

3) Manufacture of 3-(2-fluoropyridine-3-yl)-5-trimethylsilanyl-1H-[1,2,3]triazole-2-carbonic acid 512 mg of the compound 3-(2-fluoropyridine-3-yl)-5-trimethylsilanyl-1H-[1,2,3]triazole-2-ethyl carbonate was dissolved in 10 ml of ethanol. After cooling down to 0° C., 1.66 ml of 1N of potassium hydroxide aqueous solution was dropped and the mixture was stirred at room temperature for 4 hours. The reaction was stopped with 1M hydrochloric acid, and the solvents were distilled outunder reduced pressure. Saturated sodium bicarbonate aqueous solution was added to the residues, back-extracted with ethyl acetate. Water layer was extracted with ethyl acetate after neutralizing with 1M hydrochloric acid, ethyl acetate layer was washed with saturated saline solution, and dried with anhydrous sodium sulfate. The solvents were distilled outunder reduced pressure, to obtain 1.17 g of crude product the above compound as a white solid.
ESI-MS Found: m/z 281.2 [M+H]$^+$.

4) Manufacture of 3-(2-fluoropyridine-3-yl)-5-trimethylsilanyl-1-[1,2,3]triazole-2-carboxamide 634 mg of the compound 3-(2-fluoropyridine-3-yl)-5-trimethylsilanyl-1H-[1,2,3]triazole-2-carbonic acid obtained in the above 3) was dissolved in 5 ml of tetrahydrofuran. After adding 1.0 ml of triethylamine, the reaction solution was cooled down to 0° C., 5 ml of tetrahydrofuran solution with 927 mg of isobutylchloroformate was added, and the mixture was stirred for 30 min. Ammonium bicarbonate 214 mg was further added and stirred at room temperature for 5 hours. Water was added to the reaction solution, extracted with ethyl acetate. Ethyl acetate layer was washed with saturated saline solution, dried with anhydrous sodium sulfate. After distilling out the solvents under reduced pressure, the residues were separated and purified by silicagel column chromatography (hexane/ethyl acetate=1/2) to obtain 435 g of the above compound as a white solid.

5) Manufacture of 3-(2-fluoropyridine-3-yl)-5-trimethylsilanyl-4-carbonitrile-1H-[1,2,3]triazole 170 mg of the compound 3-(2-fluoropyridine-3-yl)-5-trimethylsilanyl-1H-[1,2,3]triazole-2-carboxamide obtained in the above 4) was dissolved in 10 ml of dichloromethane, 0.11 ml of trifluoroacetate was added, and the mixture was stirred for 5 min. Further, 796 mg of 2-chloro-1,3-dimethyl-2-imidazoliniumhexafluorophosphate and 0.8 ml of triethylamine were added, and the mixture was stirred for 4 hours. Water was added to the reaction solution and the solvents were distilled outunder reduced pressure. Residues were extracted with ethyl acetate. Ethyl acetate layer was washed with saturated saline solution, dried with anhydrous sodium sulfate. After distilling out the solvents under reduced pressure, the residues were separated and purified by preparative thin-layer chromatography (hexane/ethyl acetate=1/2), to obtain 79.4 mg of the above compound as a white solid.

¹HNMR (400 MHz, CDCl₃), δ: 0.50 (9H, s), 7.49-7.52 (1H, m), 8.05-8.10 (1H, m), 8.48-8.50 (1H, m), ESI-MS Found: m/z 262.2 [M+H]⁺.

6) Manufacture of 3-(2-fluoropyridine-3-yl)-5-iodo-4-carbonitrile-1H-[1,2,3]triazole 35 mg of the compound 3-(2-fluoropyridine-3-yl)-5-trimethylsilanyl-4-carbonitrile-1H-[1,2,3]tirazole obtained in the above 5) was dissolved in 1.0 ml of tetrahydrofuran, 52 mg of silvertetrafluoroborate and 168 g of iodine were added, and the mixture was stirred at room temperature for 10 hours. The reaction solution was filtrated with celite. Saturated sodium thiosulfate aqueous solution was added to the filtrate and the solvents were distilled outunder reduced pressure. Water was added to the residues, extracted with ethyl acetate, and ethyl acetate layer was washed with saturated saline solution, and dried with anhydrous sodium sulfate. After distilling out the solvents under reduced pressure, the residues were separate and purified by preparative thin-layer chromatography (hexane/ethyl acetate=2/1) to obtain 31 mg of the above compound as a white solid.

7) Manufacture of 5-(2-cyclopropyl-1-oxo-isoindoline-5-yl)-1-(2-fluoropyridine-3-yl)-4-carbonitrile-1H-[1,2,3]triazole Under nitrogen atmosphere, 35 mg of the compound 2-isopropyl-1-oxo-5-(4,4,5,5-tetramethyl[1,3,2]-dioxoborane-2-yl)-isoindoline obtained in the above 1) and 31 mg of the compound 3-(2-fluoropyridine-3-yl)-5-iodo-4-carbonitrile-1H-[1,2,3]triazole obtained in the above 6) were dissolved in 3.0 ml of dimethylformamide, 27 mg of [1,1-bis(diphenylphosphino)-ferrocene]dichloropalladium was added and the mixture was stirred by heating at 80° C. for 2 hours. The reaction solution was cooled down to room temperature, insoluble matters were removed by celite filtration. Water was added to the filtrate, the products were extracted with ethyl acetate. Ethyl acetate layer was washed with saturated saline solution and dried with anhydrous sodium sulfate. The solvents were distilled outunder reduced pressure, and the residues were separated and purified by preparative thin-layer chromatography (hexane/ethyl acetate=1/2) to obtain 0.74 mg of the above compound as a white solid.

¹HNMR (400 MHz, CDCl₃), δ: 0.93-0.98 (4H, m), 2.99-3.00 (1H, m), 4.45 (2H, s), 7.54-7.57 (1H, m), 8.01 (1H, d, J=8.0 Hz), 8.14-8.16 (1H, m), 8.21 (1H, s), 8.25 (1H, d, J=8.4 Hz), 8.55 (1H, m), ESI-MS Found: m/z 361.3 [M+H]⁺.

Example 99

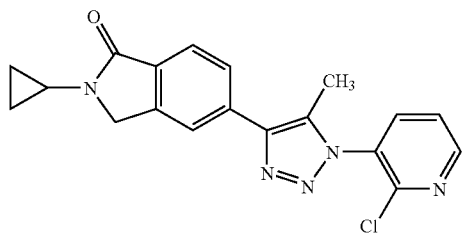

4-(2-cyclopropyl-1-oxo-isoindoline-5-yl)-1-(2-chlropyridine-3-yl)-5-methyl-1H-[1,2,3]triazole The above compound was obtained as a white solid by the same method of Example 49, by a method according thereto, or by a combination of these and ordinary methods, with the use of halogen compound obtained in Example 49, the tin reagent obtained in Reference Example 7 and tetrakistriphenylphosphinpalladium.

¹HNMR (300 MHz, CDCl₃), δ: 0.88-0.99 (4H, m), 2.46 (3H, s), 2.95-3.01 (1H, m), 4.41 (2H, s), 7.55 (1H, dd, J=4.9, 7.9 Hz), 7.81 (1H, dd, J=1.3, 7.9 Hz), 7.88-7.95 (2H, m), 7.99 (1H, d, J=0.7 Hz), 8.67 (1H, dd, J=2.0, 4.9 Hz), ESI-MS Found: m/z 366.0 [M+H]⁺.

Example 100

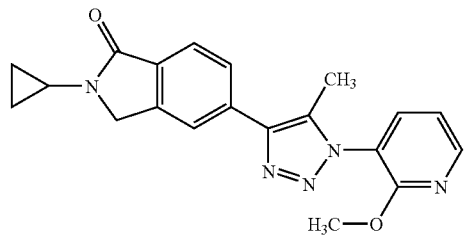

4-(2-cyclopropyl-1-oxo-isoindoline-5-yl)-1-(2-methoxypyridine-3-yl)-5-methyl-1H-[1,2,3]triazole 1) Manufacture of 4-(2-cyclopropyl-1-oxo-isoindoline-5-yl)-1-(2-hydroxypyridine-3-yl)-5-methyl-1H-[1,2,3]triazole 180 mg of 4-(2-cyclopropyl-1-oxo-isoindoline-5-yl)-1-(2-fluoropyridine-3-yl)-5-methyl-1H-[1,2,3]triazole obtained in Example 49 was dissolved in 10 ml of formic acid, and the mixture was stirred for 5 hours. After cooling down to room temperature, the residues obtained by distilling out the solvents under reduced pressure were purified by silicagel column chromatography (chloroform:methanol=90:10) to obtain 112 mg of the above compound as a white solid.

2) Manufacture of 4-(2-cyclopropyl-1-oxo-isoindoline-5-yl)-1-(2-methoxypryridine-3-yl)-5-methyl-1H-[1,2,3]triazole 70 mg of the compound obtained in 1), 83 mg of potassium carbonate, 50 μl of iodomethane were suspended in 2.0 ml of dimethylformamide, and the mixture was stirred at 60° C. for 5 hours. Water was added to the reaction solution, extracted with chloroform. Organic layer was washed with saturated saline solution, dried with anhydrous sodium sulfate. After distilling out the solvents under reduced pressure, residues were separated and purified by thin-layer basic silicagel chromatography (ethyl acetate) to obtain 3.38 mg of the above compound as a white solid.

¹HNMR (400 MHz, CDCl₃), δ: 0.83-1.00 (4H, m), 2.40 (3H, s), 2.91-3.01 (1H, m), 4.01 (3H, s), 4.40 (2H, s), 7.097.17 (1H, m), 7.75-7.83 (2H, m), 7.92 (1H, d, J=7.9 Hz), 7.98 (1H, s), 8.39 (1H, dd, J=1.9, 5.0 Hz), ESI-MS Found: m/z 362.1 [M+H]⁺.

Example 101

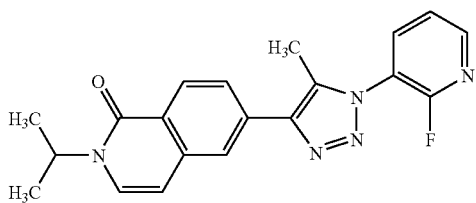

4-(2-isopropyl-1-oxo-isoquinoline-6-yl)-1-(2-fluoro-pyridine-3-yl)-5-methyl-1H-[1,2,3]triazole

1) Manufacture of 6-bromo-2-isopropylisoquinoline-1-one

Under nitrogen atmosphere, 18 mg of 60% sodium hydride was added at 0° C. to 2 ml solution of dimethylformamide with 100 mg of 6-bromo-2H-isoquinoline-1-one, and the mixture was stirred for 30 min. 0.05 ml of isopropyl iodide was added at 0° C., and the mixture was stirred at room temperature for 2 hours. Cold water was added to the reaction solution, extracted with chloroform. Chloroform layer was washed with saturated saline solution, and dried with anhydrous sodium sulfate. After distilling out the solvents under reduced pressure, residues were separated and purified by thin-layer chromatography (hexane/ethyl acetate=3/1) to obtain 17 mg of the above compound.
$^1$HNMR (400 MHz, CDCl$_3$), δ: 1.39 (6H, d, J=7.2 Hz), 5.32-5.40 (1H, m), 6.46 (1H, d, J=7.2 Hz), 7.17 (1H, d, J=7.6 Hz), 7.56 (1H, dd, J=1.8, 8.6 Hz), 7.66 (1H, d, J=2.0 Hz), 8.28 (1H, d, J=8.4 Hz), ESI-MS Found: m/z 267.9 [M+H]$^+$.

2) Manufacture of 4-(2-isopropyl-1-oxo-isoquinoline-6-yl)-1(2-fluoropyridine-3-yl)-5-methyl-1H-[1,2,3]triazole The above compound was obtained by performing coupling reaction in the same manner as Example 3, with the use of the compound obtained in the above 1) and the alkyl tin compound 1-(2-fluoropyridine-3-yl)-5-methyl-4-tributylstanyl-1H-[1,2,3]-triazole similar as Reference Example 1.
$^1$HNMR (400 MHz, CDCl$_3$), δ: 1.42 (6H, d, J=7.2 Hz), 2.54 (3H, d, J=2.4 Hz), 5.39-5.47 (1H, m), 6.64 (1H, d, J=7.2 Hz), 7.21 (1H, d, J=7.6 Hz), 7.48-7.54 (1H, m), 7.88 (1H. dd. J=1.6, 8.4 Hz), 7.99 (1H, d, J=1.6 Hz), 8.09 (1H, td, J=1.6, 7.4 Hz), 8.47 (1h, dt, J=1.5, 4.8 Hz), 8.56 (1H, d, J=8.8 Hz), ESI-MS Found: m/z 364.3 [M+H]$^+$.

Example 102

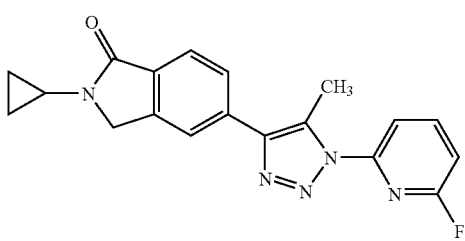

4-(2-cylcopropyl-1-oxo-isoindoline-5-yl)-1-(6-fluoropyridine-2-yl)-5-methyl-1H-[1,2,3]triazole The above compound was obtained as a white solid by the same method as Example 49, by a method according thereto, or by the combination of these and ordinary methods, with the use of halogen compound obtained in Example 49, the tin reagent obtained in Reference Example 8 and tetrakistriphenylphosphinepalladium.
$^1$HNMR (400 MHz, CDCl$_3$), δ: 0.87-0.98 (4H, m), 2.84 (3H, s), 2.95-3.01 (1H, m), 4.41 (2H, s), 7.04-7.07 (1H, m), 7.77 (1H, dd, J=1.5, 8.1 Hz), 7.85-7.86 (1H, m), 7.94 (1H, d, J=8.1 Hz), 7.99-8.10 (2H, m), ESI-MS Found: m/z 350.3 [M+H]$^+$.

Example 103

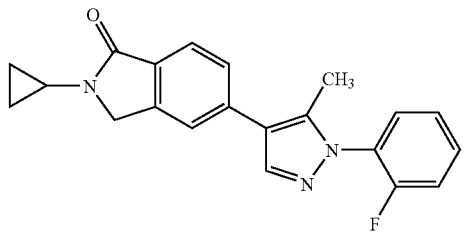

4-(2-cyclopropyl-1-oxo-isoindoline-5-yl)-1-(2-fluorophenyl)-5-methyl-1H-pyrazole

1) Manufacture of 2-cyclopropyl-5-(4,4,5,5-tetramethyl-1,3,2-dioxoborane-2-yl)isoindoline-1-one 1.01 g of 5-bromo-2-cyclopropyl-1-oxo-isoindoline obtained in Example 49, 1.02 g of bispinakoradediborane 1.18 g of potassium acetate, 110 mg of 1,1'-bis-(diphenylphosphino)ferrocene, and 163 mg of [1,1'-bis-(diphenylphosphino)-ferrocene]dichloropalladiumchloromethane complex were suspended in 15 ml of 1,4-dioxane and the mixture was stirred all night at 90° C. The obtained suspended solution was filtrated by celite, and the filtrate was concentrated under reduced pressure. The residues were purified by silicagel column chromatography (hexane:ethyl acetate=50:50) to obtain 1.46 g of the above compound as a white solid.
$^1$HNMR (400 MHz, CDCl$_3$), δ: 0.85-0.94 (4H, m) 1.24 (6H, s), 1.27 (6H, s), 2.90-3.00 (1H, m), 4.30 (2H, s), 7.81-7.90 (3H, m).

2) Manufacture of 4-bromo-1-(2-fluorophenyl)-3-methyl-1H-pyrazole 580 mg of 4-bromo-3-methylpyrazole, 1.0 g of 2-fluorophenylboric acid, 3.3 g of copper acetate, 1.0 g of molecular sieves 4A, and 1.6 ml of pyridine were suspended in 8.0 ml of dimethylformamide, and the mixture was stirred at room temperature for 3 days. The obtained suspended solution was filtrated by celite, and the filtrate was diluted with ethyl acetate. Organic layer was washed with 0.5 N sodium hydride, dried with sodium sulfate, and the solvents were distilled outunder reduced pressure. The residues were purified by silicagel column chromatography (hexane:ethyl acetate=50:50) to obtain 78 mg of the above compound as a crude product.

3) Manufacture of 4-(2-cyclopropyl-1-oxo-isoindoline-5-yl)-1-(2-fluorophenyl)-5-methyl-1H-pyrazole 90 mg of 2-cyclopropyl-5-(4,4,5,5-tetramethyl-1,3,2-dioxoborane-2-yl)isoindoline-1-one obtained in the above 1), 78 mg of 4-bromo-1-(2-fluorophenyl)-3-methyl-1H-pyrazole obtained in 2), 25 mg of [1,1'-bis-(diphenylphosphino) ferrocene]dichloropalladiumdichloromethane complex and 83 mg of potassium carbonate were suspended in 3.0 ml of dimethylformamide, and the mixture was stirred all night at 80° C. Water was added to the reaction solution, and after extracting the products with ethyl acetate, the resultant was washed with saturated ammonium chloride and water, and dried with anhydrous sodium sulfate. After distilling out the solvents under reduced pressure, the residues were purified by thin-layer chromatography (ethyl acetate) to obtain crude products. The obtained crude products were purified again by optically active column (Daicel; CHIRALPAK AD-H colum; hexane/isopropanol=1/1) to obtain 1.9 mg of the above compound as a white solid.

$^1$HNMR (400 MHz, CDCl$_3$), δ: 0.86-0.98 (4H, m), 2.50 (3H, s), 2.95-2.98 (1H, m), 4.37 (2H, s), 7.13-7.18 (2H, m), 7.48-7.54 (2H, m), 7.64-7.68 (2H, m), 7.87 (1H, d, J=7.8 Hz), 7.96 (1H, s), APCI-MS Found: m/z 348.1 [M+H]+.

Example 104

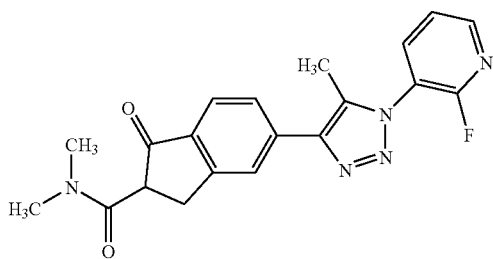

4-(2-dimethylcarbamoyl-1-oxo-indane-5-yl)-1-(2-fluoropyridine-3-yl)-5-methyl-1H-[1,2,3]triazole

1) Manufacture of 5-bromo-2-N,N-dimethylcarbamoyl-1-oxo-indane 60 mg of dimethylamine hydrochloride followed by 0.75 ml of tetrahydrofuran solution with 2M of isopropylmagnesiumchloride were added to 3 ml solution of tetrahydrofuran with 100 mg of 5-bromo-2-methoxycarbonyl-1-oxo-indane at room temperature. After stirring the mixture at room temperature for 1.5 hours, the mixture was diluted with ethyl acetate, washed with water and saturated saline solution and dried with anhydrous sodium sulfate. The solvents were distilled outunder reduced pressure, and the residues were purified by silicagel column chromatography (hexane:ethyl acetate=50:50) to obtain 24 mg of the above compound.

$^1$HNMR (300 MHz, CDCl$_3$), δ: 3.02 (3H, s), 3.17-3.26 (1H, m), 3.34 (3H, s), 3.72-3.84 (1H, m), 4.10-4.18 (1H, m), 7.50-7.70 (3H, m).

2) Manufacture of 4-(2-dimethylcarbamoyl-1-oxo-indane-5-yl)-1-(2-fluoropyridine-3yl)-5-methyl-1H-[1,2,3]triazole The above compound was obtained according to the method of Example 5, with the use of the compound obtained in the above 1) and the compound 1-(2-fluoropyridine-3-yl)-5-methyl-4-tributylstanyl-1H-[1,2,3]triazole of Reference Example 1.

$^1$HNMR (400 MHz, CDCl$_3$), δ: 2.52 (3H, d, J=2.1 Hz), 3.06 (3H, s), 3.34 (1H, dd, J=7.8, 17.1 Hz), 3.36 (3H, s), 3.87 (1H, dd, J=3.6, 17.1 Hz), 4.20 (1H, dd, J=3.6, 7.8 Hz), 7.51 (1H, ddd, J=1.2, 5.1, 7.8 Hz), 7.82-7.84 (2H, m), 7.97 (1H, s), 8.10 (1H, ddd, J=2.1, 7.8, 9.0 Hz), 8.47 (1H, dt, J=2.1, 5.1 Hz), ESI-MS Found: m/z 380.3 [M+H]$^+$.

Example 105

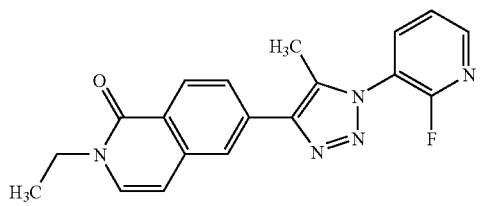

4-(2-ethyl-1-oxo-isoquinoline-6-yl)-1-(2-fluoropyridine-3-yl)-5-methyl-1H-[1,2,3]triazole

1) Manufacture of 6-bromo-2-ethylisoquinoline-1-one

Under nitrogen atmosphere, 22 mg of 60% sodium hydride was added at 0° C. to 3 ml solution of dimethylformamide with 100 mg of 6-bromo-2H-isoquinoline-1-one, and the mixture was stirred for 30 min. 0.04 ml of ethyl iodide was added at 0° C., and the mixture was stirred at room temperature for 3 hours. Cold water was added to the reaction solution, extracted with chloroform. Chloroform layer was washed with saturated saline solution, and dried with anhydrous sodium sulfate. After distilling out the solvents under reduced pressure, the residues were separated and purified by thin-layer chromatography (hexane/ethyl acetate=3/1) to obtain 30 mg of the above compound as a white solid.

$^1$HNMR (400 MHz, CDCl$_3$), δ: 1.38 (3H, t, J=7.4 Hz), 4.04 (2H, q, J=7.2 Hz), 6.41 (1H, d, J=7.2 Hz), 7.10 (1H, d, J=7.6 Hz), 7.56 (1H, dd, J=1.8, 8.6 Hz), 7.67 (1H, d, J=2.0 Hz), 8.28 (1H, d, J=8.4 Hz), ESI-MS Found: m/z 253.9 [M+H]$^+$.

2) Manufacture of 4-(2-ethyl-1-oxo-isoquinoline-6-yl)-1-(2-fluoropyridine-3-yl)-5-methyl-1H-[1,2,3]triazole The above compound was obtained as a white solid by performing coupling reaction in the same manner as Example 3, with the use of the compound obtained in the above 1) and the alkyl tin compound 1-(2-fluoropyridine-3-yl)-5-methyl-4-tributylstanyl-1H-[1,2,3]-triazole, similar as Reference Example 1.

$^1$HNMR (400 MHz, CDCl$_3$), δ: 1.42 (3H, t, J=7.4 Hz), 2.54 (3H, d, J=2.0 Hz), 4.09 (2H, q, J=7.2 Hz), 6.60 (1H, d, J=7.2 Hz), 7.14 (1H, d, J=7.2 Hz), 7.48-7.54 (1H, m), 7.88 (1H, dd,

J=2.0, 8.4 Hz), 8.00 (1H, d, J=2.0 Hz), 8.09 (1H, td, J=2.0, 7.4 Hz), 8.44-8.49 (1H, m), 8.55 (1H, d, J=8.4 Hz), ESI-MS Found: m/z 350.3 [M+H]⁺.

Example 106

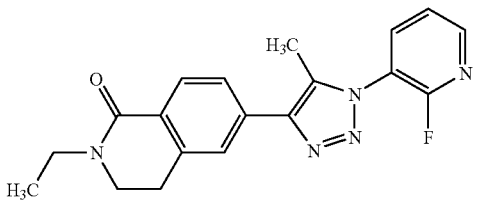

4-(2-ethyl-1-oxo-3,4-dihydroisoquinoline-6-yl)-1-(2-fluoropyridine-3-yl)-5-methyl-1H-[1,2,3]triazole 20 mg of palladium carbon was added to 10 ml solution of ethanol with 5 mg of 4-(2-ethyl-1-oxo-isoquinoline-6-yl)-1-(2-fluoropyridine-3-yl)-5-methyl-1H-[1,2,3]triazole, hydrogen was added under 4 atm of hydrogen atmosphere. 8 hours later, the reaction solution was filtrated and after distilling out the solvents of the filtrate under reduced pressure, the residues were separated and purified by thin-layer chromatography (chloroform/methanol=10/1) to obtain 1 mg of the above compound as a white solid.
¹HNMR (400 MHz, CDCl₃), δ: 1.25 (3H, t, J=7.2 Hz), 2.49 (3H, d, J=2.0 Hz), 3.09 (2H, t, J=6.6 Hz), 3.58-3.70 (4H, m), 7.47-7.53 (1H, m), 7.68 (1H, d, J=7.6 Hz), 7.74 (1H, s), 8.04-8.11 (1H, m), 8.20 (1H, d, J=8.0 Hz), 8.46 (1H, d, J=5.2 Hz), ESI-MS Found: m/z 352.0 [M+H]⁺.

Example 107

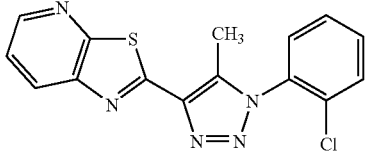

4-(thiazolo[5,4-b]pyridine-2-yl)-1-(2-chlorophenyl)-5-methyl-1H-[1,2,3]triazole

1) Manufacture of 1-(2-chlorophenyl)-5-methyl-4-trimethylsilyl-1H-[1,2,3]triazole Under nitrogen atmosphere, 50 mg of 2-chlorophenylazide and 0.49 ml of 1-(trimethylsilyl)-1-propyine were dissolved in 1 ml of toluene, and heated under reflux for 16 hours. The residues obtained by distilling out the solvents were separated and purified by thin-layer silicagel column chromatography (ethyl acetate/hexane=5/1) to obtain 66 mg of the above compound.
¹HNMR (300 MHz, CDCl₃), δ: 0.40 (9H, s), 2.20 (3H, s), 7.33-7.59 (4H, m), ESI-MS Found: m/z 266.1 [M+H]⁺.

2) Manufacture of 1-(2-chlorophenyl)-4-iode-5-methyl-1H-[1,2,3]triazole

Under nitrogen atmosphere, 65 mg of 1-(2-chlorophenyl)-5-methyl-4-trimethylsilyl-1H-[1,2,3]triazole was dissolved in 2 ml of methanol, 95 mg of tetrafluoroborate silver and 126 mg of iodine were added. The mixture was stirred at room temperature for 4 hours, and the reaction solution was filtered by celite. After diluting the sulfrate solution with chloroform, the mixture was washed with saturated sodium sulfite and water, and dried with anhydrous sodium sulfate. The residues obtained by distilling out the solvents were separated and purified by thin-layer silicagel column chromatography (ethyl acetate/hexane=10/1) to obtain 67 mg of the above compound.
¹HNMR (300 MHz, CDCl₃), δ: 2.20 (3H, s), 7.36-7.63 (4H, m).

3) Manufacture of 4-(thiazolo[5,4-b]pyridine-2-yl)-1-(2-chlorophenyl)-5-methyl-1H-[1,2,3]triazole Under nitrogen atmosphere, 344 mg of 1-(2-chlorophenyl)-4-iodo-5-methyl-[1,2,3]-triazole and 276 mg of thiazolo(5,4-b)pyridine (B. Stanovnik, Synthesis, 1974, 120) were dissolved in 3 ml of DMF. Then, 100 mg of sodium acetate and 103 mg of Herrman catalyst were added, and the mixture was stirred at 140° C. for 8 hours. After diluting the reaction solution with water, the resultant was extracted with chloroform. Organic layer was washed with saturated saline solution, and dried with anhydrous sodium sulfate. The residues obtained by distilling out the solvents were separated and purified by thin-layer silicagel column chromatography (ethyl acete/hexane=1/1) to obtain 30 mg of the above compound as a white solid.
¹HNMR (300 MHz, CDCl₃), δ: 2.69 (3H, s), 7.42-7.68 (5H, m), 8.26 (1H, dd, J=1.5 and 8.3 Hz), 8.60 (1H, dd, J=1.5 Hz, 4.6 Hz), ESI-MS Found: m/z 328.2 [M+H, ESI]

Example 108

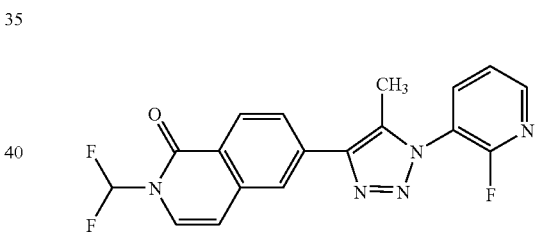

4-(2-difluoromethyl-1-oxo-isoquinoline-6-yl)-1-(2-fluoropyridine-3-yl)-5-methyl-1H-[1,2,3]triazole 1) Manufacture of 6-bromo-2-difluoromethylisoquinoline-1-one Under nitrogen atmosphere, 100 μl of oxy phosphorus trichloride, and 340 μl of N-dimethylaniline were added at room temperature to 3 ml solution of toluene with 300 mg of 6-bromo-2H-isoquinoline-1-one, and the mixture was stirred at 90° C. for 7 hours. Cold water was added to the reaction solution, and extracted with chloroform. Chloroform layer was washed with saturated saline solution, and dried with anhydrous sodium sulfate. After distilling out the solvents under reduced pressure, the residues were separated and purified by thin-layer chromatography (hexane/ethyl acetate=5/1). The obtained compound was made to 2 ml of acetonitrile solution. To this solution, 56 μl of 2,2-difluoro-2-(fluorosulfonyl)acetate and 45 mg of sodium bicarbonate were added at room temperature, and the mixture was stirred at 40° C. for 36 hours. After adding sodium bicarbonate solution to the reaction solution, the mixture was extracted with chloroform.

Chloroform layer was washed with saturated saline solution, and dried with anhydrous sodium sulfate. After distilling out the solvents under reduced pressure, the residues were separated and purified by thin-layer chromatography (hexane/ethyl acetate=1/1) to obtain 44 mg of the above compound as a white solid.

$^1$HNMR (400 MHz, CDCl$_3$), δ: 6.52 (1H, d, J=8.0 Hz), 7.28 (1H, d, J=7.6 Hz), 7.63 (1H, dd, J=1.8, 8.6 Hz), 7.70 (1H, d, J=1.6 Hz), 7.79 (1H, d, J=60.0 Hz), 8.25 (1H, d, J=8.4 Hz), ESI-MS Found: m/z 275.9 [M+H]$^+$.

2) Manufacture of 4-(2-difluoromethyl-1-oxo-isoquinoline-6-yl)-1-(2-fluoropyridine-3-yl)-5-methyl-1H-[1,2,3]triazole The above compound was obtained as a white solid by performing coupling reaction in the same manner as Example 3, with the use of the compound obtained in the above 1), and the alkyl tin compound 1-(2-fluoropyridine-3-yl)-5-methyl-4-tributylstanyl-1H-[1,2,3]triazole, similar as Reference Example 1.

$^1$HNMR (400 MHz, CDCl$_3$), δ: 2.55 (3H, d, J=2.4 Hz), 6.70 (1H, d, J=8.0 Hz), 7.31 (1H, d, J=7.6 Hz), 7.48-7.54 (1H, m), 7.85 (1H, t, J=60.4 Hz), 7.96 (1H, dd, J=1.6, 8.4 Hz), 8.03 (1H, s), 8.06-8.13 (1H, m), 8.48 (1H, d, J=4.8 Hz), 8.52 (1H, d, J=8.4 Hz), ESI-MS Found: m/z 372.0 [M+H]$^+$.

Example 109

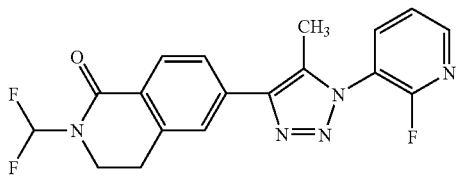

4-(2-difluoromethyl-1-oxo-3,4-dihydroisoquinoline-6-yl)-1-(2-fluoropyridine-3-yl)-5-methyl-1H-[1,2,3]triazole After adding 20 mg of palladium carbon to 10 ml solution of ethanol with 7 mg of 4-(2-difluoromethyl-1-oxo-isoquinoline-6-yl)-1-(2-fluoropyridine-3-yl)-5-methyl-1H-[1,2,3]triazole, hydrogen was added under 4 atm of hydrogen pressure. 8 hours later, the reaction solution was filtrated and after distilling out the solvents of the filtrate under reduced pressure, the residues were separated and purified by thin-layer chromatography (chloroform/methanol=10/1) to obtain 2 mg of the above compound as a white solid.

$^1$HNMR (400 MHz, CDCl$_3$), δ: 2.52 (3H, d, J=1.2 Hz), 3.16 (2H, t, J=6.6 Hz), 3.78 (2H, t, J=6.4 Hz), 7.48-7.54 (1H, m), 7.57 (1H, t, J=61.0 Hz), 7.75 (1H, d, J=8.0 Hz), 7.81 (1H, s), 8.08 (1H, t, J=8.4 Hz), 8.22 (1H, d, J=8.8 Hz), 8.47 (1H, d, J=6.0 Hz), ESI-MS Found: m/z 374.1 [M+H]$^+$.

Example 110

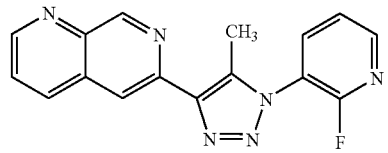

4-([1,7]naphthalidine-6-yl)-1-(2-fluoropyridine-3-yl)-5-methyl-1H-[1,2,3]triazole 1) Manufacture of trifluoromethanesulfonate 1,7-naphthalidine-6-yl ester 264 mg of 6-amino-1,7-naphthalidine (Rosita Tan, Tetrahedron Letters, 1966, 1233) and 2 ml of trifluoromethanesulfonic acid were dissolved in 4 ml of DMF. Then, 251 mg of sodium nitrite was added and the mixture was stirred at room temperature for 90 min. After diluting the reaction solution with ethyl acetate, the mixture was washed with water, saturated sodium bicarbonate aqueous solution and saturated saline solution, and dried with anhydrous sodium sulfate. The residues obtained by distilling out the solvents were separated and purified by silicagel column chromatography (ethyl acetate/hexane=1/1) to obtain 320 mg of the above compound.

$^1$HNMR (300 MHz, CDCl$_3$), δ: 7.61 (1H, s), 7.71 (1H, dd, J=4.1 and 8.5 Hz), 8.26 (1H, d, J=8.5 Hz), 9.12 (1H, d, J=4.1 Hz), 9.35 (1H, s), ESI-MS Found: m/z 279.2 [M+H]$^+$.

2) Manufacture of 4-([1,7]naphthalidine-6yl)-1-(2-fluoropyridine-3-yl)-5-methyl-1H-[1,2,3]triazole 95.2 mg of trifluoromethanesulfonate 1,7-naphthalidine-6-yl ester and 75 mg of 1-(2-fluoropyridine-3-yl)-4-tri-n-butyl-tin-5-methyl-[1,2,3]triazole prepared in Reference Example 1 was dissolved in 2 ml of DMF. 22 mg of triphenylarscine, and 11.7 mg of tris(dibenzylidenacetone)dipalladium (0) was added, and after stirring the mixture at 60° C. for 66 hours, the reaction solution was diluted with saturated sodium bicarbonate aqueous solution, and extracted with chloroform. Organic layer was washed with saturated saline solution, and dried with anhydrous sodium sulfate. The residues obtained by distilling out the solvents were separated and purified by thin-layer silicagel column chromatography (chloroform/methanole=19/1) to obtain 9.7 mg of the above compound as a white solid.

$^1$HNMR (300 MHz, CDCl$_3$), δ: 2.80 (3H, d, J=1.2 Hz), 7.47-7.52 (1H, m), 7.61-7.65 (1H, m), 8.04-8.10 (1H, m), 8.27 (1H, d, J=5.9 Hz), 8.47 (1H, d, J=4.9 Hz), 8.62 (1H, s), 9.03 (1H, d, J=4.0 Hz), 9.55 (1H, s),

ESI-MS Found: m/z 307.0 [M+H]$^+$.

EXAMPLE 111

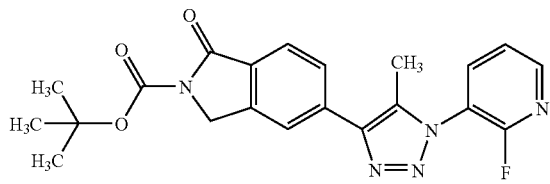

4-(2-tert-butyloxycarbonyl-1-oxo-isoindoline-5-yl)-1-(2-fluoropyridine-3-yl)-5-methyl-1H-[1,2,3]triazole 1) Manufacture of 5-bromo-2-tert-butoxycarbonyl-1-oxo-isoindoline Under nitrogen atmosphere, 1.5 mg of 5-bromo-1-oxo-isoindoline was dissolved in 20 ml of tetrahydrofuran, cooled down to 0° C. Then, 85 mg of N,N-dimethylaminopyridine and 3.0 ml of tert-butylcarbonate were added, and the mixture was stirred at room temperature for 30 min. Methanol was added to the reaction solution, and the solvents were distilled out under reduced pressure. Water was added to the residues, extracted with ethyl acetate. Ethyl acetate layer was washed with saturated saline solution, and dried with anhydrous sodium sulfate. After distilling out the solvents under reduced pressure, the residues were separated and purified by silicagel column chromatography (ethyl acetate/hexane=1/2), to obtain 300 mg of the above compound as a white solid.

$^1$HNMR (400 MHz, CDCl$_3$), δ: 1.60 (9H, s), 4.74 (2H, s), 7.62-7.65 (2H, m), 7.76 (1H, d, J=8.0 Hz),

ESI-MS Found: m/z 344.2 [M+Na]$^+$.

2) Manufacture of 1-(2-fluoropyridine-3-yl)-4-(2-tert-butoxycarbonyl-1-oxo-isoindoline-5-yl)-5-methyl-1H-[1,2,3]triazole Under nitrogen atmosphere, 1.44 g of 5-bromo-2-tert-butoxycarbonyl-1-oxo-isoindoline obtained in the above 1) and 720 mg of 1-(2-chloropyridine-3-yl)-4-tri-n-butyltin-5-methyl-[1,2,3]triazole were dissolved in N,N-dimethylformamide, 178 mg of tetrakistriphenylphosphinepalladium was added. The mixture was heated to 115° C., and stirred for 4 hours. The reaction solution was cooled down to room temperature, and insoluble matters were removed by celite filtration. Water was added to the filtrate. The resultant was extracted with ethyl acetate. Ethyl acetate layer was washed with saturated saline solution, and dried with anhydrous sodium sulfate. After distilling out the solvents under reduced pressure, the residues were separated and purified by silicagel column chromatography (ethyl acetate/hexane=2/1) to obtain 300 mg of the above compound as a white solid.

$^1$HNMR (400 MHz, CDCl$_3$), δ: 1.62 (9H, s), 2.52 (3H, d, J=2.1 Hz), 4.84 (2H, s), 7.48-7.53 (1H, m), 7.87-7.89 (1H, m), 7.99-8.01 (2H, m), 8.03 (1H, m), 8.07-8.11 (1H, m), 8.46-8.48 (1H, m),

ESI-MS Found: m/z 432.2 [M+Na]$^+$.

EXAMPLE 112

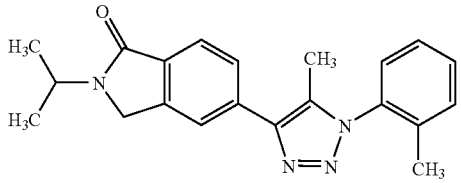

4-(2-isopropyl-1-oxo-isoindoline-5-yl)-1-(2-methylphenyl)-5-methyl-1H-[1,2,3]triazole The above compound was obtained in the same manner as Example 3, with the use of halide obtained in Example 36 and the tin reagent 1-(2-methylphenyl)-5-methyl-4-tributylstannyl-1H-[1,2,3]-triazole, obtained in Reference Example 9.

$^1$HNMR (400 MHz, CDCl$_3$), δ: 1.33 (6H, d, J=6.4 Hz), 2.12 (3H, s), 2.37 (3H, s), 4.43 (2H, s), 4.68-4.78 (1H, m), 7.15-7.35 (1H, m), 7.38-7.55 (3H, m), 7.83 (1H, dd, J=1.4, 7.8 Hz), 7.94 (1H, d, J=8.0 Hz), 8.06 (1H, s),

ESI-MS Found: m/z 347.2 [M+H]$^+$.

EXAMPLE 113

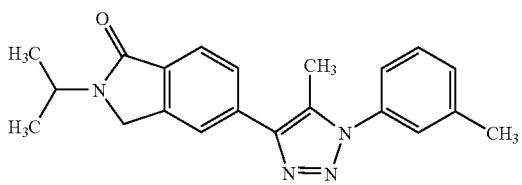

4-(2-isopropyl-1-oxo-isoindoline-5-yl)-1-(3-methylphenyl)-5-methyl-1H-[1,2,3]triazole The above compound was obtained in the same manner as Example 3, with the use of halide obtained in Example 36 and the tin reagent 1-(3-methylphenyl)-5-methyl-4-tributylstannyl-1H-[1,2,3]-triazole, obtained in Reference Example 10.

$^1$HNMR (400 MHz, CDCl$_3$), δ: 1.33 (6H, d, J=6.8 Hz), 2.48 (3H, s), 2.52 (3H, s), 4.43 (2H, s), 4.68-4.78 (1H, m), 7.25-7.42 (3H, m), 7.47 (1H, t, J=7.8 Hz), 7.8 (1H, d, J=8.0 Hz), 7.94 (1H, d, J=8.0 Hz), 8.00 (1H, s),

ESI-MS Found: m/z 347.1 [M+H]$^+$.

EXAMPLE 114

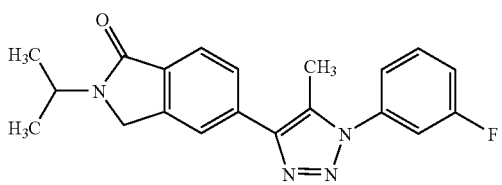

4-(2-isopropyl-1-oxo-isoindoline-5-yl)-1-(3-fluorophenyl-5-methyl-1H-[1,2,3]triazole The above compound was obtained in the same manner as Example 3, with the use of halide obtained in Example 36 and the tin reagent 1-(3-fluorophenyl)-5-methyl-4-tributylstanyl-1H-[1,2,3]-triazole, obtained in Reference Example 11.
$^1$HNMR (400 MHz, CDCl$_3$), δ: 1.33 (6H, d, J=6.8 Hz), 2.56 (3H, s), 4.43 (2H, d, J=0.4 Hz), 4.65-4.75 (1H, m), 7.25-7.39 (3H, m), 7.55-7.62 (1H, m), 7.79 (1H, d, J=8.4 Hz), 7.95 (1H, d, J=7.6 Hz), 7.99 (1H, s),
ESI-MS Found: m/z 351.1 [M+1]$^+$.

EXAMPLE 115

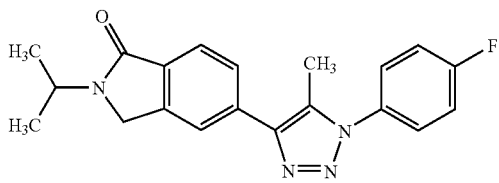

4-(2-isopropyl-1-oxo-isoindoline-5-yl)-1-(4-fluorophenyl)-5-methyl-1H-[1,2,3]triazole The above compound was obtained in the same manner as Example 3, with the use of halide obtained in Example 36 and the tin reagent 1-(4-fluorophenyl)-5-methyl-4-tributylstanyl-1H-[1,2,3]triazole, obtained in Reference Example 12.
$^1$HNMR (400 MHz, CDCl$_3$), δ: 1.33 (6H, d, J=6.8 Hz), 2.52 (3H, s), 4.43 (2H, s), 4.65-4.75 (1H, m), 7.26-7.34 (2H, m), 7.50-7.58 (2H, m), 7.79 (1H, d, J=8.8 Hz), 7.95 (1H, d, J=8.0 Hz), 8.00 (1H, s),
ESI-MS Found: m/z 351.1 [M+H]$^+$.

EXAMPLE 116

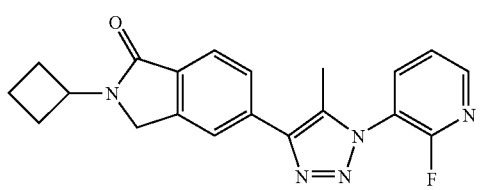

4-(2-cyclobutyl-1-oxo-isoindoline-5-yl)-1-(2-fluoropyridine-3-yl)-5-methyl-1H-[1,2,3]triazole 1) Manufacture of 5-bromo-2-cyclobutyl-1-oxo-isoindoline Under nitrogen atmosphere, 200 mg of 4-bromo-2-bromomethyl methyl benzoate was dissolved in toluene. Then, 418 mg of cyclobutylamine hydrochloride and 0.4 ml of triethylamine were added, and the mixture was heated under reflux for 2 hours. The reaction solution was cooled down to room temperature, and after distilling out the solvents under reduced pressure, the residues were separated and purified by thin-layer silicagel column chromatography (ethyl acetate/hexane=1/2) to obtain 60 mg of the above compound as a white solid.

$^1$HNMR (400 MHz, CDCl$_3$)δ: 1.74-1.80 (2H, m), 2.23-2.30 (4H, m), 4.43 (2H, s), 4.89-4.93 (1H, m), 7.58 (1H, d, J=8.0 Hz), 7.62 (1H, s), 7.68 (1H, d, J=8.0 Hz),
ESI-MS Found: m/z 266.2 [M+H]$^+$.

2) Manufacture of 1-(2-fluoropyridine-3-yl)-4-(2-cyclobutyl-1-oxo-isoindoline-5-yl)-5-methyl-1H-[1,2,3]triazole Under nitrogen atmosphere, 21 mg of 5-bromo-2-cyclobutyl-1-oxo-isoindoline obtained in the above 1) and 30 mg of 1-(2-chloropyridine-3-yl)-4-tri-n-butyltin-5-methyl-[1,2,3]triazole prepared in Reference Example 1 were dissolved in toluene. Then, 11 mg of tetrakistriphenylphosphinepalladium was added and the mixture was heated all night under reflux. The reaction solution was cooled down to room temperature, insoluble matters were removed by celite filtration. The solvents were distilled outunder reduced pressure, and the residues were separated and purified by thin-layer silicagel column chromatography (ethyl acetate/hexane=2/1) to obtain 16 mg of the above compound as a white solid.
$^1$HNMR (400 MHz, CDCl$_3$), δ:1.78-1.83 (2H, m), 2.29-2.35 (4H, m), 2.50 (3H, d, J=2.1 Hz), 4.55 (2H, s), 4.96-5.00 (1H, m), 7.49-7.52 (1H, m), 7.80-7.82 (1H, m), 7.93-7.95 (1H, m), 8.00 (1H, m), 8.07-8.11 (1H, m), 8.46-8.47 (1H, m),
ESI-MS Found: m/z 364.3 [M+H]$^+$.

EXAMPLE 117

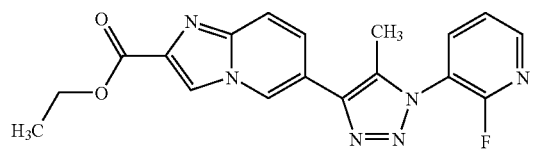

4-(2-ethoxycarbonyl-imidazo[1,2-a]pyridine-6-yl)-1-(2-fluoropyridine3-yl)-5-methyl-1H-[1,2,3]triazole The above compound was obtained as a white solid, by the same method as Example 49, by a method according thereto, or by a combination of these and ordinary methods with the use of 6-bromo-2-ethoxycarbonyl-imidazo[1,2-a]pyridine, the tin reagent obtained in Reference Example 1, and tetrakistriphenylphosphinepalladium.
$^1$HNMR (400 MHz, CDCl$_3$), δ: 1.46 (3H, t, J=7.1 Hz), 2.50 (3H, d, J=2.2 Hz), 4.49 (2H, q, J=7.1 Hz), 7.50-7.54 (1H, m), 7.65-7.69 (1H, m), 7.82 (1H, d, J=9.4 Hz), 8.05-8.12 (1H, m), 8.29 (1H, s), 8.48 (1H, d, J=4.9 Hz), 8.02 (1H, s),
ESI-MS Found: m/z 367.3 [M+H]$^+$.

EXAMPLE 118

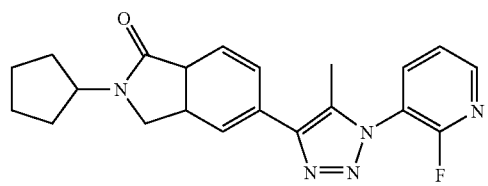

4-(2-cyclopentyl-1-oxo-isoindoline-5-yl)-1-(2-fluo-ropyridine-3-yl)-5-methyl-1H-[1,2,3]triazole 1) Manufacture of 5-bromo-2-cyclopentyl-1-oxo-isoindoline The above compound was obtained by performing the reaction in the same manner as Example 116-1), except using cyclopentylamine instead of cyclobutylamine hydrochloride which was used in Example 116-1).

¹HNMR (400 MHz, CDCl₃), δ: 1.58-1.83 (6H, m), 1.90-2.04 (2H, m), 4.34 (2H, s), 4.70-4.78 (1H, m), 7.58 (1H, d, J=8.0 Hz), 7.59 (1H, s), 7.69 (1H, d, J=8.0 Hz),

ESI-MS Found: m/z 282.2 [M+H]⁺.

2) Manufacture of 1-(2-fluoropyridine-3-yl)-4-(2-cyclopentyl-1-oxo-isoindoline-5-yl)-5-methyl-1H-[1,2,3]triazole The above compound was obtained according to the method of Example 116-2), with the use of the compound obtained in the above 1), and the compound 1-(2-fluoropyridine-3-yl)-5-methyl-4-tributylstanyl-1H-[1,2,3]-triazole of Reference Example 1.

¹HNMR (400 MHz, CDCl₃), δ: 1.70-2.04 (6H, m), 2.50 (3H, m), 4.45 (2H, s), 4.82-4.79 (1H, m), 7.49-7.52 (1H, m), 7.80-7.82 (1H, m), 7.94-7.98 (2H, m), 8.07-8.11 (1H, m), 8.46-8.47 (1H, m),

ESI-MS Found: m/z 378.3 [M+H]⁺.

EXAMPLE 119

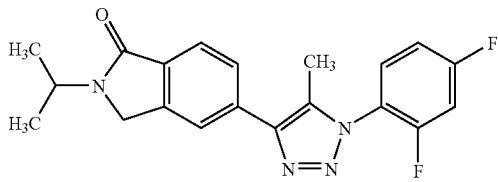

4-(2-isopropyl-1-oxo-isoindoline-5-yl)-1-(2,4-difluo-rophenyl)-5-methyl-1H-[1,2,3]triazole Under nitrogen atmosphere, 125 mg of the halide compound 5-bromo-2-isopropyl-1-oxo-isoindoline obtained in Example 36 and 280 mg of the tin compound 1-(2,4-difluorophenyl)-5-methyl-4-tributylstanyl-1H-[1,2,3]triazole of Reference Example 13 were dissolved in 3 ml of toluene, 115 mg of tetrakistriphenylphosphinepalladium was added to degas. The resultant was stirred by heating to 115° C. The reaction solution was cooled down to room temperature, and insoluble matters were removed by celite filtration. After distilling out the solvents under reduced pressure, residues were separated and purified by silicagel chromatography (ethyl acetated/hexane=1/2), washed with pentane to obtain 130 mg of the above compound as a white solid.

¹HNMR (400 MHz, CDCl₃), δ: 1.33 (6H, d, J=6.8 Hz), 2.45 (3H, d, J=1.6 Hz), 4.43 (2H, s), 4.65-4.75 (1H, m), 7.05-7.18 (2H, m), 7.55-7.61 (1H, m), 7.80 (1H, d, J=8.0 Hz), 7.95 (1H, d, J=8.0 Hz), 8.00 (1H, s),

ESI-MS Found: m/z 369.1 [M+H]⁺.

EXAMPLE 120

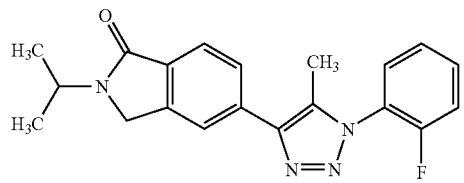

4-(2-isopropyl-1-oxo-isoindoline-5-yl)-1-(2-fluo-rophenyl)-5-methyl-1H-[1,2,3]triazole The above compound was obtained in the same manner as Example 3, with the use of halide obtained in Example 36, and the tin reagent 1-(2-fluorophenyl)-5-methyl-4-tributyl-stanyl-1H-[1,2,3]triazole obtained in Reference Example 4.

¹HNMR (400 MHz, CDCl₃), δ: 1.33 (6H, d, J=6.8 Hz), 2.47 (3H, d, J=2.0 Hz), 4.43 (2H, s), 4.65-4.75 (1H, m), 7.32-7.42 (2H, m), 7.55-7.63 (2H, m), 7.82 (1H, dd, J=1.6, 8.0 Hz), 7.95 (1H, d, J=7.6 Hz), 8.02 (1H, d, J=0.8 Hz),

ESI-MS Found: m/z 352.2 [M+H]⁺.

EXAMPLE 121

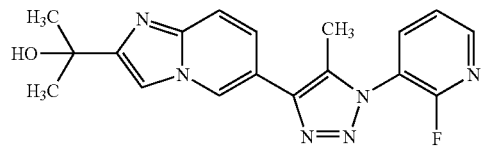

1-(2-fluoropyridine3-yl)-4-(2-(1-hydroxy-1-methyl-ethyl)-imidazo[1,2-a]pyridine-6-yl)-5-methyl-1H-[1,2,3]triazole 18.3 mg of 4-(2-ethoxycarbonyl-imidazo[1,2-a]pyridine-6-yl)-1-(2-fluoropyridine-3-yl)-5-methyl-1H-[1,2,3]triazole obtained in Example 117 was dissolved in 1.0 ml of tetrahydrofuran, cooled down to 0° C. Then, 500 μl of tetrahydrofuran with 0.93 M of methyl magnesium bromide was dropped thereto. The mixture was stirred all night at room temperature, and saturated sodium bicarbonate solution was added. The products were extracted with chloroform, dried with anhydrous sodium sulfate, and then the solvents were distilled outunder reduced pressure. The obtained residues were separated and purified by thin-layer basic silicagel chromatography (ethyl acetate) to obtain 1.02 mg of the above compound as a white solid.

¹HNMR (400 MHz, CDCl₃), δ: 1.71 (6H, s), 2.48 (3H, d, J=2.0 Hz), 2.79 (1H, brs), 7.48-7.61 (3H, m), 7.69 (1H, d, J=9.3 Hz), 8.05-8.11 (1H, m), 8.46-8.49 (1H, m), 8.57 (1H, dd, J=1.0, 1.7 Hz), APCI-MS Found: m/z 353.0 [M+H]⁺.

EXAMPLE 122

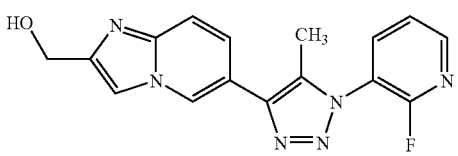

1-(2-fluoropyridine3-yl)-4-(2-hydroxymethyl-imidazo[1,2-a]pyridine-6-yl)-1-(2-fluoropyridine-3-yl)-5-methyl-1H-[1,2,3]triazole 36.6 mg of 4-(2-ethoxycarbonyl-imidazo[1,2-a]pyridine-6-yl)-1-(2-fluoropyridine-3-yl)-5-methyl-1H-[1,2,3]triazole obtained in Example 17 was dissolved in 1.0 ml of tetrahydrofuran, cooled down to 0° C., and 10 mg of lithium aluminium hydride was added. After stirring the mixture for 30 min at room temperature, sodium sulfate 10 hydrate was added, and further stirred for 2 hours. The obtained suspended solution was diluted with ethyl acetate and chloroform and the insoluble matters were filtrated. Then, the filtrate was concentrated under reduced pressure. The obtained residues were separated and purified by thin-layer silicagel chromatography (ethyl acetate and few drops of methanol) to obtain 24.6 mg of the above compound as a white solid.

¹HNMR (400 MHz, CDCl₃), δ: 2.49 (3H, d, J=2.0 Hz), 4.90 (2H, s), 7.48-7.53 (1H, m), 7.59 (1H, dd, J=1.5, 9.3 Hz), 7.65-7.71 (2H, m), 8.06-8.11 (1H, m), 8.46-8.49 (1H, m), 8.59 (1H, s),

ESI-MS Found: m/z 325.1 [M+H]⁺.

EXAMPLE 123

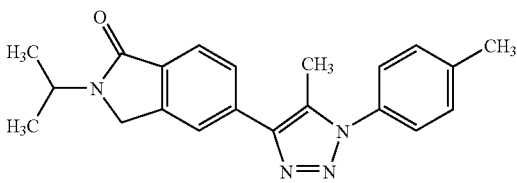

4-(2-isopropyl-1-oxo-isoindoline-5-yl)-1-(4-methylphenyl-5-methyl-1H-[1,2,3]triazole The above compound was obtained in the same manner as Example 3, with the use of halide obtained in Example 36, and the tin reagent 1-(4-methylphenyl)-5-methyl-4-tributylstanyl-1H-[1,2,3]triazole, obtained in Reference Example 14.

¹HNMR (400 MHz, CDCl₃), δ: 1.33 (6H, d, J=6.8 Hz), 2.48 (3H, s), 2.51 (3H, s), 4.42 (2H, s), 4.67-4.77 (1H, m), 7.39 (4H, s), 7.79 (1H, d, J=8.0 Hz), 7.94 (1H, d, J=7.6 Hz), 8.00 (1H, d, J=0.8 Hz),

ESI-MS Found: m/z 347.2 [M+H]⁺.

EXAMPLE 124

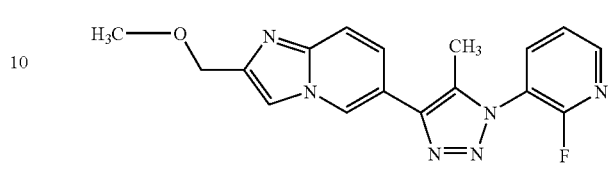

1-(2-fluoropyridine3-yl)-4-(2-methoxymethyl-imidazo[1,2-a]pyridine-6-yl)-1-(2-fluoropyridine3-yl)-5-methyl-1H-[1,2,3]triazole 20.0 mg of 1-(2-fluoropyridine-3-yl)-4-(2-hydroxymethyl-imidazo[1,2-a]pyridine-6-yl)-5-methyl-1H-[1,2,3]triazole obtained in Example 122 was dissolved in 1.0 ml of dimethylformamide, cooled down to 0° C. Then, 24 mg of 60% sodium hydride, and 50 μl of methyl iodide were added. After stirring the mixture at room temperature for 1 hour, saturated sodium bicarbonate solution was added. The products were extracted by chloroform, dried with anhydrous sodium sulfate, and the solvents were extracted under reduced pressure. The obtained residues were separated and purified by thin-layer basic silicagel chromatography (ethyl acetate) to obtain 2.91 mg of the above compound as a white solid.

¹HNMR (400 MHz, CDCl₃), δ: 2.49 (3H, d, J=2.0 Hz), 3.52 (3H, s), 4.67 (2H, s), 7.48-7.53 (1H, m), 7.56 (1H, dd, J=1.7, 9.2 Hz), 7.65-7.71 (2H, m), 8.06-8.11 (1H, m), 8.46-8.48 (1H, m), 8.58-8.60 (1H, m), APCI-MS Found: m/z 339.0 [M+H]⁺.

EXAMPLE 125

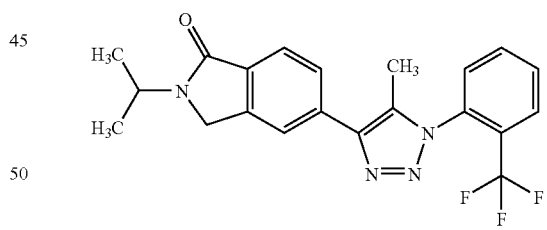

4-(2-isopropyl-1-oxo-isoindoline-5-yl)-1-(2-trifluoromethyl-phenyl)-5-methyl-1H-[1,2,3]triazole The above compound was obtained in the same manner as Example 3, with the use of halide obtained in Example 36, and the tin reagent 1-(2-trifluoromethyl-phenyl)-5-methyl-4-tributylstanyl-1H-[1,2,3]-triazole obtained in Reference Example 15.

¹HNMR (400 MHz, CDCl₃), δ: 1.33 (6H, d, J=6.8 Hz), 2.36 (3H, s), 4.43 (2H, s), 4.65-4.75 (1H, m), 7.47 (1H, d, J=7.6 Hz), 7.75-7.85 (3H, m), 7.94 (2H, d, J=8.0 Hz), 8.05 (1H, s),

ESI-MS Found: m/z 401.1 [M+H]⁺.

EXAMPLE 126

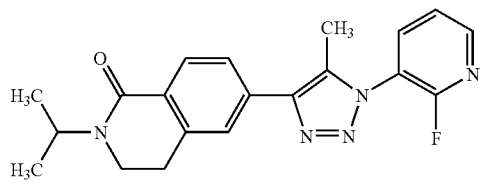

4-(2-isopropyl-1-oxo-3,4-dihydroisoquinoline-6-yl)-1-(2-fluoropyridine-3-yl)-5-methyl-1H-[1,2,3]triazole 30 mg of palladium carbon was added to 10 ml of ethanol solution with 10 mg of 4-(2-isopropyl-1-oxo-isoquinoline-6-yl)-1-(2-fluoropyridine-3-yl)-5-methyl-1H-[1,2,3]triazole, and hydrogen was added under 4 atm of hydrogen pressure. 8 hours later, the reaction solution was filtrated and after distilling out the solvents of the filtrate under reduced pressure, the residues were separated and purified by thin-layer chromatography (chloroform/methanol=10/1) to obtain 7 mg of the above compound as a white solid.

$^1$HNMR (400 MHz, CDCl$_3$), δ: 1.23 (6H, d, J=6.8 Hz), 2.49 (3H, d, J=2.0 Hz), 3.04 (2H, t, J=6.4 Hz), 3.49 (2H, t, J=6.4 Hz), 5.09-5.16 (1H, m), 7.26-7.52 (1H, m), 7.68 (1H, dd, J=1.6, 8.0 Hz), 7.74 (1H, d, J=0.4 Hz), 8.08 (1H, td, J=1.6, 8.0 Hz), 8.20 (1H, d, J=8.0 Hz), 8.44-8.48 (1H, m),

ESI-MS Found: m/z 366.1 [M+H]$^+$.

EXAMPLE 127

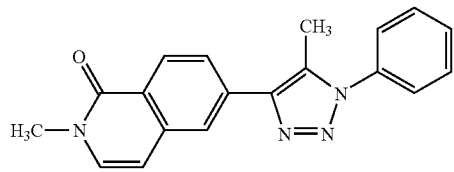

4-(2-methyl-1-oxo-isoquinoline-6-yl)-1-phenyl-5-methyl-1H-[1,2,3]triazole

The above compound was obtained in the same manner as Example 3, with the use of halide obtained in Example 94, and the tin reagent 1-phenyl-5-methyl-4-tributylstanyl-1H-[1,2,3]triazole obtained in Reference Example 5.

$^1$HNMR (400 MHz, CDCl$_3$), δ: 2.57 (3H, s), 3.64 (3H, s), 6.58 (1H, d, J=6.8 Hz), 7.12 (1H, d, J=7.6 Hz), 7.50-7.63 (5H, m), 7.88 (1H, dd, J=2.0, 8.4 Hz), 8.02 (1H, d, J=2.0 Hz), 8.54 (1H, d, J=8.4 Hz),

ESI-MS Found: m/z 317.1 [M+H]$^+$.

EXAMPLE 128

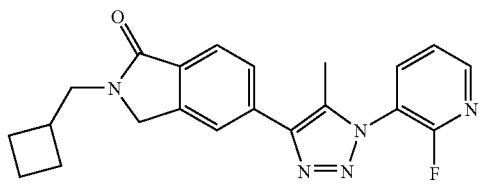

4-(2-cyclobutylmethyl-1-oxo-isoindoline-5-yl)-1-(2-fluoropyridine-3-yl)-5-methyl-1H-[1,2,3]triazole 1) Manufacture of 5-bromo-2-cyclobutylmethyl-1-oxo-isoindoline The above compound was obtained by performing the reaction by the same method as Example 116-1), except using 2-cyclobutylmethylamine instead of cyclobutylamine hydrochloride which was used in Example 116-1).

$^1$HNMR (400 MHz, CDCl$_3$), δ: 1.79-1.84 (2H, m), 1.89-1.95 (2H, m), 2.06-2.11 (2H, m), 2.65-2.69 (1H, m), 3.63 (1H, d, J=7.6 Hz), 4.32 (2H, s), 4.70-4.78 (1H, m), 7.57-7.60 (2H, m), 7.69-7.71 (1H, m),

ESI-MS Found: m/z 282.2 [M+H]$^+$.

2) Manufacture of 4-(2-cyclobutylmethyl-1-oxo-isoindoline-5-yl)-1-(2-fluoropyridine-3-yl)-5-methyl-1H-[1,2,3]triazole The above compound was obtained according to the method of Example 116-2) with the use of the compound obtained in the above 1), and the compound 1-(2-fluoropyridine-3-yl)-5-methyl-4-tributylstanyl-1H-[1,2,3]triazole of Reference Example 1.

$^1$HNMR (400 MHz, CDCl$_3$), δ: 1.83-1.99 (4H, m), 2.08-2.13 (2H, m), 2.50 (3H, d, J=1.9 Hz), 2.68-2.76 (1H, m), 3.09 (2H, d, J=7.6 Hz), 4.44 (2H, s), 7.49-7.52 (1H, m), 7.80-7.82 (1H, m), 7.94 (1H, s), 7.96 (1H, m), 8.06-8.11 (1H, m), 8.45-8.47 (1H, m),

ESI-MS Found: m/z 378.1 [M+H]$^+$.

EXAMPLE 129

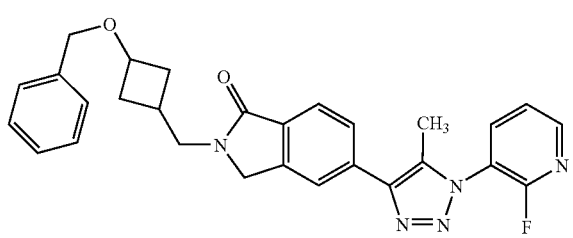

4-[2-(3-benzyloxy-cyclobutylmethyl)-1-oxo-isoindoline-5-yl]-1-(2-fluoropyridine-3-yl)-5-methyl-1H-[1,2,3]triazole 1) Manufacture of 3-benzyloxy-cyclobutylmethylazide At room temperature, 840 μl of triethylamine followed by 232 μl of methanesulfonyl chloride were added to 4 ml solution of tetrahydrofuran with 375 mg of 3-benzyloxy-cyclobutanmethanol. After stirring for 30 min at room temperature, the mixture was diluted with ethyl acetate, washed with water, saturated sodium bicarbonate water and saturated saline solution, and dried with anhydrous sodium sulfate. The solvents were distilled outunder reduced pressure. The obtained residues were dissolved in 4 ml of dimethylformamide, and 145 mg of sodium azide was added to stir all night at 80° C. The reaction solution was cooled down to room temperature, diluted with ethyl acetate, washed with water and saturated saline solution, and dried with anhydrous sodium sulfate. The residues obtained by distilling out the solvents under reduced pressure were separated and purified by silicagel column chromatography (hexane: ethyl acetate=85:15) to obtain 365 mg of the above compound as a white solid.

$^1$HNMR (300 MHz, CDCl$_3$), δ: 1.70-2.60 (5H, m), 3.25-3.35 (2H, m), 3.90-4.20 (1H, m), 4.40-4.42 (2H, m), 7.25-7.38 (5H, m).

2) Manufacture of 5-bromo-2-(3-benzyloxy-cyclobutylmethyl)-1-oxo-isoindoline

After dissolving 365 mg of 3-benzyloxy-cyclobutylmethylazide in 10 ml of methanol, 80 mg of 10% palladium-carbon was added, and the mixture was stirred under hydrogen atmosphere for 1 hour. The reaction solution was filtrated with celite, and the obtained filtrate was concentrated under reduced pressure. The obtained residues were dissolved in 5 ml of toluene, 378 g of 4-bromo-2-bromomethyl methyl benzoate and 1 ml of triethylamine were added, and the mixture was stirred all night by heating under reflux. The reaction solution was cooled down to room temperature, diluted with ethyl acetate, washed with water and saturated saline solution, and dried with anhydrous sodium sulfate. The residues obtained by distilling out the solvents under reduced pressure were separated and purified by silicagel column chromatography (ethyl acetate:hexane=80: 20) to obtain 352 mg of the above compound as a white solid.

$^1$HNMR (300 MHz, CDCl$_3$), δ: 1.75-2.70 (4H, m), 3.62-3.70 (2H, m), 3.87-4.30 (1H, m), 4.30-4.36 (2H, m), 4.40-4.42 (2H, m), 7.28-7.74 (8H, m),

ESI-MS Found: m/z 310.1 [M+H]$^+$.

3) Manufacture of 4-[2-(3-benzyloxy-cyclobutylmethyl-1-oxo-isoindoline-5-yl)-1-(2-fluoropyridine-3-yl)-5-methyl-1H-[1,2,3]]triazole The above compound was obtained according to the method of Example 5, with the use of the compound obtained in the above 2), and the compound 1-(2-fluoropyridine-3-yl)-5-methyl-4-tributylstanyl-1H-[1,2,3]triazole of Reference Example 1.

$^1$HNMR (400 MHz, CDCl$_3$), δ: 1.79-1.92 (1H, m), 2.12-2.25 (2H, m), 2.41-2.50 (3H, m), 2.62-2.75 (1H, m), 3.66-3.77 (2H, m), 3.90-4.00 (1/2H, m), 4.25-4.35 (1/2H, m), 4.40-4.49 (4H, m), 7.29-7.60 (4H, m), 7.62-7.71 (2H, m), 7.79-7.85 (1H, m), 7.93-7.99 (2H, m), 8.05-8.04 (1H, m), 8.45-8.49 (1H, m),

ESI-MS Found: m/z 484.3 [M+H]$^+$.

EXAMPLE 130

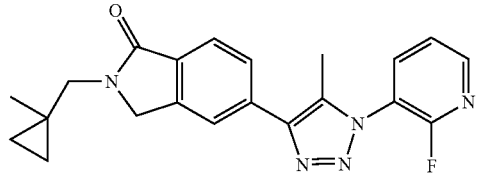

4-(2-(1-methyl-cyclopropylmethyl)-1-oxo-isoindoline-5-yl)-1-(2-fluoropyridine-3-yl)-5-methyl-1H-[1,2,3]triazole 1) Manufacture of 5-bromo-2-(1-methyl-cyclopropylmethyl)-1-oxo-isoindoline Under nitrogen atmosphere, 50 mg of 4-bromo-2-bromomethyl methyl benzoate was dissolved in methanol, 1-methyl-cyclopropylmethylamine and 0.1 ml of triethylamine were added and heated all night under reflux. The reaction solution was cooled down to room temperature. After distilling out the solvents under reduced pressure, the residues were separated and purified by silicagel column chromatography (ethyl acetate/hexane=1/2) to obtain 28 mg of the above compound as a white solid.

$^1$HNMR (400 MHz, CDCl$_3$), δ: 0.43-0.44 (2H, m), 0.50-0.53 (2H, m), 1.02 (3H, s), 3.46 (2H, s), 4.44 (2H, s), 4.89-4.93 (1H, m), 7.59-7.62 (2H, m), 7.72 (1H, d, J=8.0 Hz),

ESI-MS Found: m/z 282.1 [M+H]$^+$.

2) Manufacture of 4-(2-1-methyl-cyclopropylmethyl)-1-oxo-isoindoline-5-yl)-1-(2-fluoropyridine-3-yl)-5-methyl-1H-[1,2,3]triazole Under nitrogen atmosphere, 28 mg of 5-bromo-2-(1-methyl-cyclopropylmethyl)-1-oxo-isoindoline obtained in the above 1) and 50 mg of 1-(2-chloropyridine-3-yl)-4-tri-n-butyltin-5-methyl-[1,2,3]triazole prepared in Reference Example 1 were dissolved in toluene, 11 mg of tetrakistriphenylphosphinepalladium was added and the mixture was heated under reflux for 2 hours. The reaction solution was cooled down to room temperature, and insoluble matters were removed by celite filtration. After distilling out the solvents under reduced pressure, the residues were separated and purified by thin-layer silicagel column chromatography (ethyl acetate/hexane=2/1) to obtain 24 mg of the above compound as a white solid.

$^1$HNMR (400 MHz, CDCl$_3$), δ: 0.44-0.46 (2H, m), 0.55 (2H, m), 1.07 (3H, s), 2.51 (3H, d, J=2.15), 3.52 (2H, s), 4.55 (2H, s), 7.49-7.52 (1H, m), 7.82-7.84 (1H, m), 7.96-7.98 (2H, m), 8.07-8.12 (1H, m), 8.46-8.47 (1H, m),

ESI-MS Found: m/z 378.2 [M+H]$^+$.

EXAMPLE 131

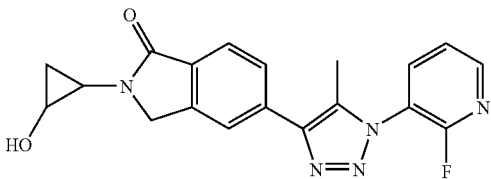

4-(2-(2-hydroxy-cyclopropyl)-1-oxo-isoindoline-5-yl)-1-(2-fluoropyridine-3-yl)-5-methyl-1H-[1,2,3]] triazole 1) Manufacture of 5-bromo-2-(2-trans*-tetrahydro-2H-2-pyranyloxy-cyclopropyl)-1-oxo-isoindoline Under nitrogen atmosphere, 30 mg of 4-bromo-2-bromomethyl methyl benzoate was dissolved in methanol, 2-tetrahydro-2H-2-pyranyloxy-cyclopropylamine and 0.1 ml of triethylamine were added and heated under reflux for 2 hours. After distilling out the solvents under reduced pressure, the residues were separated and purified by thin-layer silicagel column chromatography (ethyl acetate/hexane=1/2) to obtain a compound named trans compound for convenience as a white solid.

$^1$HNMR (400 MHz, CDCl$_3$), δ: 1.19-1.82 (8H, m), 2.87-3.11 (1H, m), 3.60-4.00 (3H, m), 4.24-4.33 (2H, m), 4.85-5.09 (1H, m), 7.56-7.58 (2H, m), 7.67 (1H, d, J=8.0 Hz),

ESI-MS Found: m/z 353.9 [M+H]$^+$.

2) Manufacture of 4-(2-(2-trans*-tetrahydro-2H-2 pyranyloxy-cyclopropyl)-1-oxo-isoindoline-5-yl)-1-(2-fluoropyridine-3-yl)-5-methyl-1H-[1,2,3]triazole Under nitrogen atmosphere, 31 mg of 5-bromo-2-(2-trans*-tetrahydro-2H-2-pyranyloxy-cyclopropyl)-1-oxo-isoindoline obtained in the above 1) and 40 mg of 1-(2-chloropyridine-3-yl)-4-tri-n-butyltin-5-methyl-[1,2,3]-triazole prepared in Reference Example 1 were dissolved in toluene, 11 mg of tetrakistriphenylphosphinepalladium was added and the mixture was heated under reflux for 2 hours. The reaction solution was cooled down to room temperature, and insoluble matters were removed by celite filtration. The solvents were distilled outunder reduced pressure, the residues were separated and purified by thin-layer silicagel column chromatography (ethyl acetate/hexane=2/1) to obtain 28 mg of the above compound as a white solid.

$^1$HNMR (400 MHz, CDCl$_3$), δ: 1.24-1.84 (8H, m), 2.93-3.18 (1H, m), 3.63-3.70 (1H, m), 3.78-3.88 (2H, m), 3.95-4.00 (1H, m), 4.35-4.44 (2H, m), 4.88-5.13 (1H, m), 7.49-7.52 (1H, m), 7.81 (1H, d, J=7.6 Hz), 7.91-7.93 (2H, m), 8.06-8.11 (1H, m), 8.45-8.47 (1H, m),

ESI-MS Found: m/z 450.3 [M+H]$^+$.

1) Manufacture of 4-(2-(1R*,2R*)-hydroxy-cyclopropyl)-1-oxo-isoindoline-5-yl)-1-(2-fluoropyridine-3-yl)-5-methyl-1H-[1,2,3]triazole and 4-(2-(1S*, 2S*)-hydroxy-cyclopropyl)-1-oxo-isoindoline-5-yl)-1-(2-fluoropyridine-3-yl)-5-methyl-1H-[1,2,3] triazole 15 mg of the compound 4-(2-(2-trans*-tetrahydro-2H-2-pyranyloxy-cyclopropyl)-1-oxo-isoindoline-5-yl)-1-(2-fluoropyridine-3-yl)-5-methyl-1H-[1,2,3]triazole obtained in the above 2) was dissolved in methanol, 1 mg of paratoluenesulphonic acid 1 hydrate was added, and the mixture was stirred at room temperature for 1 hour. The reaction solution was neutralized with saturated sodium bicarbonate solution, extracted with ethyl acetate by adding water. Ethyl acetate layer was washed with saturated saline solution, and dried with anhydrous sodium sulfate. After distilling out the solvents under reduced pressure, the residues were separated and purified by silicagel column chromatography (ethanol/hexane=1/2), optically resolved by optically active column (Daicel; CHIRALPAK OD-H column; hexane/ethanol=2/3), to obtain from the first fraction, 1.30 mg of the compound named (1R*,2R*) of the above compound for convenience, and from the latter fraction 0.60 mg of the compound named (1S*,2S*) of the above compound for convenience, both as white solid.

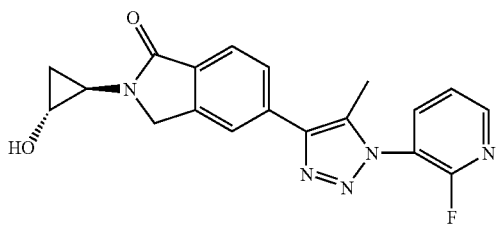

4-(2-(1R*,2R*)-hydroxy-cyclopropyl)-1-oxo-isoindoline-5-yl)-1-(2-fluoropyridine-3-yl)-5-methyl-1H-[1,2,3]triazole $^1$HNMR (400 MHz, CDCl$_3$), δ: 1.12-1.54 (2H, m), 2.50 (3H, d, J=2.0 Hz), 2.91-2.93 (1H, m), 3.77-3.79 (1H, m), 4.39 (2H, dd, J=12.4, 29.2 Hz), 7.85-7.87 (1H, m), 7.98-8.00 (3H, m), 8.07-8.11 (1H, m), 8.46-8.47 (1H, m), ESI-MS Found: m/z 366.3 [M+H]$^+$

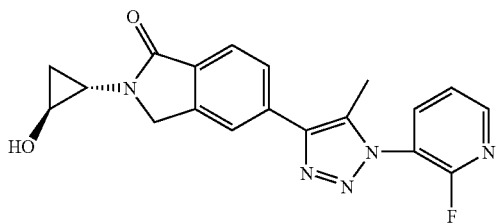

4-(2-(1S*,2S*)-hydroxy-cyclopropyl)-1-oxo-isoindoline-5-yl)-1-(2-fluoropyridine-3-yl)-5-methyl-1H-[1,2,3]triazole $^1$HNMR (400 MHz, CDCl$_3$), δ: 1.12-1.54 (2H, m), 2.50 (3H, d, J=2.0 Hz), 2.91-2.93 (1H, m), 3.77-3.79 (1H, m), 4.39 (2H, dd, J=12.4, 29.2 Hz), 7.85-7.87 (1H, m), 7.98-8.00 (3H, m), 8.07-8.11 (1H, m), 8.46-8.47 (1H, m), ESI-MS Found: m/z 366.3 [M+H]$^+$ [M+H]$^+$.

EXAMPLE 132

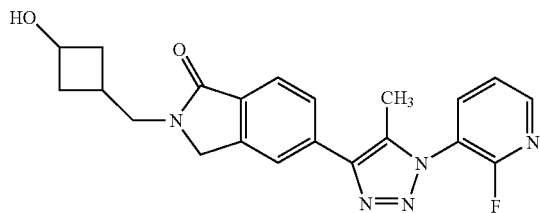

4-[2-(3-hydroxy-cyclobutylmethyl)-1-oxo-isoindo-line-5-yl]-1-(2-fluoropyridine-3-yl)-5-methyl-1H-[1,2,3]triazole After dissolving 155 mg of 4-[2-(3-benzyloxy-cyclobutyl-methyl)-1-oxo-isoindoline-5-yl]-1-(2-fluoropyridine-3-yl)-5-methyl-1H-[1,2,3]triazole obtained in Example 129 in 10 ml of methanol, 80 mg of 10% palladium-carbon was added, and the mixture was stirred all night under hydrogen atmosphere. The reaction solution was filtered by celite, and the obtained filtrate was concentrated under reduced pressure. The obtained residues were separated and purified by silica-gel column chromatography (ethyl acetate:methanol=99:1) to obtain 105 mg of the mixture of cis and trans of the above compound as a white solid. 70 mg of the obtained mixture was resolved by optically active column (Daicel; CHIRALPAK AD-H column; hexane/ethanol=400/600) to obtain cis compound of the above compound from the first fraction, and the trans compound of the above compound form the latter fraction.

C is Compound

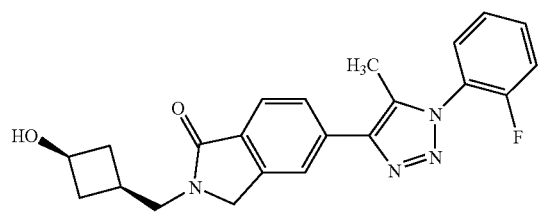

$^1$HNMR (300 MHz, CDCl$_3$), δ: 1.74-1.82 (2H, m), 1.95 (1H, d, J=6.6 Hz), 2.04-2.21 (1H, m), 2.46 (3H, d, J=1.7 Hz), 2.50-2.57 (2H, m), 3.70 (2H, d, J=7.3 Hz), 4.15-4.23 (1H, m), 4.46 (2H, s), 7.30-7.42 (2H, m), 7.56-7.62 (2H, m), 7.82 (1H, d, J=8.1 Hz), 7.94 (1H, d, J=8.1 Hz), 8.00 (1H, s),

ESI-MS Found: m/z 394.3[M+H]$^+$.

Trans Compound

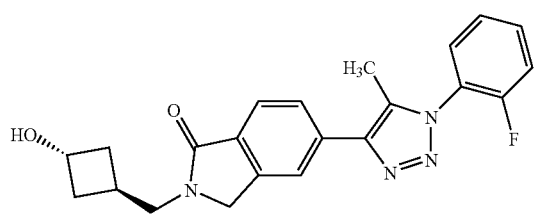

$^1$HNMR (300 MHz, CDCl$_3$), δ: 1.83 (1H, d, J=5.4 Hz), 2.04-2.15 (2H, m), 2.22-2.29 (2H, m), 2.46 (3H, d, J=1.7 Hz), 2.65-2.75 (1H, m), 3.72 (2H, d, J=8.0 Hz), 4.44 (2H, s), 4.50-4.63 (1H, m), 7.30-7.42 (2H, m), 7.56-7.62 (2H, m), 7.82 (1H, d, J=7.6 Hz), 7.95 (1H, d, J=7.6 Hz), 7.99 (1H, s),

ESI-MS Found: m/z 394.3 [M+H]$^+$.

EXAMPLE 133

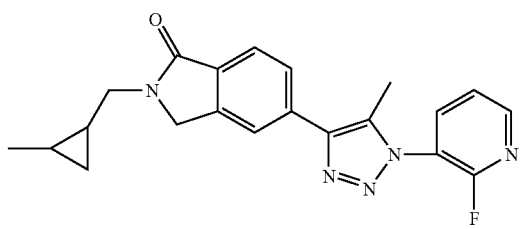

4-(2-(2-methyl-cyclopropylmethyl)-1-oxo-isoindo-line-5-yl)-1-(2-fluoropyridine-3-yl)-5-methyl-1H-[1,2,3]triazole 1) Manufacture of 5-bromo-2-(2-methyl-cyclopropy-lmethyl)-1-oxo-isoindoline The above compound was obtained by performing the reaction by the same method as Example 116-1), except using 2-methyl-cyclopropylmethylamine instead of cyclobuty-lamine hydrochloride which was used in Example 116-1).

$^1$HNMR (400 MHz, CDCl$_3$), δ: 0.31-0.35 (1H, m), 0.46-0.50 (1H, m), 0.70-0.76 (2H, m), 1.05-1.06 (3H, m), 3.93-3.44 (1H, m), 3.49-3.54 (1H, m), 4.44 (2H, s), 7.58-7.62 (2H, m), 7.70 (1H, d, J=8.4 Hz),

ESI-MS Found: m/z 282.1 [M+H]$^+$.

2) Manufacture of 4-(2-(2-methyl-cyclopropylm-ethyl)-1-oxo-isoindoline-5-yl)-1-(2-fluoropyridine-3-yl)-5-methyl-1H-[1,2,3]triazole The above compound was obtained according to the method of Example 116-2), with the use of the compound obtained in the above 1) and the compound 1-(2-fluoropyri-dine-3-yl)-5-methyl-4-tributylstanyl-1H-[1,2,3]triazole of Reference Example 1.

$^1$HNMR (400 MHz, CDCl$_3$)δ:0.34-0.37 (1H, m), 0.49-0.53 (1H, m), 0.76-0.77 (2H, m), 1.08 (3H, d, J=5.8 Hz), 2.51 (3H, d, J=2.1 Hz), 3.44-3.49 (1H, m), 3.56-3.61 (1H, m), 4.55 (2H, s), 7.49-7.52 (1H, m), 7.81-7.83 (1H, m), 7.95-7.99 (3H, m), 8.07-8.11 (1H, m(, 8.46-8.47 (1H, m),

ESI-MS Found: m/z 378.3 [M+H]$^+$.

EXAMPLE 134

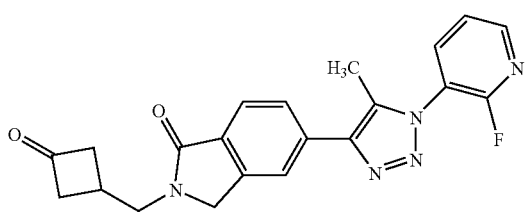

123

4-[2-(3-oxo-cyclobutylmethyl)-1-oxo-isoindoline-5-yl]-1-(2-fluoropyridine-3-yl)-5-methyl-1H-[1,2,3]triazole 20 mg of 4-[2-(3-hydroxy-cyclobutylmethyl)-1-oxo-isoindoline-5-yl]-1-(2-fluoropyridine-3-yl)-5-methyl-1H-[1,2,3]triazole obtained in Example 132 was dissolved in 1 ml of dimethylsulfoxide, and 100 μl of triethylamine followed by 40 mg of sulfur trioxide/pyridine complex were added at room temperature and the mixture was stirred for 1 hour. The reaction solution was diluted with ethyl acetate, washed with water and saturated saline solution, and dried with anhydrous sodium sulfate. The solvents were distilled outunder reduced pressure, and the residues were purified by preparative thin-layer silicagel chromatography (chloroform:methanol=20:1) to obtain 12 mg of the above compound as a white solid.

$^1$HNMR (300 MHz, CDCl$_3$), δ: 2.51 (3H, d, J=2.1 Hz), 2.80-2.93 (1H, m), 2.95-3.07 (2H, m), 3.15-3.28 (2H, m), 3.90 (2H, d, J=7.5 Hz), 4.54 (2H, s), 7.48-7.54 (1H, m), 7.84 (1H, dd, J=1.2, 8.1 Hz), 7.97 (1H, d, J=8.1 Hz), 8.00 (1H, s), 8.06-8.12 (1H, m), 8.45-8.48 (1H, m),
ESI-MS Found: m/z 392.3 [M+H]$^+$.

EXAMPLE 135

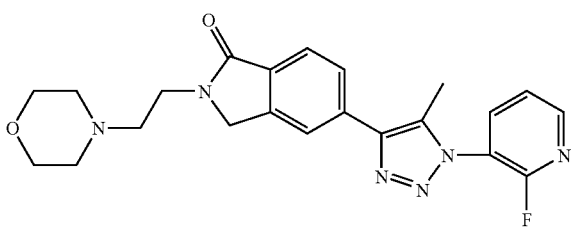

4-(2-(2-morpholine-4-ylethyl)-1-oxo-isoindoline-5-yl)-1-(2-fluoropyridine-3-yl-5-methyl-1H-[1,2,3]triazole 1) Manufacture of 5-bromo-2-(2-morpholine-4-yl-ethyl)-1-oxo-isoindoline The above compound was obtained by performing the reaction by the same method as Example 116-1), except using N-(2-aminomethylmorpholine instead of cyclobutylamine hydrochloride which was used in Example 116-1).

$^1$HNMR (400 MHz, CDCl$_3$), δ: 2.49-2.51 (4H, m), 2.61-2.65 (2H, m), 3.67-3.69 (4H, m), 3.71-3.74 (2H, m), 4.49 (2H, s), 7.58-7.60 (1H, m), 7.61 (1H, s), 7.70 (1H, d, J=8.0 Hz),
ESI-MS Found: m/z 327.2 [M+H]$^+$.

2) Manufacture of 4-(2-(2-morpholine-4-ylethyl)-1-oxo-isoindoline-5-yl)-1-(2-fluoropyridine-3-yl)-5-methyl-1H-[1,2,3]triazole The above compound was obtained according to the method of Example 116-2), with the use of the compound obtained in the above 1) and the compound 1-(2-fluoropyridine-3-yl)-5-methyl-4-tributylstanyl-1H-[1,2,3]-triazole of Reference Example 1.

$^1$HNMR (400 MHz, CDCl$_3$), δ: 2.51 (3H, d, J=1.9 Hz), 2.54 (br, 4H), 2.68 (2H, t, J=6.2 Hz), 3.70 (4H, t, J=4.6 Hz), 3.77-3.80 (2H, m), 4.59 (2H, s), 7.49-7.52 (1H, m), 7.81-7.83 (1H, m), 7.95-7.98 (2H, m), 8.07-8.11 (1H, m), 8.46-8.48 (1H, m),
ESI-MS Found: m/z 423.3 [M+H]$^+$.

EXAMPLE 136

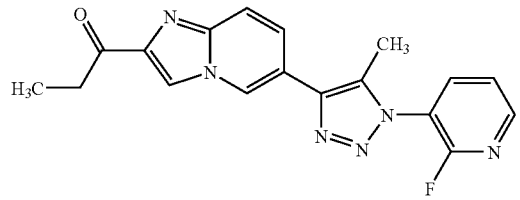

4-(2-ethylcarbonyl-imidazo[1,2-a]pyridine-6-yl)-1-(2-fluoropyridine3-yl)-5-methyl-1H-[1,2,3]triazole 1) Manufacture of 6-bromo-2-(N-methoxy-N-methyl-carbamoyl)-imidazo[1,2-a]pyridine 850 mg of 6-bromo-2-hydroxycarbonyl-imidazo[1,2-a]pyridine, 519 mg of N-methoxy-N-methyl-amine hydrochloride, and 1.12 g of 1-(3-dimethylaminopropyl)-3-ethylcarbodiimide hydrochloride were dissolved in 10 ml of pyridine, and the mixture was stirred at room temperature for 2 days. Water was added to the obtained solution, and the products were extracted with ethyl acetate. Organic layer was washed with saturated sodium chloride aqueous solution, and dried with anhydrous magnesium sulfate. Then, the solvents were distilled outunder reduced pressure. The obtained residues were purified by silicagel column chromatography (ethyl acetate) to obtain 362 mg of the above compound.

$^1$HNMR (300 MHz, CDCl$_3$), δ: 3.53 (3H, s), 3.80 (3H, s), 7.28 (1H, d, J=9.5 Hz), 7.56 (1H, d, J=9.5 Hz), 8.10 (1H, s), 8.30 (1H, s).

2) Manufacture of 6-bromo-2-ethylcarbonyl-imidazo[1,2-a]pyridine 100 mg of 6-bromo-2-(N-methoxy-N-methyl-carbamoyl)-imidazo[1,2-a]pyridine obtained in the above 1) was dissolved in 2.0 ml of tetrahydrofuran, cooled down to −78° C. Then, 1.0 ml of 1M ethylmagnesium chloride was dropped thereto. After heating to 0° C., water was added, and the products were extracted with ethyl acetate. Organic layer was dried with anhydrous sodium sulfate, and the solvents were distilled outunder reduced pressure. The obtained residues were purified by silicagel column chromatography (hexane:ethyl acetate=50:50) to obtain 60.2 mg of the above compound.

$^1$HNMR (300 MHz, CDCl$_3$), δ: 1.24 (3H, t, J=7.0 Hz), 3.19 (2H, q, J=7.0 Hz), 7.30 (1H, d, J=9.5 Hz), 7.56 (1H, d, J=9.5 Hz), 8.08 (1H, s), 8.30 (1H, s).

3) Manufacture of 4-(2-ethylcarbonyl-imidazo[1,2-a]pyridine-6-yl)-1-(2-fluoropyridine3-yl)-5-methyl-1H-[1,2,3]triazole The above compound was obtained as a white solid, by the same method as Example 49, by a method according thereto, or by a combination of these and ordinary methods, with the use of halide obtained in the above 2), the tin reagent obtained in Reference Example 7, and tetrakistriphenylphosphine-palladium.

¹HNMR (400 MHz, CDCl₃), δ: 1.28 (3H, t, J=7.3 Hz), 2.51 (3H, d, J=2.0 Hz), 3.33 (2H, q, J=7.3 Hz), 7.50-7.54 (1H, m), 7.67-7.71 (1H, m), 7.78-7.81 (1H, m), 8.06-8.12 (1H, m), 8.22 (1H, d, J=0.7 Hz), 8.47-8.50 (1H, m), 5 8.61-8.62 (1H, m), APCI-MS Found: m/z 351.0 [M+H]⁺.

EXAMPLE 137

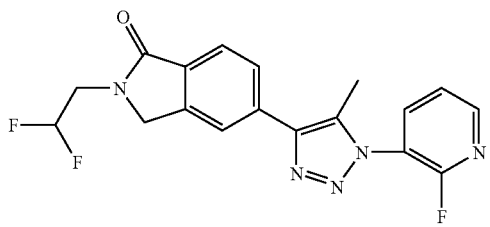

4-(2-(2,2-difluoroethyl)-1-oxo-isoindoline-5-yl)-1-(2-fluoropyridine-3-yl)-5-methyl-1H-[1,2,3]triazole 1) Manufacture of 5-bromo-2-(2,2-difluoroethyl-1-oxo-isoindoline Under nitrogen atmosphere, 100 mg of 4-bromo-2-bromomethyl methyl benzoate was dissolved in toluene, 0.1 ml of 2,2-difluoroethylamine and 0.14 ml of triethylamine were added and heated all night under reflux. The reaction solution was cooled down to room temperature, and after distilling out the solvents under reduced pressure, the residues were separated and purified by silicagel column chromatography (ethyl acetate/hexane=1/2) to obtain 45 mg of the above compound as a white solid.

¹HNMR (400 MHz, CDCl₃), δ: 3.91-4.00 (2H, m), 4.52 (2H, s), 5.84-6.14 (1H, m), 7.61-7.63 (1H, m), 7.71 (1H, s), 7.72-7.73 (1H, m), ES-MS Found: m/z 277.9 [M+H]⁺.

2) Manufacture of 4-(2-(2,2-difluoroethyl-1-oxo-isoindoline-5-yl)-1-(2-fluoropyridine-3-yl)-5-methyl-1H-[1,2,3]triazole Under nitrogen atmosphere, 45 mg of 5-bromo-2-(2,2-difluoroethyl)-1-oxo-isoindoline obtained in the above 1) and 30 mg of 1-(2-chloropyridine-3-yl)-4-tri-n-butyltin-5-methyl-[1,2,3]-triazole prepared in Reference Example 1 were dissolved in toluene, 11 mg of tetrakistriphenylphosphine-palladium was added and the mixture was heated under reflux for 6 hours. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 20 mg of the above compound as a white solid.

¹HNMR (400 MHz, CDCl₃), δ: 2.51 (3H, d, J=2.0 Hz), 3.97-4.05 (2H, m), 4.63 (2H, s), 5.89-6.17 (1H, m), 7.49-7.52 (1H, m), 7.85-7.87 (1H, m), 7.98-8.00 (2H, m), 8.06-8.11 (11H,), 8.46-8.48 (11H, m),

ESI-MS Found: m/z 374.2 [M+H]⁺.

EXAMPLE 138

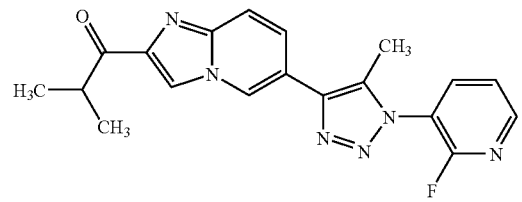

1-(2-fluoropyridine3-yl)-4-(2-isopropylcarbonyl-imidazo[1,2-a]pyridine-6-yl)-5-methyl-1H-[1,2,3]triazole 1) Manufacture of 6-bromo-2-isopropylcarbonyl-imidazo[1,2-a]pyridine 269 mg of 6-bromo-2-ethoxycarbonyl-imidazo[1,2-a]pyridine obtained in Example 117 was dissolved in 10 ml of tetrahydrofuran, cooled down to −78° C., and 0.5 ml of 2M isopropylmagnesium chloride was dropped thereto. After heating to −40° C., water was added and the products were extracted with ethyl acetate. Organic layer was dried with anhydrous magnesium sulfate, and the solvents were distilled outunder reduced pressure. The obtained residues were purified by silicagel column chromatography (hexane:ethyl acetate=50:50) to obtain 58.5 mg of the above compound.

¹HNMR (300 MHz, CDCl₃), δ: 1.26 (6H, d, J=6.7 Hz), 3.82 (1H, sept, J=6.7 Hz), 7.30 (1H, d, J=9.5 Hz), 7.58 (1H, d, J=9.5 Hz), 8.10 (1H, s), 8.30 (1H, s).

2) Manufacture of 1-(2-fluoropyridine3-yl)-4-(2-isopropylcarbonyl-imidazo[1,2-a]pyridine-6-yl)-5-methyl-1H-[1,2,3]triazole The above compound was obtained as a white solid by the same method as Example 49, by a method according thereto, or by a combination of these and ordinary methods with the use of 6-bromo-2-isopropylcarbonyl-imidazo[1,2-a]pyridine obtained in the above 1), the tin reagent obtained in Reference Example 7, and tetrakistriphenylphosphinepalladium.

¹HNMR (400 MHz, CDCl₃), δ: 1.29 (6H, d, J=7.0 Hz), 2.51 (3H, d, J=2.0 Hz), 3.87 (1H, sept, J=7.0 Hz), 7.50-7.54 (1H, m), 7.68 (1H, dd, J=1.7, 9.5 Hz), 7.80 (1H, d, J=9.5 Hz), 8.07-8.12 (1H, m), 8.23 (1H, d, J=0.7 Hz), 8.47-8.50 (1H, m), 8.61-8.62 (1H, m), APCI-MS Found: m/z 365.0 [M+H]⁺.

EXAMPLE 139

4-(2-(trans-3-hydroxy-cyclobutylmethyl-1-oxo-isoindoline-5-yl)-1-(2-fluoropyridine-3-yl)-5-methyl-1H-[1,2,3]triazole and 4-(2-(cis-3-hydroxy-cyclobutylmethyl-1-oxo-isoindoline-5-yl)-1-(2-fluoropyridine-3-yl)-5-methyl-1H-[1,2,3]triazole The mixture of cis and trans bodies of the above compound was obtained as a white solid by the same method as Examples 129 and 132, except using the tin reagents of Reference 4 instead of the tin reagent of Examples 129 and 130. The obtained mixture was resolved by optically active column (Daicel; CHIRALPAK OJ-H column; hexane/ethanol=400/600), and the trans compound of the above compound was obtained from the first fraction and the cis compound of the above compound was obtained from the latter fraction.

4-(2-(trans-3-hydroxy-cyclobutylmethyl-1-oxo-isoindoline-5-yl)-1-(2-fluoropyridine-3-yl)-5-methyl-1H-[1,2,3]triazole

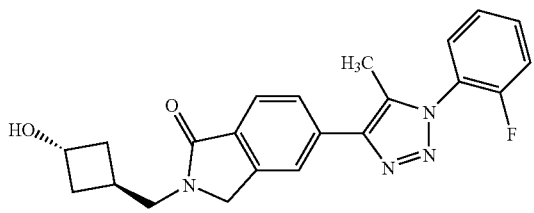

$^1$HNMR (400 MHz, CDCl$_3$), δ: 1.83 (1H, d, J=5.4 Hz), 2.04-2.15 (2H, m), 2.22-2.29 (2H, m), 2.46 (3H, d, J=1.7 Hz), 2.65-2.75 (1H, m), 3.72 (2H, d, J=8.0 Hz), 4.44 (2H, s), 4.50-4.63 (1H, m), 7.30-7.42 (2H, m), 7.56-7.62 (2H, m), 7.82 (1H, d, J=7.6 Hz), 7.95 (1H, d, J=7.6 Hz), 7.99 (1H, s), ESI-MS Found: m/z 393.3 [M+H]$^+$.

4-(2-(cis-3-hydroxy-cyclobutylmethyl-1-oxo-isoindoline-5-yl)-1-(2-fluoropyridine-3-yl)-5-methyl-1H-[1,2,3]triazole

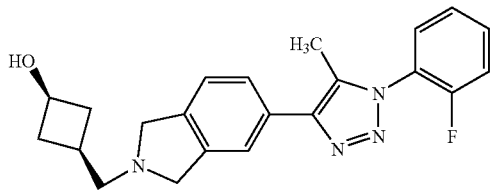

$^1$HNMR (400 MHz, CDCl$_3$), δ: 1.74-1.82 (2H, m), 1.95 (1H, d, J=6.6 Hz), 2.04-2.21 (1H, m), 2.46 (3H, d, J=1.7 Hz), 2.50-2.57 (2H, m), 3.70 (2H, d, J=7.3 Hz), 4.15-4.23 (1H, m), 4.46 (2H, s), 7.30-7.42 (2H, m), 7.56-7.62 (2H, m), 7.82 (1H, d, J=8.1 Hz), 7.94 (1H, d, J=8.1 Hz), 8.00 (1H, s), ESI-MS Found: m/z 393.3 [M+H]$^+$.

EXAMPLE 140

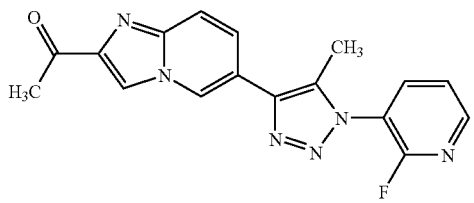

4-(2-acetyl-imidazo[[1,2-a]pyridine-6-yl]-1-(2-fluoropyridine3-yl)-5-methyl-1H-[1,2,3]triazole The above compound was obtained as a white solid by the same method as Example 49, by a method according thereto, or by a combination of these and ordinary methods, with the use of 2-acetyl-6-bromo-imidazo[1,2-a]pyridine, the tin reagent obtained in Reference Example 1, and tetrakistriphenylphosphinepalladium.

$^1$HNMR (400 MHz, CDCl$_3$), δ: 2.51 (3H, d, J=2.2 Hz), 2.75 (3H, s), 7.50-7.54 (1H, m), 7.69 (1H, dd, J=0.7, 9.5 Hz), 7.78-7.82 (1H, m), 8.07-8.12 (1H, m), 8.22 (1H, d, J=0.7 Hz), 8.47-8.49 (1H, m), 8.62 (1H, dd, J=1.2, 1.7 Hz),
ESI-MS Found: m/z 337.3 [M+H]$^+$.

EXAMPLE 141

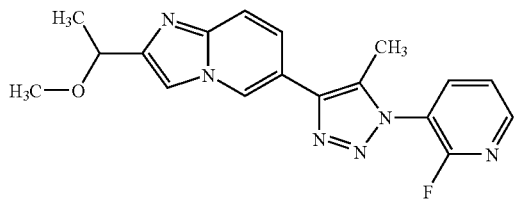

1-(2-fluoropyridine3-yl)-4-(2-(1-methoxy-ethyl)-imidazo[1,2-a]pyridine-6-yl)-5-methyl-1H-[1,2,3]triazole 1) Manufacture of 6-bromo-2-(1-methoxyethyl-imidazo[1,2-a]pyridine 60 mg of 6-bromo-2-methylcarbonyl-imidazo[1,2-a] was dissolved in 2 ml of methanol, and 38 mg of sodium borohydride was added at 0° C. After stirring the mixture for 5 min at room temperature, saturated saline solution was added. The products were extracted with ethyl acetate, dried with anhydrous sodium sulfate, and the solvents were distilled outunder reduced pressure. The obtained residues were dissolved in 2.0 ml dimethylformamide, and 30 mg of 60% sodium hydride, 47 μl of methyl iodide were added at 0° C., heated to room temperature, and stirred for 1 hour. After adding water to the obtained solution, the products were extracted with chloroform, dried with anhydrous sodium sulfate, and the solvents were distilled outunder reduced pressure. The obtained residues were purified by silicagel column chromatography (hexane:ethyl acetate=50:50) to obtain 52 mg of the above compound.

$^1$HNMR (400 MHz, CDCl$_3$), δ:1.58 (3H, d, J=6.6 Hz), 4.58 (2H, q, J=6.6 Hz), 7.21 (1H, dd, J=1.0, 9.5 Hz), 7.48 (1H, d, J=9.5 Hz), 7.51 (1H, s), 8.22-8.25 (1H, m).

2) Manufacture of 1-(2-fluoropyridine3-yl)-4-(2-(1-methoxy-ethyl)-imidazo[1,2-a]pyridine-6-yl)-5-methyl-1H-[1,2,3]triazole The above compound was obtained as a white solid by the same method as Example 49, by a method according thereto, or by a combination of these and ordinary methods, with the use of halide obtained in the above 1, the tin reagent obtained in Reference Example 1, and tetrakistriphenylphosphinepalladium.

$^1$ HNMR (400 MHz, CDCl$_3$), δ: 1.62 (3H, d, J=6.6 Hz), 2.48 (3H, d, J=2.2 Hz), 3.43 (3H, s), 4.62 (1H, q, J=6.6 Hz), 7.46-7.53 (1H, m), 7.55 (1H, dd, J=1.7, 9.5 Hz), 7.63 (1H, s), 7.69 (1H, d, J=9.4 Hz), 8.06-8.11 (1H, m), 8.46-8.48 (1H, m), 8.57-8.58 (1H, m),
ESI-MS Found: m/z 353.3 [M+H]$^+$.

EXAMPLE 142

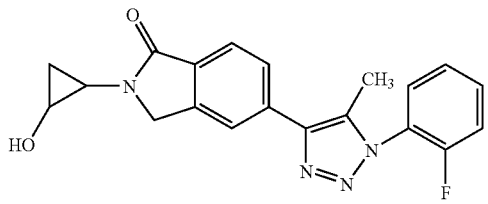

4-(2-(2-hydroxycyclopropyl)-1-oxo-isoindoline-5-yl)-1-(2-fluorobenzene-3-yl)-5-methyl-1H-[1,2,3]triazole 1) Manufacture of 4-(2-(1 R*,2R*)-hydroxy-cyclopropyl)-1-oxo-isoindoline-5-yl)-1-(2-fluorobenzene-3-yl)-5-methyl-1H-[1,2,3]triazole and 4-(2-(1S*,2S*)-hydroxy-cyclopropyl)-1-oxo-isoindoline-5-yl)-1-(2-fluorobenzene-3-yl)-5-methyl-1H-[1,2,3]triazole By using the tin reagent of Reference Example 4 instead of the tin reagent of Reference Example 1 which was used in Example 131, the same operation was performed as Example 131, and the racemic compound of the above compound was obtained. Then, the racemic compound was optically resolved by optically active column (Daicel; CHIRALPAK OJ-H column; hexane/ethanol=1/3). From the first fraction, the compound named (1R*,2R*) compound of the above compound for convenience was obtained, and from the latter fraction, the compound named (1S*,2S*) compound of the above compound for convenience was obtained, both as white solid.

$^1$HNMR (400 MHz, CDCl$_3$), δ: 1.10-1.20 (1H, m), 1.22-1.32 (1H, m), 7.45 (3H, d, J=1.8 Hz), 2.91-3.00 (1H, m), 3.54 (1H, s), 3.77-3.86 (1H, m), 4.35 (1H, d, J=16.0 Hz), 4.44 (1H, d, J=16.0 Hz), 7.30-7.42 (2H, m), 7.52-7.63 (2H, m), 7.79-7.86 (1H, m), 7.92 (1H, d, J=7.9 Hz), 7.98 (1H, s),

ESI-MS Found: m/z 365.1 [M+H]$^+$.

2) Manufacture of 4-(2-(1S*,2R*)-hydroxy-cyclopropyl)-1-oxo-isoindoline-5-yl)-1-(2-fluorobenzene-3-yl)-5-methyl-1H-[1,2,3]triazole and 4-(2-(1R*,2S*)-hydroxy-cyclopropyl)-1-oxo-isoindoline-5-yl)-1-(2-fluorobenzene-3-yl)-5-methyl-1H-[1,2,3]triazole Except using the compound named cis compound obtained as byproduct of Example 131 1) and the tin reagent of Reference Example 4, the same operation as Example 131 was performed to obtain racemic compound of the above compound. The racemic compound was optically resolved by optically active column (Daicel; CHIRALPAK AD-H column; hexane/ethanol=1/3). From the first fraction, the compound named (1S*,2R*) compound of the above compound for convenience was obtained, and from the latter fraction, the compound named (1R*,2S*) compound of the above compound for convenience was obtained, both as white solid.

$^1$HNMR (400 MHz, CDCl$_3$), δ: 0.85-0.96 (1H, m), 1.03-1.12 (1H, m), 2.47 (3H, d, J=1.8 Hz), 2.67-2.77 (1H, m), 3.82-3.94 (1H, m), 4.55 (2H, s), 4.64 (1H, s), 7.30-7.42 (2H, m), 7.52-7.65 (2H, m), 7.30-7.34 (1H, m), 7.92 (1H, d, J=8.2 Hz), 9.02 (1H, s),

ESI-MS Found: m/z 365.1 [M+H]$^+$.

EXAMPLE 143

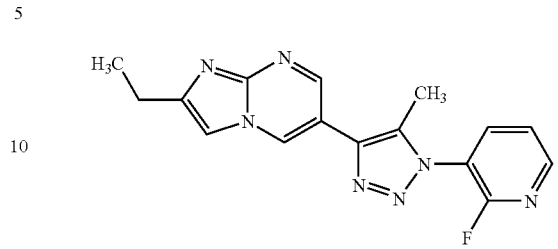

1-(2-fluoropyridine3-yl)-4-(2-ethyl-imidazo[1,2-a]pyrimidine-6-yl)-5-methyl-1H-[1,2,3]triazole 1) Manufacture of 2-ethyl-6-iodo-imidazo[1,2-a]pyrimidine 755 mg of 1-bromo-2-butanone was dissolved in 15 ml of ethanol, 1.0 g of 2-amino-5-iodopyrimidine was added and the mixture was stirred all night by heating under reflux. After cooling down to room temperature, the solvents were distilled outunder reflux, ethyl acetate followed by saturated sodium bicarbonate aqueous solution were added. Organic layer was dried with anhydrous sodium sulfate, and the solvents were distilled outunder reduced pressure. The obtained residues were purified by silicagel column chromatography (ethyl acetate) to obtain 110 mg of the above compound as a white solid.

$^1$HNMR (300 MHz, CDCl$_3$), δ: 1.38 (3H, t, J=7.0 Hz), 2.88 (2H, q, J=7.0 Hz), 7.25 (1H, s), 8.52 (1H, d, J=2.4 Hz), 8.58 (1H, d, J=2.4 Hz),

ESI-MS Found: m/z 274.0 [M+H]$^+$.

2) Manufacture of 1-(2-fluoropyridine3-yl)-4-(2-ethyl-imidazo[1,2-a]pyrimidine-6-yl)-5-methyl-1H-[1,2,3]triazole The above compound was obtained as a white solid by the same method as Example 49, by a method according thereto, or by a combination of these and ordinary method with the use of halogen compound obtained in the above, the tin reagent obtained in Reference Example 1, and tetrakistriphenylphosphinepalladium.

$^1$HNMR (400 MHz, CDCl$_3$), δ: 1.40 (3H, t, J=7.5 Hz), 2.51 (3H, d, J=2.0 Hz), 2.92 (2H, q, J=7.5 Hz), 7.27 (1H, s), 7.48-7.56 (1H, m), 8.01-8.12 (1H, m), 8.45-8.52 (1H, m), 8.80-8.90 (2H, m),

ESI-MS Found: m/z 324.2 [M+H]$^+$.

EXAMPLE 144

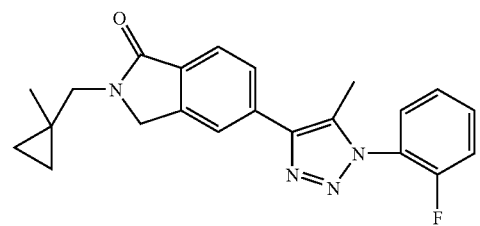

4-(2-(1-methyl-cyclopropylmethyl)-1-oxo-isoindo-
line-5-yl)-1-(2-fluorophenyl)-5-methyl-1H-[1,2,3]
triazole Under nitrogen atmosphere, 30 mg of 5-bromo-2-(1-methyl-cyclopropylmethyl)-1-oxo-isoindoline obtained in Example 131-1) and 20 mg of 1-(2-fluorophenyl)-5-methyl-4-tributylstanyl-1H-[1,2,3]triazole prepared in Reference Example 4 were dissolved in toluene, 8 mg of tetrakistriphenylphosphinepalladium was added, and the mixture was heated under reflux for 2 hours. The reaction solution was cooled down to room temperature, insoluble matters were removed by celite filtration. The solvents were distilled outunder reduced pressure, and the residues were separated and purified by thin-layer silicagel column chromatography (ethyl acetate/hexane=2/1) to obtain 6 mg of the above compound as a white solid.

$^1$HNMR (400 MHz, CDCl$_3$), δ: 0.43-0.46 (2H, m), 0.54-0.56 (2H, m), 1.07 (3H, s), 2.47 (3H, d, J=1.6 Hz), 3.51 (2H, s), 4.54 (2H, s), 7.33-7.54 (2H, m), 7.56-7.61 (2H, m), 7.82-7.84 (1H, m), 7.95-7.97 (1H, m), 8.01 (1H, s),
ESI-MS Found: m/z 377.2 [M+H]$^+$.

EXAMPLE 145

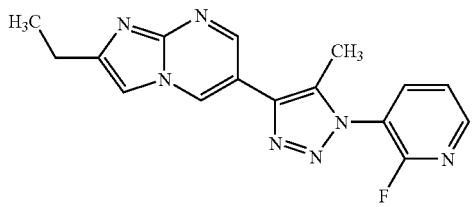

1-(2-fluoropyridine3-yl)-4-(2-ethyl-imidazo[1,2-a]
pyradine-6-yl)-5-methyl-1H-[1,2,3]triazole 1) Manufacture of
6-bromo-2-ethyl-imidazo[1,2-a]pyradine 513 mg of 1-bromo-2-butanone was dissolved in 10 ml of ethanol, 500 mg of 2-amino-5-bromopyradine was added and the mixture was stirred all night by heating under reflux. After cooling down to room temperature, the solvents were distilled outunder reduced pressure, ethyl acetate followed by saturated sodium bicarbonate aqueous solution were added. Organic layer was dried with anhydrous sodium sulfate, and the solvents were distilled outunder reduced pressure. The obtained residues were purified by silicagel column chromatography (hexane:ethyl acetate=50:50) to obtain 244 mg of the above compound as crude product.
ESI-MS Found: m/z 276.0, 228.0 [M+H]$^+$.

2) Manufacture of 1-(2-fluoropyridine3-yl)-4-(2-
ethyl-imidazo[1,2-a]pyradine-6-yl)-5-methyl-1H-[1,
2,3]triazole The above compound was obtained as a white solid by the same method as Example 49, by a method according thereto, or by a combination of these and ordinary methods, with the use of halogen compound obtained in the above, the tin reagent obtained in Reference Example 1, and tetrakistriphenylphosphinepalladium.

$^1$HNMR (400 MHz, CDCl$_3$), δ: 1.41 (3H, t, J=7.6 Hz), 2.70 (3H, d, J=1.7 Hz), 2.92 (2H, q, J=7.6 Hz), 7.46-7.52 (1H, m), 7.57 (1H, d, J=0.5 Hz), 8.01-8.06 (1H, m), 8.22-8.28 (1H, m), 8.95 (1H, d, J=1.4 Hz), 9.03-9.06 (1H, m),
ESI-MS Found: m/z 324.1 [M+H]$^+$.

EXAMPLE 146

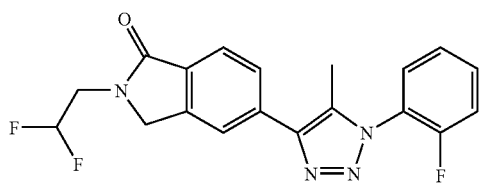

4-(2-(2,2-difluoroethyl)-1-oxo-isoindoline-5-yl)-1-
(2-fluorophenyl)-5-methyl-1H-[1,2,3]triazole Under nitrogen atmosphere, 80 mg of 5-bromo-2-(2,2-difluoroethyl)-1-oxo-isoindoline obtained in Example 137-1, and 500 mg of 1-(2-fluorophenyl)-5-methyl-4-tributylstanyl-1H-[1,2,3]triazole prepared in Reference Example 4, were dissolved in toluene and 15 mg of tetrakistriphenylphosphinepalladium was added. The mixture was stirred all night by heating under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 16 mg of the above compound as a white solid.

$^1$HNMR (400 MHz, CDCl$_3$), δ: 2.47 (3H, d, J=1.7 Hz), 3.96-4.05 (2H, m), 4.62 (2H, s), 5.89-3.16 (1H, m), 7.33-7.41 (2H, m), 7.56-7.60 (2H, m), 7.86-7.88 (1H, m), 7.96-8.01 (2H, m),
ESI-MS Found: m/z 373.1 [M+H]$^+$.

EXAMPLE 147

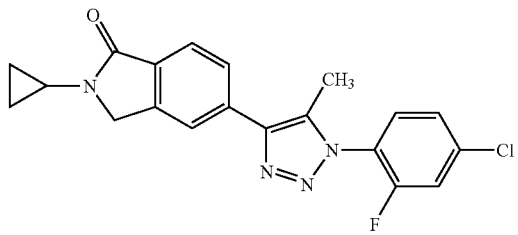

4-(2-cyclopropyl-1-oxo-isoindoline-5-yl)-1-(4-
chloro-2-fluorophenyl)-5-methyl-1H-[1,2,3]triazole The above compound was obtained as a white solid, by the same method as Example 49, by a method according thereto, by a combination of these and ordinary methods, with the use of halogen compound obtained in Example 49, the tin reagent obtained in Reference Example 16, and tetrakistriphenylphosphinepalladium.

¹HNMR (400 MHz, CDCl₃), δ: 0.88-0.98 (4H, m), 2.45 (3H, d, J=1.7 Hz), 2.94-3.01 (1H, m), 4.41 (2H, s), 7.37-7.42 (2H, m), 7.51-7.56 (1H, m), 7.79 (1H, dd, J=1.3, 7.9 Hz), 7.92-7.96 (2H, m),
ESI-MS Found: m/z 383.1 [M+H]⁺.

EXAMPLE 148

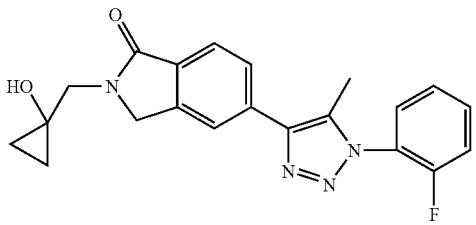

4-(2-(1-hydroxy-cyclopropylmethyl-1-oxo-isoindoline-5-yl)-1-(2-fluorophenyl)-5-methyl-1H-[1,2,3]triazole 1) Manufacture of 5-bromo-2-(1-hydroxy-cyclopropylmethyl)-1-oxo-isoindoline The above compound was obtained by performing the reaction by the same method as Example 116-1), except using 1-hydroxy-cyclopropylmethylamine, instead of cyclobutylamine hydrochloride which was used in Example 116-1).
¹HNMR (400 MHz, CDCl₃), δ: 0.67-0.70 (2H, m), 0.88-0.91 (2H, m), 3.70 (2H, s), 3.79 (1H, s), 4.54 (2H, s), 7.55-7.59 (2H, m), 7.63-7.65 (1H, m),
ESI-MS Found: m/z 284.1 [M+H]⁺.

2) Manufacture of 4-(2-(1-hydroxy-cyclopropylmethyl-1-oxo-isoindoline-5-yl)-1-(2-fluorophenyl)-5-methyl-1H-[1,2,3]triazole The above compound was obtained according to the method of Example 116-2), with the use of the compound obtained in the above 1), the compound 1-(2-fluorophenyl)-5-methyl-4-tributylstanyl-1H-[1,2,3]triazole of Reference Example 4.
¹HNMR (400 MHz, CDCl₃), δ: 0.71-0.74 (2H, m), 0.91-0.94 (2H, m), 2.47 (3H, d, J=1.75 Hz), 3.69 (1H, s), 3.78 (2H, s), 4.65 (2H, s), 7.33-7.41 (2H, m), 7.56-7.61 (2H, m), 7.82-7.84 (1H, m), 7.93-7.95 (1H, m), 8.00 (1H, m),
ESI-MS Found: m/z 379.2 [M+H]⁺.

EXAMPLE 149

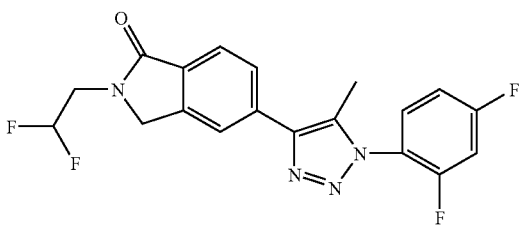

4-(2-(2,2-difluoroethyl)-1-oxo-isoindoline-5-yl)-1-(2,4-difluorophenyl)-5-methyl-1H-[1,2,3]triazole Under nitrogen atmosphere, 28 mg of 5-bromo-2-(2,2-difluoroethyl)-1-oxo-isoindoline obtained in Example 137-1), and 60 mg of 1-(2,4-difluorophenyl)-5-methyl-4-tributylstanyl-1H-[1,2,3]triazole prepared in Reference Example 13 were dissolved in toluene, 11 mg of tetrakistriphenylphosphinepalladium was added, and the mixture was heated all night under reflux. The reaction solution was cooled down to room temperature, and insoluble matters were removed by celite filtration. The solvents were distilled out under reduced pressure, and the residues were separated and purified by thin-layer silicagel column chromatography (ethyl acetate/hexane=2/1) to obtain 20 mg of the above compound as a white solid.

¹HNMR (400 MHz, CDCl₃), δ: 2.46 (3H, d, J=1.76 Hz), 3.96-4.05 (2H, m), 4.62 (2H, s), 5.89-6.16 (1H, m), 7.09-7.15 (2H, m), 7.55-7.61 (1H, m), 7.84-7.86 (1H, m), 7.96-8.00 (2H, m),
ESI-MS Found: m/z 391.1 [M+H]⁺.

EXAMPLE 150

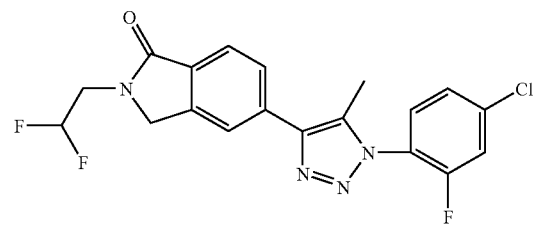

4-(2-(2,2-dufluoroethyl-1-oxo-isoindoline-5-yl)-1-(4-chloro2-fluorophenyl)-5-methyl-1H-[1,2,3]triazole Under nitrogen atmosphere, 28 mg of 5-bromo-2-(2,2-difluoroethyl)-1-oxo-isoindoline obtained in Example 137-1) and 60 mg of 1-(4-chloro-2-fluorophenyl)-5-methyl-4-tributylstanyl-1H-[1,2,3]triazole prepared in Reference Example 16 were dissolved in toluene, 11 mg of tetrakistriphenylphosphinepalladium was added, and the mixture was heated all night under reflux. The reaction solution was cooled down to room temperature, and insoluble matters were removed by celite filtration. The solvents were distilled out under reduced pressure, and the residues were separated and purified by thin-layer silicagel column chromatography (ethyl acetate/hexane=2/1) to obtain 21 mg of the above compound as a white solid.

¹HNMR (400 MHz, CDCl₃), δ: 2.47 (3H, d, J=1.7 Hz), 4.01 (2H, dt, J=4.1, 14.6 Hz), 4.62 (2H, s), 6.02 (1H, tt, J=51.4, 41 Hz), 7.39-7.41 (2H, m), 7.52-7.56 (1H, m), 7.84-7.86 (1H, m), 7.96-7.99 (2H, m),
ESI-MS Found: m/z 407.1 [M+H]⁺.

EXAMPLE 151

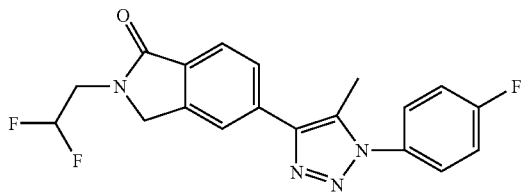

4-(2-(2,2-difluoroethyl)-1-oxo-isoindoline-5-yl)-1-(4-fluorophenyl)-5-methyl-1H-[1,2,3]triazole Under nitrogen atmosphere, 28 mg of 5-bromo-2-(2,2-difluoroethyl)-1-oxo-isoindoline obtained in Example 137-1) and 60 mg of 1-(4-fluorophenyl)-5-methyl-4-tributylstanyl-1H-[1,2,3]triazole prepared in Reference Example 12 were dissolved in toluene, 11 mg of tetrakistriphenylphosphinepalladium was added and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 22 mg of the above compound as a white solid.

$^1$HNMR (400 MHz, CDCl$_3$), δ: 2.52 (3H, m), 3.96-4.05 (2H, m), 4.62 (2H, s), 5.88-6.17 (1H, m), 7.26-7.31 (2H, m), 7.49-7.53 (2H, m), 7.83-7.85 (1H, m), 7.96-7.99 (2H, m), ESI-MS Found: m/z 373.1 [M+H]$^+$.

EXAMPLE 152

4-(2-(trans-3-methoxy-cyclobutylmethyl)-1-oxo-isoindoline-5-yl)-1-(2-fluorophenyl)-5-methyl-1H-[1,2,3]triazole and 4-(2-(cis-3-methoxy-cyclobutylmethyl)-1-oxo-isoindoline-5-yl)-1-(2-fluorophenyl)-5-methyl-1H-[1,2,3]triazole

1) Manufacture of 3-methoxy-cyclobutylmethanol 500 mg of 3-methoxycyclobutylcarbonic acid was dissolved in 10 ml of tetrahydrofuran. Under iced temperature, 292 mg of lithium aluminium hydride was added slowly, and the mixture was further stirred for 2 hours. The reaction solution was diluted with ethyl acetate, washed with 1M hydrochloric acid and saturated saline solution, and dried with anhydrous sodium sulfate. The residues obtained by distilling out the solvents under reduced pressure were separated and purified by silicagel column chromatography (ethyl acetate:hexane=40:60) to obtain 230 mg of the above compound.

$^1$HNMR (300 MHz, CDCl$_3$), δ: 1.60-2.45 (5H, m), 3.22-3.24 (3H, m), 3.59-3.66 (2H, m), 3.73-4.00 (1H, m).

2) Manufacture of 3-methoxy-cyclobutylmethylazide

530 μl of triethylamine followed by 220 μl of methanesulfonylchloride were added under iced temperature to 220 mg of 1) 3-methoxy-cyclobutylmethanol obtained in the above 1). The mixture was heated to room temperature and stirred for 30 min. The reaction solution was diluted with ethyl acetate, washed with water, saturated sodium bicarbonate water and saturated saline solution, and dried with anhydrous sodium sulfate. The residues obtained by evaporating the solvents under reduced pressure were dissolved in 4 ml of dimethylformamide. Then, 245 mg of sodium azide was added, and the mixture was stirred at 80° C. for 1.5 hours. The reaction solution was diluted with ethyl acetate, washed with water and saturated saline solution and dried with anhydrous sodium sulfate. The residues obtained by distilling out the solvents under reduced pressure were separated and purified by silicagel column chromatography (ethyl acetate:hexane=10:90) to obtain 195 mg of the above compound.

$^1$HNMR (300 MHz, CDCl$_3$), δ: 1.61-2.60 (5H, m), 3.22 (3H, s), 3.27-3.35 (2H, m), 3.72-4.01 (1H, m).

3) Manufacture of 5-bromo-(2-(3-methoxy-cyclobutylmethyl)-1-oxo-isoindoline 190 mg of 3-methoxy-cyclobutylmethylazide obtained in the above 2) was dissolved in 8 ml of methanol. After adding 10% palladium carbon of catalyst amount, the mixture was stirred under hydrogen atmosphere for 1.5 hours at room temperature. The reaction solution was filtered by celite, and the obtained filtrated solution was concentrated under reduced pressure. The obtained residues were dissolved in 3 ml of toluene, 420 mg of 4-bromo-2-bromomethyl methyl benzoate and 1 ml of triethylamine were added, and the mixture was stirred by heating all night under reflux. The reaction solution was cooled down to room temperature, diluted with ethyl acetate, washed with water and saturated saline solution, and dried with anhydrous sodium sulfate. The residues obtained by distilling out the solvents under reduced pressure were separated and purified by silicagel column chromatography (ethyl acetate:hexane=80:20) to obtain 98 mg of the above compound as a white solid.

$^1$HNMR (300 MHz, CDCl$_3$), δ: 1.67-2.67 (5H, m), 3.21 (3H, s), 3.42-4.12 (3H, m), 4.33-4.38 (2H, m), 7.43-7.78 (3H, m).

4) Manufacture of 4-(2-trans-3-methoxy-cyclobutylmethyl)-1-oxo-isoindoline-5-yl)-1-(2-fluorophenyl)-5-methyl-1H-[1,2,3]triazole; and 4-(2-(cis-3-methoxy-cyclobutylmethyl)-1-oxo-isoindoline-5-yl)-1-(2-fluorophenyl)-5-methyl-1H-[1,2,3]triazole By using 5-bromo-(2-(3-methoxy-cyclobutylmethyl)-1-oxo-isoindoline obtained in the above 3) and the compound 1-(2-fluorophenyl-3-yl)-5-methyl-4-tributylstanyl-1H-[1,2,3]triazole of Reference Example 4, a mixture of cis and trans of the above compound was obtained according to the method of Example 5. The obtained compound was resolved by optically active column (Daicel; CHIRALPAK AD-H column; hexane/ethanol=400/600). The trans compound of the above compound was obtained from the first fraction and the cis compound of the above compound from the latter fraction.

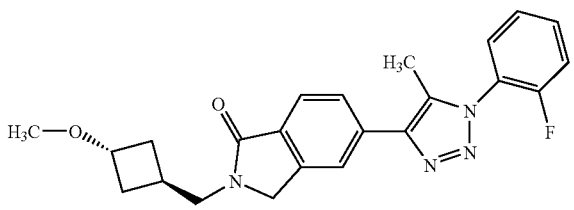

¹HNMR (300 MHz, CDCl₃), δ: 2.10-2.18 (4H, m), 2.46 (3H, d, J=1.8 Hz), 3.24 (3H, s), 3.74 (2H, d, J=8.1 Hz), 4.11 (1H, quintet, J=6.3 Hz), 4.44 (2H, s), 7.35-7.42 (2H, m), 7.55-7.61 (2H, m), 7.82 (1H, dd, J=1.5, 7.8 Hz), 7.95 (1H, d, J=7.8 Hz), 8.00 (1H, s), ESI-MS Found: m/z 407.2 [M+H]⁺.

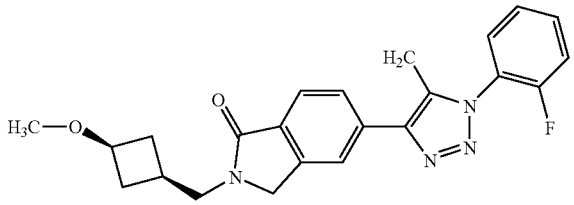

¹HNMR (300 MHz, CDCl₃), δ: 1.70-1.82 (2H, m), 2.15-2.28 (1H, m), 2.42-2.51 (2H, m), 2.46 (3H, d, J=1.8 Hz), 3.24 (3H, s), 3.69 (2H, d, J=7.2 Hz), 3.78 (1H, quintet, J=6.6 Hz), 4.46 (2H, s), 7.32-7.41 (2H, m), 7.56-7.62 (2H, m), 7.82 (1H, dd, J=1.5, 8.1 Hz), 7.94 (1H, d, J=8.1 Hz), 7.99 (1H, s), ESI-MS Found: m/z 407.2 [M+H]⁺.

EXAMPLE 153

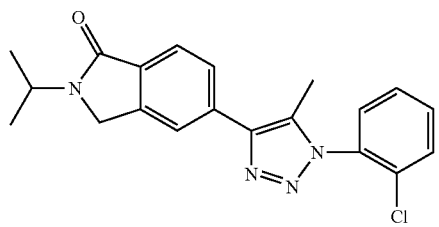

4-(2-isopropyl-1-oxo-isoindoline-5-yl)-1-(2-chlorophenyl)-5-methyl-1H-[1,2,3]triazole Under nitrogen atmosphere, 50 mg of 5-bromo-2-isopropyl-1-oxo-isoindoline obtained in Example 112-1) and 100 mg of 1-(2-chlorophenyl)-5-methyl-4-tributylstanyl-1H-[1,2,3]triazole prepared in Reference Example 25 were dissolved in toluene, 22 mg of tetrakistriphenylphosphinepalladium was added, and the mixture was heated under all night reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 18 mg of the above compound as a white solid.

¹HNMR (400 MHz, CDCl₃), δ: 1.33 (6H, d, J=6.83 Hz), 2.41 (3H, s), 4.42 (2H, s), 4.68-4.75 (1H, m), 7.50-7.51 (2H, m), 7.54-7.58 (1H, m), 7.64-7.66 (1H, m), 7.81-7.84 (1H, m), 7.93-7.95 (1H, m), 8.05 (1H, s),

ESI-MS Found: m/z 367.2 [M+H]⁺.

EXAMPLE 154

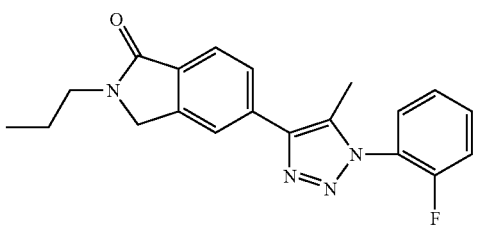

4-(2-n-propyl-1-oxo-isoindoline-5-yl)-1-(2-chlorophenyl)-5-methyl-1H-[1,2,3]triazole Under nitrogen atmosphere, 25 mg of 5-bromo-2-propyl-1-oxo-isoindoline obtained in Example 85-1) and 56 mg of 1-(2-fluorophenyl)-methyl-4-tributylstanyl-1H-[1,2,3]triazole prepared in Reference Example 11 were dissolved in toluene, 11 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 9 mg of the above compound as a white solid.

¹HNMR (400 MHz, CDCl₃), δ: 0.97-1.01 (3H, m), 1.71-1.76 (2H, m), 2.47 (3H, d, J=1.7 Hz), 3.60-3.64 (2H, m), 4.46 (2H, s), 7.35-7.41 (2H, m), 7.58 (2H, m), 7.80-7.82 (1H, m), 7.94-7.96 (1H, m), 8.01 (1H, m),

ESI-MS Found: m/z 351.2 [M+H]⁺.

EXAMPLE 155

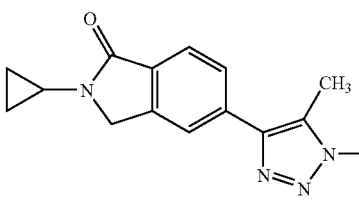

4-(2-cyclopropyl-1-oxo-isoindoline-5-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in Example 49, the tin reagent obtained in Reference Example 12, and tetrakistriphenylphosphinepalladium.

¹HNMR (400 MHz, CDCl₃), δ: 0.87-0.99 (4H, m), 2.51 (3H, s), 2.95-3.05 (1H, m), 4.41 (2H, s), 7.27-7.32 (2H, m), 7.49-7.53 (2H, m), 7.76-7.79 (1H, m), 7.93 (1H, d, J=8.1 Hz), 7.95 (1H, s),

ESI-MS Found: m/z 349.2 [M+H]⁺.

EXAMPLE 156

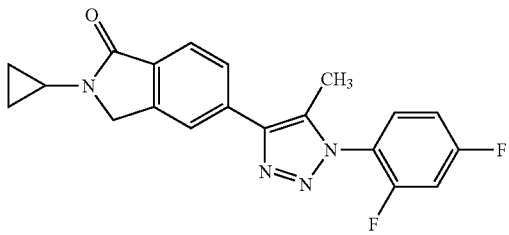

4-(2-cyclopropyl-1-oxo-isoindoline-5-yl)-1(2,4-difluorophenyl)-5-methyl-1H-[1,2,3]triazole The above compound was obtained as a white solid by the same method as Example 49, by a method according thereof, or by a combination of these and ordinary methods, with the use of halogen compound obtained in Example 49, the tin reagent obtained in Reference Example 13, and tetrakistriphenylphosphinepalladium.

$^1$HNMR (400 MHz, CDCl$_3$), δ: 0.88-0.98 (4H, m), 2.45 (3H, d, J=1.7 Hz), 2.95-3.05 (1H, m), 4.41 (2H, s), 7.08-7.17 (2H, m), 7.54-7.61 (1H, m), 7.79 (1H, d, J=8.1 Hz), 7.93 (1H, d, J=8.1 Hz), 7.96 (1H, s),

ESI-MS Found: m/z 367.1 [M+H]$^+$.

EXAMPLE 157

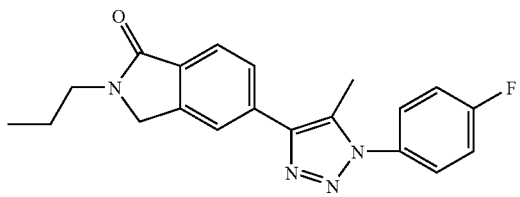

4-(2-propyl-1-oxo-isoindoline-5-yl)-1-(4-fluorophenyl)-5-methyl-1H-[1,2,3]triazole Under nitrogen atmosphere, 25 mg of 5-bromo-2-propyl-1-oxo-isoindoline obtained in Example 85-1) and 56 mg of 1-(4-fluorophenyl)-5-methyl-4-tributylstanyl-1H-[1,2,3] triazole prepared in Reference Example 12 were dissolved in toluene, 11 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 10 mg of the above compound as a white solid.

$^1$HNMR (400 MHz, CDCl$_3$), δ: 0.99 (3H, t, J=7.4 Hz), 1.68-1.78 (2H, m), 2.51 (3H, m), 3.62 (2H, t, J=7.4 Hz), 4.46 (2H, s), 7.26-7.30 (2H, m), 7.50-7.53 (2H, m), 7.77-7.79 (1H, m), 7.93-7.98 (2H, m),

ESI-MS Found: m/z 351.2 [M+H]$^+$.

EXAMPLE 158

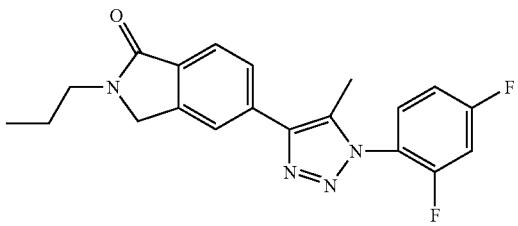

4-(2-propyl-1-oxo-isoindoline-5-yl)-1-(2,4-difluorophenyl)-5-methyl-1H-[1,2,3]triazole Under nitrogen atmosphere, 25 mg of 5-bromo-2-propyl-1-oxo-isoindoline obtained in Example 85-1), and 56 mg of 1-(2,4-difluorophenyl)-5-methyl-4-tributylstanyl-1H-[1,2,3] triazole prepared in Reference Example 13 were dissolved in toluene, 11 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 13 mg of the above compound as a white solid.

$^1$HNMR (400 MHz, CDCl$_3$), δ: 0.99 (3H, d, J=7.4 Hz), 1.69-1.78 (2H, m), 2.45 (3H, d, J=1.7 Hz), 3.62 (2H, t, J=7.4 Hz), 4.46 (2H, s), 7.09-7.16 (2H, m), 7.55-7.61 (1H, m), 7.79-7.81 (1H, m), 7.93-7.96 (1H, m), 7.99 (l H, m),

ESI-MS Found: m/z 369.2 [M+H]$^+$.

EXAMPLE 159

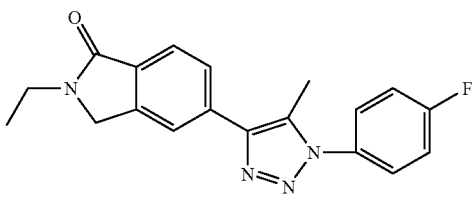

4-(2-ethyl-1-oxo-isoindoline-5-yl)-1-(4-fluorophenyl)-5-methyl-1H-[1,2,3]triazole Under nitrogen atmosphere, 150 mg of 5-bromo-2-ethyl-1-oxo-isoindoline obtained in Example 26-1), 240 mg of 1-(4-fluorophenyl)-5-methyl-4-tributylstanyl-1H-[1,2,3] triazole prepared in Reference Example 12 were dissolved in toluene, 72 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 76 mg of the above compound as a white solid.

¹HNMR (400 MHz, CDCl₃), δ: 1.31 (3H, t, J=7.2 Hz), 2.52 (3H, s), 3.69-3.74 (2H, m), 4.47 (2H, s), 7.27-7.31 (2H, m), 7.50-7.53 (2H, m), 7.77-7.79 (1H, M), 7.93-7.95 (1H, M), 7.99 (1H, M),
ESI-MS Found: m/z 337.1 [+H]⁺.

EXAMPLE 160

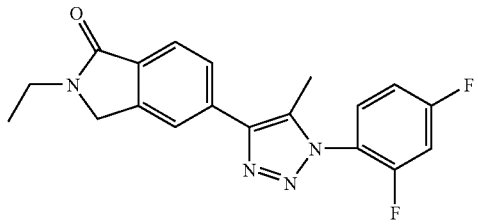

4-(2-ethyl-1-oxo-isoindoline-5-yl)-1-(2,4-difluorophenyl)-5-methyl-1H-[1,2,3]triazole Under nitrogen atmosphere, 150 mg of 5-bromo-2-ethyl-1-oxo-isoindoline obtained in Example 26-1) and 252 mg of 1-(2,4-difluorophenyl)-5-methyl-4-tributylstanyl-1H-[1,2,3]triazole prepared in Reference Example 13 were dissolved in toluene, 72 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 70 mg of the above compound as a white solid.

¹HNMR (400 MHz, CDCl₃), δ: 1.31 (3H, t, J=7.2 Hz), 2.46 (3H, d, J=1.7 Hz), 3.72 (2H, q, J=7.2 Hz), 4.47 (2H, s), 7.09-7.16 (2H, m), 7.55-7.61 (1H, m), 7.79-7.81 (1H, m), 7.93-7.95 (1H, m), 8.00 (1H, m),
ESI-MS Found: m/z 355.1 [M+H]⁺.

EXAMPLE 161

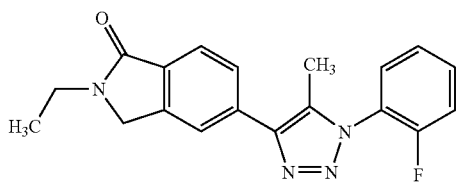

4-(2-ethyl-1-oxo-isoindoline-5-yl)-1-(2-fluorophenyl)-5-methyl-1H-[1,2,3]triazole The above compound was obtained as a white solid by the same method as Example 49, by a method according thereof, or by a combination of these and ordinary methods, with the use of halogen compound obtained in Example 72, the tin reagent obtained in Reference Example 4, and tetrakistriphenylphosphinepalladium.

¹HNMR (400 MHz, CDCl₃), δ: 1.31 (3H, t, J=7.1 Hz), 2.47 (3H, d, J=1.7 Hz), 3.72 (2H, q, J=7.1 Hz), 4.48 (2H, s), 7.33-7.42 (2H, m), 7.51-7.62 (2H, m), 7.82 (1H, d, J=7.6 Hz), 7.95 (1H, d, J=7.6 Hz), 8.01 (1H, s),
ESI-MS Found: m/z 337.1 [M+H]⁺.

EXAMPLE 162

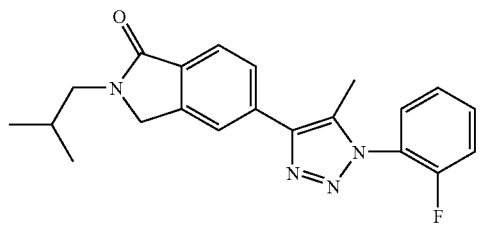

4-(2-(2-methyl-propyl)-1-oxo-isoindoline-5-yl)-1-(2-fluorophenyl)-5-methyl-1H-[1,2,3]triazole Under nitrogen atmosphere, 27 mg of 5-bromo-2-(2-methyl-propyl)-1-oxo-isoindoline obtained in Example 89-1), 56 mg of 1-(2-fluorophenyl)-5-methyl-4-tributylstanyl-1H-[1,2,3]triazole prepared in Reference Example 4 were dissolved in toluene, 11 mg of tetrakistriphenylphosphine-palladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 21 mg of the above compound as a white solid.

¹HNMR (400 MHz, CDCl₃), δ: 9.99 (6H, d, J=6.6 Hz), 2.04-2.13 (1H, m), 2.47 (3H, d, J=1.9 Hz), 3.46 (2H, d, J=7.6 Hz), 4.47 (2H, s), 7.3-7.412 (2H, m), 7.56-7.61 (2H, m), 7.81-7.83 (1H, m), 7.94-7.96 (1H, m), 8.00 (1H, m),
ESI-MS Found: m/z 365.2 [M+H]⁺.

EXAMPLE 163

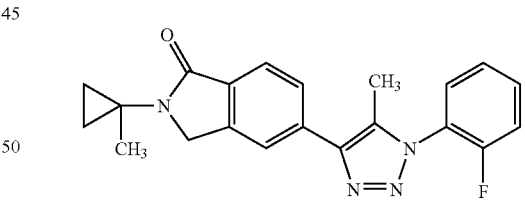

4-(2-(1-methyl-cyclopropyl)-1-oxo-isoindoline-5-yl)-1-(2-fluorophenyl)-5-methyl-1H-[1,2,3]triazole 1) Manufacture of 5-bromo-2-(1-methyl-cyclopropyl)-1-oxo-isoindoline 300 mg of 1-methyl-cyclopropylamine was dissolved in 10 ml of 10% methanol hydrochloride, and the mixture was stirred at room temperature for 10 min, concentrated under reduced pressure. The obtained residues were dissolved in 5 ml of toluene, then 540 mg of 4-bromo-2-bromomethyl benzoate and 5 ml of triethylamine were added, and the mixture was stirred all night, by heating under reflux. The reaction solution was cooled down to room temperature, diluted with ethyl acetate, washed with water and saturated saline solution, and dried with anhydrous sodium sulfate. The residues obtained by distilling out the solvents under reduced pressure were separated and purified by silicagel column chromatography (ethyl acetate:hexane=80:20) to obtain 98 mg of the above compound as a white solid.

$^1$HNMR (300 MHz, CDCl$_3$), δ: 0.78-0.84 (2H, m), 1.00-1.06 (2H, m), 1.42 (3H, s), 4.35 (2H, s), 7.55-7.69 (3H, m).

2) Manufacture of 4-(2-(1-methyl-cyclopropyl)-1-oxo-isoindoline-5-yl)-1-(2-fluorophenyl-5-methyl-1H-[1,2,3]triazole The above compound was obtained according to the method of Example 5 with the use of 5-bromo-2-(1-methyl-cyclopropyl)-1-oxo-isoindoline obtained in the above 1) and the compound 1-(2-fluorophenyl-3-yl)-5-methyl-4-tributyl-stanyl-1H-[1,2,3]triazole of Reference Example 4.

$^1$HNMR (300 MHz, CDCl$_3$), δ: 0.82-0.88 (2H, m), 1.05-1.11 (2H, m), 1.47 (3H, s), 2.46 (2H, d, J=1.8 Hz), 4.46 (2H, s), 7.32-7.42 (2H, m), 7.55-7.63 (2H, m), 7.81 (1H, dd, J=1.2, 8.1 Hz), 7.92 (1H, d, J=8.1 Hz), 7.98 (1H, s),

ESI-MS Found: m/z 363.2 [M+H]$^+$.

EXAMPLE 164

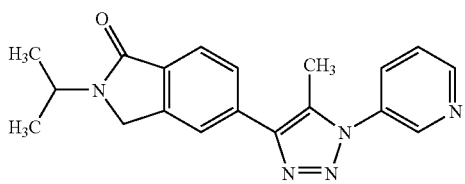

4-(2-isopropyl-1-oxo-isoindoline-5-yl)-1-(pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 36, the tin reagent obtained in Reference Example 6, and tetrakistriphenylphosphinepalladium.

$^1$HNMR (400 MHz, CDCl$_3$), δ: 1.33 (6H, d, J=6.8 Hz), 2.58 (3H, s), 4.43 (2H, s), 4.72 (1H, sept, J=6.8 Hz), 7.57-7.61 (1H, m), 7.78-7.82 (1H, m), 7.93-7.99 (3H, m), 8.81-8.86 (2H, m), ESI-MS Found: m/z 334.2 [M+H]$^+$.

EXAMPLE 165

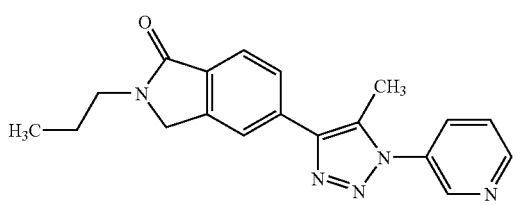

4-(2-propyl-1-oxo-isoindoline-5-yl)-1-(pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 85, the tin reagent obtained in Reference Example 6, and tetrakistriphenylphosphinepalladium.

$^1$HNMR (400 MHz, CDCl$_3$), δ: 0.99 (3H, t, J=7.3 Hz), 1.73 (2H, sept, J=7.3 Hz), 2.58 (3H, s), 3.63 (2H, t, J=7.3 Hz), 4.47 (2H, s), 7.52-7.600 (1H, m), 7.79 (1H, d, J=7.8 Hz), 7.92-7.99 (3H, m), 8.81-8.85 (2H, m), APCI-MS Found: m/z 334.2 [M+H]$^+$.

EXAMPLE 166

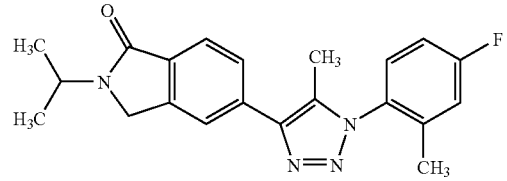

4-(2-isopropyl-1-oxo-isoindoline-5-yl)-1-(4-fluoro-2-methyl-phenyl)-5-methyl-1H-[1,2,3]triazole The above compound was obtained in the same manner as Example 3, with the use of halide obtained in Example 36, and the tin reagent 1-(4-fluoro-2-methyl-phenyl)-5-methyl-4-tributylstanyl-1H-[1,2,3]-triazole obtained in Reference Example 17.

$^1$HNMR (400 MHz, CDCl$_3$), δ: 1.33 (6H, d, J=6.8 Hz), 2.11 (3H, s), 2.36 (3H, s), 4.43 (2H, s), 4.68-4.75 (1H, m), 7.06-7.16 (2H, m), 7.26-7.31 (1H, m), 7.80-7.96 (2H, m), 8.04 (1H, s),

ESI-MS Found: m/z 365.2 [M+H]$^+$.

EXAMPLE 167

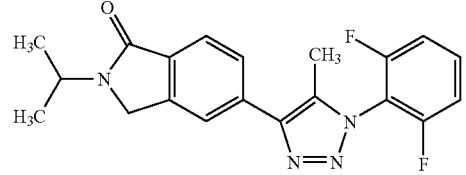

4-(2-isopropyl-1-oxo-isoindoline-5-yl)-1-(2,6-difluorophenyl)-5-methyl-1H-1,2,3]triazole The above compound was obtained in the same manner as Example 3, with the use of halide obtained in Example 36, and the tin reagent 1-(2,6-difluorophenyl)-5-methyl-4-tributylstanyl-1H-[1,2,3]-triazole obtained in Reference Example 18.

$^1$HNMR (400 MHz, CDCl$_3$), δ: 1.33 (6H, d, J=6.8 Hz), 2.45 (3H, s), 4.43 (2H, s), 4.68-4.75 (1H, m), 7.20 (2H, dt, J=1.6, 8.8 Hz), 7.55-7.62 (1H, m), 7.79-7.97 (2H, m), 8.03 (1H, s),

ESI-MS Found: m/z 369.2 [M+H]$^+$.

EXAMPLE 168

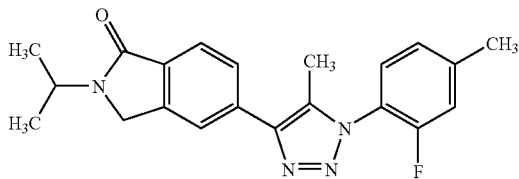

4-(2-isopropyl-1-oxo-isoindoline-5-yl)-1-(2-fluoro-
4-methyl-phenyl)-5-methyl-1H-[1,2,3]triazole The above compound was obtained in the same manner as Example 3, with the use of halide obtained in Example 36, and the tin reagent 1-(2-fluoro-4-methyl-phenyl)-5-methyl-4-tributylstanyl-1H-[1,2,3]-triazole obtained in Reference Example 19.

$^1$HNMR (400 MHz, CDCl$_3$), δ: 1.33 (6H, d, J=6.8 Hz), 2.44 (3H, d, J=2.0 Hz), 2.49 (3H, s), 4.42 (2H, s), 4.67-4.75 (1H, m), 7.14-7.19 (2H, m), 7.44 (1H, t, J=8.0 Hz), 7.79-7.95 (2H, m), 8.01 (1H, s),

ESI-MS Found: m/z 365.3 [M+H]$^+$.

EXAMPLE 169

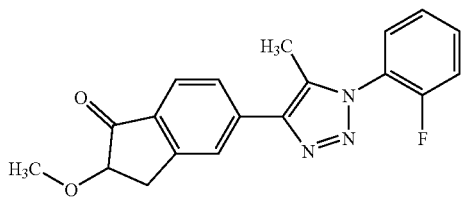

4-(2-methoxy-1-oxo-indane-5-yl)-1-(2-fluorophe-
nyl)-5-methyl-1H-[1,2,3]triazole 1) Manufacture of 5-bromo-2-methoxy-1-indanone 232 mg of [hydroxy(p-nitrobenzenesulfonyloxy)iodo] benzene was added at room temperature to 15 ml solution of acetonitrile with 100 mg of 5-bromo-1-indanone, the mixture was heated under reflux for 3 hours. The reaction solution was cooled down to room temperature, and the solvents were distilled outunder reduced pressure. The obtained residues were dissolved in 20 ml of methanol, and refluxed all night. The reaction solution was cooled down to room temperature, the solvents were distilled outunder reduced pressure, dissolved in ethyl sulfate, washed with water and saturated saline solution, and dried with anhydrous sodium sulfate. The residues obtained by distilling out the solvents under reduced pressure were purified by silicagel column chromatography (hexane:ethyl acetate=95:5) to obtain 59 mg of the above compound as a white solid.

$^1$HNMR (300 MHz, CDCl$_3$), δ: 3.00 (1H, dd, J=4.8, 17.1 Hz), 3.44 (1H, dd, J=7.5 Hz), 4.16 (1H, dd, J=4.8, 7.5 Hz), 7.52-7.66 (3H, m).

2) Manufacture of 4-(2-methoxy-1-oxo-indane-5-yl)-1(2-fluorophenyl-5-methyl-1H-[1,2,3]triazole The above compound was obtained according to the method of Example 1, with the use of 5-bromo-2-methoxy-1-indanone obtained in the above 1), and the compound 1-(2-fluorophenyl-3-yl)-5-methyl-4-tributylstanyl-1H-[1,2,3] triazole of Reference Example 4.

$^1$HNMR (300 MHz, CDCl$_3$), δ: 2.48 (3H, d, J=1.8 Hz), 3.09 (1H, dd, J=4.5, 16.8 Hz), 3.60 (1H, dd, J=7.5, 16.8 Hz), 3.67 (3H, s), 4.25 (1H, dd, J=4.5, 7.5 Hz), 7.32-7.41 (2H, m), 7.56-7.61 (2H, m), 7.80-7.89 (2H, m), 7.96 (1H, s),

ESI-MS Found: m/z 338.2 [M+H]$^+$.

EXAMPLE 170

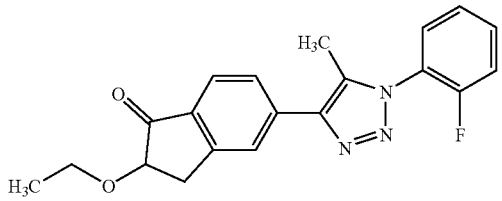

4-(2-ethoxy-1-indanone-5-yl)-1-(2-fluorophenyl)-5-
methyl-1H-[1,2,3]triazole

1) Manufacture of 5-bromo-2-ethoxy-1-indanone 310 mg of [hydroxy (p-nitrobenzenesulfonyloxy)iodo] benzene was added at room temperature to 20 ml solution of acetonitrile with 130 mg of 5-bromo-1-indanone, and the mixture was heated under reflux for 3 hours. The reaction solution was cooled down to room temperature, the solvents were distilled outunder reduced pressure. The obtained residues were dissolved in 20 ml of ethanol, and refluxed all night. The reaction solution was cooled down to room temperature, the solvents were distilled outunder reduced pressure, dissolved in ethyl acetate, washed with water and saturated saline solution, and dried with anhydrous sodium sulfate. The residues obtained by distilling out the solvents under reduced pressure were purified by silicagel column chromatography (hexane:ethyl acetate=95:5) to obtain 84 mg of the above compound as a white solid.

$^1$HNMR (300 MHz, CDCl$_3$), δ: 1.28 (3H, t, J=7.5 Hz), 2.96-3.04 (1H, m), 3.42-3.52 (1H, m), 3.68-3.78 (1H, m), 3.94-4.04 (1H, m), 4.22-4.27 (1H, m), 7.50-7.68 (3H, m).

2) Manufacture of 4-(2-ethoxy-1-indanone-5-yl)-1-
(2-fluorophenyl)-5-methyl-1H-[1,2,3]triazole The above compound was obtained according to the method of Example 1, with the use 5-bromo-2-ethoxy-1-indanone obtained in the above 1) and the compound 1-(2-fluorophenyl-3-yl)-5-methyl-4-tributylstanyl-1H-[1,2,3] triazole of Reference Example 4.

$^1$HNMR (300 MHz, CDCl$_3$), δ: 1.32 (3H, t, J=7.2 Hz), 2.47 (3H, d, J=1.8 Hz), 3.10 (1H, dd, J=4.5, 17.1 Hz), 3.59 (1H, dd, J=7.5, 17.1 Hz), 3.72-3.83 (1H, m), 3.96-4.07 (1H, m), 4.34 (1H, dd, J=4.5, 7.5 Hz), 7.31-7.42 (2H, m), 7.55-7.61 (2H, m), 7.79-7.89 (2H, m), 7.95 (1H, s),

ESI-MS Found: m/z 352.2 [M+H]$^+$.

EXAMPLE 171

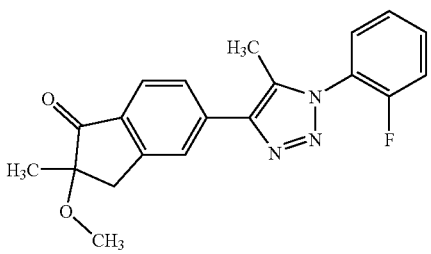

4-(2-methoxy-2-methyl-1-indanone-5-y)-1-(2-fluorophenyl)-5-methyl-1H-[1,2,3]triazole 4-((2S*)-methoxy-(2R*)-methyl-1-oxoindane-5-yl)-1-(2-fluorophenyl-3-yl)-5-methyl-1H-[1,2,3]triazole; and 4-((2R*)-methoxy-(2S*)-methyl-1-oxoindane-5-yl)-1-(2-fluorophenyl-3-yl)-5-methyl-1H-[1,2,3]triazole By using 5-bromo-2-methoxy-2-methyl-1-indanone obtained in Example 53-2), and the compound 1-(2-fluorophenyl-3-yl)-5-methyl-4-tributylstanyl-1H-[1,2,3]triazole of Reference Example 4, the racemic compound of the above compound was obtained according to the method of Example 1. Then, the obtained compound was optically resolved by optically active column (Daicel; CHIRALPAK AD-H column; hexane/ethanol=500/500). From the first fraction, the compound named (2S*,2R*) compound of the above compound for convenience was obtained, and from the latter fraction, the compound named (2R*,2S*) compound of the above compound for convenience was obtained, both as white solid.

$^1$HNMR (300 MHz, CDCl$_3$), δ: 1.49 (3H, s), 2.48 (3H, d, J=1.8 Hz), 3.15 (1H, d, J=17.1 Hz), 3.33 (3H, s), 3.45 (1H, d, J=17.1 Hz), 7.32-7.43 (2H, m), 7.56-7.63 (2H, m), 7.80-7.84 (1H, m), 7.89 (1H, d, J=7.8 Hz), 7.96 (1H, s),
ESI-MS Found: m/z 352.2 [M+H]$^+$.

EXAMPLE 172

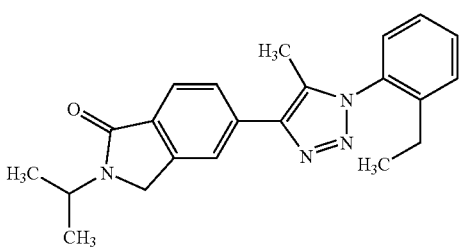

4-(2-isopropyl-1-oxo-isoindoline-5-yl)-1-(2-ethylphenyl)-5-methyl-1H-[1,2,3]triazole The above compound was obtained in the same manner as Example 3, with the use of halide obtained in Example 36, and the tin reagent 1-(2-ethylphenyl)-5-methyl-4-tributylstanyl-1H-[1,2,3]triazole obtained in Reference Example 20.

$^1$HNMR (400 MHz, CDCl$_3$), δ: 1.13 (3H, t, J=7.6 Hz), 1.33 (6H, d, J=6.8 Hz), 2.37 (3H, s), 2.40 (2H, q, J=7.4, 15.0 Hz), 4.42 (2H, s), 4.67-4.77 (1H, m), 7.36-7.57 (3H, m), 7.83 (1H, d, J=8.8 Hz), 7.94 (1H, d, J=7.6 Hz), 8.07 (1H, d, J=0.8 Hz),
ESI-MS Found: m/z 361.3[M+H]$^+$.

EXAMPLE 173

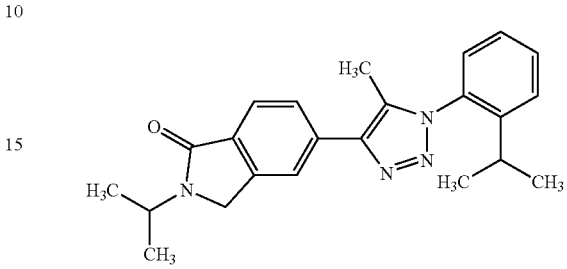

4-(2-isopropyl-1-oxo-isoindoline-5-yl)-1-(2-isopropylphenyl)-5-methyl-1H-[1,2,3]triazole The above compound was obtained in the same manner as Example 3, with the use of halide obtained in Example 36, the tin reagent 1-(2-isopropylphenyl)-5-methyl-4-tributylstanyl-1H-[1,2,3]-triazole obtained in Reference Example 21.

$^1$HNMR (400 MHz, CDCl$_3$), δ: 1.19 (6H, d, J=6.8 Hz), 1.33 (6H, d, J=6.8 Hz), 2.37 (3H, s), 2.49-2.56 (1H, m), 4.43 (2H, s), 4.68-4.76 (1H, m), 7.21-7.26 (1H, m), 7.38 (1H, dt, J=2.0, 7.4 Hz), 7.53-7.80 (2H, m), 7.84 (1H, d, J=6.4 Hz), 7.91-7.97 (1H, m), 8.07 (1H, s),
ESI-MS Found: m/z 375.3[M+H]$^+$.

EXAMPLE 174

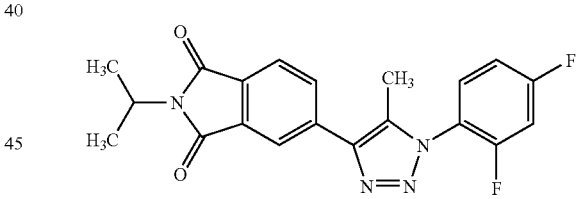

4-(2-isopropyl-1,3-dioxo-isoindoline-5-yl)-1-(2,4-difluorophenyl)-5-methyl-1H-[1,2,3]triazole 37 mg of the compound obtained in Example 119 was dissolved in 2.0 ml of acetic acid, then 41 mg of sodium acetate and 3 drops of bromine were added and the mixture was stirred at room temperature for 20 min. After adding saturated hydrogen carbonate water and ethyl acetate, organic layer was separated, and dried with anhydrous sodium sulfate. The residues obtained by distilling out the solvents under reduced pressure were purified by thin-layer silicagel chromatography (hexane:ethyl acetate=50:50) to obtain 19.5 mg of the above compound as a white solid.

$^1$HNMR (300 MHz, CDCl$_3$), δ: 1.52 (6H, d, J=6.9 Hz), 2.48 (3H, d, J=1.8 Hz), 4.57 (1H, sept, J=7.0 Hz), 7.09-7.19 (2H, m), 7.51-7.62 (1H, m), 7.93 (1H, d, J=7.8 Hz), 8.16 (1H, d, J=1.5 Hz), 8.24 (1H, dd, J=1.5, 7.8 Hz),
ESI-MS Found: m/z 383.1 [M+H]$^+$.

EXAMPLE 175

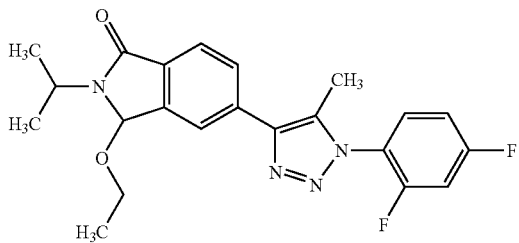

4-(2-isopropyl-3-ethoxy-1-oxo-isoindoline-5-yl)-1-(2,4-difluorophenyl)-5-methyl-1H-[1,2,3]triazole 9.2 mg of the above compound was obtained as a byproduct of Example 174.

$^1$HNMR (300 MHz, CDCl$_3$), δ: 1.13 (3H, t, J=7.0 Hz), 1.42 (3H, d, J=6.9 Hz), 1.45 (3H, d, J=6.9 Hz), 2.45 (3H, d, J=1.7 Hz), 3.01-3.12 (1H, m), 3.27-3.40 (1H, m), 4.45 (1H, sept, J=6.9 Hz), 7.08-7.19 (2H, m), 7.51-7.61 (1H, m), 7.83-7.91 (2H, m), 8.01 (1H, s), ESI-MS Found: m/z 435.1 [M+Na]

EXAMPLE 176

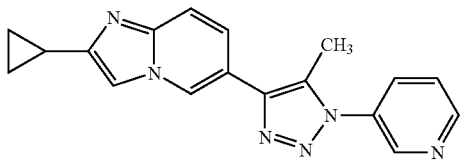

4-(2-cyclopropyl-imidazo[1,2-a]pyridine-6-yl)-1-(pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 48, the tin reagent obtained in Reference Example 6, and tetrakistriphenylphosphinepalladium.

$^1$HNMR (400 MHz, CDCl$_3$), δ: 0.96-1.04 (4H, m), 2.01-2.05 (1H, m), 2.55 (3H, s), 7.45-7.49 (2H, m), 7.52-7.63 (2H, m), 7.91-7.95 (1H, m), 8.51-8.52 (1H, m), 8.81-8.84 (2H, m),

ESI-MS Found: m/z 317.2 [M+H]$^+$.

EXAMPLE 177

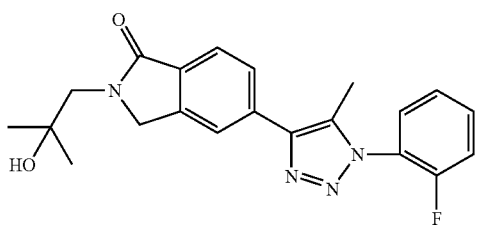

4-(2-(2-hydroxy-2-methyl-propyl)-1-oxo-isoindoline-5-yl)-1-(2-fluorophenyl)-5-methyl-1H-[1,2,3]triazole

1) Manufacture of 5-bromo-2-(2-hydroxy-2-methyl-propyl)-1-oxo-isoindoline

Under nitrogen atmosphere, 3.4 g of 4-bromo-2-bromomethyl methyl benzoate was dissolved in toluene, 2-hydroxy-2-methyl-propylamine and 4.85 ml of triethylamine were added and the mixture was heated all night under reflux. The reaction solution was cooled down to room temperature, the solvents were distilled out under reduced pressure, and the residues were separated and purified by silicagel column chromatography (ethyl acetate/hexane=1/2) to obtain 3.73 g of the above compound as a white solid.

$^1$HNMR (400 MHz, CDCl$_3$), δ: 1.29 (6H, s), 2.76 (1H, s), 3.59 (2H, s), 4.59 (2H, s), 7.60-7.62 (2H, m), 7.72 (1H, d, J=8.4 Hz), ES-MS Found: m/z 286.1 [M+H]$^+$.

2) Manufacture of 4-(2-(2-hydroxy-2-methyl-propyl)-1-oxo-isoindoline-5-yl)-1-(2-fluorophenyl)-5-methyl-1H-[1,2,3]triazole Under nitrogen atmosphere, 106 mg of 5-bromo-2-(2-hydroxy-2-methyl-propyl)-1-oxo-isoindoline obtained in the above 1), and 100 mg of 1-(2-fluorophenyl)-5-methyl-4-tributylstanyl-1H-[1,2,3]triazole prepared in Reference Example 4 were dissolved in toluene, 43 mg of tetrakistriphenylphosphinepalladium was added, and the mixture was heated under reflux for 6 hours. The reaction solution was cooled down to room temperature, and insoluble matters were removed by celite filtration. The solvents were distilled out under reduced pressure, and the residues were separated and purified by silicagel column chromatography (ethyl acetate/hexane=1/2) to obtain 73 mg of the above compound as a white solid.

$^1$HNMR (400 MHz, CDCl$_3$), δ: 1.32 (6H, s), 2.47 (3H, d, J=1.7 Hz), 3.13 (1H, s), 3.65 (2H, s), 4.68 (2H, s), 7.33-7.41 (2H, m), 7.56-7.61 (2H, m), 7.83-7.85 (1H, m), 7.95-7.97 (1H, m), 8.00 (1H, br),

ESI-MS Found: m/z 381.2[M+H]$^+$.

EXAMPLE 178

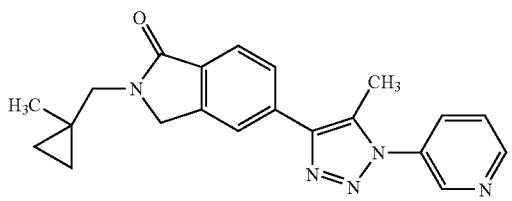

4-(2-(1-methyl-cyclopropylmethyl)-1-oxo-isoindoline-5-yl)-1-(pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 130, the tin reagent obtained in Reference Example 6, and tetrakistriphenylphosphinepalladium.

¹HNMR (400 MHz, CDCl₃), δ: 0.43-0.51 (2H, m), 0.54-0.87 (2H, m), 1.07 (3H, s), 2.58 (3H, s), 3.52 (2H, s), 4.56 (2H, s), 7.52-7.61 (1H, m), 7.81 (1H, dd, J=1.6, 7.7 Hz), 7.93-7.99 (3H, m), 8.81-8.86 (2H, m),
ESI-MS Found: m/z 360.2 [M+H]⁺.

EXAMPLE 179

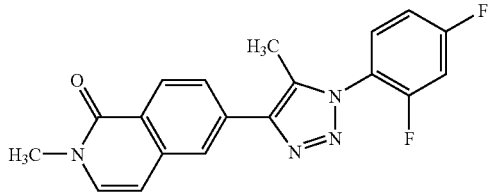

4-(2-methyl-1-oxo-isoquinoline-6-yl)-1-(2,4-difluorophenyl)-5-methyl-1H-[1,2,3]triazole The above compound was obtained in the same manner as Example 3, with the use of halide obtained in Example 94 and the tin reagent 1-(2,4-difluorophenyl)-5-methyl-4-tributylstanyl-1H-[1,2,3]-triazole obtained in Reference Example 13.

¹HNMR (400 MHz, CDCl₃), δ: 2.49 (3H, d, J=1.6 Hz), 3.63 (3H, s), 6.57 (1H, d, J=7.2 Hz), 7.10-7.71 (4H, m), 7.88 (1H, dd, J=2.0, 8.4 Hz), 8.01 (1H, d, J=1.2 Hz), 8.54 (1H, d, J=8.4 Hz),
ESI-MS Found: m/z 353.1 [M+H]⁺.

EXAMPLE 180

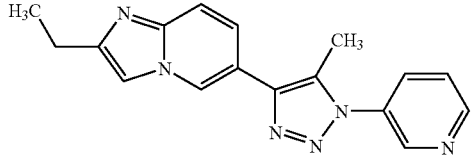

4-(2-ethyl-imidazo[1,2-a]pyridine-6-yl)-1-(pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 95, the tin reagent obtained in Reference Example 6, and tetrakistriphenylphosphinepalladium.

¹HNMR (400 MHz, CDCl₃), δ: 1.38 (3H, t, J=7.6 Hz), 2.55 (3H, s), 2.86 (2H, q, J=7.6 Hz), 7.44 (1H, s), 7.49 (1H, dd, J=2.0, 9.4 Hz), 7.52-7.61 (1H, m), 7.63-7.66 (1H, d, J=9.4 Hz), 7.92-7.95 (1H, m), 8.54 (1H, d, J=1.7 Hz), 8.54-8.85 (2H, m),
ESI-MS Found: m/z 305.2 [M+H]⁺.

EXAMPLE 181

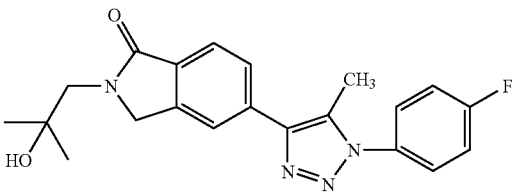

4-(2-(2-hydroxy-2-methyl-propyl)-1-oxo-isoindoline-5-yl)-1-(4-fluorophenyl)-5-methyl-1H-[1,2,3]triazole Under nitrogen atmosphere, 85 mg of 5-bromo-2-(2-hydroxy-2-methyl-propyl-1-oxo-isoindoline obtained in Example 177-1) and 100 mg of 1-4-fluorophenyl)-5-methyl-4-tributylstanyl-1H-[1,2,3]triazole prepared in Reference Example 12 were dissolved in toluene, 35 mg of tetrakistriphenylphosphinepalladium was added and the mixture was heated under reflux for 6 hours. The reaction solution was cooled down to room temperature, and insoluble matters were removed by celite filtration. The solvents were distilled out under reduced pressure, and the residues were separated and purified by thin-layer silicagel column chromatography (ethyl acetate/hexane=1/2) to obtain 31 mg of the above compound as a white solid.

¹HNMR (400 MHz, CDCl₃), δ: 1.32 (6H, s), 2.52 (3H, s), 3.08 (1H, s), 3.65 (2H, s), 4.68 (2H, s), 7.27-7.31 (2H, m), 7.50-7.53 (2H, m), 7.80-7.82 (1H, m), 7.95-7.98 (2H, m),
ESI-MS Found: m/z 381.2 [M+H]⁺.

EXAMPLE 182

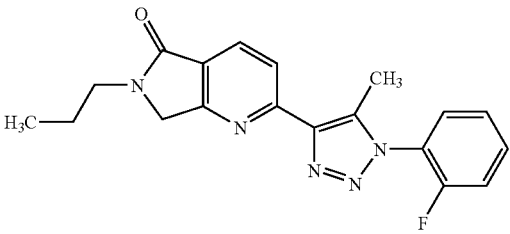

1-(2-fluorophenyl)-4-(6-propyl-6,7-dihydro-5H-pyrrolo[3,4-b]pyridine-5-one-2-yl)-5-methyl-1H-[1,2,3]triazole 1) Manufacture of 2-(benzyloxy)-6-propyl-5H-pyrrolo[3,4-b]pyridine-5,7 (6H)-dione 510 mg of 2-(benzyloxy)flo[3,4-b]pyridine-5,7-dione was dissolved in 10 ml of toluene, then 354 μg of propylamine, 835 μl of triethylamine were added and the mixture was stirred all night by heating under reflux. After cooling down to room temperature, the solvents were distilled out under reduced pressure, the obtained residues were purified by silicagel chromatography (hexane:ethyl acetate=50:50) to obtain 56 mg of the above compound as a white solid.

¹HNMR (300 MHz, CDCl₃), δ: 0.96 (3H, t, J=7.3 Hz), 1.63-1.79 (2H, m)3.68 (2H, t, J=7.3 Hz), 5.07 (2H, s), 7.03 (1H, d, J=8.3 Hz), 7.30-7.52 (5H, m), 7.98 (1H, d, J=8.3 Hz),

ESI-MS Found: m/z 297.2 [M+H]⁺.

2) Manufacture of 2-(benzyloxy)-6-propyl-6,7-dihydro-5H-pyrrolo[3,4-b]pyridine-5-one 23 mg of the compound obtained in the above 1) was dissolved in 1.0 ml of acetic acid, then 20 mg of zinc was added thereto and the mixture was stirred at 80° C. for 1.5 hours. After cooling down the obtained mixture to room temperature, water and 3N sodium hydride aqueous solution were added, and the products were extracted with ethyl acetate. After drying with anhydrous sodium sulfate, the solvents were distilled outunder reduced pressure. The obtained residues were dissolved in 2.0 ml of chloroform, 127 μl of triethylsilane was added, cooled at 0° C., and 30 μl of trifluoroacetic acid was dropped. After stirring all night at room temperature, the solvents were distilled outunder reduced pressured, ethyl acetate and saturated sodium bicarbonate aqueous solution were added to the obtained residues, and organic layer was dried with anhydrous sodium sulfate. The solvents were distilled outunder reduced pressure, the obtained residues were purified by basic thin-layer silicagel chromatography (hexane:ethyl acetate=50:50) to obtain 14.2 mg of the above compound.

¹HNMR (300 MHz, CDCl₃), δ: 0.97 (3H, t, J=7.3 Hz), 1.60-1.80 (2H, m), 3.58 (2H, t, J=7.3 Hz), 4.32 (2H, s), 5.44 (2H, s), 6.84 (1H, d, J=8.3 Hz), 7.25-7.49 (5H, m), 7.96 (1H, d, J=8.3 Hz),

ESI-MS Found: m/z 283.2 [M+H]⁺.

3) Manufacture of 5-oxo-6-propyl-6,7-dihydro-5H-pyrrolo[3,4-b]pyridine-2-yltrifluoromethanesulfonate 12 mg of the compound obtained in the above 2) was dissolved in 2.5 ml of methanol, 10 mg of 10% palladium carbon was added and the mixture was stirred under hydrogen atmosphere for 6 hours. The catalysts were filtrated, and the filtrate was concentrated under reduced pressure. The obtained residues were dissolved in 1 ml of methylene chloride, cooled down to 0° C., and 50 μl of pyridine, and 15 μl of trifluoromethanesulfonate anhydride were added. After stirring 2 hours at room temperature, water was added and the products were extracted with ethyl acetate. Organic layer was dried with anhydrous sodium sulfate, the solvents were distilled outunder reduced pressure, to obtain the above compound as crude product.

4) Manufacture of 1-(2-fluorophenyl)-4-(6-propyl-6,7-dihydro-5H-pyrrolo[3,4-b]pyridine-5-one-2-yl)-5-methyl-1H-[1,2,3]triazole The above compound was obtained as a white solid by the same method as Example 49, by a method according thereof, or by a combination of these and ordinary methods, with the use of the compound obtained in the above 3), the tin reagent obtained in Reference Example 4, and tetrakistriphenylphosphinepalladium.

¹HNMR (400 MHz, CDCl₃), δ: 1.00 (3H, t, J=7.4 HZ), 1.71-1.77 (2H, m), 2.68 (3H, d, J=1.7 Hz), 3.65 (2H, t, J=7.3 Hz), 4.47 (2H, s), 7.32-7.41 (2H, m), 7.52-7.62 (2H, m), 8.20 (1H, d, J=8.1 Hz), 8.38 (1H, d, J=8.1 Hz),

ESI-MS Found: m/z 352.2 [M+H]⁺.

EXAMPLE 183

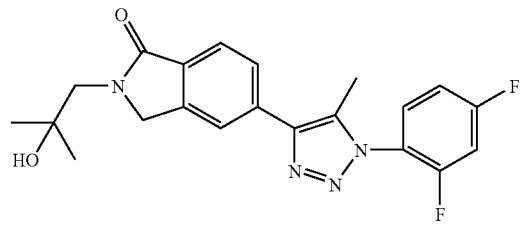

4-(2-(2-hydroxy-2-methyl-propyl)-1-oxo-isoindoline-5-yl)-1-(2,4-difluorophenyl)-5-methyl-1H-[1,2,3]triazole Under nitrogen atmosphere, 85 mg of 5-bromo-2-(2-hydroxy-2-methyl-propyl)-1-oxo-isoindoline obtained in Example 177-1), and 100 mg of 1-(2,4-difluorophenyl)-5-methyl-4-tributylstanyl-1H-[1,2,3]triazole prepared in Reference Example 13 were dissolved in toluene, 35 mg of tetrakistriphenylphosphinepalladium was added, and the mixture was heated under reflux for 6 hours. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=1/2) to obtain 20 mg of the above compound as a white solid.

¹HNMR (400 MHz, CDCl₃), δ: 1.32 (6H, s), 2.46 (3H, d, J=1.76 Hz), 3.08 (1H, s), 3.65 (2H, s), 4.68 (2H, s), 7.10-7.12 (2H, m), 7.52-7.59 (2H, m), 7.82-7.84 (1H, m), 7.95-7.99 (2H, m),

ESI-MS Found: m/z 399.2 [M+H]⁺.

EXAMPLE 184

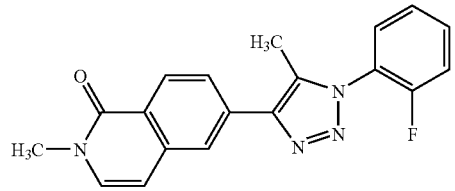

4-(2-methyl-1-oxo-isoquinoline-6-yl)-1-(2-fluorophenyl)-5-methyl-1H-[1,2,3]triazole The above compound was obtained in the same manner as Example 3, with the use of halide obtained in Example 94, the tin reagent 1-(2-fluorophenyl)-5-methyl-4-tributylstanyl-1-H-[1,2,3]-triazole obtained in Reference Example 13.

¹HNMR (400 MHz, CDCl₃), δ: 2.50 (3H, d, J=2.0 Hz), 3.64 (3H, s), 6.58 (1H, d, J=7.6 Hz), 7.12 (1H, d, J=7.6 Hz), 7.32-7.42 (2H, m), 7.55-7.62 (2H, m), 7.90 (1H, dd, J=2.0, 8.4 Hz), 8.03 (1H, d, J=1.6 Hz), 8.69 (1H, d, J=8.0 Hz),

ESI-MS Found: m/z 335.1 [M+H]⁺.

EXAMPLE 185

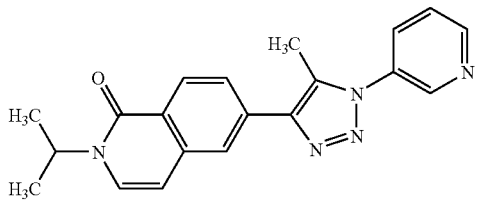

4-(2-isopropyl-1-oxo-isoquinoline-6-yl)-1-(pyridine-3-yl)-5-methyl-1H-[1,2,3]triazole The above compound was obtained in the same manner as Example 3, with the use of halide obtained in Example 101, the alkyl tin compound 1-(pyridine-3-yl)-5-methyl-4-tributylstanyl-1H-[1,2,3]-triazole similar as Reference Example 6.

$^1$HNMR (400 MHz, CDCl$_3$), δ: 1.23 (6H, d, J=6.8 Hz), 2.56 (3H, m), 3.04 (2H, t, J=6.6 Hz), 3.49 (2H, t, J=6.4 Hz), 5.09-5.15 (1H, m), 7.55-7.60 (1H, m), 7.66 (1H, dd, J=1.6, 8.4 Hz), 7.74 (1H, d, J=0.8 Hz), 7.91-7.95 (1H, m), 8.19 (1H, d, J=8.4 Hz), 8.79-8.85 (2H, m),

ESI-MS Found: m/z 348.2 [M+H]$^+$.

EXAMPLE 186

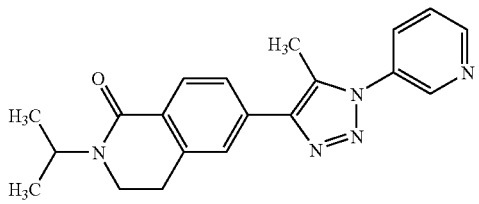

4-(2-isopropyl-1-oxo-3,4-dihydroisoquinoline-6-yl)-1-(pyridine-3-yl)-5-methyl-1H-[1,2,3]triazole After adding 50 mg of palladium carbon to 10 ml solution of ethanol with 25 mg of 4-(2-isopropyl-1-oxo-isoquinoline-6-yl)-1-(pyridine-3-yl)-5-methyl-1H-[1,2,3]triazole, hydrogen was added under 4 atm of hydrogen pressure. 8 hours later, the reaction solution was filtrated, the solvents of the filtrate were distilled outunder reduced pressure, and the residues were separated and purified by thin-layer chromatography (chloroform/methanol=10/1) to obtain 23 mg of the above compound as a white solid.

$^1$HNMR (400 MHz, CDCl$_3$), δ: 1.42 (6H, d, J=6.8 Hz), 2.60 (3H, s), 5.38-5.48 (1H, m), 6.64 (1H, d, J=7.2 Hz), 7.21 (1H, d, J=7.6 Hz), 7.56-7.61 (1H, m), 7.86 (1H, dd, J=1.6, 8.4 Hz), 7.92-7.97 (1H, m), 7.99 (1H, d, J=2.0 Hz), 8.56 (1H, d, 8.4 Hz), 8.80-8.87 (2H, m),

ESI-MS Found: m/z 346.2 [M+H]$^+$.

EXAMPLE 187

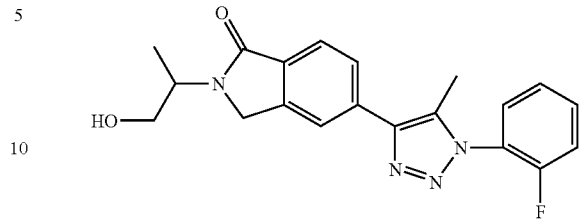

4-(2-(2-hydroxy-1-methyl-ethyl)-1-oxo-isooindoline-5-yl)-1-(2-fluorophenyl)-5-methyl-1H-[1,2,3]triazole Under nitrogen atmosphere, 10 mg of 5-bromo-2-(2-hydroxy-1-methyl-ethyl)-1-oxo-isoindoline obtained in Example 76-1) and 20 mg prepared in Reference Example 4 were dissolved in toluene, 35 mg of tetrakistriphenylphosphinepalladium was added, and the mixture was heated under reflux for 6 hours. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 7 mg of the above compound as a white solid.

$^1$HNMR (400 MHz, CDCl$_3$), δ: 1.37 (3H, d, J=2.9 Hz), 2.45 (3H, d, J=1.7 Hz), 3.77-3.81 (1H, m), 3.89-3.93 (1H, m), 4.44-4.50 (1H, m), 4.45-4.60 (2H, m), 7.32-7.41 (2H, m), 7.55-7.61 (2H, m), 7.79-7.81 (1H, m), 7.90-7.92 (1H, m), 7.98-7.99 (1H, m),

ESI-MS Found: m/z 367.2 [M+H]$^+$.

EXAMPLE 188

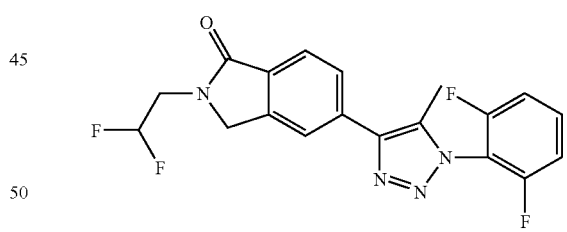

4-(2-2,2-difluoro-ethyl)-1-oxo-isoindoline-5-yl)-1-(2,6-difluorophenyl)-5-methyl-1H-[1,2,3]triazole Under nitrogen atmosphere, 100 mg of 5-bromo-2-(2,2-difluoroethyl)-1-oxo-isoindoline obtained in Example 137-1) and 175 mg of 1-(2,6-difluorophenyl)-5-methyl-4-tributylstanyl-1H-[1,2,3]triazole prepared in Reference Example 18 were dissolved in toluene, 41 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 95 mg of the above compound as a white solid.

$^1$HNMR (400 MHz, CDCl$_3$), δ: 2.45 (3H, s), 3.97-4.05 (2H, m), 4.62 (2H, s), 5.89-6.18 (1H, m), 7.18-7.22 (2H, m), 7.55-7.62 (1H, m), 7.86-7.87 (1H, m), 7.97-7.99 (1H, m), 8.02 (1H, m),

ESI-MS Found: m/z 391.1 [M+H]$^+$.

EXAMPLE 189

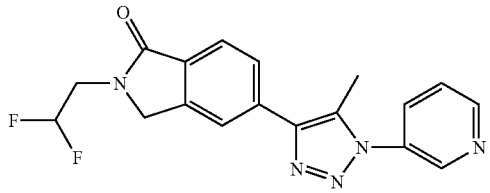

4-(2-(2,2-difluoro-ethyl-1-oxo-isoindoline-5-yl)-1-(pyridine-3-yl)-5-methyl-1H-[1,2,3]triazole Under nitrogen atmosphere, 100 mg of 5-bromo-2-(2,2-difluoroethyl)-1-oxo-isoindoline obtained in Example 137-1), and 162 mg of 1-(pyridine-3-yl)-5-methyl-4-tributylstanyl-1H-[1,2,3]triazole prepared in Reference Example 6 were dissolved in toluene, 41 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 15 mg of the above compound as a white solid.

$^1$HNMR (400 MHz, CDCl$_3$), δ: 2.58 (3H, s), 3.97-4.05 (2H, m), 4.63 (2H, s), 5.89-6.17 (1H, m), 7.57-7.60 (1H, m), 7.84-7.86 (1H, m), 7.92-7.95 (1H, m), 7.98-7.99 (1H, m), 8.81-8.84 (2H, m),

ESI-MS Found: m/z 356.2 [M+H]$^+$.

EXAMPLE 190

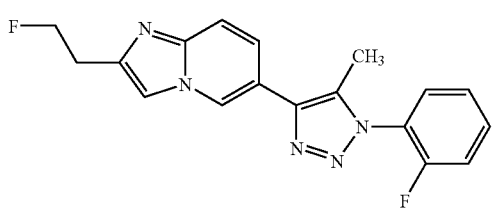

4-(2-(2-fluoroethyl)-imidazo[1,2-a]pyridine-6-yl)-1-(2-fluorophenyl)-5-methyl-1H-[1,2,3]triazole 1) Manufacture of ethyl(6-bromoimidazo[1,2-a]pyridine-2-yl)acetate 4.90 ml of ethyl4-chloro-3-oxobutanoate was dissolved in 50 ml of ethanol, 5.19 g of 2-amino-5-bromopyridine was added, and the mixture was stirred all night by heating under reflux. After cooling down to room temperature, the solvents were distilled outunder reduced pressure, and then, ethyl acetate followed by saturated sodium bicarbonate aqueous solution were added. Organic layer was dried with anhydrous sodium sulfate, and the solvents were distilled outunder reduced pressure. The obtained residues were purified by preparative thin-layer chromatography (hexane:ethyl acetate=60:40) to obtain 9.49 mg of the above compound as a white solid.

$^1$HNMR (300 MHz, CDCl$_3$), δ: 1.29 (3H, t, J=7.6 Hz), 3.86 (2H, s), 4.16 (2H, q, J=7.6 Hz), 7.18-7.25 (1H, m), 7.45 (1H, d, J=8.0 Hz), 7.58 (1H, s), 8.21-8.24 (1H, m).

2) Manufacture of 2-(6-bromoimidazo[1,2-a]pyridine-2-yl)ethanol 4.25 g of ester compound obtained in the above 1) was dissolved in 50 ml of tetrehydrofuran, cooled down to 0° C., and 570 mg of lithium aluminium hydride was added. After stirring for 30 min at room temperature, sodium sulfate 10-hydrate was added and the mixture was further stirred for 2 hours. The obtained chloroform was diluted, and after filtrating insoluble matters, the filtrate was concentrated under reduced pressure. The obtained residues were separated and purified by silicagel column chromatography (chloroform:methano=7:1) to obtain 1.23 g of the above compound as crude product.

3) 6-bromo-(2-fluoroethyl)-imidazo[1,2-a]pyridine 139 mg of alcoholic compound obtained in the above 2) was dissolved in 2.0 ml of tetrahydrofuran and after cooling down to −78° C., 225 μl of diethylaminosulfate trifluoride was added. After heating to room temperature, the mixture was stirred for 5 min, saturated sodium bicarbonate aqueous solution was added and the products were extracted with ethyl acetate. Organic layer was dried with sodium sulfate anhydride, and the solvents were distilled outunder reduced pressure. The obtained residues were separated and purified by silicagel column chromatography (hexane:ethyl acetate=1:1) to obtain 10.2 mg of the above compound.

$^1$HNMR (300 MHz, CDCl$_3$), δ: 3.20 (2H, td, J=6.0, 26.1 Hz), 4.82 (2H, td, J=6.0, 94.3 Hz), 7.22 (1H, d, J=8.0 Hz), 7.51-7.57 (2H, m), 8.22 (1H, s).

4) Manufacture of 4-(2-(2-fluoroethyl)-imidazo[1,2-a]pyridine-6-yl)-1-(2-fluorophenyl)-5-metyl-1H-[1,2,3]triazole The above compound was obtained as a white solid by the same method as Example 49, by a method according thereof, or by a combination of these and ordinary methods, with the use of the compound obtained in the above 3), the tin reagent obtained in Reference Example 1, and tetrakistriphenylphosphinepalladium.

$^1$HNMR (400 MHz, CDCl$_3$), δ: 2.44 (3H, d, J=2.0 Hz), 3.24 (2H, td, J=6.2, 24.9 Hz), 4.85 (2H, td, J=6.2, 47.1 Hz), 7.30-7.42 (2H, m), 7.52-7.67 (5H, m), 8.55-8.57 (1H, m),

ESI-MS Found: m/z 340.3 [M+H]$^+$.

EXAMPLE 191

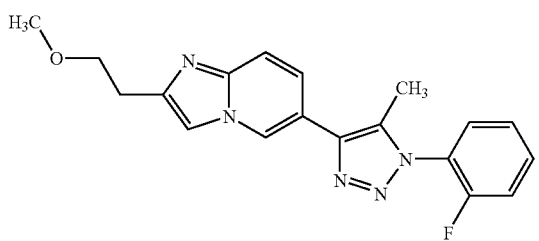

1-(2-fluorophenyl)-4-(2-(2-methoxyethyl)-imidazo[1,2-a]pyridine-6-yl)-5-methyl-1H-[1,2,3]triazole

1) Manufacture of 6-bromo-2-methoxyethyl-imidazo[1,2-a]pyridine 110 mg of the alcoholic compound obtained in Example 190-2) was dissolved in 2.0 ml of dimethylformamide, 56 mg of 60% sodium hydride was added under iced temperature, heated to room temperature, cooled down again to 0° C., and 56 µL of methyl iodide was added. After stirring the mixture all night at room temperature, water was added and the products were extracted with ethyl acetate. The obtained residues were separated and purified by silicagel column chromatography (hexane:ethyl acetate=1:1) to obtain 24 mg of the above compound.

$^1$HNMR (300 MHz, CDCl$_3$), δ: 3.06 (2H, t, J=6.3 Hz), 3.40 (3H, s), 3.77 (2H, t, J=6.3 Hz), 7.15-7.20 (1H, m), 7.40-7.46 (2H, m), 8.20 (1H, s).

2) Manufacture of 1-(2-fluorophenyl)-4-(2-(2-methoxyethyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of the compound obtained in the above 1), the tin reagent obtained in Reference Example 1, and tetrakistriphenylphosphinepalladium.

$^1$HNMR (400 MHz, CDCl$_3$), δ: 2.43 (3H, d, J=2.0 Hz), 3.10 (2H, t, J=6.6 Hz), 3.41 (3H, s), 3.82 (2H, t, J=6.6 Hz), 7.32-7.44 (2H, m), 7.52-7.66 (5H, m), 8.53-8.55 (1H, m),

ESI-MS Found: m/z 352.3 [M+H]$^+$.

EXAMPLE 192

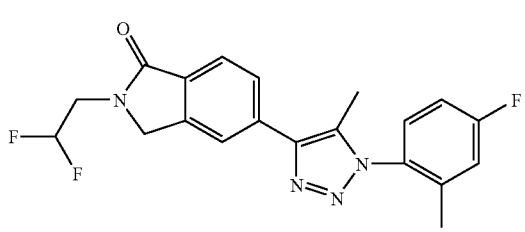

4-(2-(2,2-difluoro-ethyl)-1-oxo-isoindoline-5-yl)-1-(4-fluoro-2-methyl-phenyl)-5-methyl-1H-[1,2,3]triazole Under nitrogen atmosphere, 100 mg of 5-bromo-2-(2,2-difluoroethyl)-1-oxo-isoindoline obtained in Example 137-1), and 173 mg of 1-(4-fluoro-2-methyl-phenyl)-5-methyl-4-tributylstanyl-1H-[1,2,3]triazole prepared in Reference Example 17 were dissolved in toluene, 41 mg of tetrakistriphenylphosphinepalladium was added, and the mixture was heated under reflux all night. The reaction solution was cooled down to room temperature, and insoluble matters were removed by celite filtration. The solvents were distilled out under reduced pressure, and the residues were separated and purified by thin-layer silicagel column chromatography (ethyl acetate/hexane=2/1) to obtain 80 mg of the above compound as a white solid.

$^1$HNMR (400 MHz, CDCl$_3$), δ: 2.10 (3H, s), 2.37 (3H, s), 4.01 (2H, dt, J=4.3 Hz,14.6 Hz), 4.62 (2H, s), 6.03 (1H, tt, J=4.3 Hz, 55.7 Hz), 7.07-7.16 (2H, m), 7.27-7.30 (1H, m), 7.85-7.88 (1H, m), 7.96-7.98 (1H, m), 8.03-8.04 (1H, m),

ESI-MS Found: m/z 387.2 [M+H]$^+$.

EXAMPLE 193

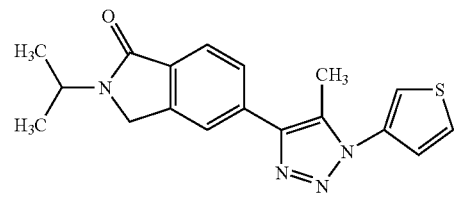

4-(2-isopropyl-1-oxo-isoindoline-5-yl)-1-(thiophene-3-yl)-5-methyl-1H-[1,2,3]triazole The above compound was obtained in the same manner as Example 3, with the use of halide obtained in Example 36, the tin reagent 1-(thiophene-3-yl)-5-methyl-4-tributylstanyl-1-H-[1,2,3]-triazole obtained in Reference Example 22.

$^1$HNMR (400 MHz, CDCl$_3$), δ: 1.33 (6H, d, J=6.8 Hz), 2.58 (3H, s), 4.42 (2H, s), 4.56-4.75 (1H, m), 7.36 (1H, dd, J=0.8, 5.2 Hz), 7.51-7.56 (2H, m), 7.78 (1H, d, J=7.6 Hz), 7.94 (1H, d, J=8.4 Hz), 7.98 (1H, s),

ESI-MS Found: m/z 339.2 [M+H]$^+$.

EXAMPLE 194

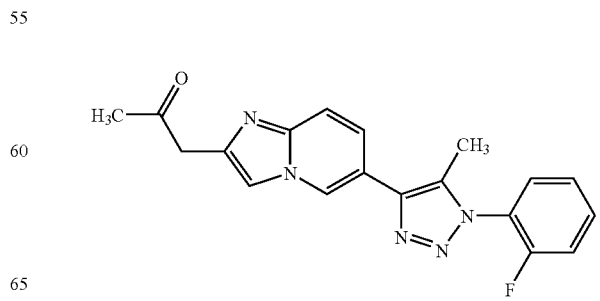

4-(2-acetylmethyl-imidazo[1,2-a]pyridine-6-yl)-1-(2-fluorophenyl)-5-methyl-1H-[1,2,3]triazole 1) Manufacture of 1-(6-bromoimidazo[1,2-a]pyridine-2-yl)acetone 425 mg of ester compound obtained in Example 190-1) was dissolved in 10 ml of tetrahydrofuran, cooled down to −20° C., and 8.1 ml of 0.93 M methylmagnesiumbromide was added. After stirring the mixture for 30 min at −10° C., water was added and the products were extracted with ethyl acetate. Organic layer was dried with anhydrous sodium sulfate, and the solvents were distilled outunder reduced pressure. The obtained residues were separated and purified by silicagel column chromatography (hexane:ethyl acetate=1:1) to obtain 84 mg of the above compound.

$^1$HNMR (300 MHz, CDCl$_3$), δ: 2.29 (3H, s), 3.91 (2H, s), 7.19-7.29 (1H, m), 7.45 (1H, d, J=8.7 Hz), 7.52 (1H, s), 8.44 (1H, s).

2) Manufacture of 4-(2-acetylmethyl-imidazo[1,2-a]pyridine-6-yl)-1-(2-fluorophenyl)-5-methyl-1H-[1,2,3]triazole The above compound was obtained as a white solid by the same method as Example 49, by a method according thereof, or by a combination of these and ordinary methods, with the use of the compound obtained in the above 1), the tin reagent obtained in Reference Example 4, and tetrakistriphenylphosphinepalladium.

$^1$HNMR (400 MHz, CDCl$_3$), δ: 2.31 (3H, s), 2.44 (3H, d, J=1.7 Hz), 3.97 (2H, s), 7.30-7.42 (2H, m), 7.56-7.68 (5H, m), 8.55-8.57 (1H, m),

ESI-MS Found: m/z 350.2 [M+H]$^+$.

EXAMPLE 195

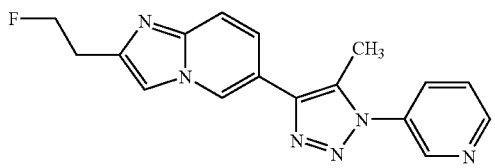

4-(2-(2-fluoroethyl)-imidazo[1,2-a]pyridine-6-yl)-1-(pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 190, the tin reagent obtained in Reference Example 6, and tetrakistriphenylphosphinepalladium.

$^1$HNMR (400 MHz, CDCl$_3$), δ: 2.55 (3H, s), 3.24 (2H, dd, J=6.1, 25.1 Hz), 4.84 (2H, dd, J=6.1, 47.1 Hz), 7.52-7.60 (3H, m), 7.66 (1H, d, J=9.3 Hz), 7.92-7.96 (1H, m), 8.54 (1H, d, J=1.2 Hz), 8.81-8.85 (2H, m),

ESI-MS Found: m/z 323.2 [M+H]$^+$.

EXAMPLE 196

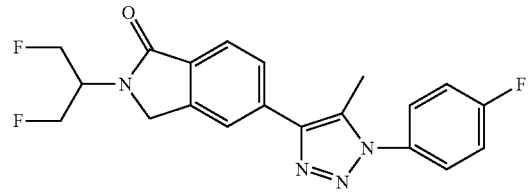

4-(2-(2-fluoro-1-fluoromethyl-ethyl-1-oxo-isoindoline-5-yl)-1-(4-fluorophenyl)-5-methyl-1H-[1,2,3]triazole 1) Manufacture of 5-bromo-2-(2-fluoro-1-fluoromethyl-ethyl)-1-oxo-isoindoline Under nitrogen atmosphere, 100 mg of 4-bromo-2-bromomethyl methyl benzoate was dissolved in toluene, 120 mg of 2-fluoro-1-fluoromethyl-ethylamine hydrochloride and 0.20 ml of triethylamine were added, and the mixture was heated under reflux all night. The reaction solution was cooled down to room temperature, and the solvents were distilled outunder reduced pressure. The residues were separated and purified by thin-layer silicagel column chromatography (ethyl acetate/hexane=2/1) to obtain 5 mg of the above compound as a white solid.

$^1$HNMR (400 MHz, CDCl$_3$), δ: 4.70-4.75 (2H, m), 4.80-4.87 (3H, m), 7.61-7.62 (1H, m), 7.64 (1H, s), 7.73-7.75 (1H, m), ES-MS Found: m/z 292.0 [M+H]$^+$.

2) Manufacture of 4-(2-(2-fluoro-1-fluoromethyl-ethyl)-1-oxo-isoindoline-5-yl)-1-(4-fluorophenyl)-5-methyl-1H-[1,2,3]triazole Under nitrogen atmosphere, 10 mg of 5-bromo-2-(2-fluoro-1-fluoromethyl-ethyl)-1-oxo-isoindoline obtained in the above 1) and 30 mg of 1-(4-fluorophenyl)-5-methyl-4-tributylstanyl-1H-[1,2,3]triazole prepared in Reference Example 12 were dissolved in toluene, 11 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=1/2) to obtain 2 mg of the above compound as a white solid.

$^1$HNMR (400 MHz, CDCl$_3$), δ: 2.52 (3H, s), 4.65 (2H, s), 4.73-4.93 (5H, m), 7.27-731 (2H, m), 7.50-7.53 (2H, m), 7.83-7.85 (1H, m), 7.973-7.99 (2H, m),

ESI-MS Found: m/z 387.2 [M+H]$^+$.

EXAMPLE 197

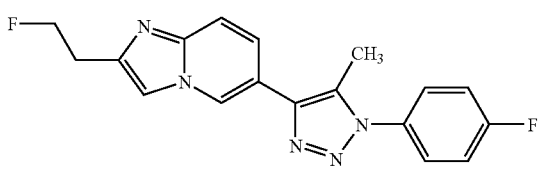

4-(2-(2-fluoroethyl)-imidazo[1,2-a]pyridine-6-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in Example 190, the tin reagent obtained in Reference Example 12, and tetrakistriphenylphosphinepalladium.

$^1$HNMR (400 MHz, CDCl$_3$), δ: 2.49 (3H, s), 3.18-3.29 (2H, m), 4.84 (2H, dt, J=47.0, 6.1 Hz), 7.27-7.33 (2H, m), 7.49-7.57 (4H, m), 7.65 (1H, d, J=9.3 Hz), 8.53-8.55 (1H, m),
ESI-MS Found: m/z 340.2 [M+H]$^+$.

EXAMPLE 198

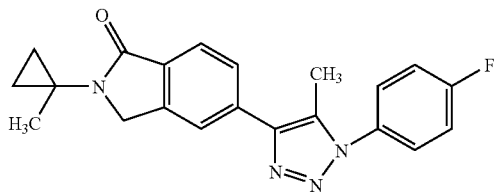

4-(2-(1-methyl-cyclopropyl)-1-oxo-isoindoline-5-yl)-1-(4-fluorophenyl)-5-methyl-1H-[1,2,3]triazole The above compound was obtained according to the method of Example 5, with the use of 5-bromo-2-(1-methylcyclopropyl)-1-oxo-isoindoline obtained in Example 163-1), and the compound 1-(4-fluorophenyl-3-yl)-5-methyl-4-tributylstanyl-1H-[1,2,3]triazole of Reference Example 12.

$^1$HNMR (400 MHz, CDCl$_3$), δ: 0.81-0.86 (2H, m), 1.05-1.10 (2H, m), 1.47 (3H, s), 2.51 (3H, s), 4.46 (2H, s), 7.26-7.32 (2H, m), 7.49-7.54 (2H, m), 7.77 (1H, d, J=8.1 Hz), 7.92 (1H, d, J=8.1 Hz), 7.96 (1H, s),
ESI-MS Found: m/z 363.2 [M+H]$^+$.

EXAMPLE 199

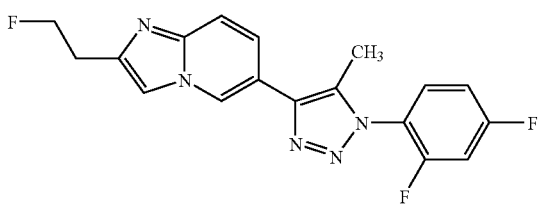

1-(2,4-difluorophenyl)4-(2-(2-fluoroethyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of halogen compound obtained in Example 190, the tin reagent obtained in Reference Example 13, and tetrakistriphenylphosphinepalladium.

$^1$HNMR (400 MHz, CDCl$_3$), δ: 2.43 (3H, d, J=1.7 Hz), 3.19-3.27 (2H, m), 4.84 (2H, dt, J=46.9, 6.2 Hz), 7.09-7.17 (2H, m), 7.54-7.68 (4H, m), 8.55 (1H, dd, J=0.9, 1.7 Hz),
ESI-MS Found: m/z 358.2 [M+H]$^+$.

EXAMPLE 200

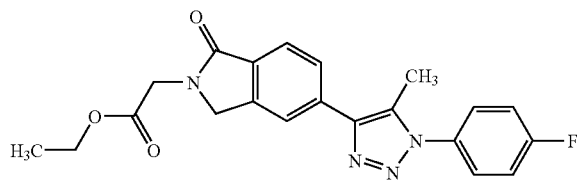

4-(2-ethoxycarbonylmethyl-1-oxo-isoindoline-5-yl)-1-(4-fluorophenyl)-5-methyl-1H-[1,2,3]triazole 1) Manufacture of ethyl(5-bromo-1-oxo-1,3-dihydro-2H-isoindole-2-yl)acetate The above compound was obtained by performing the reaction in the same manner as Example 49-1), except using glycineethylester instead of cyclopropylamine which was used in Example 49-1.

$^1$HNMR (300 MHz, CDCl$_3$), δ: 1.29 (3H, t, J=7.6 Hz), 4.22 (2H, q, J=7.6 Hz), 4.38 (2H, s), 4.51 (2H, s)7.54-7.67 (2H, m), 7.74 (1H, d, J=8.0 Hz),

2) Manufacture of 4-(2-ethoxycarbonylmethyl-1-oxo-isoindoline-5-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in the above 1), the tin reagent obtained in Reference Example 12, and tetrakistriphenylphosphinepalladium.

$^1$HNMR (400 MHz, CDCl$_3$), δ: 1.31 (3H, t, J=7.1 Hz), 2.52 (3H, s), 4.24 (2H, q, J=7.1 Hz), 4.44 (2H, s), 4.62 (2H, s), 7.26-7.32 (2H, m), 7.50-7.54 (2H, m), 7.81 (1H, d, J=7.6 Hz), 7.97-8.00 (2H, m),
ESI-MS Found: m/z 395.2 [M+H]$^+$.

EXAMPLE 201

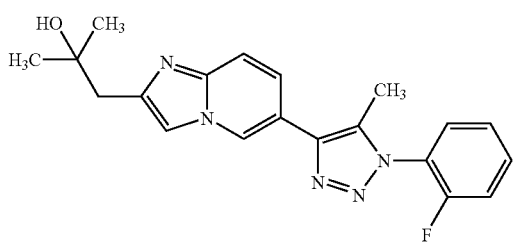

1-(2-fluorophenyl)-4-(2-(2-hydroxy-2-methyl-propyl)-imidazo[1,2-a]pyridine-6-yl)-5-methyl-1H-[1,2,3]triazole

1) Manufacture of 1-(6-bromoimidazo[1,2-a]pyridine-2-yl)-2-methylpropane-2-ol 5.66 g of the compound obtained in Example 190-1) was dissolved in 50 ml of diethylether, and after cooling down to 0° C., 30 ml of 3.0 M methylmagnesiumiodide was added. After stirring the mixture at room temperature for 1 hour, saturated ammonium chloride aqueous solution was added and the products were extracted with ethyl acetate. Organic layer was dried with anhydrous sodium sulfate, and the solvents were distilled outunder reduced pressure. The obtained residues were separated and purified by silicagel column chromatography (ethyl acetate) to obtain 1.17 g of the above compound as a white solid.

$^1$HNMR (300 MHz, CDCl$_3$), δ: 1.24 (6H, s), 2.89 (2H, s), 4.54 (1H, s), 7.20-7.25 (1H, m), 7.37 (1H, s)7.41-7.46 (1H, m), 8.22-8.23 (1H, m).

2) Manufacture of 1-(2-fluorophenyl)4-(2-(2-hydroxy-2-methyl-propyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of halogen compound obtained in the above 1), the tin reagent obtained in Reference Example 4, and tetrakistriphenylphosphinepalladium.

$^1$HNMR (400 MHz, CDCl$_3$), δ: 1.27 (6H, s), 2.44 (3H, d, J=1.7 Hz), 2.93 (2H, s), 7.33-7.42 (2H, m), 7.49 (1H, s), 7.52-7.67 (4H, m), 8.58-8.60 (1H, m),

ESI-MS Found: m/z 366.3 [M+H]$^+$.

EXAMPLE 202

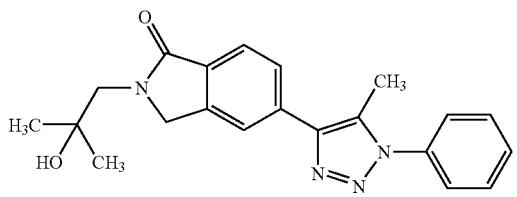

4-(2-(2-hydroxy-2-methyl-propyl)-1-oxo-isoindoline-5-yl)-1-phenyl-5-methyl-1H-[1,2,3]triazole The above compound was obtained as a white solid by the same method as Example 49, by a method according thereof, or by a combination of these and ordinary methods, with the use of halogen compound obtained in Example 177, the tin reagent obtained in Reference Example 5, and tetrakistriphenylphosphinepalladium.

$^1$HNMR (400 MHz, CDCl$_3$), δ: 1.32 (6H, s), 2.17 (3H, s), 3.50 (2H, s), 3.65 (2H, s), 7.52-7.63 (5H, m), 7.83 (1H, d, J=8.0 Hz), 7.96 (1H, d, J=8.0 Hz), 8.00 (1H, s),

ESI-MS Found: m/z 363.3 [M+H]$^+$.

EXAMPLE 203

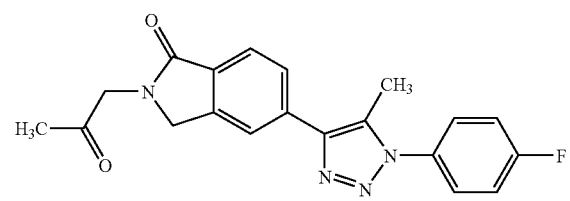

4-(2-acetylmethyl-1-oxo-isoindoline-5-yl)-1-(4-fluorophenyl)-5-methyl-1H-[1,2,3]triazole

1) Manufacture of 5-bromo-2-(2-oxopropyl)isondoline-1-one 4.78 g of the compound obtained in Example 200-1) was dissolved in 100 ml of diethylether, cooled down to 0° C., and 24 ml of 3.0 M methylmagnesium iodide was added. After stirring the mixture for 1 hour at room temperature, water was added and the products were extracted with ethyl acetate. Organic layer was dried with anhydrous sodium sulfate, and the solvents were distilled outunder reduced pressure. The obtained residues were separated and purified by silicagel column chromatography (hexane:ethyl acetate=1:1) to obtain 232 mg of the above compound.

$^1$HNMR (400 MHz, CDCl$_3$), δ: 2.24 (3H, s), 4.44 (2H, s), 4.47 (2H, s), 7.60-7.65 (2H, m), 7.71-7.75 (1H, m).

2) Manufacture of 4-(2-acetylmethyl-1-oxo-isoindoline-5-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in the above 1), the tin reagent obtained in Reference Example 12, and tetrakistriphenylphosphinepalladium.

$^1$HNMR (400 MHz, CDCl$_3$), δ: 2.26 (3H, s), 2.52 (3H, s), 4.49 (2H, s), 4.57 (2H, s), 7.26-7.32 (2H, m), 7.50-7.54 (2H, m), 7.82 (1H, dd, J=1.5, 8.0 Hz), 7.97 (1H, d, J=8.0 Hz), 7.98 (1H, d, J=1.5 Hz),

ESI-MS Found: m/z 365.2 [M+H]$^+$.

EXAMPLE 204

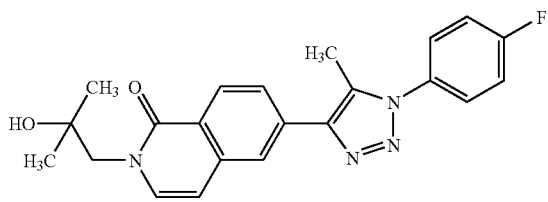

4-(2-(2-hydroxy-2-methyl-propyl)-1-oxo-isoquinoline-6-yl)-1-(4-fluorophenyl)-5-methyl-1H-[1,2,3]triazole

1) Manufacture of 6-bromo-2-(2-hydroxy-2-methyl-propyl)-isoquinoline-1-one

Under nitrogen atmosphere, 23 mg of 60% of sodium hydride was added at 0° C. to 2 ml solution of dimethylformamide with 62 mg of 6-bromo-2H-isoquinoline-1-one, and the mixture was stirred for 30 30 min. Then, 0.055 ml of 3-bromo-2-methyl-propene was added at 0° C., and the mixture was stirred at room temperature for 2 hours. Cold water was added to the reaction solution, extracted with chloroform. Chloroform layer was washed with saturated saline solution, and dried with anhydrous sodium sulfate. The solvents were distilled outunder reduced pressure, and the residues were separated and purified by thin-layer chromatography (hexane/ethyl acetate=3/1). The obtained compounds were dissolved in concentrated hydrochloric acid, stirred at 100° C. for 3 hours, and then cooled down to room temperature. After making it alkaline with 50% sodium hydride aqueous solution, the mixture was stirred at room temperature for 3 hours. Cold water was added to the reaction solution, and extracted with chloroform. Chloroform layer was washed with saturated saline solution, and dried with anhydrous sodium sulfate. The solvents were distilled outunder reduced pressure, and the residues were separated and purified by thin-layer chromatography (hexane/ethyl acetate=3/1) to obtain 20 mg of the above compound as a white solid.

$^1$HNMR (400 MHz, CDCl$_3$), δ: 1.29 (6H, s), 3.56 (1H, s), 4.07 (2H, s), 6.43 (1H, d, J=7.6 Hz), 7.17 (1H, d, J=7.2 Hz), 7.58 (1H, dd, J=1.8, 8.6 Hz), 7.70 (1H, d, J=1.6 Hz), 8.27 (1H, d, J=8.4 Hz),

ESI-MS Found: m/z 238.1 [M+H]$^+$.

2) Manufacture of 4-(2-(2-hydroxy-2-methyl-propyl)-1-oxo-isoquinoline-6-yl)-1-(4-fluorophenyl)-5-methyl-1H-[1,2,3]triazole Under nitrogen atmosphere, 100 mg of the halide compound 6-bromo-2-(2-hydroxy-2-methyl-propyl)-isoquinoline-1-one obtained in the above 1) and 200 mg of the alkyl tin compound 1-(4-fluorophenyl)-5-methyl-4-tributylstanyl-1H-[1,2,3]-triazole, similar as Reference Example 12 were dissolved in 3 ml of toluene, and 100 mg of tetrakistriphenylphosphinepalladium was added to degas. Then, the mixture was stirred by heating to 115° C. The reaction solution was cooled down to room temperature, and insoluble matters were removed by celite filtration. The solvents were distilled outunder reduce pressure, and the residues were separated and purified by silicagel chromatography (ethyl acetate/hexane=1/2) to obtain 95 mg of the above compound as a white solid.

$^1$HNMR (400 MHz, CDCl$_3$), δ: 1.32 (6H, s), 2.55 (3H, s), 3.88 (1H, s), 4.12 (2H, s), 6.62 (1H, d, J=7.6 Hz), 7.17 (1H, d, J=7.6 Hz), 7.25-7.33 (2H, m), 7.49-7.55 (2H, m), 7.89 (1H, dd, J=1.6, 8.4 Hz), 8.03 (1H, d, J=1.6 Hz), 8.53 (1H, d, J=8.4 Hz),

ESI-MS Found: m/z 393.2 [M+H]$^+$.

EXAMPLE 205

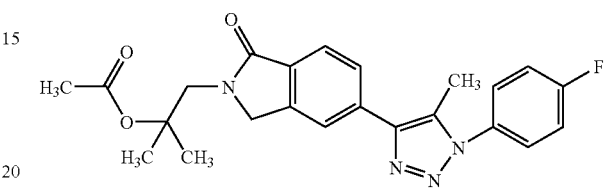

4-(2-(2-methyl-2-acetyloxy-propyl-1-oxo-isoindoline-5-yl)-1-(4-fluorophenyl)-5-methyl-1H-[1,2,3]triazole

1) Manufacture of 5-bromo-2-(2-methyl-2-acetyloxy-propyl)-1-oxo-isoindoline

Under nitrogen atmosphere, 50 mg of 5-bromo-2-(2-hydroxy-2-methyl-propyl)-1-oxo-isoindoline obtained in Example 177-1) was dissolved in tetrahydrofuran. 21 mg of acetatic anhydride and 20 mg of sodium hydride were added and the mixture was heated under reflux for 4 hours. The reaction solution was cooled down to room temperature, water was added and the products were extracted with ethyl acetate. Ethyl acetate layer was washed with saturated saline solution and dried with anhydrous sodium sulfate. The solvents were distilled outunder reduced pressure, and the residues were separated and purified by silicagel column chromatography (ethyl acetate/hexane=1/2) to obtain 44 mg of the above compound as a white solid.

$^1$HNMR (400 MHz, CDCl$_3$), δ: 1.52 (6H, s), 2.05 (3H, s), 3.84 (2H, s), 4.49 (2H, s), 7.60-7.63 (2H, m), 7.71-7.73 (1H, m), ES-MS Found: m/z 326.1 [M+H]$^+$.

2) Manufacture of 4-(2-(2-methyl-2-acetyloxy-propyl-1-oxo-isoindoline-5-yl)-1-(4-fluorophenyl)-5-methyl-1H-[1,2,3]triazole Under nitrogen atmosphere, 44 mg of 5-bromo-2-(fluoro-1-fluoromethyl-ethyl)-1-oxo-isoindoline obtained in the above 1), and 76 mg of 1-(4-fluorophenyl)-5-methyl-4-tributylstanyl-1H-[1,2,3]triazole prepared in Reference Example 12 were dissolved in toluene, 16 mg of tetrakistriphenylphosphinepalladium was added, and the mixture was heated under reflux for 6 hours. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 20 mg of the above compound as a white solid.

$^1$HNMR (400 MHz, CDCl$_3$), δ: 1.56 (6H, d, J=9.2 Hz), 2.07 (3H, s), 2.52 (3H, s), 3.89 (2H, s), 4.60 (2H, s), 7.27-7.31 (2H, m), 7.50-7.53 (2H, m), 7.79-7.82 (1H, m), 7.96-8.00 (2H, m),

ESI-MS Found: m/z 423.3 [M+H]$^+$.

EXAMPLE 206

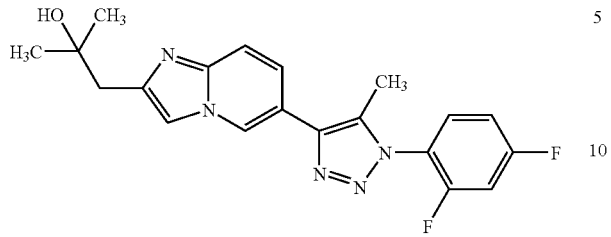

1-(2,4-difluorophenyl)4-(2-(2-hydroxy-2-methyl-propyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of halogen compound obtained in Example 201, the tin reagent obtained in Reference Example 13, and tetrakistriphenylphosphinepalladium.

$^1$HNMR (400 MHz, CDCl$_3$), δ: 1.27 (6H, s), 2.44 (3H, d, J=1.7 Hz), 2.93 (2H, s), 7.10-7.16 (2H, m), 7.49 (1H, s), 7.52-7.66 (3H, m), 8.58 (1H, s),

ESI-MS Found: m/z 384.3 [M+H]$^+$.

EXAMPLE 207

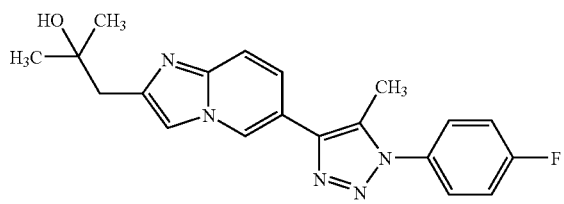

1-(4-fluorophenyl)4-(2-(2-hydroxy-2-methyl-propyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of halogen compound obtained in Example 201, the tin reagent obtained in Reference Example 12, and tetrakistriphenylphosphinepalladium.

$^1$HNMR (400 MHz, CDCl$_3$), δ: 1.27 (6H, s), 2.50 (3H, s), 2.93 (2H, s), 7.25-7.32 (2H, m), 7.49-7.55 (4H, m), 7.65 (1H, d, J=9.3 Hz), 8.57 (1H, s),

ESI-MS Found: m/z 366.2[M+H]$^+$.

EXAMPLE 208

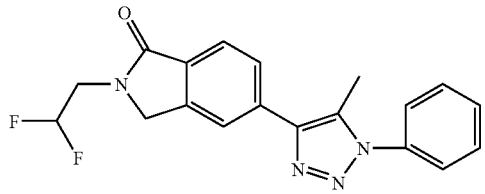

4-(2,2-difluoro-ethyl-1-oxo-isoindoline-5-yl)-1-phenyl-5-methyl-1H-[1,2,3]triazole Under nitrogen atmosphere, 100 mg of 5-bromo-2-(2,2-difluoroethyl)-1-oxo-isoindoline obtained in Example 137-1), and 162 mg of 1-phenyl-5-methyl-4-tributylstanyl-1H-[1,2,3]triazole were dissolved in toluene, 41 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by thin-layer silicagel column chromatography (ethyl acetate/hexane=2/1) to obtain 55 mg of the above compound as a white solid.

$^1$HNMR (400 MHz, CDCl$_3$), δ: 2.54 (3H, s), 3.96-4.05 (2H, m), 4.62 (2H, s), 5.88-6.17 (1H, m), 7.51-7.63 (5H), 7.84-7.86 (1H), 7.96-8.00 (2H, m),

ESI-MS Found: m/z 355.2 [M+H]$^+$.

EXAMPLE 209

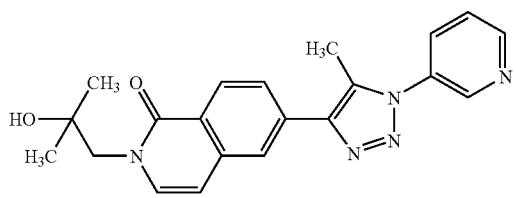

4-(2-(2-hydroxy-2-methyl-propyl)-1-oxo-isoquinoline-6-yl)-1-(pyridine-3-yl)-5-methyl-1H-[1,2,3]triazole The above compound was obtained in the same manner as Example 3, with the use of halide obtained in Example 204, the alkyl tin compound 1-(pyridine-3-yl)-5-methyl-4-tributylstanyl-1H-[1,2,3]-triazole similar as Reference Example 6.

$^1$HNMR (400 MHz, CDCl$_3$), δ: 1.33 (6H, s), 2.61 (3H, s), 3.82 (1H, s), 4.12 (2H, s), 6.63 (1H, d, J=7.6 Hz), 7.19 (1H, d, J=7.2 Hz), 7.57-7.61 (1H, m), 7.90 (1H, dd, J=0.8, 8.4 Hz), 7.95 (1H, ddd, J=0.8, 2.4, 8.0 Hz), 8.54 (1H, d, J=9.4 Hz), 8.81-8.86 (2H, m), ESI-MS Found: m/z 376.2 {M+H}$^+$.

EXAMPLE 210

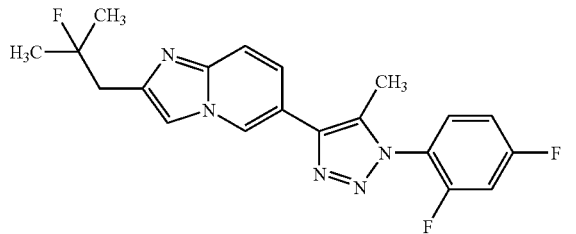

1-(2,4-difluorophenyl)-4-(2-(2-fluoro-2-methyl-propyl)-imidazo[1,2-a]pyridine-6-yl)-5-methyl-1H-[1,2,3]triazole

1) Manufacture of 6-bromo-2-(2-fluoro-2-methylpropyl)imidazo[1,2-a]pyridine 135 mg of the compound obtained in Example 201-1) was dissolved in 5.0 ml of methylene chloride, cooled down to −78° C., and 198 µl of diethylaminosulfate trifluoride was added. After heating the mixture to room temperature, saturated sodium bicarbonate aqueous solution was added and the products were extracted with ethyl acetate. Organic layer was dried with anhydrous sodium sulfate, and the solvents were distilled outunder reduced pressure. The obtained residues were separated and purified by silicagel column chromatography (hexane:ethyl acetate=2:1) to obtain 96.1 mg of the above compound.

$^1$HNMR (400 MHz, CDCl$_3$), δ: 1.43 (6H, d, J=21.5 Hz), 3.11 (2H, d, J=20.5 Hz), 7.15-7.22 (1H, m), 7.42-7.48 (2H, m), 8.21-8.23 (1H, m),
ESI-MS Found: m/z 271.1, 273.1 [M+H]$^+$.

2) Manufacture of 1-(2,4-difluorophenyl)-4-(2-2-fluoro-2-methyl-propyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of halogen compound obtained in the above 1), the tin reagent obtained in Reference Example 13, and tetrakistriphenylphosphinepalladium.

$^1$HNMR (400 MHz, CDCl$_3$), δ: 1.47 (6H, d, J=21.5 Hz), 2.43 (3H, d, J=1.9 Hz), 3.16 (2H, d, J=20.5 Hz), 7.09-7.15 (2H, m), 7.53-7.61 (3H, m), 7.66 (1H, d, J=9.2 Hz), 8.55 (1H, d, J=1.4 Hz),
ESI-MS Found: m/z 386.2 [M+H]$^+$.

EXAMPLE 211

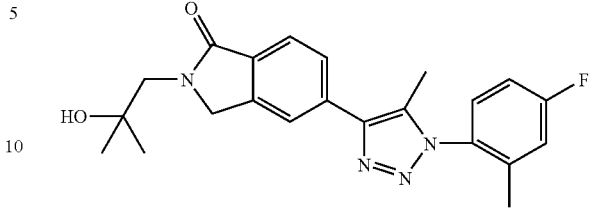

4-(2-(2-hydroxy-2-methyl-propyl)-1-oxo-isoindoline-5-yl)-1-(4-fluoro-2-methyl-phenyl)-5-methyl-1H-[1,2,3]triazole Under nitrogen atmosphere, 100 mg of 5-bromo-2-(2-hydroxy-2-methyl-propyl)-1-oxo-isoindoline obtained in Example 177-1), and 170 mg of 1-(4-fluoro-2-methyl-phenyl)-5-methyl-4-tributylstanyl-1H-[1,2,3]triazole prepared in Reference Example 17 were dissolved in toluene, 40 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by silicagel column chromatography (ethyl acetate/hexane=1/2) to obtain 61 mg of the above compound as a white solid.

$^1$HNMR (400 MHz, CDCl$_3$), δ: 1.32 (6H, s), 2.10 (3H, s), 2.37 (3H, s), 3.10 (1H, s), 3.65 (2H, s), 4.63 (2H, s), 7.10-7.15 (2H, m), 7.26-7.30 (1H, m), 7.83-7.85 (1H, m), 7.95-7.97 (1H, m), 8.03 (1H, m),
ESI-MS Found: m/z 395.2 [M+H]$^+$.

EXAMPLE 212

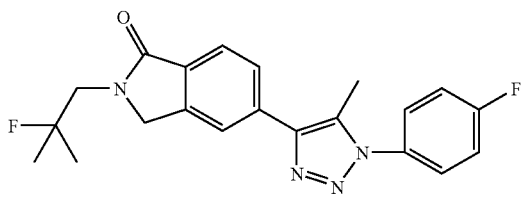

4-(2-(2-fluoro-2-methyl-propyl)-1-oxo-isoindoline-5-yl)-1-(4-fluorophenyl)-5-methyl-1H-[1,2,3]triazole Under nitrogen atmosphere, 100 mg of 4-(2-(2-hydroxy-2-methyl-propyl)-1-oxo-isoindoline-5-yl)-1-(4-fluorophenyl)-5-methyl-1H-[1,2,3]triazole obtained in Example 181) was dissolved in 1,2-dichloromethane, after cooling down to −78° C., 0.1 ml of diethylaminosulfate trifluoride was added and the mixture was stirred for 10 min. Water was added and the products were extracted with ethyl acetate. Ethyl acetate layer was washed with saturated sodium bicarbonate aqueous solution and saturated saline solution, and dried with anhydrous sodium sulfate. The solvents were distilled outunder reduce pressure, and the residues were separated and purified by thin-layer silicagel column chromatography (ethyl acetate/hexane=1/1) to obtain 30 mg of the above compound as a white solid.

¹HNMR (400 MHz, CDCl₃), δ: 1.42 (6H, d, J=21.4 Hz), 2.52 (3H, s), 3.78 (2H, d, J=23.6 Hz), 4.64 (2H, s), 7.26-7.32 (2H, m), 7.49-7.54 (2H, m), 7.82-7.84 (1H, m), 7.96-7.97 (2H, m),

ESI-MS Found: m/z 383.2 [M+H]⁺.

EXAMPLE 213

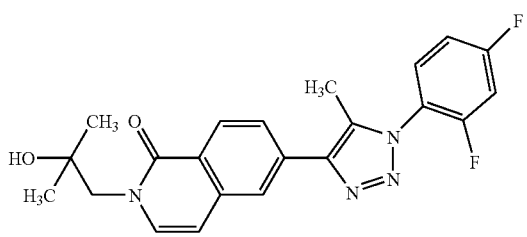

4-(2-(2-hydroxy-2-methyl-propyl)-1-oxo-isoquinoline-6-yl)-1-(2,4-difluorophenyl)-5-methyl-1H-[1,2,3]triazole The above compound was obtained in the same manner as Example 3, with the use of halide obtained in Example 204, and the alkyl tin compound 1-(2,4-difluorophenyl)-5-methyl-4-tributylstanyl-1H-[1,2,3]-triazole similar as Reference Example 13.

¹HNMR (400 MHz, CDCl₃), δ: 1.32 (6H, s), 2.49 (3H, d, J=1.6 Hz), 3.88 (1H, s), 4.12 (2H, s), 6.62 (1H, d, J=7.2), 7.08-7.20 (2H, m), 7.55-7.63 (1H, m), 7.91 (1H, dd, J=2.0, 8.4 Hz), 8.05 (1H, d, J=1.6 Hz), 8.53 (1H, d, J=8.4 Hz),

ESI-MS Found: m/z 411.3 [M+H]⁺.

EXAMPLE 214

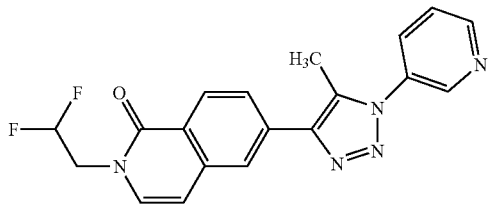

4-(2-(2,2-difluoroethyl)-1-oxo-isoquinoline-6-yl)-1-(pyridine-3-yl)-5-methyl-1H-[1,2,3]triazole 1) Manufacture of 6-bromo-2-(2,2-difluoroethyl)-isoquinoline-1-one Under nitrogen atmosphere, 44 mg of 60% sodium hydride was added at room temperature to 2 ml solution of dimethylformamide with 49 mg of 6-bromo-2H-isoquinoline-1-one and the mixture was stirred for 30 min. Then, 169 mg of 2,2-difluoroethyliodide was added and stirred at room temperature for 6 hours. Cold water was added to the reaction solution, the products were extracted with chloroform. Chloroform layer was washed with saturated saline solution and dried with anhydrous sodium sulfate. The solvents were distilled out under reduced pressure, and the residues were separated and purified by thin-layer chromatography (chloroform/methyl alcohol=10/1) to obtain 41 mg of the above compound as a white solid.

2) Manufacture of 4-(2-(2,2-difluoroethyl)-1-oxo-isoquinoline-6-yl)-1-(pyridine-3-yl)-5-methyl-1H-[1,2,3]triazole The above compound was obtained by performing coupling reaction in the same manner as Example 3, with the use the compound obtained in the above 1), and the alkyl tin compound 1-(pyridine-3-yl)-5-methyl-4-tributylstanyl-1H-[1,2,3]triazole similar as Reference Example 6.

¹HNMR (400 MHz, CDCl₃), δ: 2.61 (3H, s), 4.34 (2H, td, J=4.4, 13.6 Hz), 6.18 (1H, tt, J=4.4, 56.0 Hz), 6.63 (1H, d, J=7.2 Hz), 7.12 (1H, d, J=7.2 Hz), 7.59 (1H, dd, J=4.8, 8.0 Hz), 7.89-7.97 (2H, m), 8.02 (1H, d, J=1.6 Hz), 8.52 (1H, d, J=8.4 Hz), 8.81-8.87 (2H, m),

ESI-MS Found: m/z 368.2 [M+H]⁺.

EXAMPLE 215

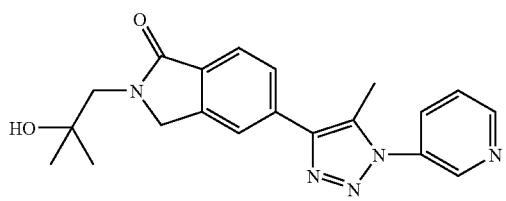

4-(2-(2-hydroxy-2-methyl-propyl)-1-oxo-isoindoline-5-yl)-1-(pyridine-3-yl)-5-methyl-1H-[1,2,3]triazole Under nitrogen atmosphere, 100 mg of 5-bromo-2-(2-hydroxy-2-methyl-propyl)-1-oxo-isoindoline obtained in Example 177-1) and 150 mg of 1-(pyridine-3-yl)-5-methyl-4-tributylstanyl-1H-[1,2,3]triazole prepared in Reference Example 6 were dissolved in toluene, 40 mg of tetrakistriphenylphosphinepalladium was added, and the mixture was heated all night under reflux. The reaction solution was cooled down to room temperature, and insoluble matters were removed by celite filtration. The solvents were distilled out under reduced pressure, and the residues were separated and purified by thin-layer silicagel column chromatography (ethyl acetate/hexane=1/2) to obtain 4 mg of the above compound as a white solid.

¹HNMR (400 MHz, CDCl₃), δ: 2.58 (3H, s), 3.65 (2H, s), 4.69 (2H, s), 7.50-7.60 (1H, m), 7.82 (1H, d, J=8.4 Hz), 7.92-7.98 (2H, m), 7.81-8.84 (2H, m),

ESI-MS Found: m/z 364.2 [M+H]⁺.

EXAMPLE 216

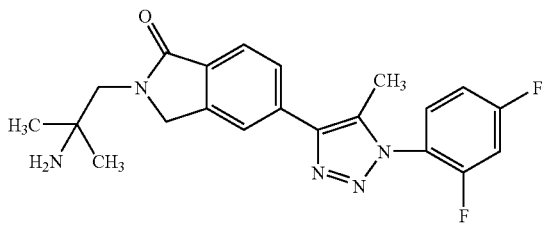

4-(2-(2-amino-2-methyl-propyl)-1-oxo-isoindoline-5-yl)-1-(2,4-difluoro-phenyl)-5-methyl-1H-[1,2,3]triazole 1) Manufacture of 2-(2-amino-2-methylpropyl)-5-bromoisoindoline-1-one The above compound was obtained by performing the reaction by the same method as Example 49-1), except using 1,2-diamino-2-methylpropane instead of cyclopropylamine which was used in Example 49-1).
$^1$HNMR (300 MHz, CDCl$_3$), δ: 1.17 (6H, s), 3.48 (2H, s), 4.62 (2H, s), 7.59-7.62 (2H, m), 7.72 (1H, d, J=8.0 Hz).

2) Manufacture of 4-(2-(2-amino-2-methyl-propyl)-1-oxo-isoindoline-5-yl)-1-(2,4-difluoro-phenyl)-5-methyl-1H-[1,2,3]triazole The above compound was obtained as a white solid by the same method as Example 49, by a method according thereof, or by a combination of these and ordinary methods, with the use of halogen compound obtained in the above 1), the tin reagent obtained in Reference Example 13, and tetrakistriphenylphosphinepalladium.
$^1$HNMR (400 MHz, CDCl$_3$), δ: 1.56 (6H, s), 2.46 (3H, d, J=1.5 Hz), 3.54 (2H, s), 4.71 (2H, s), 7.09-7.23 (2H, m), 7.56-7.61 (1H, m), 7.83 (1H, d, J=7.8 Hz), 7.95-7.98 (2H, m),
ESI-MS Found: m/z 398.2 [M+H]$^+$.

EXAMPLE 217

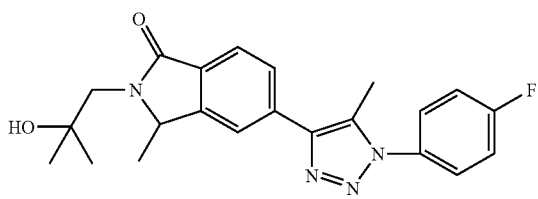

4-(2-(2-hydroxy-2-methyl-propyl)-3-methyl-1-oxo-isoindoline-5-yl)-1-(2,4-difluoro-phenyl)-5-methyl-1H-[1,2,3]triazole 1) Manufacture of 5-bromo-2-(2-hydroxy-2-methyl-propyl)-3-methyl-1-oxo-isoindoline Under nitrogen atmosphere, 100 mg of 5-bromo-2-(2-hydroxy-2-methyl-propyl)-1-oxo-isoindoline obtained in Example 177-1) was dissolved in tetrahydrofuran, 40 mg of sodium hydride, 0.4 ml of methyl iodide were added and the mixture was heated under reflux for 2 hours. The reaction solution was cooled down to room temperature, water was added, and the products were extracted with ethyl acetate. Ethyl acetate layer was washed with saturated saline solution and dried with anhydrous sodium sulfate. The solvents were distilled outunder reduced pressure, and the residues were separated and purified by thin-layer silicagel column chromatography (ethyl acetate) to obtain 7 mg of the above compound as a white solid.
$^1$HNMR (400 MHz, CDCl$_3$), δ: 1.23 (3H, s), 1.30 (3H, s), 1.48 (3H, d, J=6.8 Hz), 3.23 (1H, d, J=14.8 Hz), 3.88 (1H, d, J=14.4 Hz), 4.79-4.80 (1H, m), 7.58-7.62 (2H, m), 7.70-7.72 (1H, m), 2) Manufacture of 4-(2-(2-hydroxy-2-methyl-propyl)-3-methyl-1-oxo-isoindoline-5-yl)-1-(2,4-difluoro-phenyl)-5-methyl-1H-[1,2,3]triazole Under nitrogen atmosphere, 7 mg of 5-bromo-2-(2-hydroxy-2-methyl-propyl)-3-methyl-1-oxo-isoindoline obtained in the above 1) and 10 mg of 1-(4-fluorophenyl)-5-methyl-4-tributylstanyl-1H-[1,2,3]triazole prepared in Reference Example 12 were dissolved in toluene, 2 mg of tetrakistriphenylphosphinepalladium was added, and the mixture was heated all night under reflux. The reaction solution was cooled down to room temperature, and insoluble matters were removed by celite filtration. The solvents were distilled outunder reduced pressure, and the residues were separated and purified by silicagel column chromatography (ethyl acetate/hexane=1/2) to obtain 5 mg of the above compound as a white solid.
$^1$HNMR (400 MHz, CDCl$_3$), δ: 1.30 (1H, d, J=9.5 Hz), 1.55 (3H, d, J=6.8 Hz), 2.52 (3H, s), 3.31 (1H, d, J=14.6 Hz), 3.90 (1H, d, J=14.6 Hz), 4.85-4.87 (1H, m), 7.26-7.31 (2H, m), 7.50-7.53 (2H, m), 7.76-7.78 (1H, m), 7.93-7.95 (1H, m)7.99 (1H, br),
ESI-MS Found: m/z 395.2 [M+H]$^+$.

EXAMPLE 218

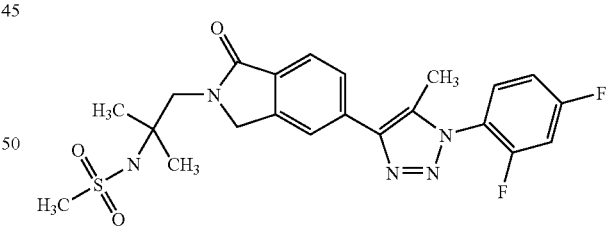

4-(2-(2-methanesulfonylamino-2-methyl-propyl)-1-oxo-isoindoline-5-yl)-1-(2,4-difluoro-phenyl)-5-methyl-1H-[1,2,3]triazole 10 mg of the compound obtained in Example 217 was dissolved in 2 ml of chloroform, 20 μl of methanesulfonylchloride and 20 μl of triethylamine were added, and after 30 min at room temperature, the solvents were distilled outunder reduced pressure. The obtained residues were purified by silicagel thin-layer chromatography (ethyl acetate) to obtain 12.3 mg of the above compound as a white solid.

¹HNMR (400 MHz, CDCl₃), δ: 1.51 (6H, s), 2.46 (3H, d, J=1.5 Hz), 3.06 (3H, s), 3.75 (2H, s), 4.74 (2H, s), 5.48 (1H, s), 7.09-7.16 (2H, m), 7.56-7.61 (1H, m), 7.88 (1H, d, J=8.2 Hz), 7.95-7.97 (2H, m),
ESI-MS Found: m/z 476.1 [M+H]⁺.

EXAMPLE 219

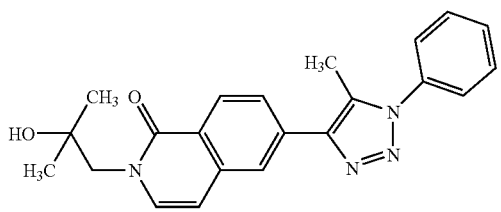

4-(2-(2-hydroxy-2-methyl-propyl-1-oxo-isoquinoline-6-yl)-1-phenyl-5-methyl-1H-[1,2,3]triazole The above compound was obtained in the same manner as Example 3, with the use of halide obtained in Example 204, and the alkyl tin compound 1-phenyl-5-methyl-4-tributylstannyl-1H-[1,2,3]triazole similar as Reference Example 5.

¹HNMR (400 MHz, CDCl₃), δ: 1.32 (6H, s), 2.57 (3H, s), 3.92 (1H, s), 4.12 (2H, s), 6.62 (1H, d, J=8.0 Hz), 7.17 (1H, d, J=8.0 Hz), 7.51-7.69 (5H, m), 7.90 (1H, dd, J=4.0, 8.0 Hz), 8.04 (1H, s), 8.52 (1H, d, J=8.0 Hz),
ESI-MS Found: m/z 375.3 [M+H]⁺.

EXAMPLE 220

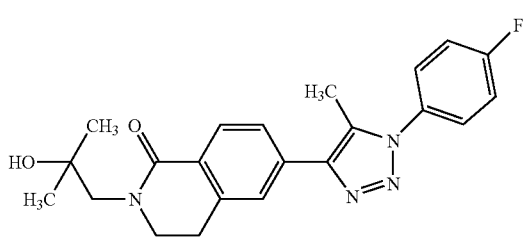

4-(2-(2-hydroxy-2-methyl-propyl)-1-oxo-3,4-dihydroisoquinoline-6-yl)-1-(4-fluorophenyl)-5-methyl-1H-[1,2,3]triazole 50 mg of palladium carbon was added to 10 ml solution of ethanol with 30 mg of 4-(2-2-hydroxy-2-methyl-propyl)-1-oxo-isoquinoline-6-yl)-1-(4-fluorophenyl)-5-methyl-1H-[1,2,3]triazole, and hydrogen was added under 4 atm of hydrogen pressure. 8 hours later, the reaction solution was filtrated, the solvents of the filtrate was distilled outunder reduced pressure, and the residues were separated and purified by thin-layer chromatography (chloroform/methanol=10/1) to obtain 19 mg of the above compound as a white solid.

¹HNMR (400 MHz, CDCl₃), δ: 1.33 (6H, s), 2.51 (3H, s), 3.12 (2H, t, J=6.6 Hz), 3.62 (2H, s), 3.76 (2H, t, J=6.6 Hz), 4.06 (1H, brs), 7.26-7.32 (2H, m), 7.48-7.54 (2H, m), 7.67 (1H, dd, J=1.4, 8.2 Hz), 7.79 (1H, s), 8.16 (1H, d, J=8.0 Hz),
ESI-MS Found: m/z 395.3 [M+H]⁺.

EXAMPLE 221

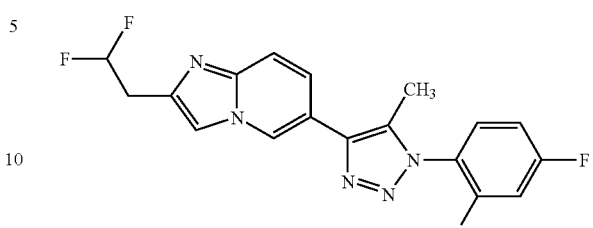

4-(2-(2,2-difluoroethyl)-(2,4-difluorophenyl)-imidazo[1,2-a]pyridine-6-yl)-1-5-methyl-1H-[1,2,3]triazole 1) Manufacture of 2-(6-bromoimidazo[1,2-a]pyridine-2-yl)-N-methoxy-N-methylacetoamide 2.0 g of ester compound obtained in Example 190-1) was dissolved in 5 ml of ethanol, 5 ml of 3N sodium hydride aqueous solution was added and the mixture was stirred all night. 6 N chloric acid solution was added to the obtained mixture to neutralize. The solvents were distilled outunder reduced pressure. Chloroform-methanol was added to the residues, insoluble matters were filtrated, the filtrate was concentrated under reduced pressure to obtain 1.26 mg of carbonic acid as a mixture. 810 mg of the obtained carbonic acid was dissolved in 10 ml of pyridine, 466 mg of N,O-dimethylhydroxyamine dichloride and 1010 mg of 1-(3-dimethylaminopropyl)-3-ethylcarbodiimide hydrochloride were added, and the mixture was stirred at room temperature for 3 hours. Water was added to the obtained solution and the products were extracted with ethyl acetate. Organic layer was washed with saturated sodium chloride solution, dried with anhydrous sodium sulfate and the solvents were distilled outunder reduced pressure. The obtained residues were purified by basic silicagel colum chromatography (ethyl acetate) to obtain 630 mg of the above compound.

¹HNMR (400 MHz, CDCl₃), δ: 3.24 (3H, s), 3.75 (3H, s), 4.01 (2H, s), 7.17-7.22 (1H, m), 7.44 (1H, d, J=8.4 Hz), 7.61 (1H, s), 8.20-8.22 (1H, m).

2) Manufacture of 6-bromoimidazo-2-(2,2-difluoroethyl)-imidazo[1,2-a]pyridine 630 mg of the compound obtained in the above 1) was dissolved in 15 ml of tetrahydrofuran, cooled down to −5° C., and 80 mg of lithium alminium hydride was added. The mixture was stirred at room temperature for 1 hour, diluted hydrochloric acid was added and washed with ethyl acetate. Saturated sodium bicarbonate was added to the water layer to make a basic solution, and the products were extracted with chloroform. Organic layer was dried with anhydrous sodium sulfate, the solvents were distilled outunder reduced pressure, to obtain 530 mg of aldehyde as a mixture. 530 mg of the obtained aldehyde was dissolved in 20 ml of methylene chloride, cooled dowin to −15° C. 880 μl of diethylaminosulfate trifluoride was added and the mixture was stirred for 30 min. After adding saturated sodium bicarbonate aqueous solution to the obtained solution, the products were extracted with ethyl sulfate. Organic layer was dried with anhydrous sodium sulfate, the solvents were distilled outunder reduced pressure.

The residues were purified by basic silicagel column chromatography (hexane:ethyl acetate), followed by thin-layer silicagel chromatograpy (hexane:ethyl acetate=2:1) to obtain 17.1 mg of the above compound.

$^1$HNMR (400 MHz, CDCl$_3$), δ: 3.35 (2H, dt, J=4.7, 16.9 Hz), 6.16 (1H, tt, J=4.7, 56.4 Hz), 7.22-7.28 (1H, m), 7.43 (1H, d, J=8.0 Hz), 7.48 (1H, s), 8.23-8.24 (1H, m).

3) Manufacture of 4-(2-(2,2-difluoroethyl)-(2,4-difluorophenyl)-imidazo[1,2-a]pyridine-6-yl)-1-5-methyl-1H-[1,2,3]triazole The above compound was obtained as a white solid by the same method as Example 49, by a method according thereof, or by a combination of these and ordinary methods, with the use of halogen compound obtained in the above 2), the tin reagent obtained in Reference Example 13, and tetrakistriphenylphosphinepalladium.

$^1$HNMR (400 MHz, CDCl$_3$), δ: 2.44 (3H, d, J=1.4 Hz), 3.40 (2H, dt, J=4.7, 16.9 Hz), 6.22 (1H, tt, J=4.7, 56.4 Hz), 7.10-7.17 (2H, m), 7.55-7.61 (3H, m), 7.67 (1H, d, J=9.3 Hz), 8.56-8.58 (1H, m),

ESI-MS Found: m/z 376.1 [M+H]$^+$.

EXAMPLE 222

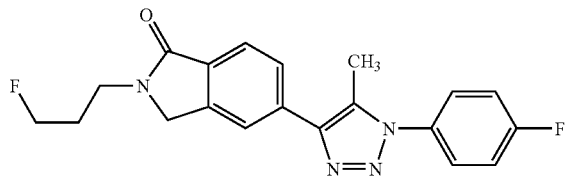

4-(2-(3-fluoro-propyl)-1-oxo-isoindoline-6-yl)-1-(4-fluorophenyl)-5-methyl-1H-[1,2,3]triazole 1) Manufacture of 5-bromo-2-(3-hydroxypropyl)-isoindoline-1-one The above compound was obtained by performing the reaction in the same manner as Example 49-1), except using 3-aminopropanol instead of cyclopropylamine which was used in Example 49-1).

$^1$HNMR (400 MHz, CDCl$_3$), δ: 1.80-1.88 (2H, m), 3.44-3.46 (1H, m), 3.55-3.61 (2H, m), 3.77 (2H, t, J=7.0 Hz), 4.39 (2H, s), 7.60-7.64 (2H, m), 7.71 (1H, d, J=8.0 Hz).

2) Manufacture of 3-(5-bromo-1-oxo-1,3-dihydro-2H-isoindole-2-yl)propylmethansulfonate 270 mg of the compound obtained in the above 1) was dissolved in 5 ml of chloroform, cooled down to 0° C., 93 μl of methanesulfonylchloride and 167 μl of triehtylamine were added, and the mixture was stirred all night at room temperature. Saturated sodium bicarbonate aqueous solution was added to the obtained solution, and the products were extracted with chloroform. Organic layer was washed with anhydrous sodium sulfate, and the solvents were distilled outunder reduced pressure. The obtained residues were purified by silicagel colum chromatography (hexane:ethyl acetate=75:35) to obtain 310 mg of the above compound.

$^1$HNMR (400 MHz, CDCl$_3$), δ: 2.12-2.20 (2H, m), 3.03 (3H, s), 3.75 (2H, t, J=7.0 Hz), 4.30 (2H, t, J=7.0 Hz), 4.41 (2H, s), 7.60-7.64 (2H, m), 7.70 (1H, d, J=8.0 Hz).

3) Manufacture of 5-bromo-2-(3-fluoropropyl)-isoindoline-1-one

The compound obtained in the above 2) was dissolved in 4 ml of acetonitrile, 350 mg of tetrabutylammonium fluoride 3 hydride was added and the mixture was stirred at 80° C. for 1 hour. The mixture was cooled down to room temperature, water was added and the products were extracted with ethyl acetate. Organic layer was dried with anhydrous sodium sulfate, and the products were distilled outunder reduced pressure. The obtained residues were purified by silicagel column chromatography (hexane:ethyl acetate=75:25) to otbtain 27.7 mg of the above compound.

$^1$HNMR (300 MHz, CDCl$_3$), δ: 2.02-2.19 (2H, m), 3.75 (2H, t, J=7.0 Hz), 4.31 (2H, s), 4.41 (2H, s), 4.42-4.65 (2H, m), 7.53-7.63 (2H, m), 7.71 (1H, d, J=8.0 Hz).

3) Manufacture of 4-(2-(3-fluoro-propyl)-1-oxo-isoindoline-6-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in the above 3), the tin reagent obtained in Reference Example 12, and tetrakistriphenylphosphinepalladium.

$^1$HNMR (400 MHz, CDCl$_3$), δ: 2.03-2.19 (2H, m), 2.52 (3H, s), 3.80 (2H, t, J=7.0 Hz), 4.49-4.64 (4H, m), 7.26-7.31 (2H, m), 7.50-7.53 (2H, m), 7.80 (1H, d, J=7.7 Hz), 7.95 (1H, d, J=7.7 Hz), 7.99 (1H, s),

ESI-MS Found: m/z 369.2 [M+H]$^+$.

EXAMPLE 223

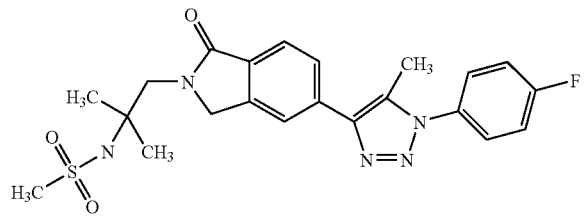

4-(2-(2-methanesulfonylamino-2-metyhyl-propyl)-1-oxo-isoindoline-5-yl)-1-(4-fluorophenyl)-5-methyl-1H-[1,2,3]triazole 1) Manufacture of 2-(2-amino-2-methylpropyl)-5-[1-(2,4-difluorophenyl)-5-methyl-1H-1,2,3-triazole4-yl]isoindoline-1-one The above compound was obtained as a white solid by the same method as Example 217, by a method according thereof, or by a combination of these and ordinary methods, with the use of halogen compound obtained in Example 218-1), the tin reagent obtained in Reference Example 13, and tetrakistriphenylphosphinepalladium.

2) Manufacture of 4-(2-(2-methanesulfonylamino-2-methyl-propyl)-1-oxo-isoindoline-5-yl)-1-(4-fluorophenyl)-5-methyl-1H-[1,2,3]triazole 57 mg of the compound obtained in the above 1) was dissolved in 2 ml of chloroform, 23 µl of methanesulfonyl chloride, and 42 µl of triethylamine were added. The mixture was stirred for 30 min at room temperature, and the solvents were distilled outunder reduced pressure. The obtained residues were purified by silicagel thin-layer chromatography (ethyl acetate) to obtain 62 mg of the above compound.
$^1$HNMR (400 MHz, CDCl$_3$), δ: 1.55 (6H, s), 2.52 (3H, s), 3.06 (3H, s), 3.75 (2H, s), 4.74 (2H, s), 5.44 (1H, s), 7.26-7.31 (2H, m), 7.50-7.54 (2H, m), 7.87 (1H, d, J=8.8 Hz), 7.95-7.97 (2H, m),
ESI-MS Found: m/z 458.2 [M+H]$^+$.

EXAMPLE 224

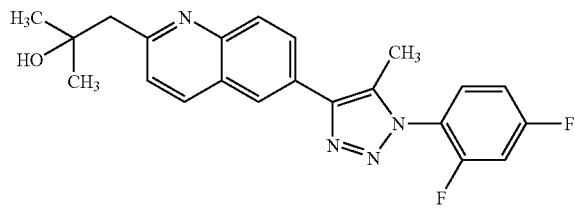

1-(2,4-difluorophenyl)-5-methyl-4-(2-(2-hydroxy-2-methyl-propyl)-quinoline-6-yl)-1H-[1,2,3]triazole 1) Manufacture of 1-(6-bromoquinoline-2-yl)-2-methylpropane-2-ol 20 ml of diethylether was added to 2.22 g of 6-bromoquinaldine, and 3.76 ml of 2.66 M normal butyl lithium was dropped thereto at −78° C. The obtained suspension was stirred for 5 min, 2 ml of anhydrous acetone was added and the mixture was further stirred for 10 min, and water was added. The products were extracted with ethyl acetate, organic layer was dried with anhydrous sodium sulfated and the solvents were distilled outunder reduced pressure. The obtained residues were separated and purified by silicagel colum chromatography (hexane:ethyl acetate=2:1) to obtain 1.14 g of the above compound.
$^1$HNMR (400 MHz, CDCl$_3$), δ: 1.28 (6H, s), 3.09 (2H, s), 5.81 (1H, s), 7.28 (1H, d, J=8.3 Hz), 7.77 (1H, dd, J=2.4, 8.6 Hz), 7.90 (1H, d, J=8.6 Hz), 7.97 (1H, d, J=2.4 Hz), 8.03 (1H, d, J=8.3 Hz).

2) Manufacture of 1-(2,4-difluorophenyl)-5-methyl-4-(2-(2-hydroxy-2-methyl-propyl)-quinoline-6-yl)-1H-[1,2,3]triazole The above compound was obtained as a white solid by the same method as Example 49, by a method according thereof, or by a combination of these and ordinary methods, with the use of halogen compound obtained in the above 1), the tin reagent obtained in Reference Example 13, and tetrakistriphenylphosphinepalladium.
$^1$HNMR (400 MHz, CDCl$_3$ ), δ: 1.31 (6H, s), 2.51 (3H, d, J=1.5 Hz), 3.13 (2H, s), 6.05 (1H, brs), 7.10-7.17 (2H, m), 7.31 (1H, d, J=8.3 Hz), 7.57-7.63 (1H, m), 8.12-8.17 (2H, m), 8.19 (1H, d, J=8.3 Hz), 8.24 (1H, s),
ESI-MS Found: m/z 395.3[M+H]$^+$.

EXAMPLE 225

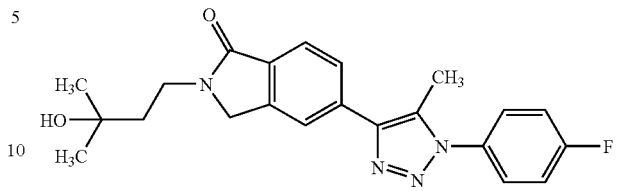

4-(2-(3-hydroxy-3-methyl-butyl)-1-oxo-isoindoline-5-yl)-1-(4-fluorophenyl)-5-methyl-1H-[1,2,3]triazole 1) Manufacture of methyl3-(5-bromo-1-oxo-1,3-dihydro-2H-isoindole-2-yl)propionate The above compound was obtained by performing the reaction by the same method as Example 49-1, except using methyl □-alanine instead of cyclopropylamine which was used in Example 49-1).
$^1$HNMR (400 MHz, CDCl$_3$), δ: 2.75 (2H, t, J=6.4 Hz), 3.69 (3H, s), 3.89 (2H, t, J=6.4 Hz), 4.46 (2H, s), 7.56-7.61 (2H, m), 7.71 (1H, d, J=8.8 Hz).

2) Manufacture of 5-bromo-2-(3-hydroxy-3-methyl-butyl)-isoindoline-1-one 312 mg of the compound obtained in the above 1) was dissolved in 2 ml of diethylether, cooled down to 0° C., and 1.33 ml of 3.0 M methyl magnesium iodide was added. The mixture was stirred for 1 hour at room temperature, water was added the products were extracted with ethyl acetate. Organic layer was dried with anhydrous sodium sulfate and the solvents were distilled outunder reduced pressure. The obtained residues were purified by sicagel column chromatography (hexane:ethyl acetate=1:1) to obtain 83.3 mg of the above compound.
$^1$HNMR (400 MHz, CDCl$_3$), δ: 1.28 (6H, s), 1.83 (2H, t, J=7.3 Hz), 3.76 (2H, t, J=7.3 Hz), 4.40 (2H, s), 7.58-7.62 (2H, m), 7.70 (1H, d, J=8.3 Hz).

3) Manufacture of 4-(2-(3-hydroxy-3-methyl-butyl)-1-oxo-isoindoline-5-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in the above 2), the tin reagent obtained in Reference Example 12, and tetrakistriphenylphosphinepalladium.
$^1$HNMR (400 MHz, CDCl$_3$), δ: 1.31 (6H, s), 1.86 (2H, t, J=7.6 Hz), 2.26 (1H, brs), 2.52 (3H, s), 3.81 (2H, t, J=7.6 Hz), 4.51 (2H, s), 7.26-7.32 (2H, m), 7.49-7.53 (2H, m), 7.78 (1H, d, J=7.8 Hz), 7.93 (1H, d, J=7.8 Hz), 7.99 (1H, s),
ESI-MS Found: m/z 395.2 [M+H]$^+$.

EXAMPLE 226

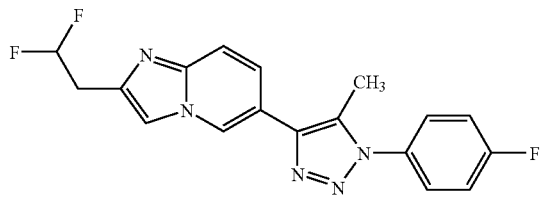

4-(2-(2,2-difluoroethyl)-imidazo[1,2-a]pyridine-6-yl)-1-(4-fluorophenyl)-5-methyl-1H-[1,2,3]triazole The above compound was obtained as a white solid by the same method as Example 49, by a method according thereof, or by a combination of these and ordinary methods, with the use of halogen compound obtained in Example 221, the tin reagent obtained in Reference Example 12, and tetrakistriphenylphosphinepalladium.

$^1$HNMR (400 MHz, CDCl$_3$), δ: 2.50 (3H, s), 3.39 (2H, tt, J=4.6, 16.9 Hz), 6.20 (1H, tt, J=4.6, 56.6 Hz), 7.24-7.32 (2H, m), 7.49-7.60 (4H, m), 7.67 (1H, d, J=9.3 Hz), 8.55 (1H, s),

ESI-MS Found: m/z 358.2 [M+H]$^+$.

EXAMPLE 227

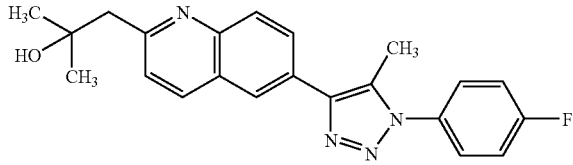

1-(4-fluorophenyl)-5-methyl-4-(2-(2-hydroxy-2-methyl-propyl-quinoline-6-yl)-1H-[1,2,3]triazole The above compound was obtained as a white solid by the same method as Example 49, by a method according thereof, or by a combination of these and ordinary methods, with the use of halogen compound obtained in Example 224, the tin reagent obtained in Reference Example 12, and tetrakistriphenylphosphinepalladium.

$^1$HNMR (400 MHz, CDCl$_3$), δ: 1.31 (6H, s), 2.57 (3H, s), 3.13 (2H, s), 6.05 (1H, brs), 7.25-7.33 (3H, m), 7.50-7.57 (2H, m), 8.13-8.24 (4H, m), ESI-MS Found: m/z 377.2 [M+H]$^+$.

EXAMPLE 228

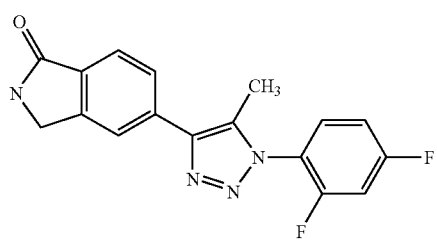

4-(1-oxo-isoindoline-5-yl)-1(2,4-difluorophenyl)-5-methyl-1H-[1,2,3]triazole

The above compound was obtained by the same method as Example 81 except using the tin reagent of Reference Example 13 instead of the tin reagent which was used in Example 81.

$^1$HNMR (400 MHz, CDCl$_3$), δ: 2.47 (3H, d,=1.5 Hz), 4.55 (2H, s), 6.29 (1H, brs), 7.08-7.17 (2H, m), 7.55-7.62 (1H, m), 7.85 (1H, d, J=7.3 Hz), 7.99 (1H, d, J=7.3 Hz), 8.02 (1H, s), ESI-MS Found: m/z 327.1 [M+H]$^+$.

EXAMPLE 229

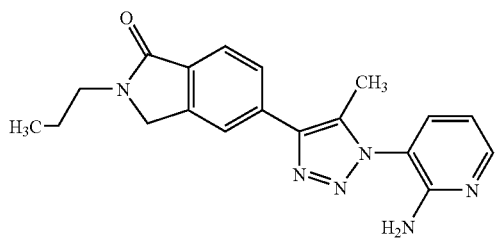

4-(2-propyl-1-oxo-isoindoline-5-yl)-1-(2-amino-pyridine-3-yl)-5-methyl-1H-[1,2,3]triazole 72 g of the compound obtained in Example 8 was added to 52 mg of isopropanole and 2 ml of 25% aqueous ammonium. The mixture was stirred at 120° C. for 2 days. The solvents were distilled out under reduced pressure, and the obtained residues were purified by thin-layer silicagel chromatography, to obtain 15.7 mg of the above compound as a white solid.

$^1$HNMR (400 MHz, CDCl$_3$), δ: 0.99 (3H, t, J=7.6 Hz), 1.70-1.78 (2H, m), 2.46 (3H, s), 3.63 (2H, t, J=7.3 Hz), 4.47 (2H, s), 4.78 (2H, brs), 6.81-6.91 (1H, m), 7.46-7.50 (1H, m), 7.81 (1H, d, J=8.1 Hz), 7.96 (1H, d, J=8.1 Hz), 7.99 (1H, s), 8.27-8.30 (1H, m), ESI-MS Found: m/z 349.2 [M+H]$^+$.

EXAMPLE 230

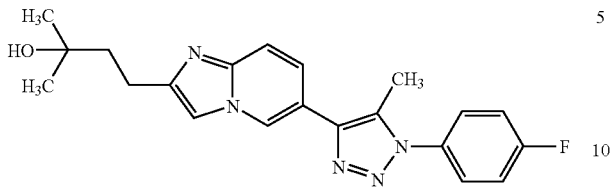

1-(4-fluorophenyl)-4-(2-(3-hydroxy-3-methyl-butyl)-imidazo[1,2-a]pyridine-6-yl)-5-methyl-1H-[1,2,3]triazole

1) Manufacture of ethyl 3-(6-bromoimidazo[1,2-a]pyridine-2-yl)propionate 4.28 mg of ethyl 5-chloro-3-oxopentanoate was dissolved in 40 ml of ethanol, 2.94 g of 2-amino-5-bromopyridine was added and the mixture was stirred all night by heating under reflux. The mixture was cooled down to room temperature, and the solvents were distilled outunder reduced pressure. Ethyl acetate followed by saturated sodium bicarbonate aqueous solution were added. Organic layer was dried with anhydrous sodium sulfate, and the solvents were distilled outunder reduced pressure. The obtained residues were purified by preparative thin-layer silicagel chromatography (hexane:ethyl acetate=50:50) to obtain 990 mg of the above compound as crude product.

2) Manufacture of 4-(6-bromoimidazo[1,2-a]pyridine-2-yl)2-methylbutane-2-ol 225 mg of the ester compound obtained in the above 1) was dissolved in 4 ml of diethylether, the mixture was cooled down to 0° C., and 1.27 ml solution of diethylethyer with 3M methylmagnesium iodide was added. After stirring the mixture at room temperature for 30 min, water was added and the products were extracted with chloroform. Organic layer was dried with anhydrous sodium sulfate, and the solvents were distilled outunder reduced pressure. The obtained residues were purified by silicagel column chromatography (hexane:ethyl acetate=1:4) to obtain 195 mg of the above compound as crude product.

$^1$HNMR (400 MHz, CDCl$_3$), δ: 1.32 (6H, s), 1.95 (2H, t, J=7.3 Hz), 2.92 (2H, t, J=7.3 Hz), 7.16-7.21 (1H, m), 7.33 (1H, s), 7.41 (1H, d, J=7.8 Hz), 8.18-8.20 (1H, m).

3) Manufacture of 1-(4-fluorophenyl)-4-(2-(3-hydroxy-3-methyl-butyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of the compound obtained in the above 2), the tin reagent obtained in Reference Example 12, and tetrakistriphenylphosphinepalladium.

$^1$HNMR (400 MHz, CDCl$_3$), δ: 1.26 (6H, s), 1.99 (2H, t, J=7.6 Hz), 2.49 (3H, s), 2.96 (2H, t, J=7.6 Hz), 7.23-7.32 (2H, m), 7.45-7.54 (4H, m), 7.61 (1H, d, J=9.2 Hz), 8.54 (1H, d, J=1.0 Hz),

ESI-MS Found: m/z 380.2 [M+H]$^+$.

EXAMPLE 231

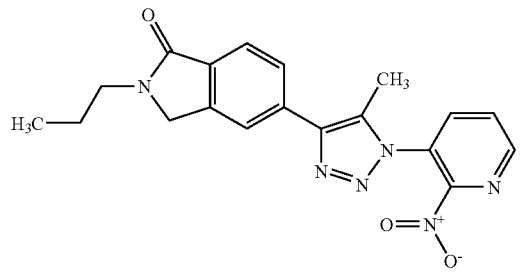

4-(2-propyl-1-oxo-isoindoline-5-yl)-1-(2-nitro-pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 85, the tin reagent obtained in Reference Example 23, and tetrakistriphenylphosphinepalladium.

$^1$HNMR (400 MHz, CDCl$_3$), δ: 1.00 (3H, t, J=7.4 Hz), 1.71-1.78 (2H, m), 2.49 (3H, s), 3.63 (2H, t, J=7.4 Hz), 4.48 (2H, s), 7.80 (1H, d, J=7.8 Hz), 7.89-8.01 (3H, m), 8.10 (1H, dd, j=1.5, 7.8 Hz), 8.83 (1H, dd, J=2.1, 4.7 Hz),

ESI-MS Found: m/z 379.2 [M+H]$^+$.

EXAMPLE 232

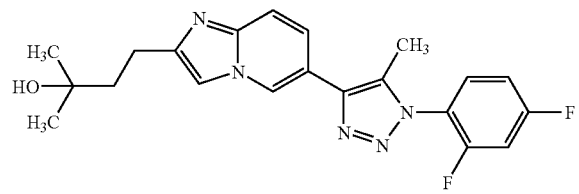

1-(2,4-difluorophenyl)-4-(2-(3-hydroxy-3-methyl-butyl)-imidazo[1,2-a]pyridine-6-yl)-5-methyl-1H-[1,2,3]triazole The above compound was obtained as a white solid by the same method as Example 49, by a method according thereof, or by a combination of these and ordinary methods, with the use of the compound obtaine in Example 230, the tin reagent obtained in Reference Example 13, and tetrakistriphenylphosphinepalladium.

$^1$HNMR (400 MHz, CDCl$_3$), δ: 1.31 (6H, s), 1.99 (2H, t, J=7.3 Hz), 2.43 (3H, d, J=1.4 Hz), 2.96 (2H, t, J=7.6 Hz), 7.09-7.16 (2H, m), 7.45 (1H, s), 7.50-7.63 (3H, m), 8.55 (1H, d, J=1.0 Hz),

ESI-MS Found: m/z 398.2 [M+H]$^+$.

EXAMPLE 233

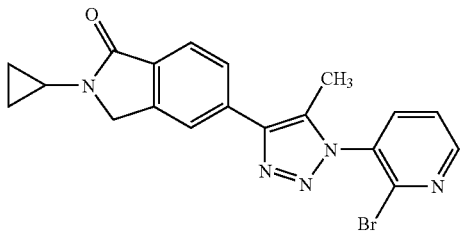

4-(2-cyclopropyl-1-oxo-isoindoline-5-yl)-1-(2-bromo-pyridine-3-yl)-5-methyl-1H-[1,2,3]triazole The above compound was obtained as a white solid by the same method as Example 49, by a method according thereof, or by a combination of these and ordinary methods, with the use of halogen compound obtained in Example 85, the tin reagent obtained in Reference Example 24, and tetrakistriphenylphosphinepalladium.

$^1$HNMR (400 MHz, CDCl$_3$), δ: 0.89-0.99 (4H, m), 2.46 (3H, s), 2.94-3.02 (1H, m), 4.41 (2H, s), 7.55-7.79 (1H, m), 7.80-7.86 (2H, m), 7.94 (1H, d, J=7.8 Hz), 8.00 (1H, s), 8.64 (1H, dd, J=2.0,4.9 Hz),

ESI-MS Found: m/z 412.0 [M+H]$^+$.

REFERENCE EXAMPLE 1

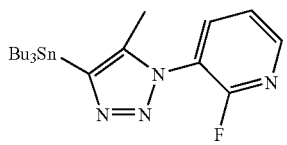

1-(2-fluoropyridine-3-yl)-5-methyl-4-tributylstanyl-1H-[1,2,3]triazole

1) Manufacture of 3-azide-2-fluoropyridine

Under nitrogen atmosphere, 10 ml solution of tetrahydrofuran with 5.3 ml of diisopropylamine was cooled down to −78° C., and 24 ml of 1.58 M n-butyl lithium/hexane solution was dropped thereto. The reaction solution was heated to 0° C., stirred for 5 min, cooled down again to −78° C., and 10 ml solution of tetrahydrofuran with 3.7 mg of 2-fluoropyridine was added thereto. After stirring at −78° C. for 10 min, 10 ml solution of tetrahydrofuran with 8.9 g of n-dodecylbenzene sulfoneazide was added and stirred. The reaction solution was heated to −60° C., water was added and the reaction was stopped. The products were extracted with ethyl acetate and dried with anhydrous sodium sulfate, and the solvents were distilled outunder reduced pressure. The obtained residues were purified by silicagel column chromatography (hexane:ethyl acetate=75:25) to obtain 3.02 g of the above compound as liver oily crude product.

2) Manufacture of 1-(2-fluoropyridine-3-yl)-5-methyl-4-tributylstanyl-1H-[1,2,3]triazole 10 g of tributyl (1-propinyl)tin was added to 10 ml solution of toluene with 3.02 g of the compound obtained in the above 1), and the mixture was stirred at 120° C. for 3 hours. The obtained solution was cooled down to room temperature, and purified by silicagel column chromatography (hexane:ethyl acetate=75:25) to obtain 6.40 g of the above compound as yellow oily substance.

$^1$HNMR (400 MHz, CDCl$_3$), δ: 0.90 (9H, t, J=7.4 Hz), 1.19-1.29 (12H, m), 1.35-1.66 (6H, m), 2.28 (3H, d, J=1.6 Hz), 7.41-7.46 (1H, m), 7.97-8.02 (1H, m), 8.37-8.39 (1H, m),

ESI-MS Found: m/z 469.3 [M+H]$^+$.

REFERENCE EXAMPLE 2

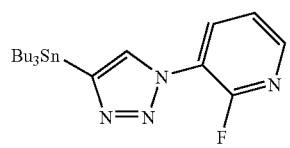

1-(2-fluoropyridine-3-yl)-4-tributylstanyl-1H-[1,2,3]triazole 958 mg of tributyl(1-ethynyl)tin was added to 3.0 ml solution of toluene with 280 mg of the compound 3-azide-2-fluoropyridine obtained in Reference Example 1-1. The reaction solution was stirred all night at 80° C., and 2 hours at 100° C. The obtained solution was cooled down to room temperature, purified by silicagel column chromatography (hexane:ethyl acetate=80:20) to obtain 380 mg of the above compound as a colorless oily substance.

$^1$HNMR (300 MHz, CDCl$_3$), δ: 0.90 (9H, t, J=7.3 Hz), 1.03-1.43 (12H, m), 1.44-1.73 (6H, m), 7.38-7.45 (1H, m), 8.08 (1H, d, J=3.3 Hz), 8.22-8.30 (1H, m), 8.46-8.57 (1H, m), APCI-MS Found: m/z 454.9 [M+H]$^+$.

REFERENCE EXAMPLE 3

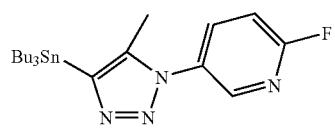

1-(2-fluoropyridine-5-yl)-5-methyl-4-tributylstanyl-1H-[1,2,3]triazole

1) Manufacture of 5-azide-2-fluoropyridine

Under nitrogen atmosphere, 40 ml solution of diethylether with 3.5 mg of 5-bromo-2-fluoropyridine was cooled down to −78° C., and 8.3 ml of 2.6 M n-butyl lithium was dropped thereto. The reaction solution was stirred at −78° C. for 10 min, 20 ml solution of diethylether with 5.1 g of 2,4,6-triisopropylbenzenesulfoneazide was added and the mixture was stirred. After heating to −65° C., water was added and the reaction was stopped. The products were extracted with diethylether, dried with anhydrous sodium sulfate, and the solvents were distilled outunder reduced pressure. The obtained residues were purified by silicagel column chromatography (hexane:ethyl acetate=75:25) to obtain 1.80 g of the above compound as liver oily crude product.

2) Manufacture of 1-(2-fluoropyridine-5-yl)-5-methyl-4-tributylstanyl-1H-[1,2,3]triazole 4.33 g of tributyl(1-propynyl)tin was added to 15 ml solution of toluene with 1.80 g of the compound obtained in the above 1), and the mixture was stirred all nigh at 120° C. The obtained solution was cooled down to room temperature, purified by silicagel column chromatography (hexane:ethyl acetate=75:25) to obtain 3.90 g of the above compound as yellow oily substance.

$^{1}$I H (400 MHz, CDCl$_3$), δ: 0.91 (9H, t, J=7.6 Hz), 1.15-1.24 (6H, m), 1.30-1.42 (6H, m) 1.53-1.65 (6H, m), 2.36 (3H, t, J=2.0 Hz)7.20 (1H, dd, J=3.2,8.8 Hz), 7.95-8.00 (1H, m), 8.37 (1H, dd, J=0.8,2.8 Hz),

ESI-MS Found: m/z 469.6 [M+H]$^{+}$.

REFERENCE EXAMPLE 4

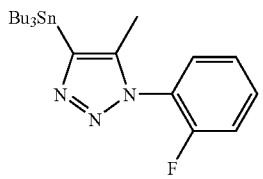

1-(2-fluorophenyl)-5-methyl-4-tributylstanyl-1H-[1,2,3]triazole

1) Manufacture of 1-azide-2-fluorobenzene 510 mg of sodium nitrite dissolved in 2 ml of water was dropped under iced temperature to 5 ml of concentrated hydrochloric acid with 1.0 g of 2-fluorophenylhydrazine hydrochloride and 6 ml solution of diethylether. The reaction solution was heated to room temperature, and stirred for 2 hours. The reaction solution was diluted with diethyl ether, washed with water followed by saturated saline solution and dried with anhydrous sodium sulfate. The solvents were distilled outunder reduced pressure to obtain 400 mg of the above compound as crude bronze oily substance.

2) Manufacture of 1-(2-fluorophenyl)-5-methyl-4-tributylstanyl-1H-[1,2,3]triazole 2.9 g of tributyl(1-propinyl)tin was added to 5 ml solution of toluene with 400 mg of the compound obtained in the above 1), and the mixture was stirred at 120° C. for 4.5 hours. The obtained solution was cooled down to room temperature, saturated potassium fluoride aqueous solution was added to the reaction solution and the products were extracted with ethyl acetate. The resultants were washed with saturated saline solution and dried with anhydrous sodium sulfate. The solvents were distilled outunder reduced pressure, and the residues were purified by silicagel column chromatography (hexane:ethyl sulfate=90:10) to obtain 680 mg of the above compound as yellow oily substance.

$^{1}$HNMR (300 MHz, CDCl$_3$), δ: 0.90 (9H, t, J=7.5 Hz), 1.19-1.29 (12H, m), 1.35-1.66 (6H, m), 2.32 (3H, s), 7.19-7.24 (2H, m), 7.42-7.49 (2H, m), APCI-MS Found: m/z 468.5 [M+H]$^{+}$.

REFERENCE EXAMPLE 5

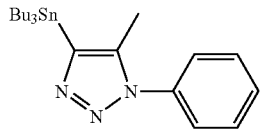

1-phenyl-5-methyl-4-tributylstanyl-1H-[1,2,3]triazole

1) Manufacture of azidebenzene 4.1 g of sodium nitrite dissolved in 5 ml of water was dropped under iced temperature to 50 ml of concentrated chrolic acid with 5 ml of phenylhydrazine and 15 ml solution of diethylether. The reaction solution was heated to room temperature, and stirred for 4 hours. The reaction solution was diluted with ethyl acetate, washed with water followed by saturated saline solution and dried with anhydrous sodium sulfate. The solvents were distilled outunder reduced pressure to obtain 3.2 g of the above compound as crude bronze oily substance.

2) Manufacture of 1-phenyl-5-methyl-4-tributylstanyl-1H-[1,2,3]triazole 1.7 g of tributyl(1-propynyl)tin was added to 1 ml solution of toluene with 120 mg of the compound obtained in 1), and the mixture was stirred at 120° C. for 12 hours. The obtained solution was cooled down to room temperature and the reaction solution was directly purified by silicagel column chromatography (hexane:ethyl acetate=90:10) to obtain 246 mg of the above compound as yellow oily substance.

$^{1}$HNMR (300 MHz, CDCl$_3$), δ: 0.90 (9H, t, J=7.5 Hz), 1.15-1.42 (12H, m), 1.54-1.66 (6H, m)2.32 (3H, s), 7.42-7.59 (5H, m),

ESI-MS Found: m/z 450.1 [M+H]$^{+}$.

REFERENCE EXAMPLE 6

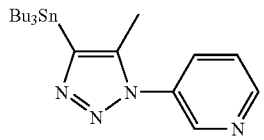

1-(3-pyridyle)-5-methyl-4-tributylstanyl-1H-[1,2,3]triazole

1) Manufacture of 3-azidepyridine 1.5 g of sodium azide dissolved in 5 ml of water was dropped under iced temperature to 15 ml solution of 10% chloric acid with 2.0 g of 3-aminopyridine. After stirring the mixture under iced temperature for 20 min, 1.8 g of sodium nitrite dissolved in 5 ml of water was dropped thereto. The reaction solution was heated to room temperature and stirred for 1 hour. The reaction solution was diluted with chloroform, and washed with water followed by saturated saline solution, dried with anhydrous sodium sulfate. The solvents were distilled out under reduced pressure to obtain 2.5 g of the above compound as crude bronze oily substance.

2) Manufacture of 1-(3-pyridyle)-5-methyl-4-tributylstanyl-1H-[1,2,3]triazole 1.2 g of tributyl(1-propynyl)tin was added to 10 ml solution of toluene with 800 mg of the compound obtained in the above 1), and the mixture was stirred at 120° C. for 6 hours. The obtained solution was cooled down to room temperature, the solvents were concentrated under reduced pressure and the obtained residues were purified by silicagel column chromatography (hexane:diethylether=90:10) to obtain 610 mg of the above compound as yellow oily substance.

$^1$ HNMR (400 MHz, CDCl$_3$), δ: 0.91 (9H, t, J=7.5 Hz), 1.20-1.41 (12H, m), 1.56-1.62 (6H, m), 2.38 (3H, s), 7.49-7.53 (1H, m), 7.86-7.89 (1H, m), 8.74-8.74 (1H, m), 8.74-8.78 (1H, m),
ESI-MS Found: m/z 451.1 [M+H]$^+$.

REFERENCE EXAMPLE 7

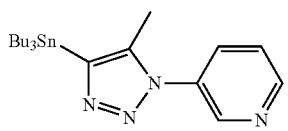

1-(2-chloropyridine-3-yl)-5-methyl-4-tributylstanyl-1H-[1,2,3]triazole

1) Manufacture of 3-azide-2-chloropiridine

Under nitrogen atmosphere, 7.0 ml solution of tetrahydrofuran with 1.4 ml of diisopropylamine was cooled to −78° C., and 6.3 ml of 1.58 M n-butyl lithium/hexane solution was dropped thereto. The reaction solution was heated to 0° C., stirred for 5 min, cooled down again to −78° C., and 5.0 ml solution of tetrahydrofuran with 1.13 g of 2-chloropyridine was added. After stirring the mixture for 10 min at −78° C., 7.0 ml solution of tetrahydrofuran with 1.62 g of 2,4,6-triisopropylbenzenesulfoneazide was added and stirred. The reaction solution was heated to −60° C., water was added and the reaction was stopped. The products were extracted with ethyl acetate, dried with anhydrous sodium sulfate, and the solvents were distilled out under reduced pressure. The obtained residues were purified by silicagel column chromatography (hexane:ethyl acetate=80:20) to obtain 102 g of the above compound as liver oily crude substance.

2) Manufacture of 1-(2-chloropyridine-3-yl)-5-methyl-4-tributylstanyl-1H-[1,2,3]triazole 1.65 g of tributyl(1-propynyl)tin was added to 4.0 ml solution of toluene with 685 mg of the compound obtained in the above 1), and the mixture was stirred all night at 120° C. The obtained solution was cooled down to room temperature and purified by silicagel column chromatography (hexane:ethyl acetate=80:20) to obtain 1.10 g of the above compound as yellow oily substance.

$^1$HNMR (400 MHz, CDCl$_3$), δ: 0.90 (9H, t, J=8.0 Hz), 1.16-1.40 (12H, m), 1.50-1.67 (6H, m), 2.23 (3H, s)7.45-7.50 (1H, m), 7.79-7.83 (1H, m), 8.70-8.60 (1H, m).

REFERENCE EXAMPLE 8

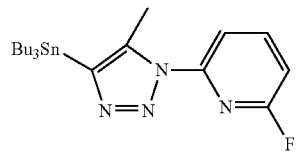

1-(2-fluoropyridine-6-yl)-4-tributylstanyl-1H-[1,2,3]triazole

1) Manufacture of 6-azide-2-fluorobenzene 325 mg of the sodium nitrite dissolved in 3 ml of water was dropped under iced temperature to 10 ml of concentrated chloric acid with 500 mg of 6-fluorophenylhydrazine hydrochloride and 6 ml solution of diethylether. The reaction solution was heated to room temperature and stirred for 2.5 hours. The reaction solution was diluted with diethylether, washed with water followed by saturated saline solution, and dried with anhydrous sodium sulfate. The solvents were distilled out under reduced pressure to obtain 424 mg of the above compound as crude bronze oily substance.

2) Manufacture of 1-(2-fluoropyridine-6-yl)-5-methyl-4-tributylstanyl-1H-[1,2,3]triazole 1.32 g tributyl(1-propynyl)tin was added to 2 ml solution of toluene with 424 mg of the compound obtained in 1), and the mixture was stirred at 120° C. for 4 hours. The obtained solution was cooled down to room temperature. The solvents were distilled out under reduced pressure and the residues were purified by silicagel column chromatography (hexane:ethyl acetate=90:10) to obtain 910 mg of the above compound as yellow oily substance.

$^1$HNMR (300 MHz, CDCl$_3$), δ: 0.90 (9H, t, J=7.3 Hz), 1.16-1.40 (12H, m), 1.43-1.70 (6H, m), 2.67 (3H, s), 6.92-6.99 (1H, m), 7.95-8.02 (2H, m).

REFERENCE EXAMPLE 9

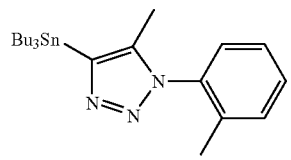

1-(2-methylphenyl)-5-methyl-4-tributylstanyl-1H-[1,2,3]triazole

1) Manufacture of 1-azide-2-methylbenzene 1.7 g of sodium nitrite dissolved in 10 ml of water was dropped under iced temperature to 20 ml of concentrated chloric acid with 3.5 g of 2-methylphenylhydrazine hydrochloride and 35 ml solution of diethylether. The reaction solution was heated to room temperature and stirred for 2 hours. The reaction solution was diluted with diethylether, washed with water followed by saturated saline solution, and dried with anhydrous sodium sulfate. The solvents were distilled outunder reduced pressure to obtain 2.2 g of the above compound as crude brown oily substance.

2) Manufacture of 1-(2-methylphenyl)-5-methyl-4-tributylstanyl-1H-[1,2,3]triazole 1.9 ml of tributyl(1-propynyl)tin was added to 5 ml solution of toluene with 1 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 2.0 g of the above compound as yellow oily substance.

$^1$HNMR (400 MHz, CDCl$_3$), δ: 0.90 (9H, t, J=7.2 Hz), 1.15-1.65 (18H, m), 2.00 (3H, s), 2.13 (3H, t, 1.8 Hz), 7.20-7.24 (1H, m), 7.32-7.43 (3H, m),

ESI-MS Found: m/z 468.0 [M+H]$^+$.

REFERENCE EXAMPLE 10

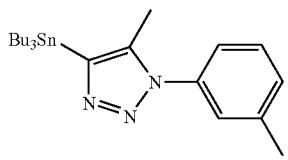

1-(3-methylphenyl)-5-methyl-4-tributylstanyl-1H-[1,2,3]triazole

1) Manufacture of 1-azide-3-methylbenzene 2.6 g of sodium nitrite dissolved in 5 ml of water was dropped under iced temperature to 16 ml of concentrated chloric acid with 2.5 g of 3 methylphenylhydrazine hydrochloride and 25 mlf solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 1.2 g of the above compound as crude bronze oily substance.

2) Manufacture of 1-(3-methylphenyl)-5-methyl-4-tributylstanyl-1H-[1,2,3]triazole 1.6 ml of tributyl(1-propynyl)tin was added to 5 ml solution of toluene with 780 mg of the compound obtained in 1), and the mixture was stirred all night at 120° C. The obtained solution was cooled down to room temperature, and saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 620 mg of the above compound as yellow oily substance.

$^1$HNMR (400 MHz, CDCl$_3$), δ: 0.90 (9H, t, J=7.4 Hz), 1.16-1.64 (18H, m), 2.32 (3H, t, 2.0 Hz), 2.43 (3H, s), 7.21-7.29 (3H, m), 7.37-7.42 (1H, m),

ESI-MS Found: m/z 468.0 [M+H]$^+$.

REFERENCE EXAMPLE 11

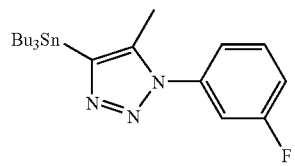

1-(3-fluorophenyl)-5-methyl-4-tributylstanyl-1H-[1,2,3]triazole

1) Manufacture of 1-azide-3-fluorobenzene 2.5 g of sodium nitrite dissolved in 30 ml of water was dropped under iced temperature to 30 ml of concentrated chloric acid with 4.8 g of 3-fluorophenylhydrazine hydrochloride and 50 ml solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 2.2 g of the above compound as crude bronze oily substance.

2) Manufacture of 1-(3-fluorophenyl)-5-methyl-4-tributylstanyl-1H-[1,2,3]triazole 3.8 ml of tributyl(1-propynyl)tin was added to 5 ml solution of toluene with 2 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 2.7 g of the above compound as yellow oily substance.

$^1$HNMR (400 MHz, CDCl$_3$), δ: 0.90 (9H, t, J=7.4 Hz), 1.16-1.65 (18H, m), 2.35 (3H, t, 2.0 Hz), 7.16-7.34 (3H, m), 7.47-7.54 (1H, m),

ESI-MS Found: m/z 467.9 [M+H]$^+$.

REFERENCE EXAMPLE 12

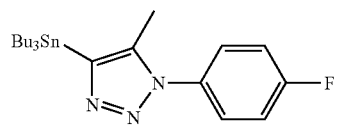

1-(4-fluorophenyl)-5-methyl-4-tributylstanyl-1H-[1,2,3]triazole

1) Manufacture of 1-azide-4-fluorobenzene 2.5 g of sodium nitrate dissolved in 30 ml of water was dropped under iced temperature to 30 ml of concentrated chloric acid with 4.8 g of 4-fluorophenylhydrazine hydrochloride and 50 ml solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 1.9 g of the above compound as crude bronze oily substance.

2) Manufacture of 1-(4-fluorophenyl)-5-methyl-4-tributylstanyl-1H-[1,2,3]triazole 3.6 ml of tributyl(1-propynyl)tin was added to 5 ml solution of toluene with 1.9 mg of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 2.3 g of the above compound as yellow oily substance.

$^1$HNMR (400 MHz, CDCl$_3$), δ: 0.90 (9H, t, J=7.4 Hz), 1.15-1.65 (18H, m), 2.32 (3H, t, 2.0 Hz), 7.21 (2H, dd, J=8.2, 9.0 Hz), 7.44 (2H, dd, J=4.6, 9.0 Hz),

ESI-MS Found: m/z 467.9 [M+H]$^+$.

REFERENCE EXAMPLE 13

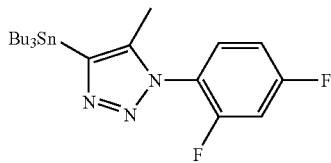

1-(2,4-fluorophenyl)-5-methyl-4-tributylstanyl-1H-[1,2,3]triazole

1) Manufacture of 1-azide-2,4-difluorobenzene 2.2 g of sodium nitrite dissolved in 5 ml of water was dropped under iced temperature to 13 ml of concentrated chloric acid with 2 g of 2,4-difluorophenylhydrazine hydrochloride and 25 ml solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 1.7 g of the above compound as crude bronze oily substance.

2) Manufacture of 1-(2,4-difluorophenyl)-5-methyl-4-tributylstanyl-1H-[1,2,3]triazole 3.4 ml of tributyl(1-propynyl)tin was added to 5 ml solution of toluene with 1.7 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 3.1 g of the above compound as yellow oily substance.

$^1$HNMR (400 MHz, CDCl$_3$), δ: 0.90 (9H, t, J=7.4 Hz), 1.17-1.65 (18H, m), 2.23-2.25 (3H, m), 7.01-7.09 (2H, m), 7.46-7.53 (1H, m),

ESI-MS Found: m/z 490.0 [M+H]$^+$.

REFERENCE EXAMPLE 14

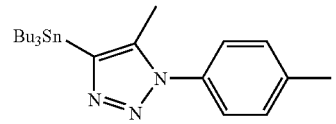

1-(4-methylphenyl)-5-methyl-4-tributylstanyl-1H-[1,2,3]triazole

1) Manufacture of 1-azide-4-methylbenzene 2.5 g of sodium nitrite dissolved in 30 ml of water was dropped under iced temperature to 30 ml of concentrated chloric acid with 4.8 g of 4-methylphenylhydrazine hydrochloride and 50 ml solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 2.1 g of the above compound as crude bronze oily substance.

2) Manufacture of 1-(4-methylphenyl)-5-methyl-4-tributylstanyl-1H-[1,2,3]triazole 1.3 ml of tributyl(1-propynyl)tin was added to 5 ml solution of toluene with 620 mg of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 690 mg of the above compound as yellow oily substance.

$^1$HNMR (400 MHz, CDCl$_3$), δ: 0.90 (9H, t, J=7.2 Hz), 1.15-1.65 (18H, m), 2.31 (3H, t, 1.8 Hz), 2.43 (3H, s), 7.32 (4H, d, J=2.4 Hz),

ESI-MS Found: m/z 468.0 [M+H]$^+$.

REFERENCE EXAMPLE 15

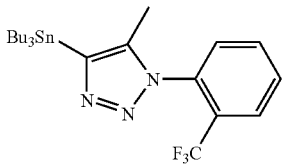

1-(2-trifluoromethyl-phenyl)-5-methyl-4-tributylstanyl-1H-[1,2,3]triazole

1) Manufacture of 1-azide-2-trifluoromethyl-benzene 1.9 g of sodium nitrite dissolved in 8 ml of water was dropped under iced temperature to 7.5 ml of concentrated chloric acid with 1.8 g of 2-trifluoromethyl-aniline, 10 ml of water and 35 ml of ethanol. The mixture was stirred under iced temperature for 30 min and 2.0 g of sodium azide dissolved in 8 ml of water was dropped thereto. The reaction solution was heated to room temperature and stirred for 2 hours. The reaction solution was neutralized with sodium bicarbonate, and the products were extracted with chloroform. Then, organic layer was washed with saturated saline solution and dried with anhydrous sodium sulfate. The solvents were distilled outunder reduced pressure to obtain 1.5 g of the above compound as crude bronze oily substance.

2) Manufacture of 1-(2-trifluoromethyl-phenyl)-5-methyl-4-tributylstanyl-1H-[1,2,3triazole 1.5 ml of tributyl(1-propynyl)tin was added to 5 ml solution of toluene with 0.7 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 0.9 g $^1$HNMR (400 MHz, CDCl$_3$), δ: 0.90 (9H, t, J=7.2 Hz), 1.16-1.64 (18H, m), 2.13 (3H, t, J=2.0 Hz), 7.37 (1H, d, J=7.6 Hz), 7.66-7.76 (2H, m), 7.84-7.89 (1H, m), ESI-MS Found: m/z 517.9 [M+H]$^+$.

REFERENCE EXAMPLE 16

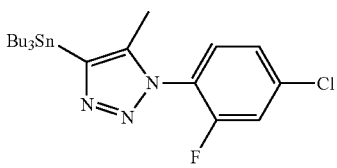

1-(4-chloro-2-fluorobenzene-6-yl)-4-tributylstanyl-1H-[1,2,3]triazole

1) Manufacture of 6-azide-4-chloro-2-fluorobenzene 10 ml of ethanol, 4 ml of water and 4 ml of concentrated chloric acid were added to 728 mg of 4-chloro-2-fluoroaniline. The mixture was cooled down to 0° C., and a solution with 380 g of sodium nitrite dissolved in 4 ml of water was added thereto. After stirring at room temperature for 1 hour, the mixture was cooled down again to 0° C., and the solution with 390 mg of sodium azide dissolved in 4 ml of water was added. After stirring the mixture at room temperature all night, the products were extracted with ether, dried with anhydrous sodium sulfate. The solvents were distilled outunder reduced pressure, to obtain crude product of the above compound.

2) Manufacture of 1-(4-chloro-2-fluoropyridine-6-yl)-5-methyl-4-tributylstanyl-1H-[1,2,3]triazole 1.65 g of tributyl(1-propynyl)tin was added to 4 ml solution of toluene with the compound obtained in 1), and the mixture was stirred at 120° C. for 4 hours. The obtained solution was cooled down to room temperature. The solvents were distilled outunder reduced pressure, and the residues were purified by silicagel column chromatography (hexane:ethyl acetate=80:20) to obtain 1.29 g of the above compound as yellow oily substance.

$^1$HNMR (300 MHz, CDCl$_3$), δ: 0.90 (9H, t, J=7.3 Hz), 1.08-1.42 (12H, m), 1.43-1.72 (6H, m)2.24 (3H, d, J=1.7 Hz), 7.29-7.49 (3H, m).

REFERENCE EXAMPLE 17

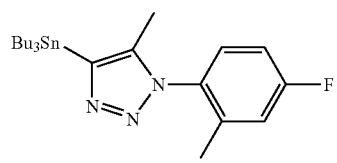

1-(4-fluoro-2-methyl-phenyl)-5-methyl-4-tributylstanyl-1H-[1,2,3]triazole

1) Manufacture of 1-azide-4-fluoro-2-methyl-benzene 2.9 g of sodium nitrite dissolved in 11 ml of water was dropped under iced temperature to 9.3 ml of concentrated chloric acid with 2.5 g of 4-fluoro-2-methyl-aniline, 14 ml of water and 50 ml of ethanol. After stirring the mixture under iced temperature for 30 min, 3.0 g of sodium azide dissolved in 11 ml of water was dropped thereto. The reaction solution was heated to room temperature and stirred for 1 hour. The reaction solution was neutralized with sodium carbonate, and the products were extracted with chloroform. Organic layer was washed with saturated saline solution and dried with anhydrous sodium sulfate. The solvents were distilled outunder reduced pressure to obtain 2.3 g of the above compound as crude brown oily substance.

2) Manufacture of 1-(4-fluoro-2-methyl-phenyl)-5-methyl-4-tributylstanyl-1H-[1,2,3]triazole 3.0 ml of tributyl(1-propynyl)tin was added to 10 ml solution of toluene with 1.5 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled out under reduced pressure, and the residues were purified by silicagel column chromatography (hexane:ethyl acetate=90:10) to obtain 2.1 g of the above compound as yellow oily substance.

$^1$HNMR (400 MHz, CDCl$_3$), δ: 0.86 (9H, t, J=7.2 Hz), 1.13-1.62 (18H, m), 1.96 (3H, s), 2.10 (3H, t, J=1.8 Hz), 6.95-7.07 (2H, m), 7.18 (1H, dd, J=5.2, 8.8 Hz),

ESI-MS Found: m/z 482.3 [M+H]$^+$.

REFERENCE EXAMPLE 18

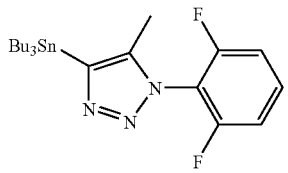

1-(2,6-difluorophenyl)-5-methyl-4-tributylstanyl-1H-[1,2,3]triazole

1) Manufacture of 1-azide-2,6-difluorobenzene

2.9 g of sodium nitrite dissolved in 11 ml of water was dropped under iced temperature to 9.3 ml of concentrated chloric acid with 2.5 g of 2,6-difluoroaniline, 14 ml of water, and 50 ml of ethanol. After stirring the mixture under iced temperature for 30 min, 3.0 g of sodium azide dissolved in 11 ml of water was dropped thereto. The reaction solution was heated to room temperature and stirred for 1 hour. The reaction solution was neutralized with sodium carbonate, and the products were extracted with chloroform. Organic layer was washed with saturated saline solution and dried with anhydrous sodium sulfate. The solvents were distilled out under reduced pressure to obtain 2.1 g of the above compound as crude bronze oily substance.

2) Manufacture of 1-(2,6-difluorophenyl)-5-methyl-4-tributylstanyl-1H-[1,2,3]triazole 3.0 ml of tributyl(1-propynyl)tin was added to 10 ml solution of toluene with 1.6 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled out under reduced pressure, and the residues were purified by silicagel column chromatography (hexane:ethyl acetate=90:10) to obtain 2.8 g of the above compound as yellow oily substance.

ESI-MS Found: m/z 486.2 [M+H]$^+$.

REFERENCE EXAMPLE 19

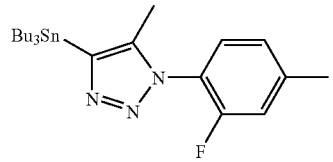

1-(2-fluoro-4-methyl-phenyl)-5-methyl-4-tributylstanyl-1H-[1,2,3]triazole

1) Manufacture of 1-azide-2-fluoro-4-methyl-benzene 2.9 g of sodium nitrate dissolved in 11 ml of water was dropped under iced temperature to 9.3 ml of concentrated chloric acid with 2.5 g of 2-fluoro-4-methyl-aniline, 14 ml of water, and 50 ml of ethanol.

After stirring the mixture under iced temperature for 30 min, 3.0 mg of sodium azide dissolved in 11 ml of water was dropped thereto. The reaction solution was heated to room temperature and stirred for 1 hour. The reaction solution was neutralized with sodium carbonate, and the products were extracted with chloroform. Organic layer was washed with saturated saline solution and dried with anhydrous sodium sulfate. The solvents were distilled out under reduced pressure to obtain 2.6 g of the above compound as crude bronze oily substance.

2) Manufacture of 1-(2-fluoro-4-methyl-phenyl)-5-methyl-4-tributylstanyl-1H-[1,2,3]triazole 2.0 ml of tributyl(1-propynyl)tin was added to 10 ml solution of toluene with 1.0 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled out under reduced pressure, and the residues were purified by silicagel column chromatography (hexane:ethyl acetate=90:10) to obtain 1.8 g of the above compound as yellow oily substance.

ESI-MS Found: m/z 482.3 [M+H]$^+$.

REFERENCE EXAMPLE 20

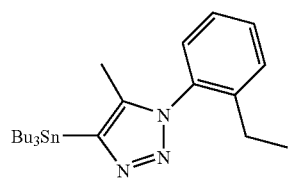

1-(2-ethylphenyl)-5-methyl-4-tributylstanyl-1H-[1,2,3]triazole

1) Manufacture of 1-azide-2-ethylbenzene 1.7 g of sodium nitrite dissolved in 20 ml of water was dropped under iced temperature to 20 ml of concentrated chloric acid with 3.5 g of 2-ethylphenylhydrazine hydrochloride and 35 ml solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 2.2 g of the above compound as crude brown oily substance.

2) Manufacture of 1-(2-ethylphenyl)-5-methyl-4-tributylstanyl-1H-[1,2,3]triazole 1.9 ml of tributyl(1-propynyl)tin was added to 5 ml solution of toluene with 1.0 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 2.0 g of the above compound as yellow oily substance.
$^1$HNMR (400 MHz, CDCl$_3$), δ: 0.90 (9H, t, J=7.2 Hz), 1.05 (3H, t, J=7.6 Hz), 1.17-1.65 (18H, m), 2.14 (3H, t, 2.0 Hz), 2.31 (2H, q, J=7.7 Hz), 7.19 (1H, dd, J=1.0, 7.8 Hz), 7.33 (1H, dd, J=1.6, 7.6 Hz), 7.39-7.49 (2H, m),
ESI-MS Found: m/z 478.3 [M+H]$^+$.

REFERENCE EXAMPLE 21

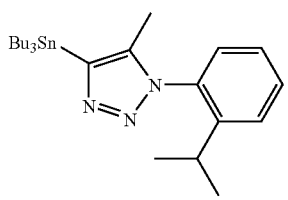

1-(2-isopropylphenyl)-5-methyl-4-tributylstanyl-1H-[1,2,3]triazole

1) Manufacture of 1-azide-2-isopropylbenzene 2.9 g of sodium nitrite dissolved in 11 ml of water was dropped under iced temperature to 9.3 ml of concentrated chloric acid with 2.6 g of 2-isopropylaniline, 14 ml of water, and 50 ml of ethanol. After stirring the mixture under iced temperature for 30 min, 3.0 g of sodium azide dissolved in 11 ml of water was dropped thereto. The reaction solution was heated to room temperature and stirred for 1 hour. The reaction solution was neutralized with sodium carbonate, and the products were extracted with chloroform. Organic layer was washed with saturated saline solution and dried with anhydrous sodium sulfate. The solvents were distilled outunder reduced pressure to obtain 1.7 g of the above compound as crude bronze oily substance.

2) Manufacture of 1-(2-isopropylphenyl)-5-methyl-4-tributylstanyl-1H-[1,2,3]triazole 1.7 ml of tributyl(1-propynyl)tin was added to 5 ml solution of toluene with 1.0 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 1.1 g of the above compound as yellow oily substance.
$^1$HNMR (400 MHz, CDCl$_3$), δ: 0.90 (9H, t, J=7.4 Hz), 1.13 (6H, d, J=7.2 Hz), 1.17-1.65 (18H, m), 2.12 (3H, t, 1.8 Hz), 2.37-2.45 (1H, m), 7.14-7.19 (1H, m), 7.29-7.34 (1H, m), 7.47-7.51 (2H, m),
ESI-MS Found: m/z 492.3 [M+H]$^+$.

REFERENCE EXAMPLE 22

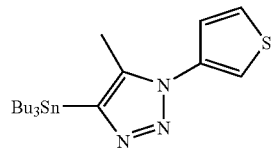

1-(thiophene-3-yl)-5-methyl-4-tributylstanyl-1H-[1,2,3]triazole

1) Manufacture of 3-azidethiophene 2.9 g of sodium nitrite dissolved in 11 ml of water was dropped under iced temperature to 9.3 ml of concentrated chloric acid with 1.8 g of 3-aminothiophene, 14 ml of water, and 50 ml of ethanol. After stirring the mixture under iced temperature for 30 min, 3.0 g of sodium azide dissolved in 11 ml of water was dropped thereto. The reaction solution was heated to room temperature and stirred for 1 hour. The reaction solution was neutralized with sodium carbonate, and the products were extracted with chloroform. Organic layer was washed with saturated saline solution and dried with anhydrous sodium sulfate. The solvents were distilled outunder reduced pressure to obtain 1.3 g of the above compound as crude bronze oily substance.

2) Manufacture of 1-(thiophene-3-yl)-5-methyl-4-tributylstanyl-1H-[1,2,3]triazole 1.5 ml of tributyl(1-propynyl)tin was added to 5 ml solution of toluene with 1.0 g of the compound obtained in 1), and the mixture was stirred all night at 120° C. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=90:10) to obtain 1.0 g of the above compound as yellow oily substance.

ESI-MS Found: m/z 456.2 [M+H]⁺.

REFERENCE EXAMPLE 23

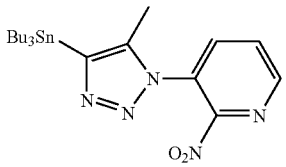

1-(2-nitropyridine-5-yl)-5-methyl-4-tributylstanyl-1H-[1,2,3]triazole 5.89 mg of tributyl(1-propynyl)tin was added to 6 ml solution of toluene with 1.29 g of 5-azide-2-nitropyridine, and the mixture was stirred all night at 120° C. The obtained solution was cooled down to room temperature and purified by silicagel column chromatography (hexane:ethyl acetate=75:25) to obtain 962 mg of the above compound as yellow oily substance.

$^1$HNMR (400 MHz, CDCl$_3$), δ: 0.91 (9H, t, J=8.0 Hz), 1.12-1.28 (6H, m), 1.29-1.40 (6H, m) 1.51-1.65 (6H, m), 2.26 (3H, s), 7.81-7.86 (1H, m), 7.99-8.03 (1H, m), 8.72-8.76 (1H, m).

REFERENCE EXAMPLE 24

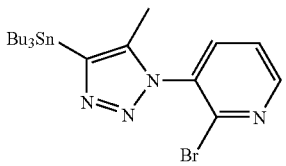

1-(2-bromopyridine-3-yl)-5-methyl-4-tributylstanyl-1H-[1,2,3]triazole

1) Manufacture of 3-azide-2-bromopyridine

Under nitrogen atmosphere, 10 ml solution of tetrahydrofuran with 0.53 ml of diisopropylamine was cooled down to −78° C., and 2.3 ml of 1.58 M n-butyl lithium/hexane solution was dropped thereto. The reaction solution was heated to 0° C., stirred for 5 min, cooled down again to −78° C., and 1.0 ml solution of tetrahydrofuran with 569 mg of 2-bromopyridine was added thereto. After stirring at −78° C. for 10 min, 1.0 ml solution of tetrahydrofuran with 1.05 g of n-dodecylbenzene sulfoneazide was added and stirred. The reaction solution was heated to −60° C., water was added and the reaction was stopped. The products were extracted with ethyl acetate, dried with anhydrous sodium sulfate and the solvents were distilled outunder reduced pressure. The obtained residues were purified by silicagel column chromatography (hexane:ethyl acetate=90:10) to obtain the above compound as crude liver oily product.

2) Manufacture of 1-(2-bromopyridine-3-yl)-5-methyl-4-tributylstanyl-1H-[1,2,3]triazole 987 mg of tributyl(1-propynyl)tin was added to 2.0 ml solution of toluene with the compound obtained in 1), and the mixture was stirred at 120° C. for 3 hours. The obtained solution was cooled down to room temperature, and purified by silicagel column chromatography (hexane:ethyl acetate=75:25) to obtain 190 mg of the above compound as yellow oily substance.

$^1$HNMR (400 MHz, CDCl$_3$), δ: 0.90 (9H, t, J=8.0 Hz), 1.12-1.40 (12H, m), 1.48-1.68 (6H, m), 2.22 (3H, s), 7.46-7.51 (1H, m), 7.73-7.77 (1H, m), 8.55-8.58 (1H, m).

REFERENCE EXAMPLE 25

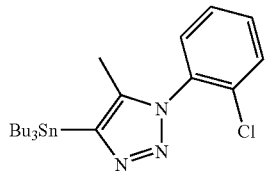

1-(2-chlorophenyl)-5-methyl-4-tributylstanyl-1H-1,2,3]triazole

1) Manufacture of 1-azide-2-chlorobenzene 8.28 g of sodium nitrate dissolved in 50 ml of water was dropped under iced temperature to 100 ml of concentrated chloric acid with 17.9 g of 2-chlorophenylhydrazine hydrochloride and 150 ml solution of diethylether. The reaction solution was heated to room temperature and stirred for 2 hours. The reaction solution was diluted with diethylether, washed with water followed by saturated saline solution and dried with anhydrous sodium sulfate. The solvents were distilled outunder reduced pressure to obtain 16 g of the above compound as crude bronze oily substance.

2) Manufacture of 1-(2-chlorophenyl)-5-methyl-4-tributylstanyl-1=H-[1,2,3]triazole 12 g of tributyl(1-propynyl)tin was added to 20 ml solution of toluene with 16 g of the compound obtained in 1), and the mixture was stirred at 120° C. for 6 hours. The obtained solution was cooled down to room temperature, saturated potassium fluoride aqueous solution was added to the reaction solution. The products were extracted with ethyl acetate, washed with saturated saline solution and dried with anhydrous sodium sulfate. The solvents were distilled outunder reduced pressure, and the residues were purified by silicagel column chromatography (hexane:ethyl acetate=9:1) to obtain 10 g of the above compound as yellow oily substance.

$^1$HNMR (400 MHz, CDCl$_3$), δ: 0.86 (9H, m), 1.11-1.22 (6H, m), 1.31-1.40 (6H, m), 1.51-1.66 (6H, m), 2.18 (3H, s), 7.41-7.51 (3H, m), 7.58 (1H, d, J=8.0 Hz),

ESI-MS Found: m/z 484.1 [M+H]⁺.

Pharmacological test examples shown in the following were performed by using the compound of the present invention as test compounds.

PHARMACOLOGICAL TEST EXAMPLE 1 mGluR1 Inhibiting Effect

MGlu1 inhibiting effect was measured by using the compound of the present invention.
(Cell Culture)
With the use of Lipofectamine (Gibco BRL), cDNA of human metabotropic glutamate receptor 1a (mGluR1a) were transfected to CHO cells, to obtain cells expressing mGluR1a in a stable manner. CHO cells which expressed mGluR1a were cultured in DMEM medium containing 10% dialysis fetal bovine serum, 1% proline, 100 units/ml of penicillin, 0.1 mg of streptomycin sulfate and 2 nM glutamine.
(Measurement of Intracellular Calcium Concentration)
4 μM of Fluo-3 was incubated to mGluR1a-expressing CHO cells plated with 50000 cells per 1 well of 96-well black plate (Packard, Viewplate) the day before the measurement, in a CO2 incubator for 1 hour. The cells were washed 4 times with HBSS solution containing 20 mM HEPES and 25 mM probenecid, and the intracellular calcium concentration was measured with the use of Fluorescence Imaging Plate Reader (FLIPR; Mollecular Device). The test compounds and glutamic acid were adjusted with HBSS solution containing 20 mM HEPES and 2.5 mM Probenecid. The test compounds were added 5 min before agonist stimulation, and 10 μM of glutamic acid was used as agonist.

As a result, the compounds of the present invention shown in the following table 1 did not exhibit agonistic property until the amount reached 10 μM. The calcium increased with 10 μM of glutamic acid was suppressed dose-dependently. The IC 50 levels are shown in Table 1.

TABLE 1

| | IC 50 (nM) |
|---|---|
| Example 34 | 2.3 |
| Example 36 | 6.5 |
| Example 49 | 3.2 |
| Example 85 | 4.4 |
| Example 87 | 4.3 |
| Example 119 | 4.3 |
| Example 151 | 2.5 |
| Example 181 | 18 |
| Example 204 | 3.4 |
| Example 227 | 2.4 |

As for animal models to which existing antipsychotic drugs such as Haloperidol and Risperidone are effective, spontaneous movement-increased models and prepulse inhibition decreased models by Amphetamine administration are known. In both tested systems, the drug effect having mGluR1 antagonistic effect was investigated.

PHARMACOLOGICAL TEST EXAMPLE 2

Suppressing Effect of the Compound to Mouse Spontaneous Movement Level Increased by methamphetamine With the use of male ICR(CD-1) mouse (20-40 g), movement level was measured with the use of movement level-measuring device detecting animal migration by infrared radiation sensor (Neuroscience). Compounds or appropriate solvents were administered to mice, and after administrating normal saline solution or 2 mg/kg of methamphetamine 30 min later, the movement level during 60 min from after the administration was measured. By making the difference between the movement level of the methamphetamine-administered group and that of the solvents-administered group during measuring period as 100%, the movement level of test compound-administered group was shown by inhibition % for estimation. The movement level during 60 min after the admistration was significantly increased by subcutaneous methamphetamine administration. By administrating orally the compound of the present invention having mGluR1 antagonist effect (3 mg/kg) 30 min before administration of metanephetamine, increase of movement level due to methapheamine was significantly suppressed. The results are shown in Table 2.

From these results, the compounds of the present invention or pharmaceutically acceptable salts thereof were shown to have obvious antagonist effect to enhance spontaneous movement level induced by methamphetamine.

TABLE 2

| Compounds of Examples | Movement level (inhibition %) |
|---|---|
| Example 34 | >50% |
| Example 36 | >50% |
| Example 49 | >50% |
| Example 85 | >50% |
| Example 87 | >50% |
| Example 119 | >50% |
| Example 151 | >50% |
| Example 181 | >50% |
| Example 204 | >50% |
| Example 227 | >50% |

PHARMACOLOGICAL TEST EXAMPLE 3

Suppressing Effect of the Compound Toward the Prepulse Inhibition Reduced by methamphetamine Systems tested for prepulse inhibition which can detect specifically antipsychotic effect were also investigated. By using startle reflex measuring device (San Diego Instruments) which can dectect movement of rats, startle reaction to 120 dB-sound stimulation (pulse stimulation) combined with 63, 66 and 72 dB-sound stimulation prior to pulse stimulation (prepulse) was measured in the presence of 60 dB-background sound. The compounds of the present invention or appropriate solvents were administered to rats, and normal saline solution or 3 mg/kg of methamphetamine was administered 30 min later, to measure startle reation. Startle reactions to pulse stimulation and to stimulation with prepulse were named A and B respectively, and the prepulse inhibition (herein referred to as PPI) level was calculated with the following formula.

Calculating formula of PPI:PPI(%)=100×$(A-B)/A$

In contrast to startle reaction toward pulse stimulation, in the presence of preminary prepulse of 72 dB, startle reaction decreased by about 50% (prepulse inhibition). When pretreating with methamphemine, strate reaction decreased only by about 20%, and decrease of prepulse inhibition was observed. Moreover, by administrating orally the compounds having mGluR1 antagonist effect 30 min before methamphetamine administration to the present models, decrease of prepulse inhibition by methamphetamine had tendance to recover. The significant suppressing effects to PPI, which decreases with methamphemine, are shown in the following Table 3.

From these results, the compounds of the present invention are suggested to recover PPI disorder induced by methamphemine.

TABLE 3

| Compounds of Examples | Inhibition effect to PPI disorder |
|---|---|
| Example 34 | yes |
| Example 36 | yes |
| Example 49 | yes |
| Example 85 | yes |
| Example 87 | yes |
| Example 119 | yes |
| Example 151 | yes |
| Example 181 | yes |
| Example 204 | yes |
| Example 227 | yes |

From the above results of Pharmacological Test Examples 2 and 3, the compounds of the present invention having mGluR1 inhibiting effect, were shown to have similar effect as schizophrenia-treating agents in model animals to which schizophrenia-treating agents such as Haloperidol and Risperidone are effective.

Therefore, the compounds of the present invention having mGluR1 antagonist effect were demonstrated to be useful agent for treating and/or preventing schizopherenia.

INDUSTRIAL APPLICABILITY

The present invention provides novel substances having mGluR1 inhibiting effect. Diaryl-substituted hetero 5-membered derivatives shown by formula (I) or pharmaceutical salts thereof have strong mGluR1 inhibiting effect, and are useful for preventing or treating convulsion, acute pain, inflammatory pain, chronic pain, brain disorder such as cerebral infarction or transient ischemick attack, psychotic disorder such as schizophrenic, anxiety, drug dependence, Parkinson's disease or gastrointestinal disorder.

the invention claimed is:
1. A compound of the formula (I):

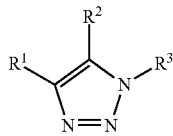

wherein:
$R^1$ is selected from the group consisting of:
quinoline-6-yl, quinoline-7-yl, isoquinoline-7-yl, isoquinoline-6-yl, 2-methylquinoline-6-yl, isoquinoline-3-yl, 2-methoxyquinoline-6-yl, 3-methoxyquinoline-6-yl, 2-dimethylamino-quinoline-6-yl, 2-chloro-3-ethyl-quinoline-6-yl, 2-morpholine-4-yl-quinoline-6-yl, 2-(4-methylpiperazine-1-yl)-quinoline-6-yl, 2-pyrrolidine-1-yl-quinoline-6-yl, 2-methanesulfonyl-quinoline-6-yl, 2-isopropyl-methylamino-quinoline-6-yl, 2-(2-hydroxy-2-methyl-propyl)-quinoline-6-yl, and 2-(2-hydroxy-2-methyl-propyl)-1-oxo-isoquinoline-6-yl;

$R^2$ represents a substituent selected from the group consisting of:
hydrogen atom, lower alkyl group, cyano group, lower alkyloxy group, lower alkyloxycarbonyl group, and trialkylsilyl group;

R3 is a phenyl group, which is unsubstituted or substituted with 1 to 3 groups selected from the group consisting of:
halogen atom, lower alkyl group, cyano group, nitro group, lower alkyloxy group, hydroxy group, and amino group, wherein the lower alkyl group is unsubstituted or substituted with a halogen atom;

or a pharmaceutically acceptable salt thereof.

2. The compound of claim 1 wherein $R^1$ is 2-(2-hydroxy-2-methyl-propyl)-quinoline-6-yl.

3. The compound of claim 1 wherein $R^1$ is 2-(2-hydroxy-2-methyl-propyl)-1-oxo-isoquinoline-6-yl.

4. The compound of claim 1 wherein $R^2$ represents a substituent selected from the group consisting of: lower alkyl group, and cyano group.

5. A compound which is selected from the group consisting of:
5-methyl-1-phenyl-4-(quinoline-6-yl)-1H-[1,2,3]triazole,
4-(2-(2-hydroxy-2-methyl-propyl)-1-oxo-isoquinoline-6-yl)-1-(4-fluorophenyl)-5-methyl-1H-[1,2,3]triazole, and
1-(4-fluorophenyl)-5-methyl-4-(2-(2-hydroxy-2-methyl-propyl)-quinoline-6-yl)-1H-[1,2,3]triazole,
or a pharmaceutically acceptable salt thereof.

6. The compound of claim 5 which is selected from the group consisting of:
4-(2-(2-hydroxy-2-methyl-propyl)-1-oxo-isoquinoline-6-yl)-1-(4-fluorophenyl)-5-methyl-1H-[1,2,3]triazole;
or a pharmaceutically acceptable salt thereof.

7. A compound which is selected from the group consisting of:
1-(4-fluorophenyl)-5-methyl-4-(2-(2-hydroxy-2-methyl-propyl)-quinoline-6-yl)-1H-[1,2,3]triazole,
or a pharmaceutically acceptable salt thereof.

8. The compound of claim 7 which is:
1-(4-fluorophenyl)-5-methyl-4-(2-(2-hydroxy-2-methyl-propyl)-quinoline-6-yl)-1H-[1,2,3]triazole.

9. A pharmaceutical composition which comprises an inert carrier and the compound of claim 1, or a pharmaceutically acceptable salt thereof.

10. A pharmaceutical composition which comprises an inert carrier and the compound of claim 5, or a pharmaceutically acceptable salt thereof.

11. A pharmaceutical composition which comprises an inert carrier and the compound of claim 6, or a pharmaceutically acceptable salt thereof.

12. A pharmaceutical composition which comprises an inert carrier and the compound of claim 7, or a pharmaceutically acceptable salt thereof.

13. A pharmaceutical composition which comprises an inert carrier and the compound of claim 8, or a pharmaceutically acceptable salt thereof.

* * * * *